US012703697B2

(12) United States Patent
August et al.

(10) Patent No.: US 12,703,697 B2
(45) Date of Patent: Aug. 11, 2026

(54) BCAT MODULATION

(71) Applicant: Icagen, LLC, Emeryville, CA (US)

(72) Inventors: Paul R. August, Durham, NC (US); Margaret Kenney, Durham, NC (US); Jacques Mauger, Durham, NC (US); Mark Drew, Durham, NC (US); Weixi Kong, Durham, NC (US)

(73) Assignee: Icagen, LLC, Emeryville, CA (US)

( * ) Notice: Subject to any disclaimer, the term of this patent is extended or adjusted under 35 U.S.C. 154(b) by 892 days.

(21) Appl. No.: 17/625,607

(22) PCT Filed: Jul. 8, 2020

(86) PCT No.: PCT/US2020/041254
§ 371 (c)(1),
(2) Date: Jan. 7, 2022

(87) PCT Pub. No.: WO2021/007350
PCT Pub. Date: Jan. 14, 2021

(65) Prior Publication Data

US 2022/0274967 A1 Sep. 1, 2022

Related U.S. Application Data

(60) Provisional application No. 62/871,828, filed on Jul. 9, 2019.

(51) Int. Cl.

| | |
|---|---|
| ***C07D 409/14*** | (2006.01) |
| ***A61P 13/02*** | (2006.01) |
| ***C07D 401/04*** | (2006.01) |
| ***C07D 405/14*** | (2006.01) |
| ***C07D 409/12*** | (2006.01) |
| ***C07D 413/14*** | (2006.01) |
| ***C07D 471/04*** | (2006.01) |
| ***C07D 487/04*** | (2006.01) |

(52) U.S. Cl.
CPC ............ *C07D 409/14* (2013.01); *A61P 13/02* (2018.01); *C07D 401/04* (2013.01); *C07D 405/14* (2013.01); *C07D 409/12* (2013.01); *C07D 413/14* (2013.01); *C07D 471/04* (2013.01); *C07D 487/04* (2013.01)

(58) Field of Classification Search
CPC ............ A61K 2300/00; A61K 31/4035; A61K 45/06; A61P 13/02; A61P 3/00; C07D 235/18; C07D 401/04; C07D 405/14; C07D 409/12; C07D 409/14; C07D 413/14; C07D 471/04; C07D 487/04
See application file for complete search history.

(56) References Cited

U.S. PATENT DOCUMENTS

2012/0289476 A1 11/2012 Barth
2015/0057363 A1 2/2015 Miller et al.

OTHER PUBLICATIONS

Taheri et. al. (Green Chem., 17, 812-816) (Year: 2015).*
CAS Registry File 1275679-54-3; entered into STN Apr. 6, 2011; obtained from the internet Nov. 4, 2025 (Year: 2011).*
CAS Registry File 1461651-06-8; entered into STN Oct. 21, 2013; obtained from the internet Nov. 4, 2025 (Year: 2013).*
CAS Registry File 1478952-80-5; entered into STN Nov. 22, 2013; obtained from the internet Nov. 4, 2025 (Year: 2013).*
CAS Registry File 1480438-63-8; entered into STN Nov. 25, 2013; obtained from the internet Nov. 4, 2025 (Year: 2013).*
CAS Registry File 1485203-90-4; entered into STN Dec. 2, 2013; obtained from the internet Nov. 4, 2025 (Year: 2013).*
CAS Registry File 1712010-58-6; entered into STN May 25, 2015; obtained from the internet Nov. 5, 2025 (Year: 2015).*
CAS Registry File 1854752-02-5; entered into STN Jan. 28, 2016; obtained from the internet Nov. 5, 2025 (Year: 2016).*
Deng et. al., "Discovery and Optimization of Potent, Selective, and in Vivo Efficacious 2-Aryl Benzimidazole BCATm Inhibitors", ACS Med Chem Lett, 7, 379-384 (Year: 2016).*
Meanwell, "Fluorine and Fluorinated Motifs in the Design and Application of Bioisosteres for Drug Design", J Med Chem, 61, 5822-5880 (Year: 2018).*
Brunetti-Pierri et al., 2011, Phenylbutyrate therapy for maple syrup urine disease, Human Molecular Genetics, 20(4):631-640.
CAS Registry No. 1225152-21-5; STN Entry Date May 26, 2010; 2- Quinazolinamine, N-(3-chloro-4-methoxyphenyl)-4-(1-pyrrolidinyl).
Deng et al., 2016, Discovery and Optimization of Potent, Selective, and inVivo Efficacious 2/Aryl Benzimidazole BCATm Inhibitors, ACS Med. Chem. Lett., 7:379-384.
During et al., Apr. 1989, Controlled release of dopamine from a polymeric brain implant: in vivo characterization, Ann. Neurol. 25(4):351-356.
Goodson, 1984, Dental Applications, in Langer et al., eds., Medical Applications of Controlled Release, vol. II: Application and Evaluation, CRC Press Inc., Boca Raton, FL, pp. 115-138.
Greene and Wutts, 1999, Protective Groups in Organic Synthesis, 3rd Edition, John Wiley & Sons, Inc., New York (TOC).
Howard et al., 1989, Intracerebral drug delivery in rats with lesion-induced memory deficits, J. Neurosurg. 71:105-112.
Kawamoto, 2015, Maple syrup urine disease, Japanese Society of Inherited Metabolic Disorders, Medical Guide for Diseases Submited to Neonatal Mass Screening, p. 17.
Langer and Peppas, 1983, Chemical and physical structure of polymers as carriers for controlled release of bioactive agents: a review, J. Macromol. Sci. Rev. Macromol. Chem. 23:61-126.
Langer, Sep. 28, 1990, New methods of drug delivery, Science 249:1527-1533.

(Continued)

*Primary Examiner* — Jeffrey H Murray
*Assistant Examiner* — Daniel John Burkett
(74) *Attorney, Agent, or Firm* — Knobbe, Martens, Olson & Bear, LLP

(57) ABSTRACT

This disclosure relates to, in part, the treatment of an organic acidemia in a subject in need thereof via administration of a therapeutically effective amount of compounds that inhibit BCAT2. The disclosure also relates to, in part, methods for identifying a candidate compound for treatment of organic acidemias such as maple syrup urinary disease, methylmalonic acidemia, propionic acidemia and isovaleric acidemia.

21 Claims, 6 Drawing Sheets

(56) References Cited

OTHER PUBLICATIONS

Levy et al., 1985, Inhibition of calicifcation of bioprosthetic heart valves by local controlled-release diphosphonate, Science 228:190-192.
Manoli et al., 2016, Disorders of branched chain amino acid metabolism, Translational Science of Rare Diseases, 1:91-110.
Schiff et al., 2016, Branched-chain Organic Acidurias/Acidaemias, in Saudubray et al., eds., Inborn Metabolic Diseases, Springer Verlag, Berlin, pp. 278-294.
Smith et al., eds., 2001, March's Advanced Organic Chemistry, 5th Edition, John Wiley & Sons, Inc., New York (TOC).
Smolen et al., eds., 1984, Controlled Drug Bioavailability, vol. 1: Drug Product Design and Performance, John Wiley & Sons, New York (TOC).
Treat et al., 1989, Liposome encapsulated doxorubicin preliminary results of phase 1 and phase 11 trials, in Lopez-Berestein et al., eds., Liposomes in the Therapy of Infectious Disease and Cancer, Allan R. Liss, Inc., New York, pp. 353-365.
Tso et al., 2014, Benzothiophene Carboxylate Derivatives as Novel Allosteric Inhibitors of Branched-chain α-Ketoacid Dehydrogenase Kinase, J. Biol. Chem., 289(30):20583-20593.
International Search Report and Written Opinion dated Sep. 18, 2020, in application No. PCT/US2020/041254.
CAS Registry No. 1156931-43-9, entered STN: Jun. 14, 2009, 1 p.
CAS Registry No. 1461651-06-8, entered STN: Oct. 21, 2013, 1 p.
CAS Registry No. 1890633-69-8, entered STN Apr. 15, 2016, 1 p.
CAS Registry No. 1893594-33-6, entered STN Apr. 20, 2016, 1 p.
CAS Registry No. 1893969-89-5, entered STN Apr. 20, 2016, 1 p.
CAS Registry No. 1893971-84-0, entered STN Apr. 20, 2016, 1 p.
CAS Registry No. 1896038-54-2, entered STN Apr. 24, 2016, 1 p.
Sonnet et al., Jul. 4, 2016, Metformin inhibits branched chain amino acid (BCAA) derived ketoacidosis and promotes metabolic homeostasis in MSUC, Scientific Reports, 6:28775.
Azepine Product List (http://azepine.com/) obtained from the CHEMCATS database, publication date Mar. 1, 2019.Catalogue Nos. (CAS Reg. Nos. ) AZ05304148 (1893969-89-5), AZ05304728 (1893971-84-0), AZ05302690 (1896038-54-2), AZ05304665 (1890633-69-8),AZ05302266 (1893594-33-6), AZ01202979 (1156931-43-9), AZ01664001 (1461651-06-8).

* cited by examiner

A

BCAT MODULATION

CROSS REFERENCE TO RELATED APPLICATIONS

This application is U.S. National Phase under 35 U.S.C. § 371 of International Application No. PCT/US2020/041254, filed Jul. 8, 2020, designating the U.S., which claims the benefit of U.S. Provisional Application No. 62/871,828, filed Jul. 9, 2019, each of which is incorporated herein by reference in its entirety.

FIELD

This disclosure relates to methods and compositions that are useful for targeting a branched-chain amino acid aminotransferase (BCAT) for the treatment of genetic disorders of amino acid metabolism.

BACKGROUND

Branched chain organic acidurias and/or organic acidemias are a group of disorders that result from an abnormality of specific enzymes involving the catabolism of branched chain amino acids (BCAA)—leucine, isoleucine, and valine. Organic acidemias are a subset of rare diseases that affect approximately 150,000 patients worldwide. Patients afflicted with an organic acidemia over-produce metabolites in the mitochondria that result in the toxic accumulation of substrate molecules. Some of the toxic molecules negatively impact normal metabolic pathways by allosterically inhibiting key enzymes. The effects on cell metabolism result in neurodevelopmental pathologies and failure to thrive pathologies, which can lead to death if not treated. Maple syrup urine disease (MSUD), isovaleric acidaemia (IVA), propionic aciduria (PA) and methylmalonic aciduria (MMA) represent the most commonly encountered abnormal organic acidemias. However, any mutation in the BCAA metabolic pathway which results in the accumulation of a metabolic intermediate also would be considered an organic acidemia. MMA, PA and IVA present with a severe dehydration, leuconeutropenia and thrombopenia which can mimic sepsis. These disorders can be diagnosed by newborn genetic screening and identifying acylcarnitine and other organic acid compounds in plasma and urine by gas chromatography mass spectrometry or tandem MS-MS.

The BCAAs include a first step in their catabolism that is common to all three, involving the BCAA aminotransferase (BCAT) and branched chain α-keto acid dehydrogenase (BCKD). Their further metabolism employs distinct pathways to different end products (e.g., glucose and/or ketone bodies). However, the fact that the flux-generating step (involving BCKD) for the catabolism of the three BCAAs occurs at one of the common steps indicates that the production of these downstream products are not individually regulated and, hence, may not play important individual roles. The catabolism of the BCAAs is highly regulated by both allosteric and covalent mechanisms. BCKD is inhibited by phosphorylation and activated by dephosphorylation. Allosteric inhibition of the kinase by the branched-chain keto acids (BCKA) (particularly by α-ketoisocaproate) serves both as a mechanism for promoting the catabolism of excess quantities of these amino acids as well as for conserving low concentrations of these dietary essential amino acids. Cytosolic and mitochondrial isoenzymes of BCAT have been identified.

SUMMARY

In some embodiments, provided herein is a method of treating an organic acidemia, comprising administering a therapeutically effective amount of a BCAT2 inhibitor compound described herein.

In some embodiments, provided herein is a method of reducing toxic branched-chain amino acid (BCAA) metabolites, comprising administering a therapeutically effective amount of a BCAT2 inhibitor compound described herein.

In some embodiments, provided herein is a method of reducing a toxic load burden in cells of a patient having organic acidemia, comprising administering a therapeutically effective amount of a BCAT2 inhibitor described herein.

In some embodiments, the compounds described herein are compounds having the structure of Formula (I) or a pharmaceutically acceptable salt thereof:

(I)

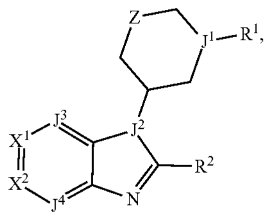

wherein

Z may be $CH_2$, $CF_2$, O, or a bond;

each of $J^1$, $J^2$, $J^3$, and $J^4$ may be independently CH or N;

$X^1$ is N or $CR^{5A}$;

$X^2$ is N or $CR^{5B}$;

$R^1$ may be $C_1$-$C_6$ alkyl, —$NR^3S(O)R^4$, —$NR^3SO_2R^4$, —$NR^3C(O)R^4$, —$C(O)(CH_2)_mNR^3R^4$, $C_6$-$C_{10}$ aryl, 5-10-membered heteroaryl, or (5-10-membered heteroaryl)-$C_1$-$C_6$ alkyl;

$R^2$ may be —$NR^6R^7$, $C_1$-$C_6$ alkyl, $C_3$-$C_8$ cycloalkyl, $C_6$-$C_{10}$ aryl, or 5-10 membered heteroaryl, wherein each aryl or heteroaryl may be optionally substituted with one, two, or three substituents $R^{2'}$ independently selected from halo, —CN, —$NO_2$, $C_1$-$C_6$ alkyl, $C_1$-$C_6$ alkoxy, halo$C_1$-$C_6$ alkyl, halo$C_1$-$C_6$ alkoxy, $C_2$-$C_6$ alkenyl, $C_2$-$C_6$ alkynyl, —$C(O)NR^6R^7$, —$C(O)R^6$, —$NR^6R^7$, —$NR^6C(O)R^7$, —OH, —S-(halo$C_1$-$C_6$ alkyl), $C_6$-$C_{10}$ aryl, and 5-10 membered heterocyclyl; or two $R^{2'}$ substituents together with the atoms to which they are attached may form a five-membered heterocyclyl or $C_3$-$C_8$ cycloalkyl, each optionally substituted with halo;

$R^3$ may be H or $C_1$-$C_6$ alkyl;

$R^4$ may be H, $C_1$-$C_6$ alkyl, $C_2$-$C_6$ alkenyl, $C_6$-$C_{10}$ aryl, or 5-10 membered heteroaryl, wherein each aryl or heteroaryl may be optionally substituted with one, two, or three substituents $R^{4'}$ independently selected from halo, —CN, —$NO_2$, $C_1$-$C_6$ alkyl, halo$C_1$-$C_6$ alkyl, $C_1$-$C_6$ alkoxy, $C_2$-$C_6$ alkenyl, $C_3$-$C_8$ cycloalkyl, $C_6$-$C_{10}$ aryl, —$(CH_2)_qNR^8C(O)R^9$, —$C(O)NR^8R^9$, —$C(O)OR^9$, $C(O)R^9$, and 5-10 membered heterocyclyl;

$R^{5A}$ may be H, halo, —CN, $C_1$-$C_6$ alkyl, halo$C_1$-$C_6$ alkyl, $C_1$-$C_6$ alkoxy, —$(CH_2)_rOH$, —$C(O)NR^8R^9$, —$NR^8COR^9$, 5-10 membered heteroaryl, —$C(O)R^8$, or —$C(O)OR^8$;

$R^{5B}$ is H, halo, —CN, $C_1$-$C_6$ alkyl, halo$C_1$-$C_6$ alkyl, $C_1$-$C_6$ alkoxy, —$(CH_2)_r$OH, —C(O)$NR^8R^9$, —$NR^8COR^9$, 5-10 membered heteroaryl, —C(O)$R^8$, or —C(O)O$R^8$;

or $R^{5A}$ and $R^{5B}$ together with the atoms to which they are attached may form a six-membered heterocyclyl ring optionally substituted with oxo;

$R^6$ and $R^7$ may be independently H, $C_1$-$C_6$ alkyl, or $C_3$-$C_8$ cycloalkyl;

each $R^8$ may be independently H. $C_1$-$C_6$ alkyl, or $C_3$-$C_8$ cycloalkyl;

each $R^9$ may be independently H, $C_1$-$C_6$ alkyl, $C_2$-$C_6$ alkenyl, or $C_3$-$C_8$ cycloalkyl;

m may be 0 or 1;

q may be 0 or 1; and r may be 0 or 1.

In some embodiments, $R^{5A}$ is not hydrogen.

In some embodiments, $R^{5B}$ is not hydrogen or —C(O)$NR^8R^9$.

In some embodiments, $R^2$ is not unsubstituted aryl or unsubstituted heteroaryl. In some embodiments, $R^2$ is not $C_6$-$C_{10}$ aryl substituted with one —S—$C_1$-$C_6$ alkyl. In some embodiments, $R^2$ is not 5-10 membered heteroaryl substituted with one $C_1$-$C_6$ alkyl.

In some embodiments, the compound of Formula (I) is not selected from the group consisting of:

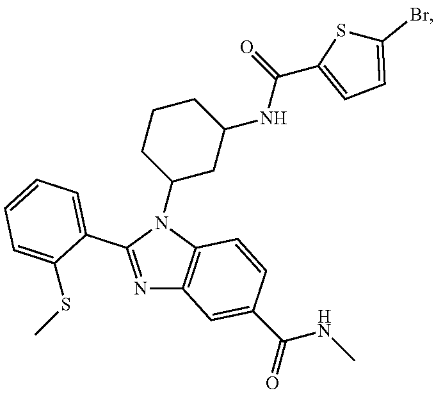

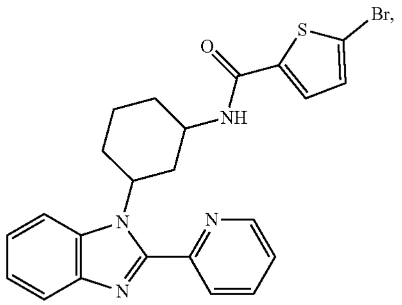

-continued

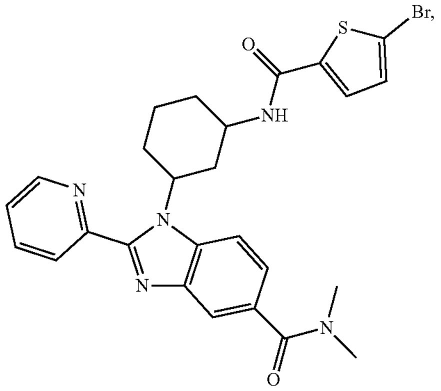

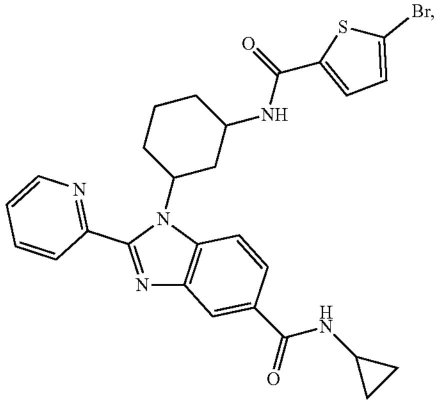

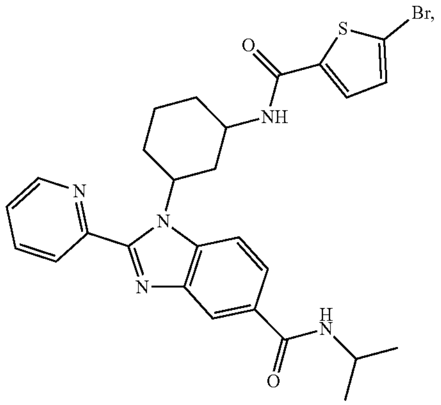

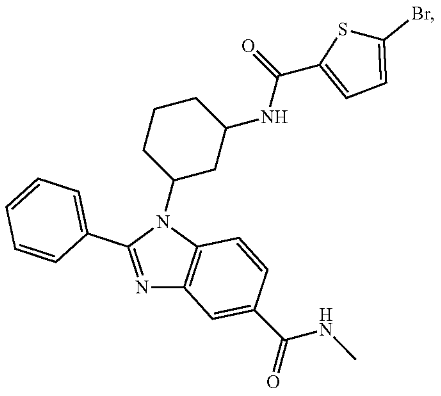

-continued
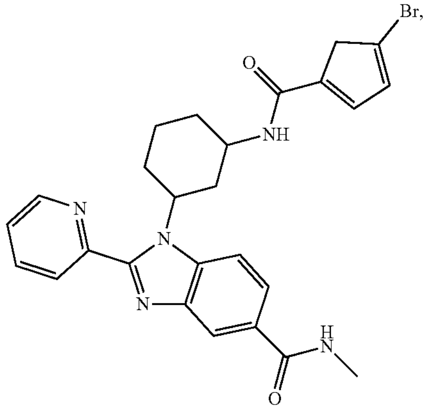
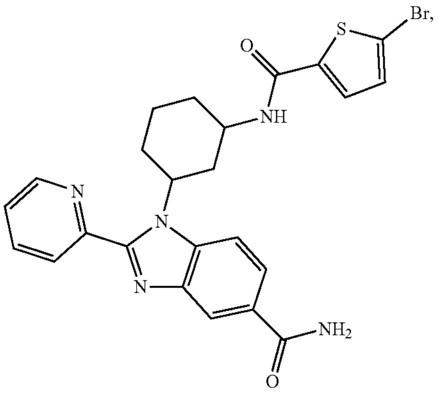
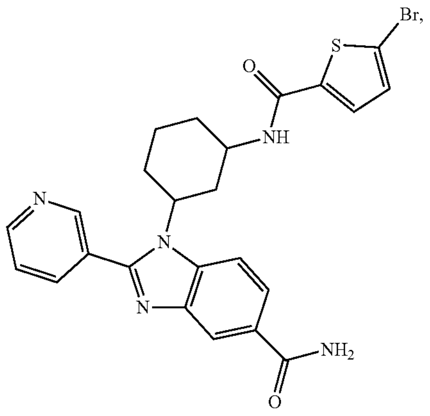
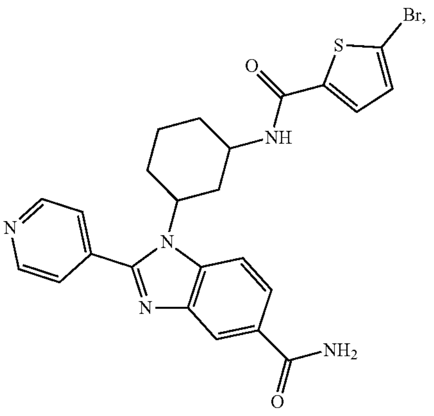
-continued
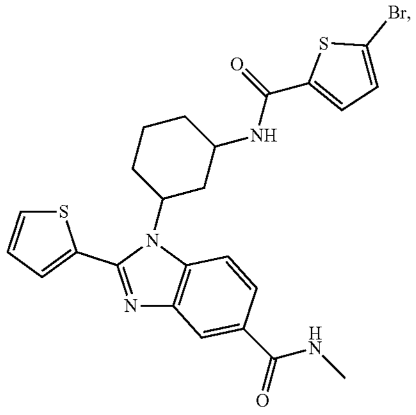
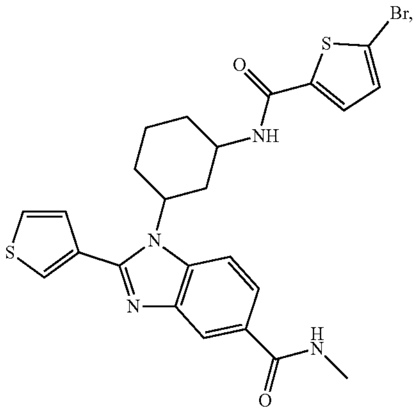
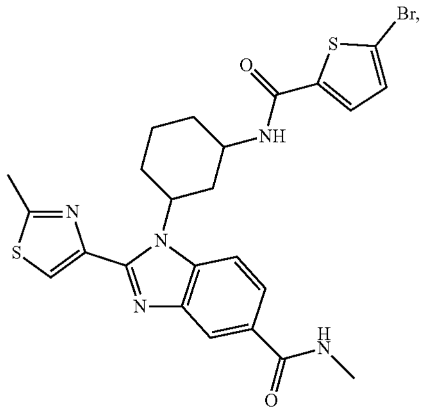
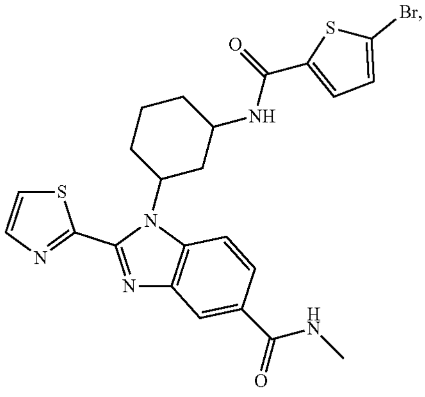

-continued
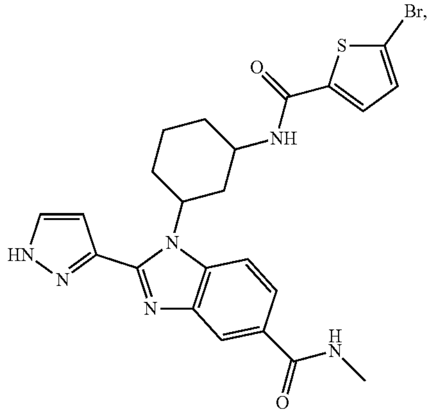
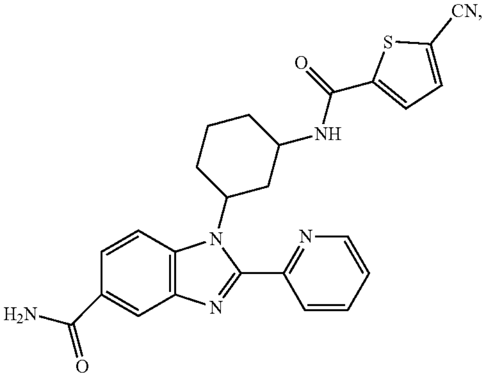
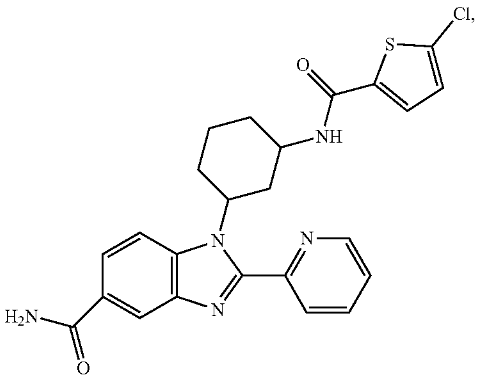
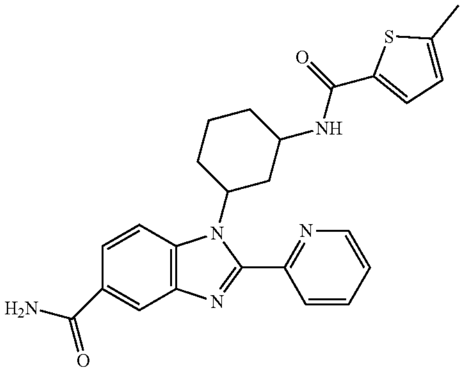
,
-continued
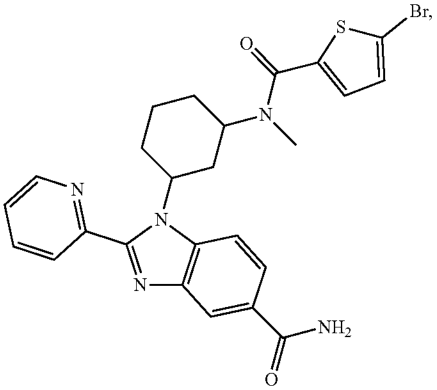
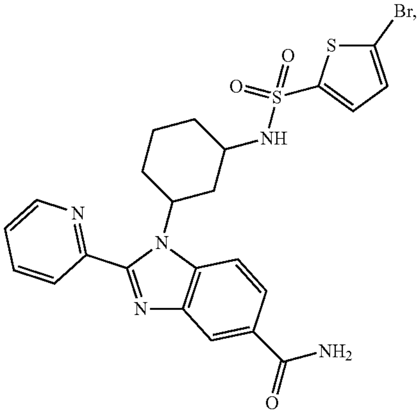
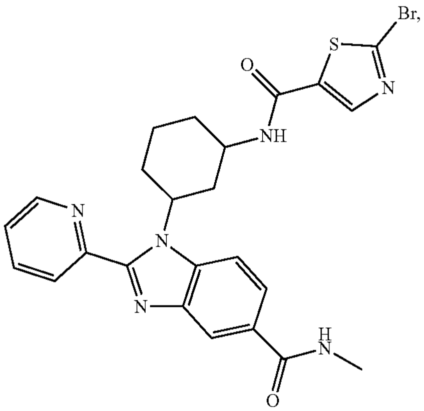
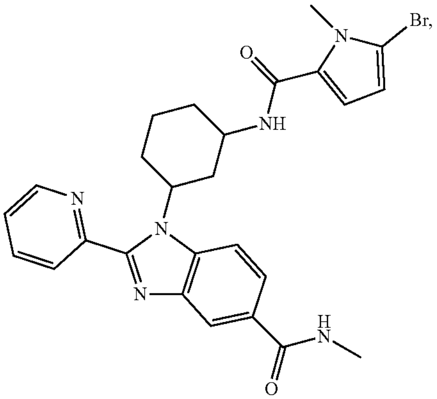

-continued

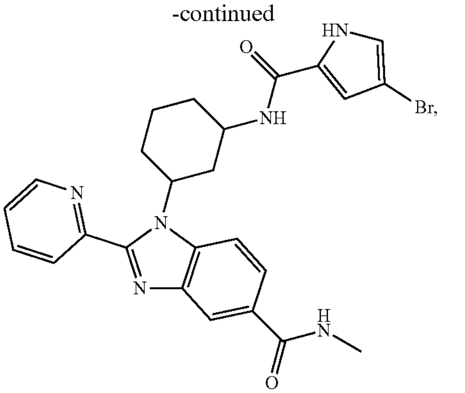

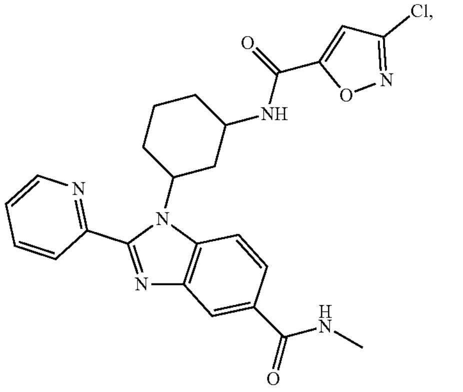

and pharmaceutically acceptable salts and stereoisomers thereof.

In some embodiments, Z may be $CH_2$. In other embodiments, Z may be $CF_2$. In yet other embodiments, Z may be O. In still yet other embodiments, Z may be a bond.

In some embodiments, $J^1$ may be CH. In other embodiments, $J^1$ may be N.

In some embodiments, $J^2$ may be CH. In other embodiments, $J^2$ may be N.

In some embodiments, $J^3$ is CH. In other embodiments, $J^3$ may be N.

In some embodiments, $J^4$ may be CH. In other embodiments, $J^4$ may be N.

In some embodiments, $X^1$ may be N. In other embodiments, $X^1$ may be $CR^{5A}$.

In some embodiments, $X^2$ may be N. In other embodiments, $X^2$ may be $CR^{5B}$.

In some embodiments, $J^2$ may be N and $X^1$ may be N. In other embodiments, $J^2$ may be N and $J^3$ may be N. In yet other embodiments, $J^2$ may be N and $J^4$ may be N. In still yet other embodiments, $J^2$ may be N and $X^2$ may be N. In some embodiments, each of $J^2$, $J^3$, and $J^4$ may be CH; $X^1$ may be $CR^{5A}$; and $X^2$ may be $CR^{5B}$.

In some embodiments, $R^1$ may be $NR^3C(O)R^4$. In other embodiments, $R^1$ may be $—C(O)(CH_2)_mNR^3R^4$.

In some embodiments, $R^3$ may be hydrogen. In other embodiments, $R^1$ may be $C_{1-6}$ alkyl.

In some embodiments, $R^4$ may be $C_{6-10}$ aryl or 5-10 membered heteroaryl, each optionally substituted with one, two, or three substituents $R^{4'}$. In some embodiments, $R^4$ may be selected from the phenyl, thiophene, oxazole, isoxazole, thiazole, furan, and pyrrole, each of which may be optionally substituted with one, two, or three substituents $R^{4'}$, wherein each $R^{4'}$ may be independently selected from the group consisting of —F, —Cl, —Br, —CN, $—NO_2$, $—CF_3$, $—CH_3$, $—CH(CH_3)_2$, $—C(O)CH_3$, $—C(O)OCH_3$, phenyl, cyclopropyl, and morpholinyl.

In some embodiments, m may be 0. In other embodiments, m may be 1.

In some embodiments, $R^2$ may be $C_{6-10}$ aryl or 5-10 membered heteroaryl, each optionally substituted with one, two, or three substituents $R^{2'}$. In some embodiments, $R^2$ may be selected from the group consisting of phenyl, pyridine, pyrimidine, pyridazine, pyrazine, imidazole, or thiophene, each of which may be optionally substituted with one, two, or three substituents $R^{2'}$, wherein each $R^{2'}$ may be independently selected from the group consisting of —F, —Cl, —Br, —CN, $NO_2$, $—CH_3$, $—CF_2H$, $—C{\equiv}CH$, —C(O)H, $—CONH_2$, $—C(O)NHCH_3$, —OH, $—OCH_3$, $—OCF_3$, $—SCF_3$, $—NH_2$, $—NHC(O)CH_3$, and morpholine.

In some embodiments, $X^2$ may be $CR^{5B}$ and $R^{5B}$ may be $—C(O)NR^8R^9$. In other embodiments, $X^2$ may be $CR^{5B}$ and $R^{5B}$ may be halo, —CN, $C_1$-$C_6$ alkyl, halo$C_1$-$C_6$ alkyl, $C_1$-$C_6$ alkoxy, $—(CH_2)_rOH$, $—NR^8COR^9$, 5-10 membered heteroaryl, $—C(O)R^8$, or $—C(O)OR^8$. In yet other embodiments, $X^2$ may be $CR^{5B}$ and $R^{5B}$ may be $—NR^8COR^9$. In some embodiments, $X^2$ may be $CR^{5B}$ and $R^{5B}$ may be $—C(O)OR^8$. In some embodiments, $X^2$ may be $CR^{5B}$ and $R^{5B}$ may be $—CF_3$, $—COCH_3$, $—CH_2OH$, —CN, or tetrazole.

In some embodiments, $R^8$ may be hydrogen. In other embodiments, $R^8$ may be $—C_{1-6}$ alkyl.

In some embodiments, $R^9$ may be hydrogen. In other embodiments, $R^9$ may be $—C_{1-6}$ alkyl.

In some embodiments, the compounds provided herein are compounds of Formula (I) having the structure of Formula (Ia) or pharmaceutically acceptable salts thereof:

(Ia)

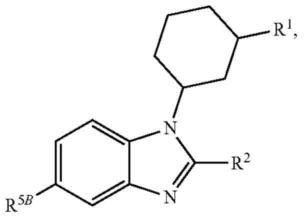

wherein $R^1$ may be $C_1$-$C_6$ alkyl, $—NR^3S(O)R^4$, $—NR^3SO_2R^4$, $—NR^3C(O)R^4$, $—C(O)(CH_2)_mNR^3R^4$, $C_6$-$C_{10}$ aryl, or 5-10-membered heteroaryl;

$R^2$ may be $C_1$-$C_6$ alkyl, $C_6$-$C_{10}$ aryl, or 5-10-membered heteroaryl;

$R^4$ may be $C_6$-$C_{10}$ aryl or 5-10-membered heteroaryl;

$R^{5B}$ may be $—C(O)NR^8R^9$; and $R^8$ and $R^9$ are independently H, $C_1$-$C_6$ alkyl, or $C_3$-$C_8$ cycloalkyl.

In some embodiments, provided herein is a compound of Formula (Ia) or a pharmaceutically acceptable salt thereof, wherein:

$R^1$ may be $—NR^3SO_2R^4$ or $—NR^3C(O)R^4$;

$R^2$ may be aryl or 5-10-membered heteroaryl;

$R^3$ may be H or $C_1$-$C_6$ alkyl;

$R^4$ may be $C_6$-$C_{18}$ aryl or 5-10-membered heteroaryl;

$R^{5B}$ may be $—C(O)NR^8R^9$; and $R^8$ and $R^9$ may independently be H or $C_1$-$C_6$ alkyl.

In some embodiments, provided herein is a compound of Formula (Ia) or a pharmaceutically acceptable salt thereof, wherein:

$R^1$ may be —$NR_3C(O)R_4$;

$R^2$ may be $C_6$-$C_{10}$ aryl or 5-10-membered heteroaryl;

$R^3$ may be H or methyl;

$R^4$ may be $C_6$-$C_{10}$ aryl or 5-10-membered heteroaryl;

$R^{5B}$ may be —$C(O)NR^8R^9$; and $R^8$ and $R^9$ may be independently H or $C_1$-$C_6$ alkyl.

In some embodiments, provided herein is a compound of Formula (Ia) or a pharmaceutically acceptable salt thereof, wherein:

$R^1$ may be —$NR_3C(O)R_4$;

$R^2$ may be $C_6$-$C_{10}$ aryl or 5-10-membered heteroaryl;

$R^3$ may be H or methyl;

$R^4$ may be $C_6$-$C_{10}$ aryl or 5-10-membered heteroaryl;

$R^5$ may be —$C(O)NR^8R^9$; and $R^8$ may be $R^9$ are independently H or methyl.

In some embodiments, the compound of the present disclosure may be 1-(3-(5-bromothiophene-2-carboxamido)cyclohexyl)-N-methyl-2-(2-(methylthio)phenyl)-1H-benzo[d]imidazole-5-carboxamide, 1-(3-(5-bromothiophene-2-carboxamido)cyclohexyl)-N-methyl-2-phenyl-1H-benzo[d]imidazole-5-carboxamide, 1-(3-(5-bromothiophene-2-carboxamido)cyclohexyl)-N-methyl-2-(pyridin-2-yl)-1H-benzo[d]imidazole-5-carboxamide, 1-(3-(5-bromothiophene-2-carboxamido)cyclohexyl)-2-(pyridin-2-yl)-1H-benzo[d]imidazole-5-carboxamide, 1-(3-(5-bromothiophene-2-carboxamido)cyclohexyl)-2-(pyridin-3-yl)-1H-benzo[d]imidazole-5-carboxamide, 1-(3-(5-bromothiophene-2-carboxamido)cyclohexyl)-2-(pyridin-4-yl)-1H-benzo[d]imidazole-5-carboxamide, 1-(3-(5-bromothiophene-2-carboxamido)cyclohexyl)-N-methyl-2-(thiophen-2-yl)-1H-benzo[d]imidazole-5-carboxamide, 1-(3-(5-bromothiophene-2-carboxamido)cyclohexyl)-N-methyl-2-(thiophen-3-yl)-1H-benzo[d]imidazole-5-carboxamide, 1-(3-(5-bromothiophene-2-carboxamido)cyclohexyl)-N-methyl-2-(2-methylthiazol-4-yl)-1H-benzo[d]imidazole-5-carboxamide, 1-(3-(5-bromothiophene-2-carboxamido)cyclohexyl)-N-methyl-2-(thiazol-2-yl)-1H-benzo[d]imidazole-5-carboxamide, 1-(3-(5-bromothiophene-2-carboxamido)cyclohexyl)-N-methyl-2-(1H-pyrazol-3-yl)-1H-benzo[d]imidazole-5-carboxamide, 1-(3-(5-cyanothiophene-2-carboxamido)cyclohexyl)-2-(pyridin-2-yl)-1H-benzo[d]imidazole-5-carboxamide, 1-(3-(5-chlorothiophene-2-carboxamido)cyclohexyl)-2-(pyridin-2-yl)-1H-benzo[d]imidazole-5-carboxamide, 1-(3-(5-methylthiophene-2-carboxamido)cyclohexyl)-2-(pyridin-2-yl)-1H-benzo[d]imidazole-5-carboxamide, 1-(3-(5-bromo-N-methylthiophene-2-carboxamido)cyclohexyl)-2-(pyridin-2-yl)-1H-benzo[d]imidazole-5-carboxamide, 1-(3-((5-bromothiophene)-2-sulfonamido)cyclohexyl)-2-(pyridin-2-yl)-1H-benzo[d]imidazole-5-carboxamide, 2-bromo-N-(3-(5-(methylcarbamoyl)-2-(pyridin-2-yl)-1H-benzo[d]imidazol-1-yl)cyclohexyl)thiazole-5-carboxamide, 1-(3-(5-bromo-1-methyl-1H-pyrrole-2-carboxamido)cyclohexyl)-N-methyl-2-(pyridin-2-yl)-1H-benzo[d]imidazole-5-carboxamide, 1-(3-(4-bromo-1H-pyrrole-2-carboxamido)cyclohexyl)-N-methyl-2-(pyridin-2-yl)-1H-benzo[d]imidazole-5-carboxamide, 3-chloro-N-(3-(5-(methylcarbamoyl)-2-(pyridin-2-yl)-1H-benzo[d]imidazol-1-yl)cyclohexyl)isoxazole-5-carboxamide, 5-bromo-N-(3-(2-(pyridin-2-yl)-1H-benzo[d]imidazol-1-yl)cyclohexyl)thiophene-2-carboxamide, 1-(3-(5-bromothiophene-2-carboxamido)cyclohexyl)-N,N-dimethyl-2-(pyridin-2-yl)-1H-benzo[d]imidazole-5-carboxamide, 1-(3-(5-bromothiophene-2-carboxamido)cyclohexyl)-N-cyclopropyl-2-(pyridin-2-yl)-1H-benzo[d]imidazole-5-carboxamide, and 1-(3-(5-bromothiophene-2-carboxamido)cyclohexyl)-N-isopropyl-2-(pyridin-2-yl)-1H-benzo[d]imidazole-5-carboxamide; or a pharmaceutical acceptable salt thereof.

In further embodiments, provided herein may be a compound of Formula (I) having the structure of Formula (II):

(II)

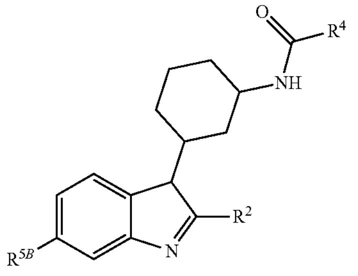

or a pharmaceutically acceptable salt thereof, wherein $R^2$ may be $C_6$-$C_{10}$ aryl or 5-10 membered heteroaryl, wherein each aryl or heteroaryl may be optionally substituted with one, two, or three substituents $R^{2'}$ independently selected from halo, —CN, —$NO_2$, $C_1$-$C_6$ alkyl, $C_1$-$C_6$ alkoxy, halo$C_1$-$C_6$ alkyl, halo$C_1$-$C_6$ alkoxy, $C_2$-$C_6$ alkenyl, $C_2$-$C_6$ alkenyl, —$C(O)NR^6R^7$, —$C(O)R^6$, —$NR^6R^7$, —$NR^6C(O)R^7$, —OH, —S-(halo$C_1$-$C_6$ alkyl), $C_6$-$C_{10}$ aryl, and 5-10 membered heterocyclyl; or two $R^{2'}$ substituents together with the atoms to which they are attached may form a five-membered heterocyclyl or $C_3$-$C_8$ cycloalkyl, each optionally substituted with halo;

$R^4$ may be 5-10 membered heteroaryl, optionally substituted with one, two, or three substituents $R^{4'}$ independently selected from halo, —CN, —$NO_2$, $C_1$-$C_6$ alkyl, halo$C_1$-$C_6$ alkyl, $C_1$-$C_6$ alkoxy, $C_2$-$C_6$ alkenyl, $C_3$-$C_8$ cycloalkyl, $C_6$-$C_{10}$ aryl, —$(CH_2)_qNR^BC(O)R^9$, —$C(O)NR^8R^9$, —$C(O)OR^9$, —$C(O)R^9$, and 5-10 membered heterocyclyl; and $R^{5B}$ may be —$C(O)NR^8R^9$.

In some embodiments, $R^2$ may be phenyl optionally substituted with one, two, or three substituents $R^2$ independently selected from halo, —CN, —$NO_2$, and $C_1$-$C_6$ alkyl. In other embodiments, $R^2$ is 5-10 membered heteroaryl optionally substituted with one, two, or three substituents $R^{2'}$ independently selected from halo, —CN, —$NO_2$, and $C_1$-$C_6$ alkyl.

In some embodiments, $R^4$ may be thiophene optionally substituted with halo or phenyl.

In further embodiments, the compounds provided herein may compounds of Formula (I) having the structure of Formula (III):

(III)

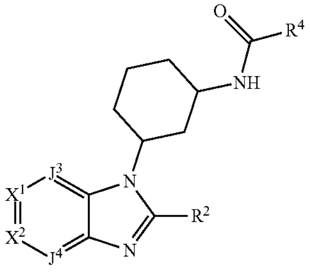

or a pharmaceutically acceptable salt thereof wherein each $J^3$ and $J^4$ is independently CH or N;

$X^1$ may be N or $CR^{5A}$;

$X^2$ may be N or $CR^{5B}$;

wherein one, two, three, or four of $J^3$, $J^4$, $X^1$, and $X^2$ is N;

$R^2$ may be $C_6$-$C_{10}$ aryl or 5-10 membered heteroaryl, wherein each aryl or heteroaryl may be optionally substituted with one, two, or three substituents $R^{2'}$ independently selected from halo, —CN, —$NO_2$, $C_1$-$C_6$ alkyl, $C_1$-$C_6$ alkoxy, halo$C_1$-$C_6$ alkyl, halo$C_1$-$C_6$ alkoxy, $C_2$-$C_6$ alkenyl, $C_2$-$C_6$ alkynyl, —C(O)$NR^6R^7$, —C(O)$R^6$, —$NR^6R^7$, —$NR^6C(O)R^7$, —OH, —S-(halo$C_1$-$C_6$ alkyl). $C_6$-$C_{10}$ aryl, and 5-10 membered heterocyclyl; or two $R^{2'}$ substituents together with the atoms to which they are attached form a five-membered heterocyclyl or $C_3$-$C_8$ cycloalkyl, each optionally substituted with halo; and $R^4$ may be H, $C_1$-$C_6$ alkyl, $C_2$-$C_6$ alkenyl, $C_6$-$C_{10}$ aryl, or 5-10 membered heteroaryl, wherein each aryl or heteroaryl may be optionally substituted with one, two, or three substituents $R^{4'}$ independently selected from halo, —CN, —$NO_2$, $C_1$-$C_6$ alkyl, halo$C_1$-$C_6$ alkyl, $C_1$-$C_6$ alkoxy, $C_2$-$C_6$ alkenyl, $C_3$-$C_8$ cycloalkyl, $C_6$-$C_{10}$ aryl, —$(CH_2)_q NR^8C(O)R^9$, —C(O)$NR^8R^9$, —C(O)$OR^9$, —C(O)$R^9$, and 5-10 membered heterocyclyl.

In some embodiments, $R^2$ may be phenyl optionally substituted with one, two, or three substituents $R^{2'}$ independently selected from halo, —CN, —$NO_2$, and $C_1$-$C_6$ alkyl. In other embodiments, $R^2$ is 5-10 membered heteroaryl optionally substituted with one, two, or three substituents $R^{2'}$ independently selected from halo, —CN, —$NO_2$, and $C_1$-$C_6$ alkyl.

In some embodiments, $R^4$ may be thiophene optionally substituted with halo or phenyl.

In some embodiments, $X^2$ may be $CR^{5B}$; $R^{5B}$ may be selected from hydrogen, -halo, —C(O)$NR^8R^9$, —$NR^8COR^9$, or —C(O)$OR^8$; and $R^8$ and $R^9$ may each independently be H or $C_1$-$C_6$ alkyl.

In further embodiments, the compounds provided herein may be compounds of Formula (I) having the structure of Formula (IV):

(IV)

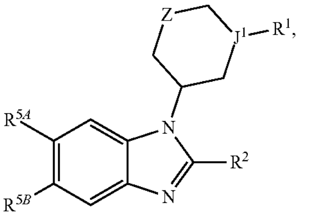

or a pharmaceutically acceptable salt thereof, wherein $R^1$ is $C_1$-$C_6$ alkyl, —$NR^3C(O)R^4$, —C(O)$(CH_2)_m NR^3R^4$, $C_6$-$C_{10}$ aryl, 5-10-membered heteroaryl, or (5-10-membered heteroaryl)-$C_1$-$C_6$ alkyl; and $R^2$ is —$NR^6R^7$, $C_1$-$C_6$ alkyl, $C_3$-$C_8$ cycloalkyl, $C_6$-$C_{10}$ aryl, or 5-10 membered heteroaryl, wherein each aryl or heteroaryl is substituted with one, two, or three substituents $R^2$ independently selected from halo, —CN, —$NO_2$, $C_1$-$C_6$ alkoxy, halo$C_1$-$C_6$ alkyl, halo$C_1$-$C_6$ alkoxy, $C_2$-$C_6$ alkenyl, $C_2$-$C_6$ alkynyl, —C(O)$NR^6R^7$, —C(O)$R^6$, —$NR^6R^7$, —$NR^6C(O)R^7$, —OH, $C_6$-$C_{10}$ aryl, and 5-10 membered heterocyclyl; or two $R^2$ substituents together with the atoms to which they are attached form a five-membered heterocyclyl or $C_3$-$C_8$ cycloalkyl, each optionally substituted with halo.

In yet further embodiments, provided herein may be a compound of Formula (I) having the structure of Formula (V):

(V)

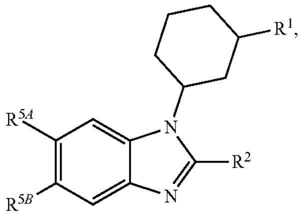

or a pharmaceutically acceptable salt thereof wherein $R^{5A}$ is halo, —CN, $C_1$-$C_6$ alkyl, halo$C_1$-$C_6$ alkyl. $C_1$-$C_6$ alkoxy, —$(CH_2)_r OH$, —C(O)$NR^8R^9$, —$NR^8COR^9$, 5-10 membered heteroaryl, —C(O)$R^8$, or —C(O)$OR^8$;

$R^{5B}$ is H, halo, —CN, $C_1$-$C_6$ alkyl, halo$C_1$-$C_6$ alkyl, $C_1$-$C_6$ alkoxy, —$(CH_2)_r OH$, —C(O)$NR^8R^9$, —$NR^8COR^9$, 5-10 membered heteroaryl, —C(O)$R^8$, or —C(O)$OR^8$; and or $R^{5A}$ and $R^{5B}$ together with the atoms to which they are attached may form a six-membered heterocyclyl ring optionally substituted with oxo.

In still yet further embodiments, provided herein may be a compound of Formula (I) having the structure of Formula (VI):

(VI)

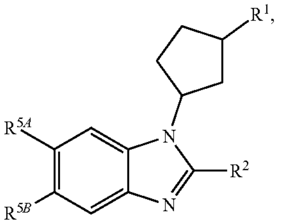

or a pharmaceutically acceptable salt thereof.

In still yet further embodiments, provided herein may be a compound of Formula (I) having the structure of Formula (VII), or a pharmaceutically acceptable salt thereof:

(VII)
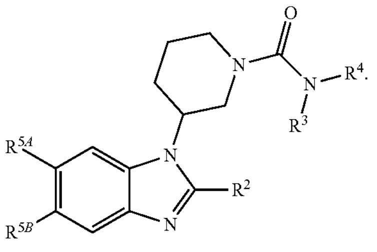
In still yet further embodiments, provided herein are compounds selected from the group consisting of:
106
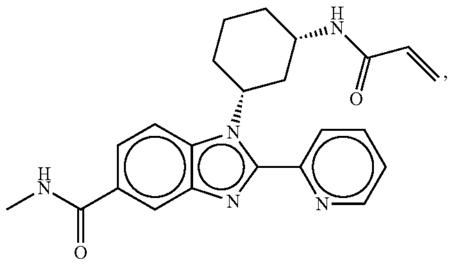
107
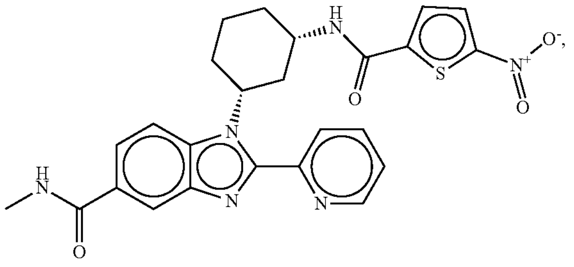
108
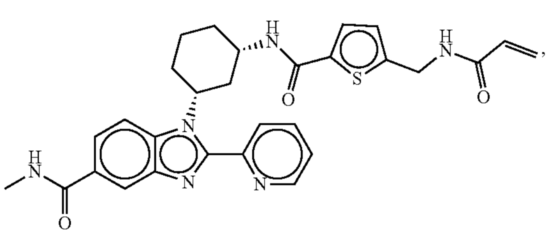
109
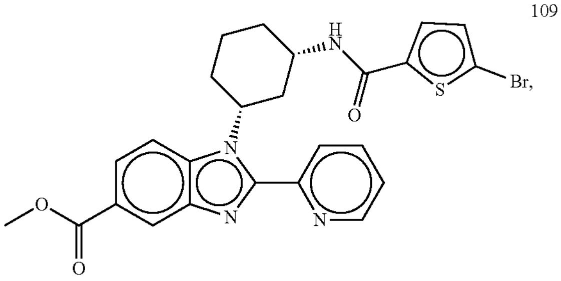
-continued
110
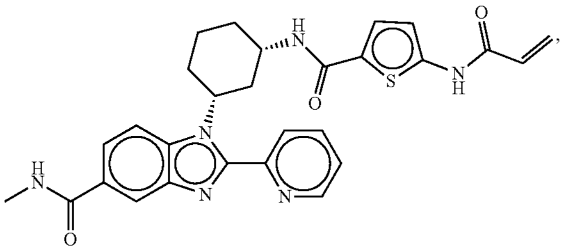
111
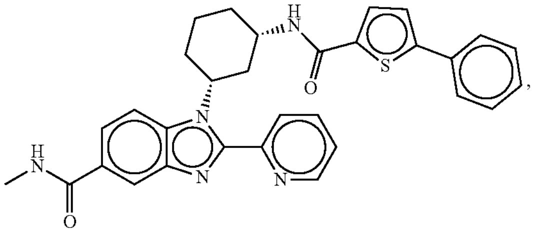
112
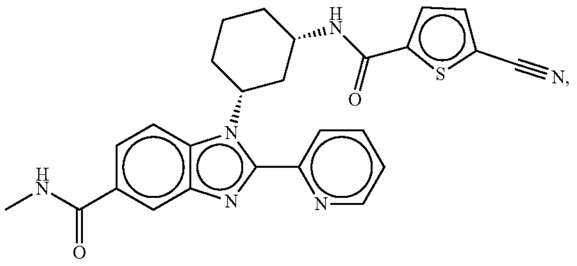
113
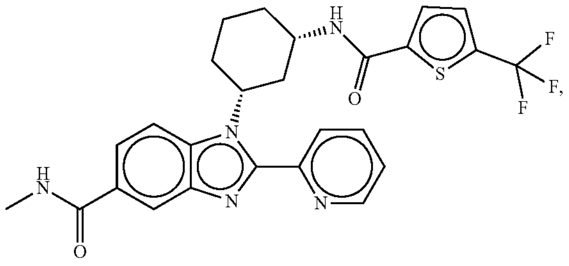
114
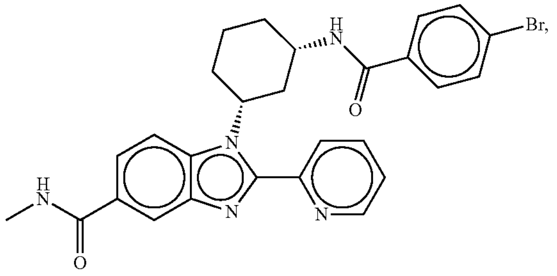

-continued
115
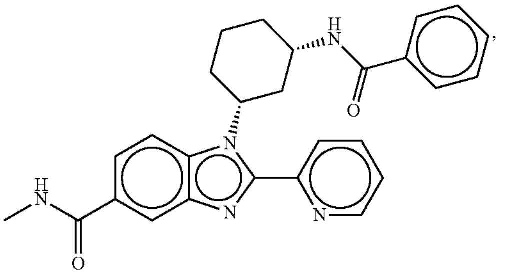
116
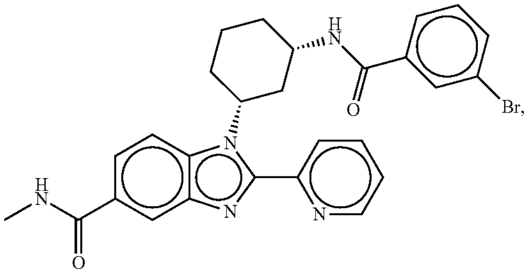
117
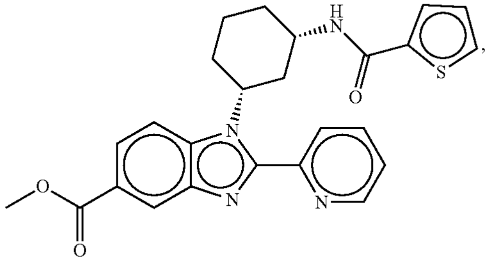
118
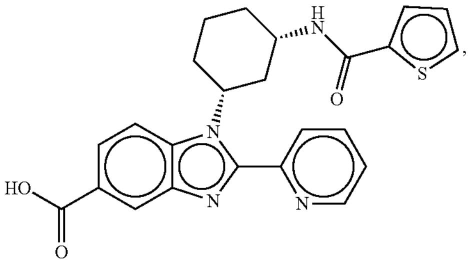
119
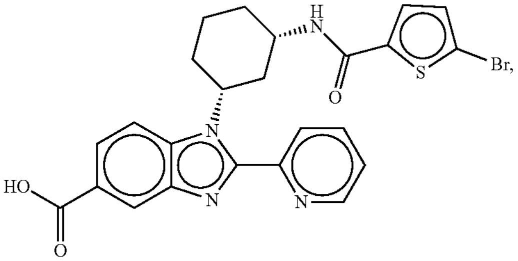
-continued
120
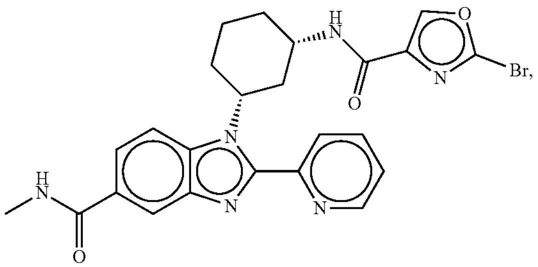
121
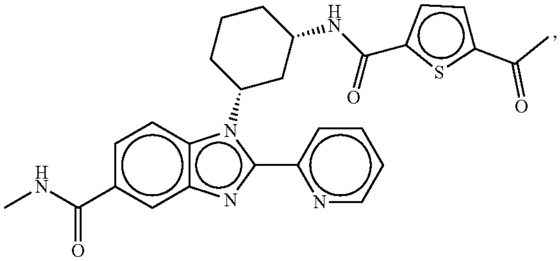
122
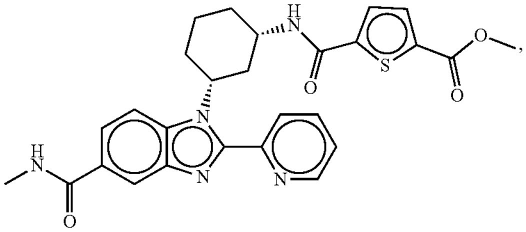
123
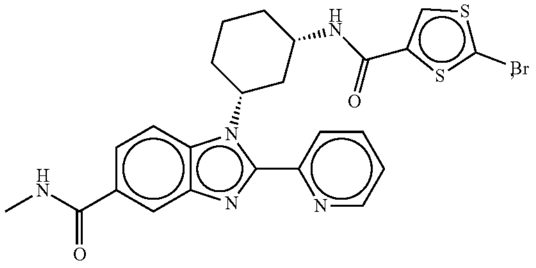
124
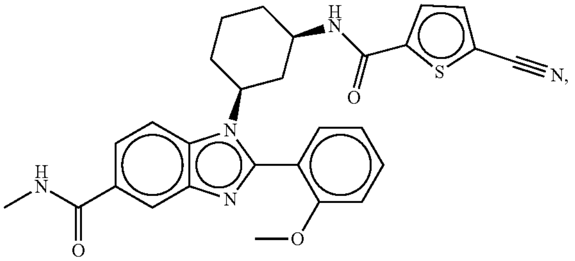

-continued
125
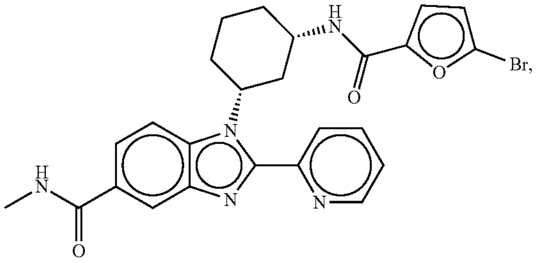,
126
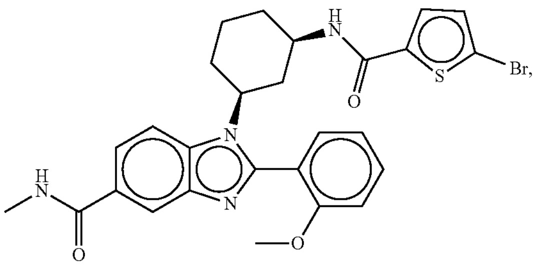,
127
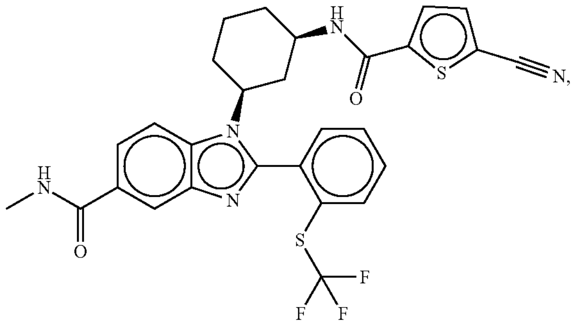,
128
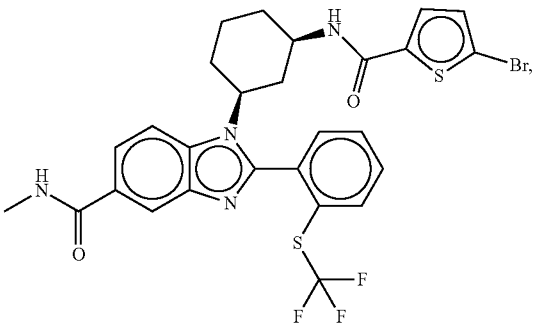,
129
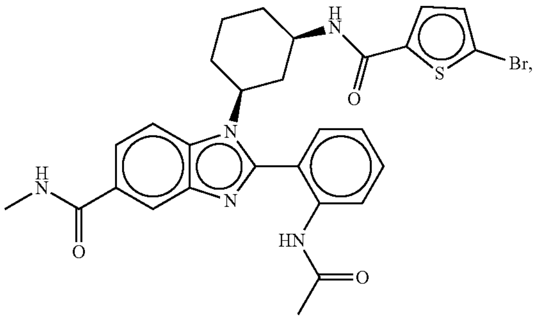,
-continued
130
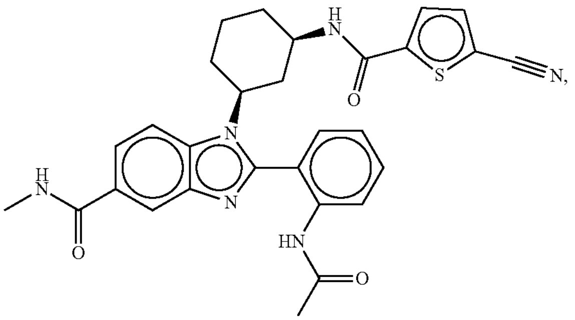,
131
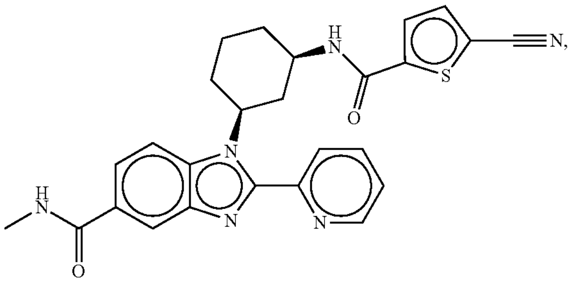,
132
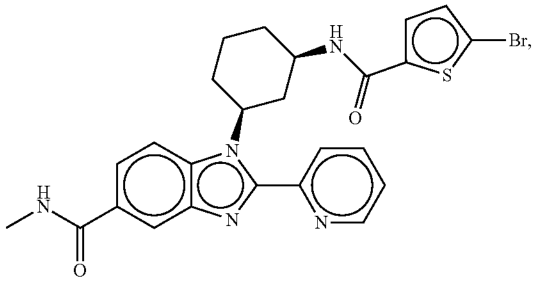,
133
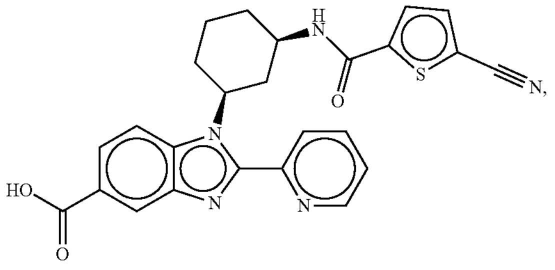,
134
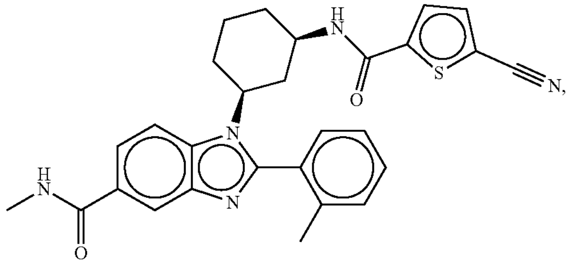, -continued
135
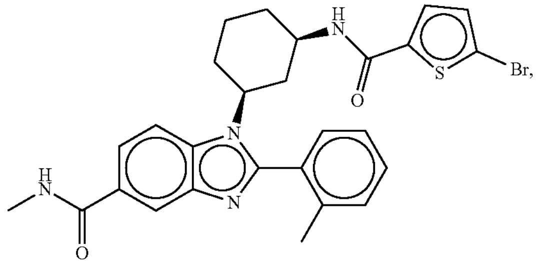
136
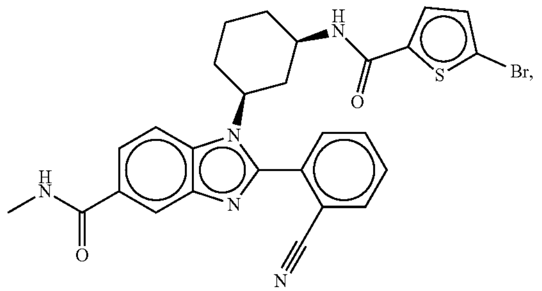
137
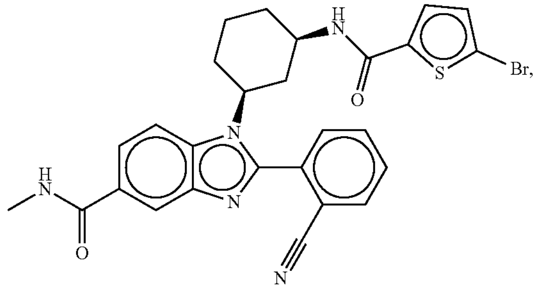
138
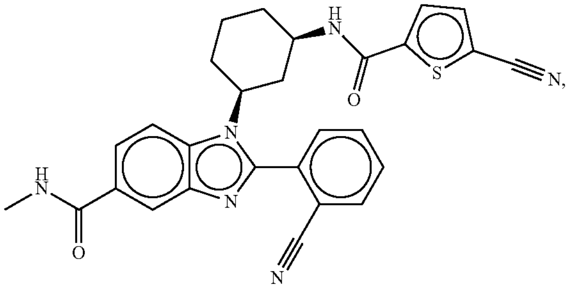
139
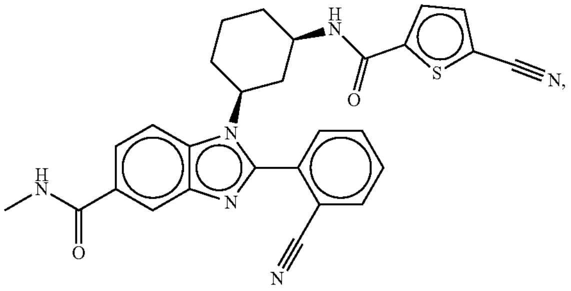
-continued
140
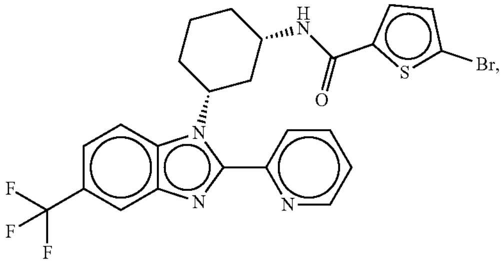
141
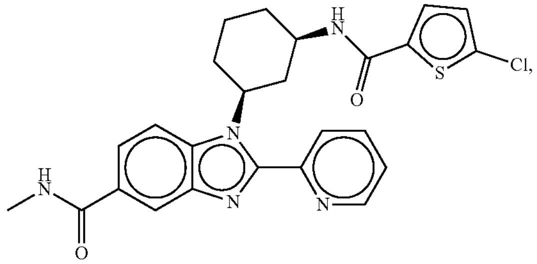
142
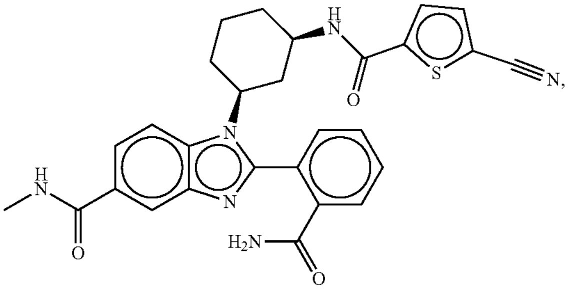
143
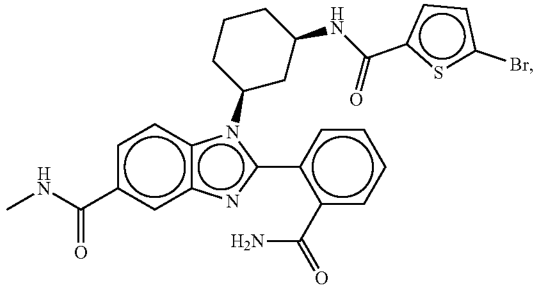
144
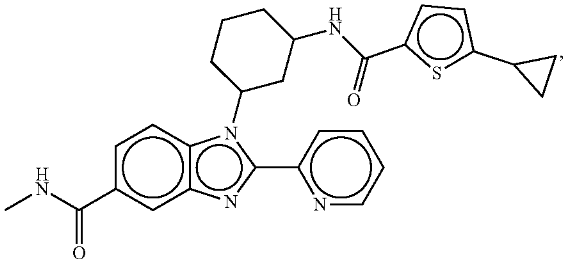

-continued
145
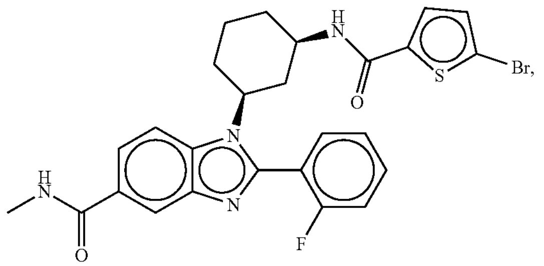
146
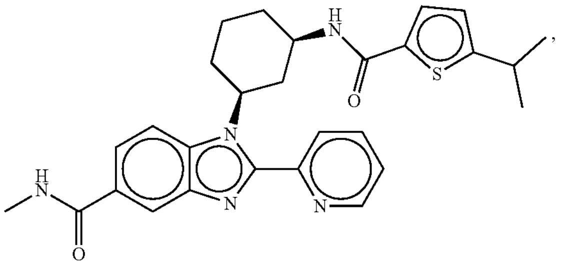
147
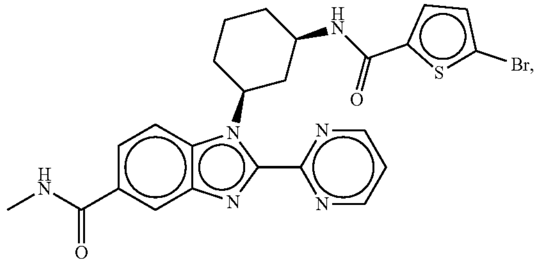
148
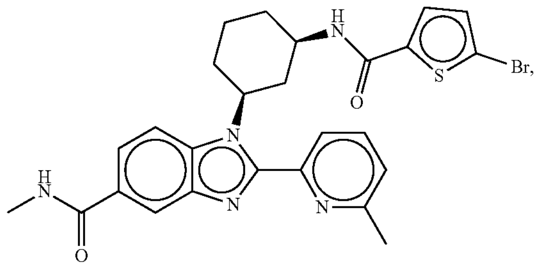
149
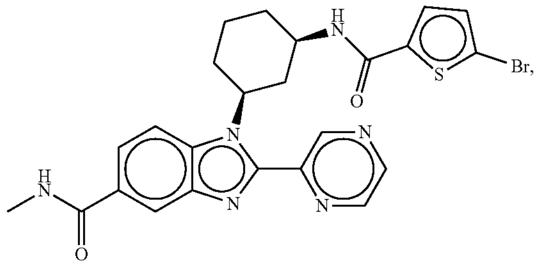
-continued
150
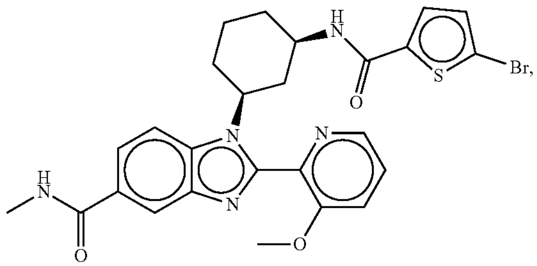
151
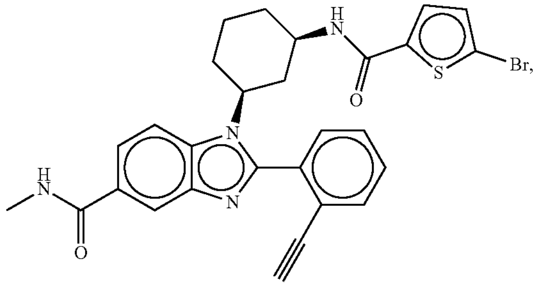
152
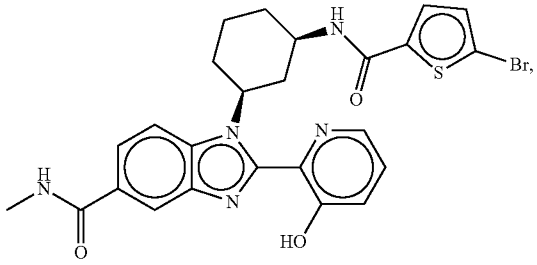
153
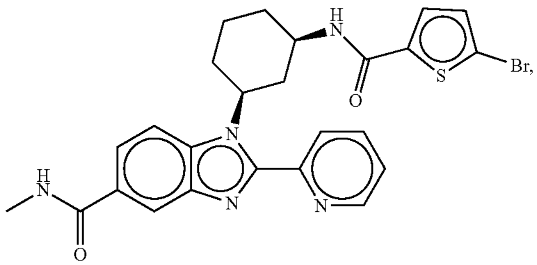
154
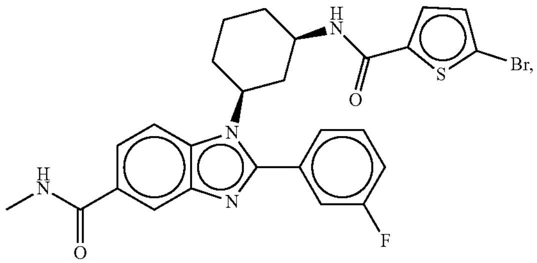

-continued
155
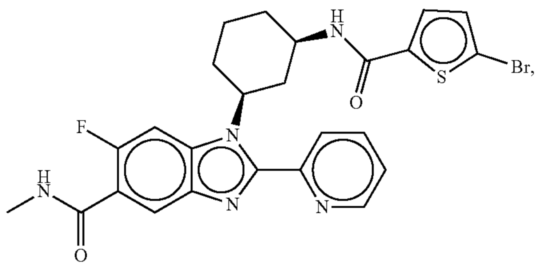
156
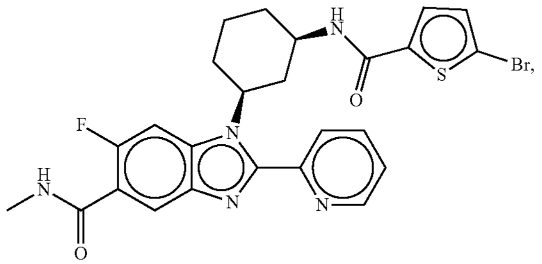
157
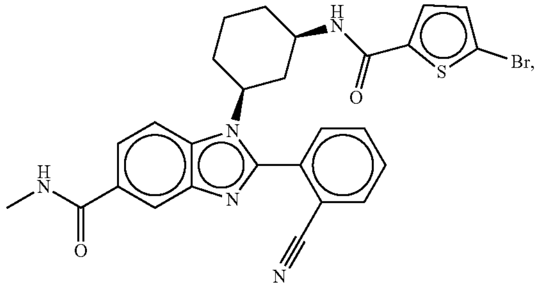
158
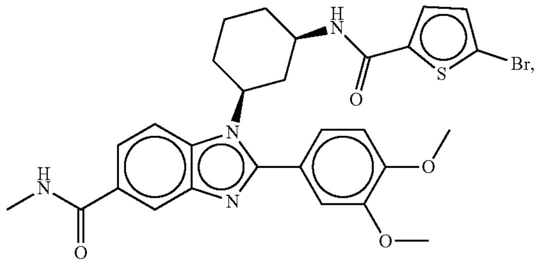
159
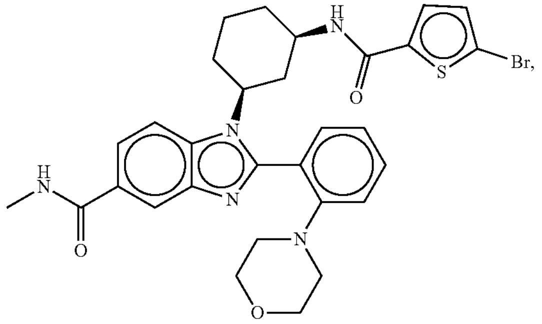
-continued
160
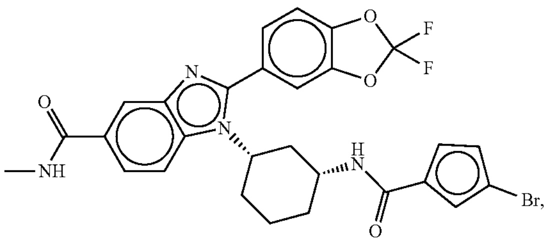
161
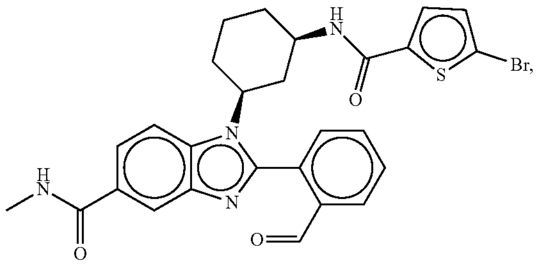
162
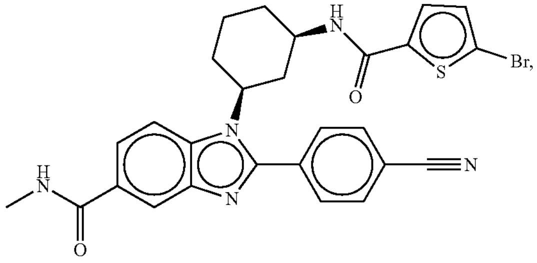
163
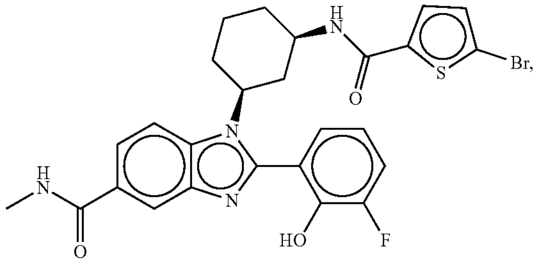
164
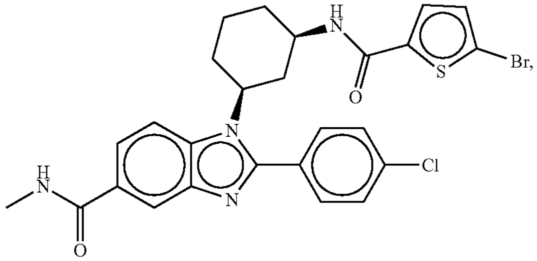

-continued
165
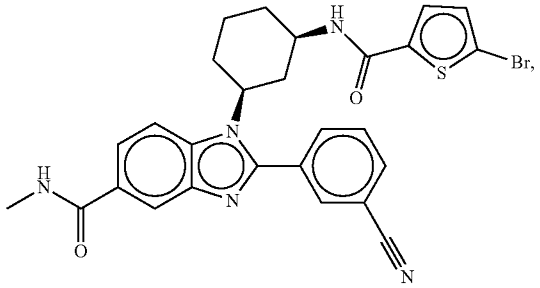
166
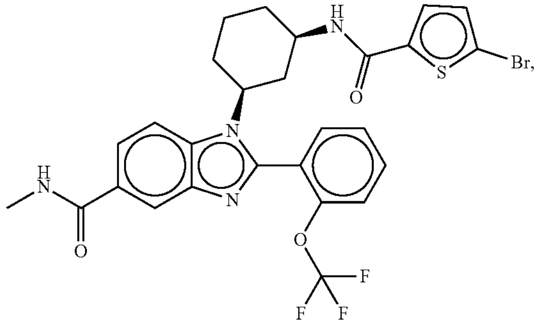
167
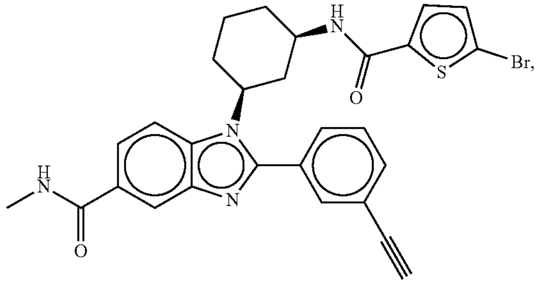
168
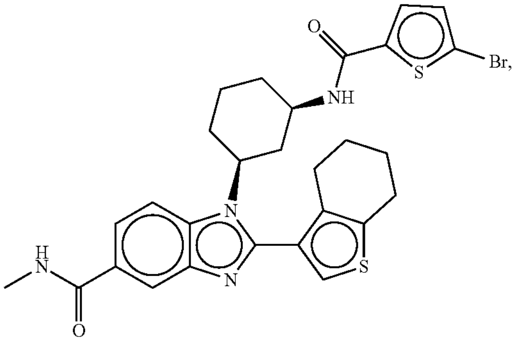
169
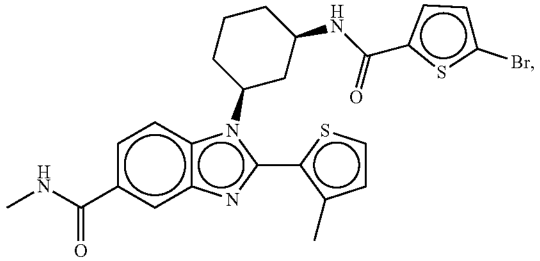
-continued
170
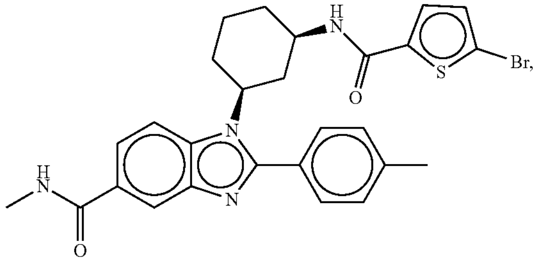
171
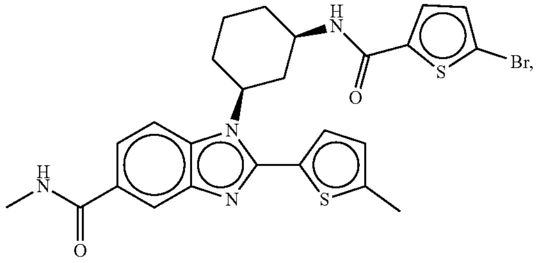
172
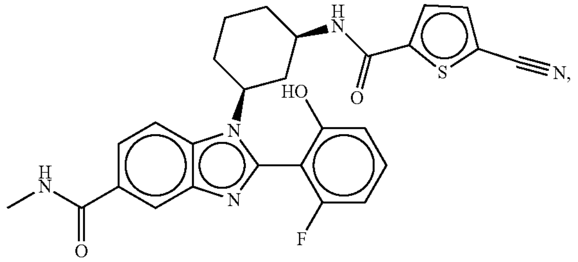
173
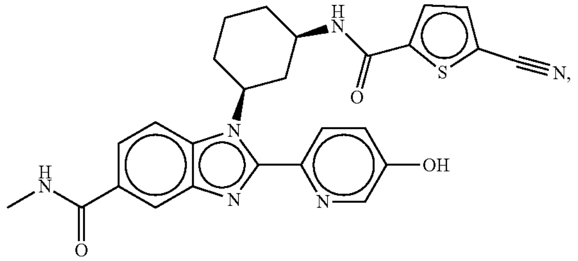
174
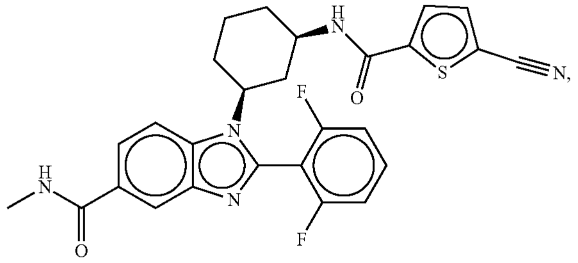

-continued
175
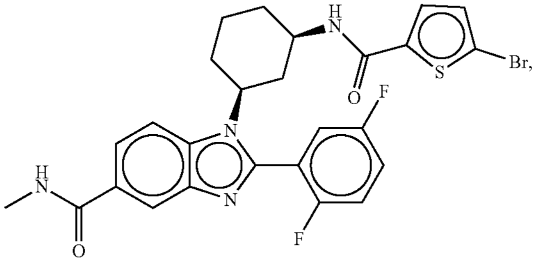
176
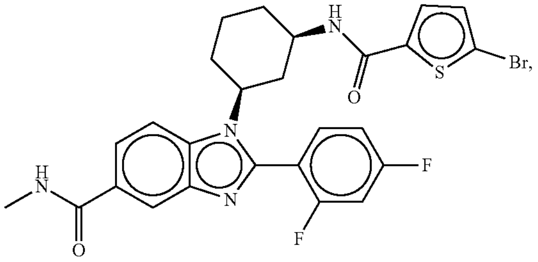
177
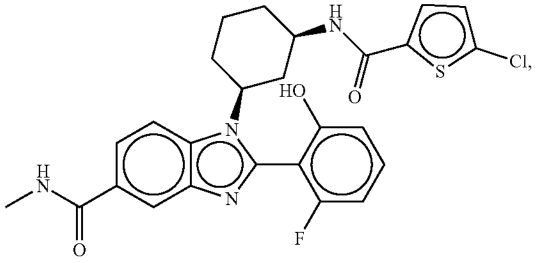
178
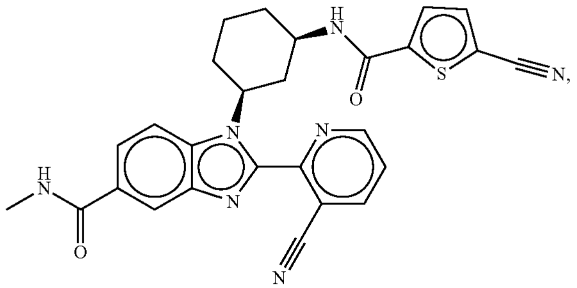
179
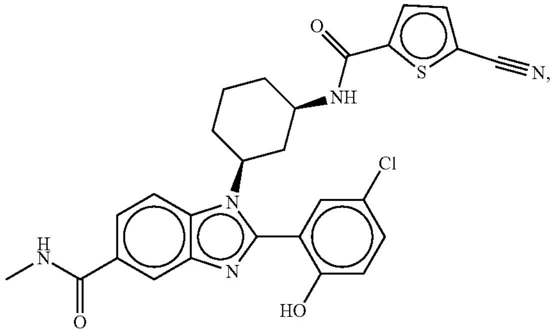
-continued
180
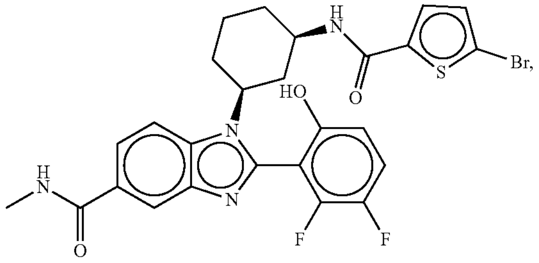
181
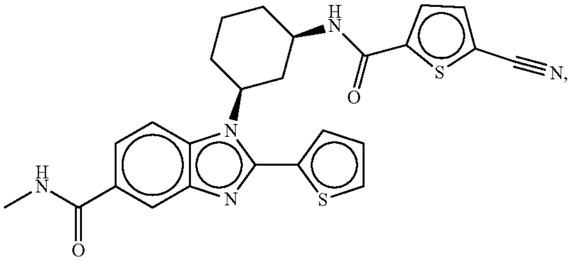
182
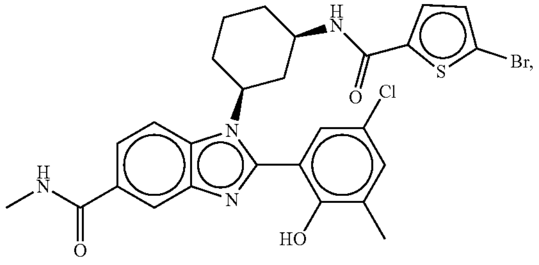
183
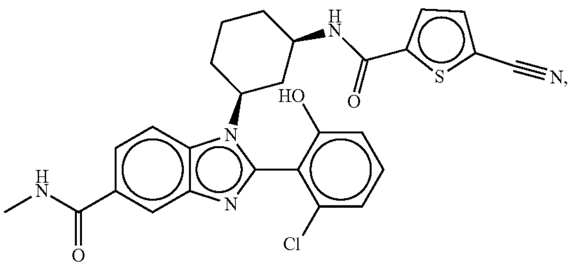
184
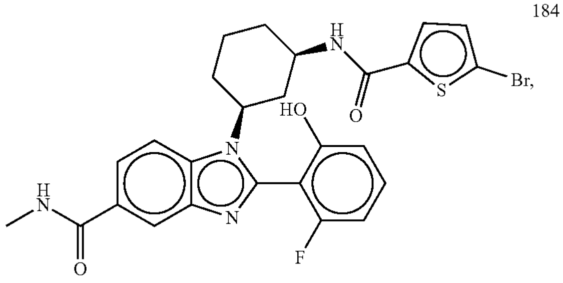

-continued
185
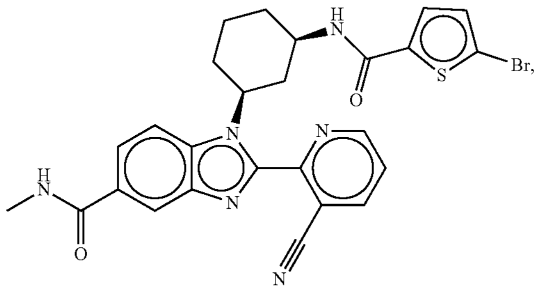
186
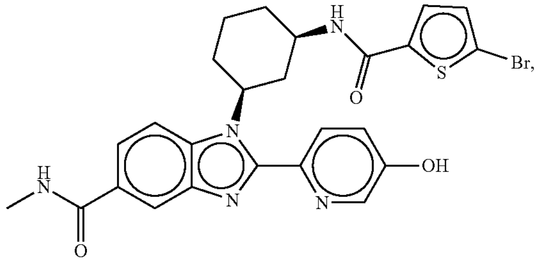
187
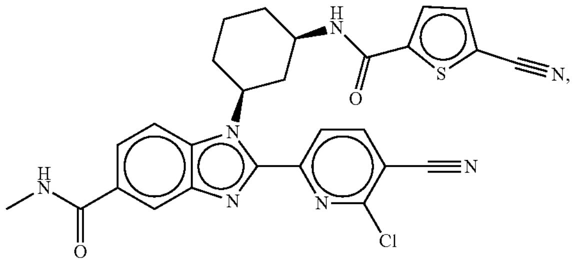
188
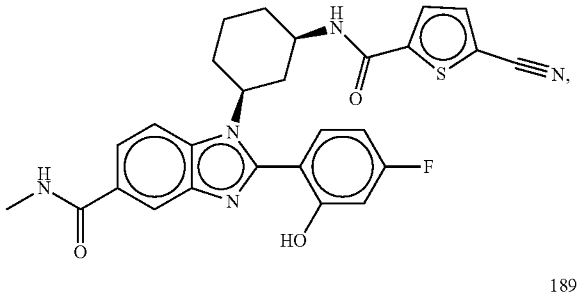
189
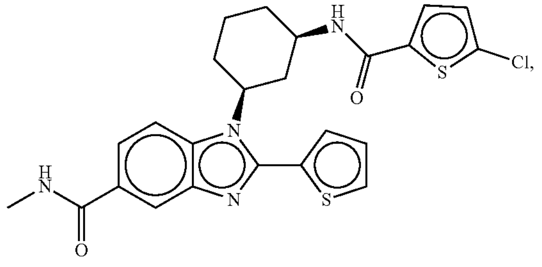
-continued
190
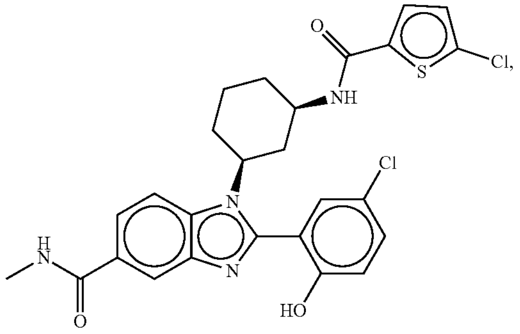
191
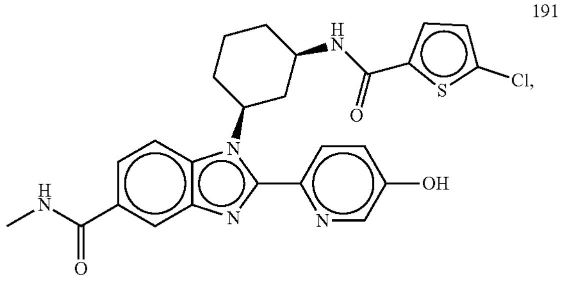
192
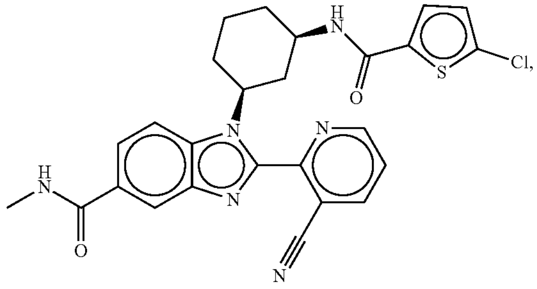
193
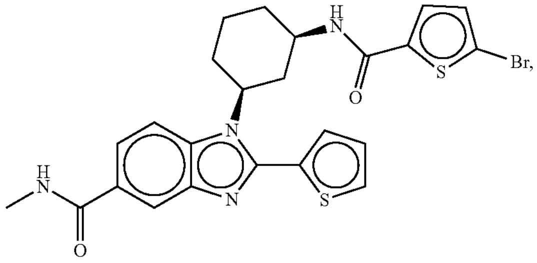
194
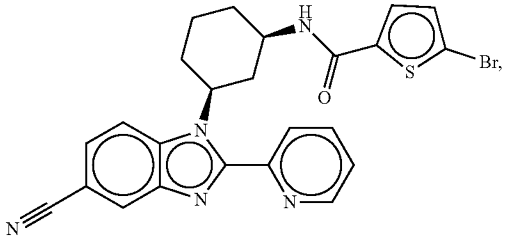

-continued
195
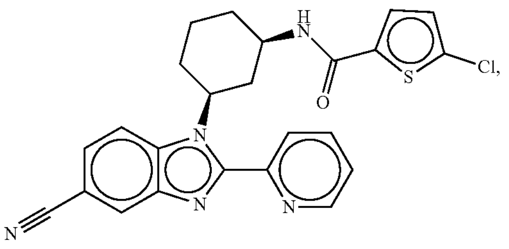
196
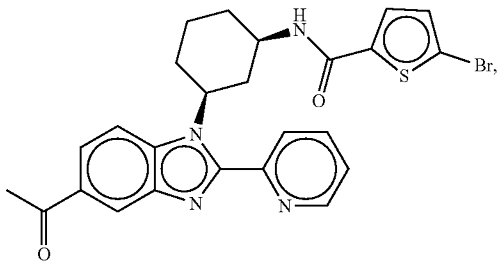
197
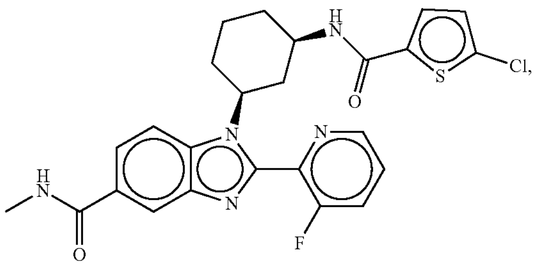
198
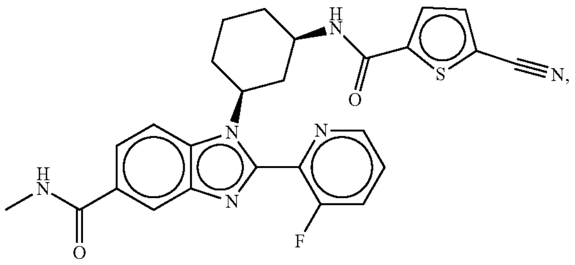
199
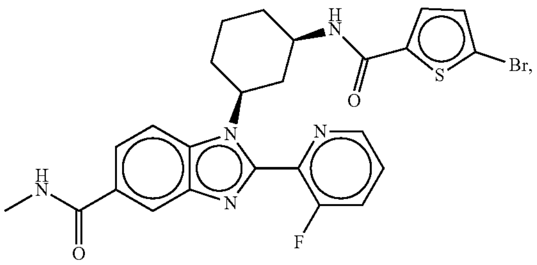
-continued
200
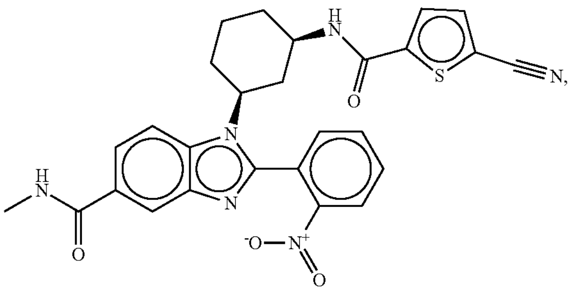
201
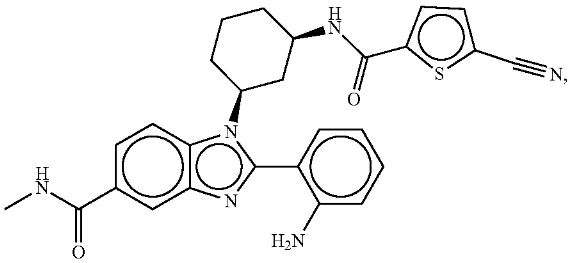
202
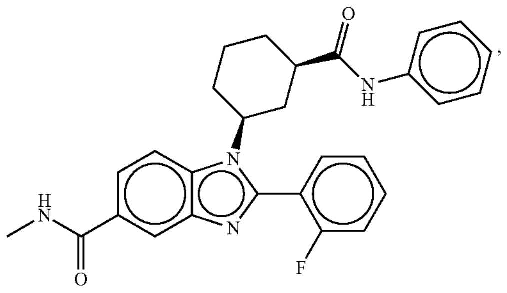
203
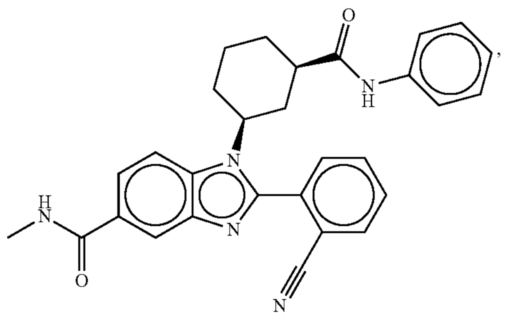
204
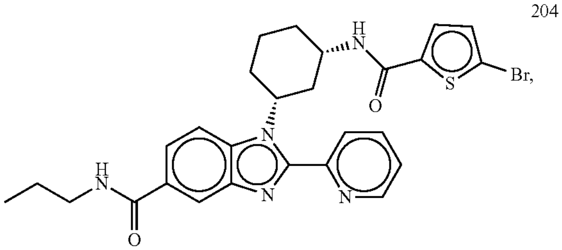

-continued
205
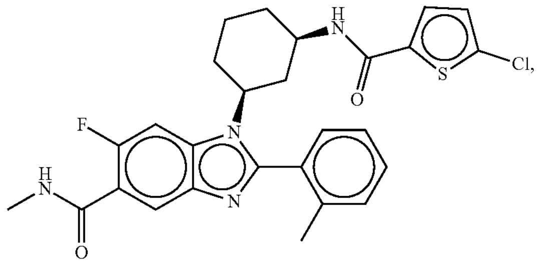
206
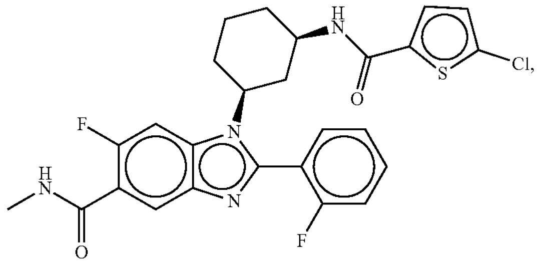
207
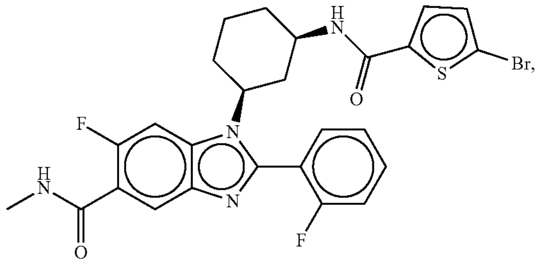
208
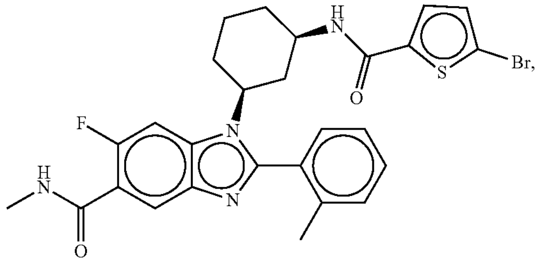
209
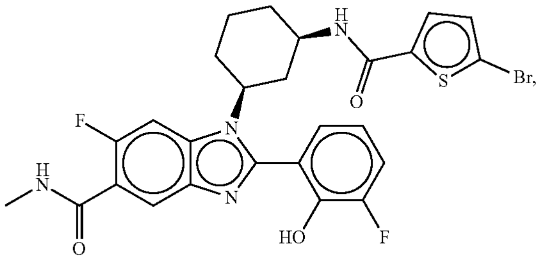
-continued
210
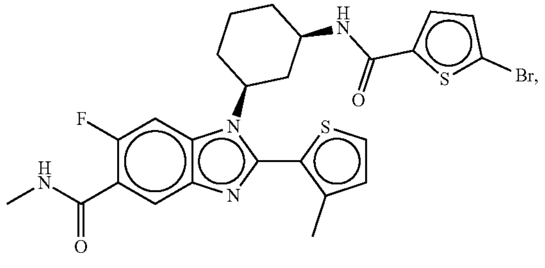
211
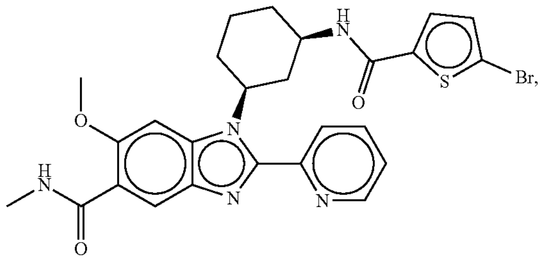
212
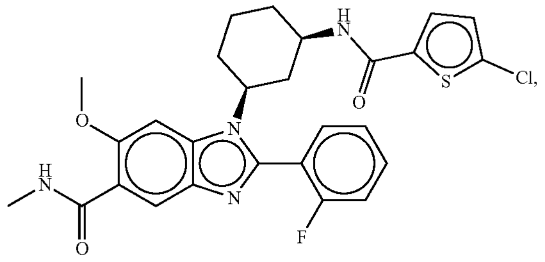
213
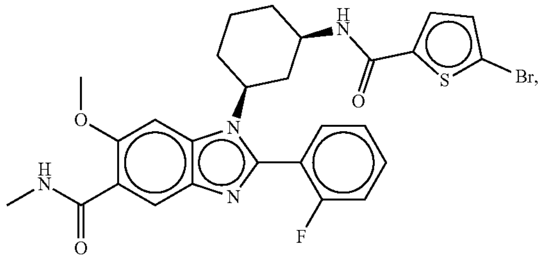
214
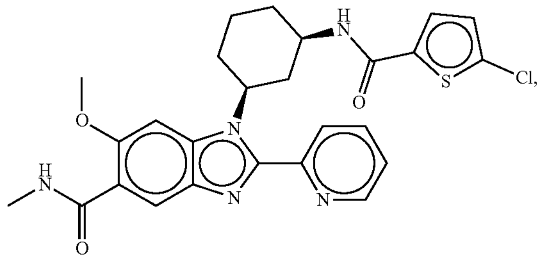

-continued
215
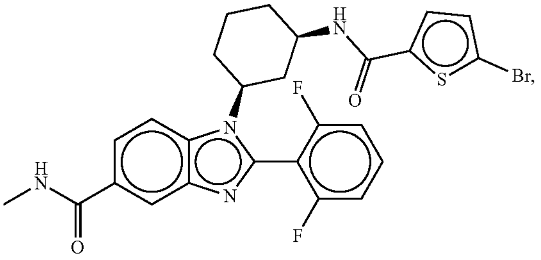
216
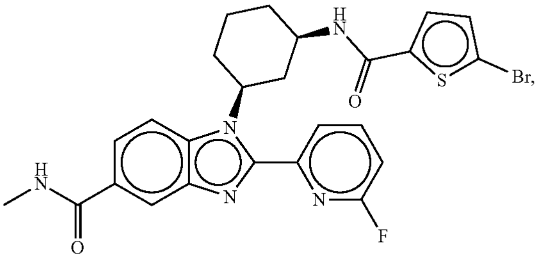
217
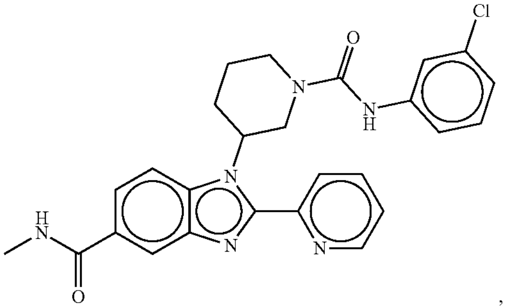
,
218
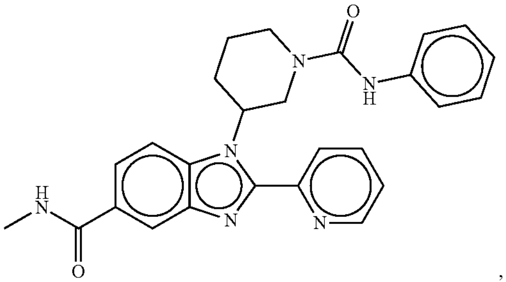
,
219
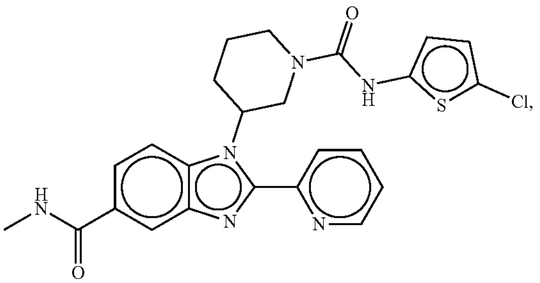
-continued
220
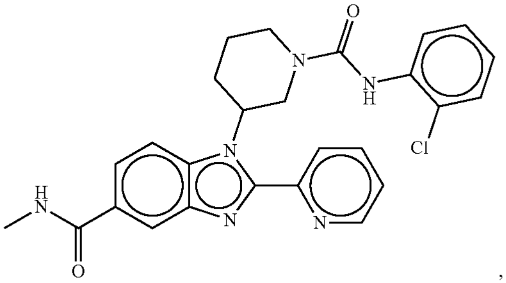
,
221
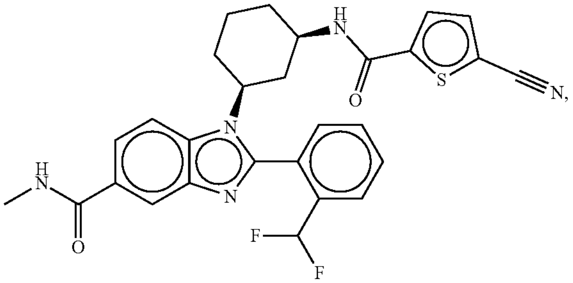
222
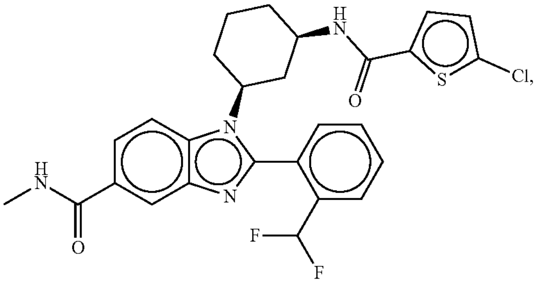
223
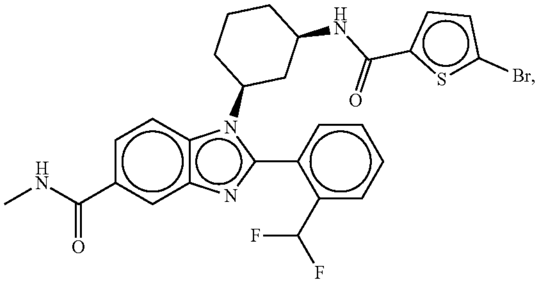
224
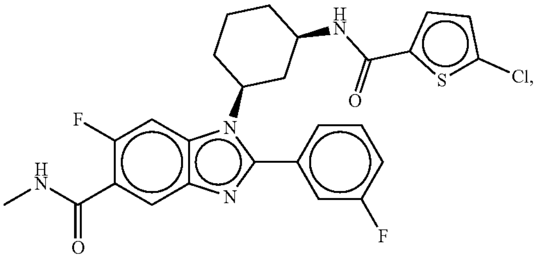

-continued
225
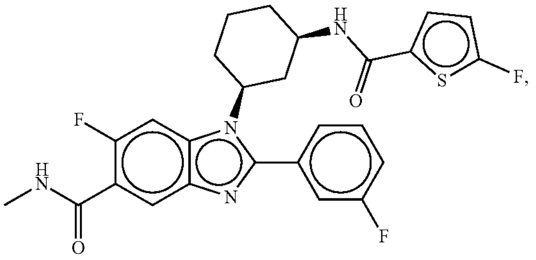
226
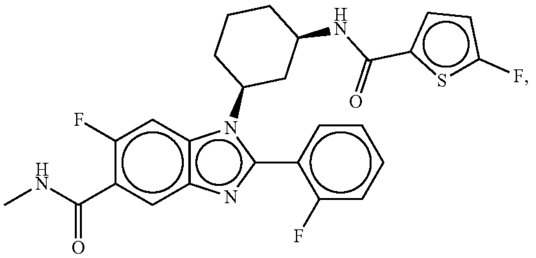
227
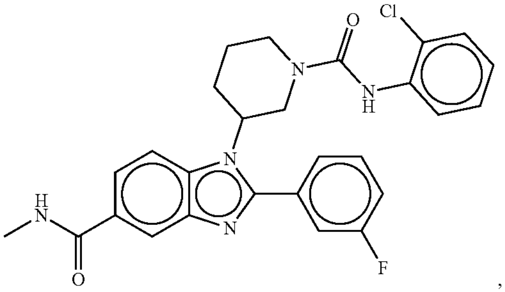
,
228
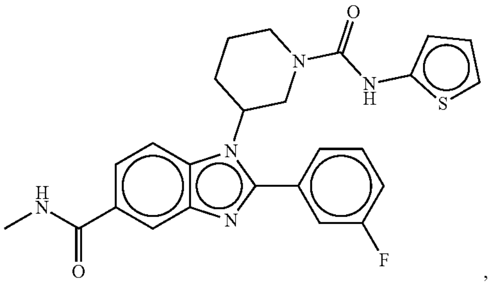
,
229
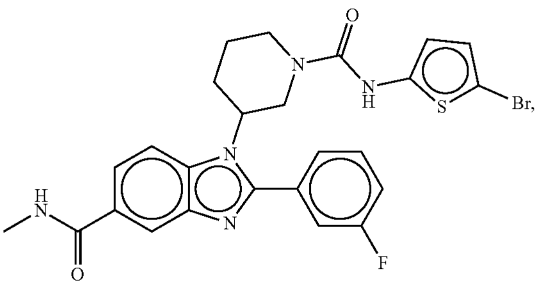
-continued
230
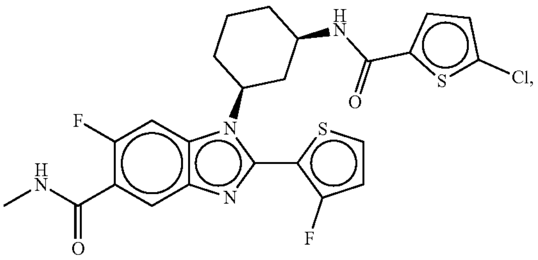
231
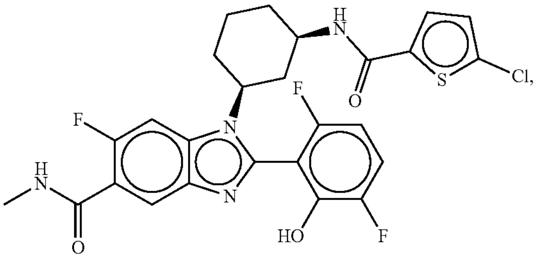
232
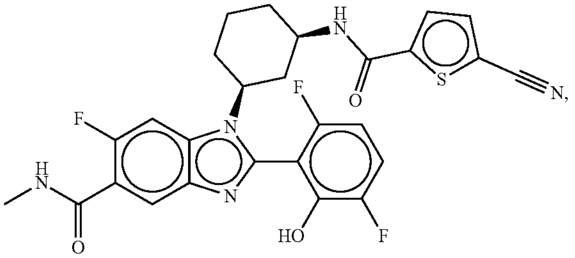
233
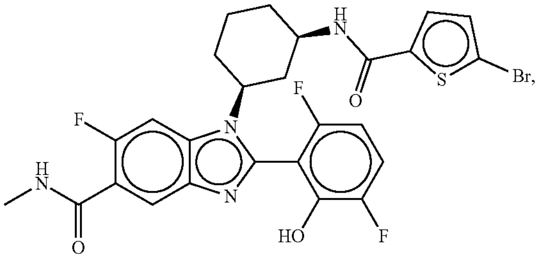
234
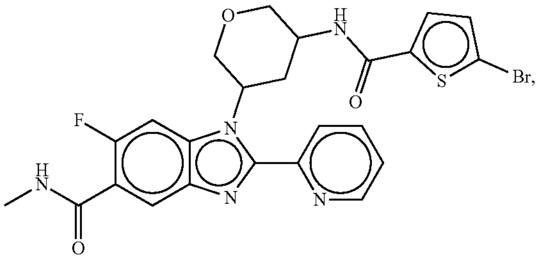

-continued
235
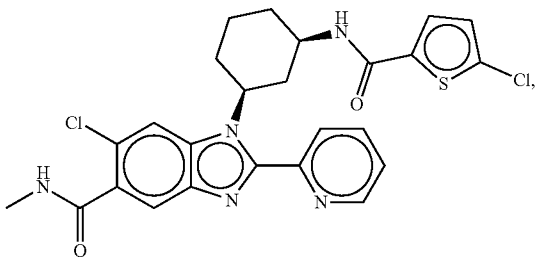
236
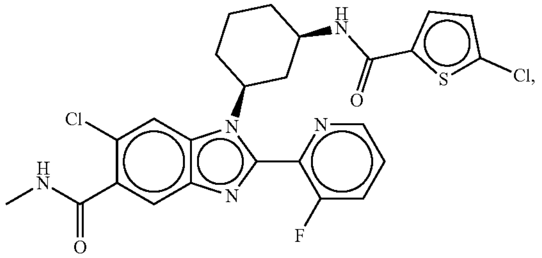
237
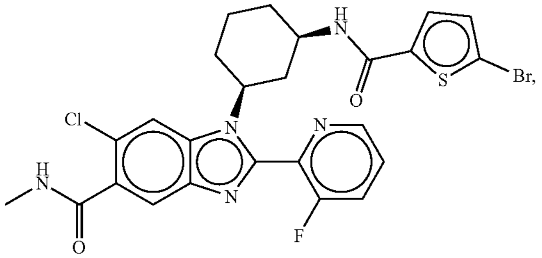
238
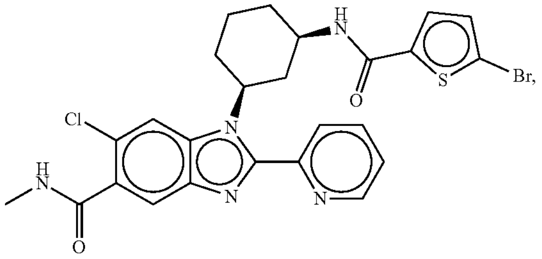
239
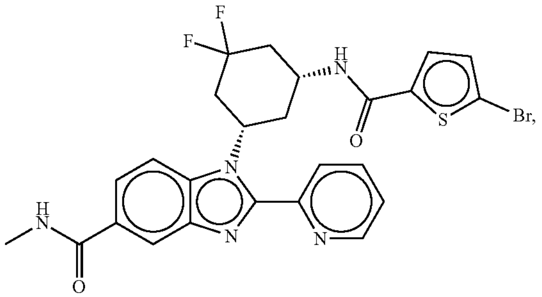
-continued
240
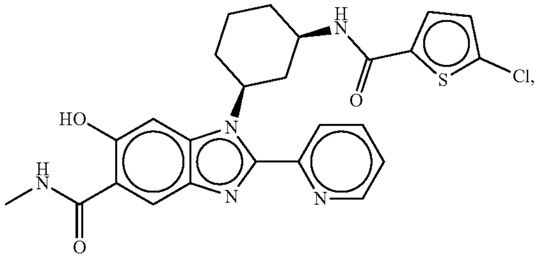
241
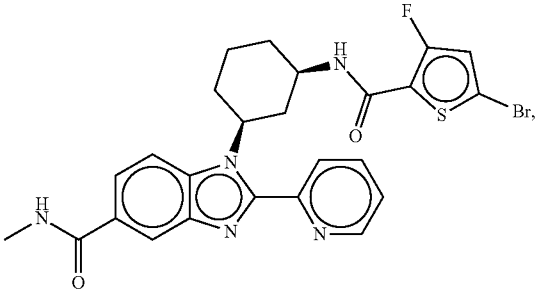
242
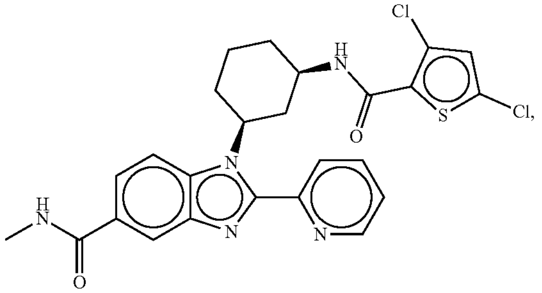
243
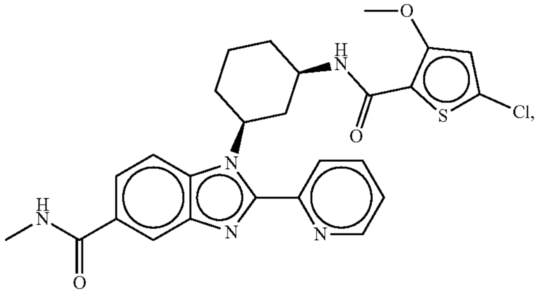
244
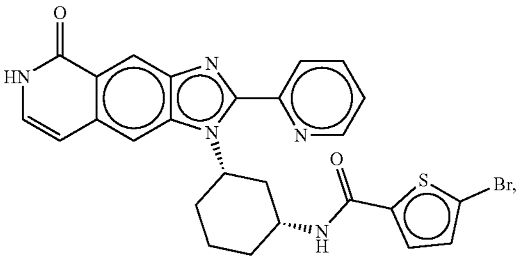

-continued
245
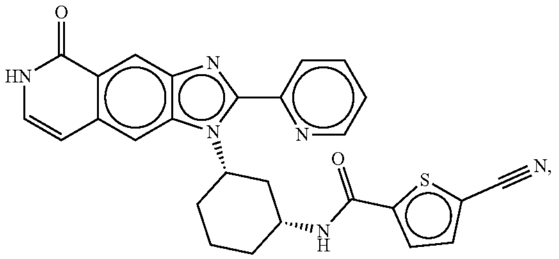
246
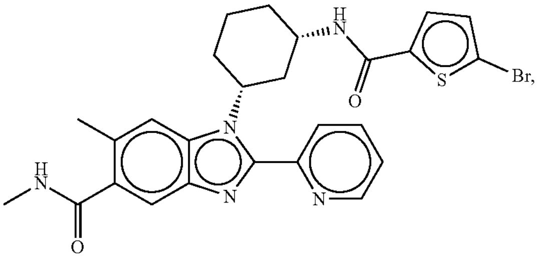
247
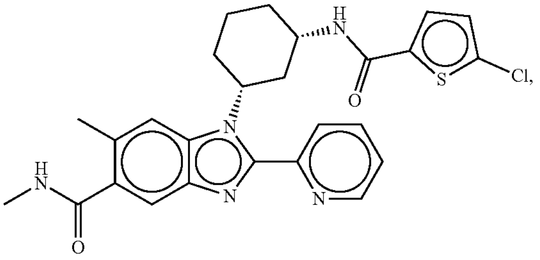
248
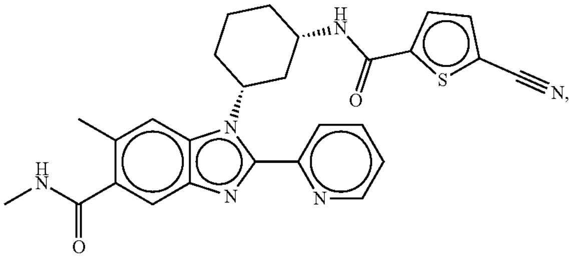
249
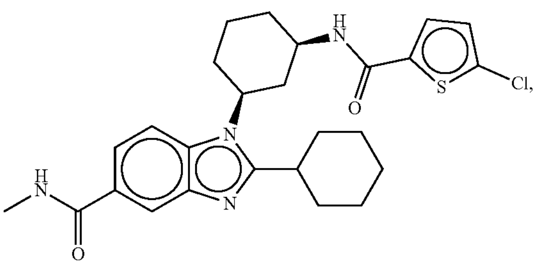
-continued
250
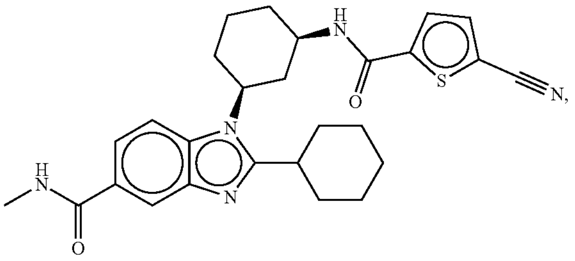
251
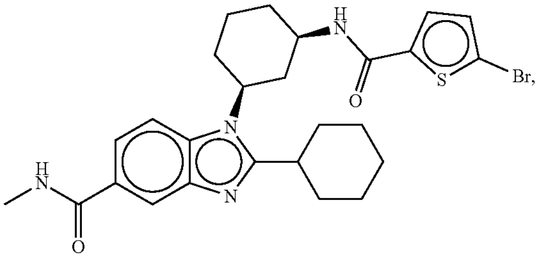
252
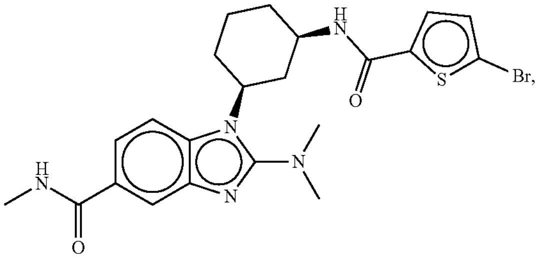
253
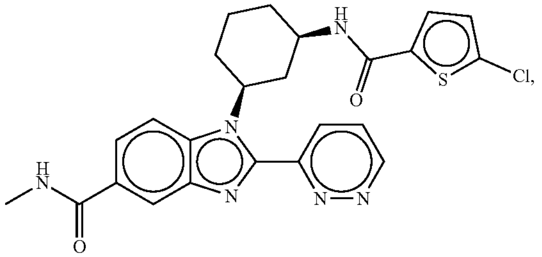
254
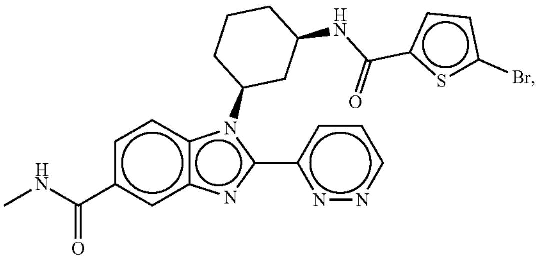

-continued
255
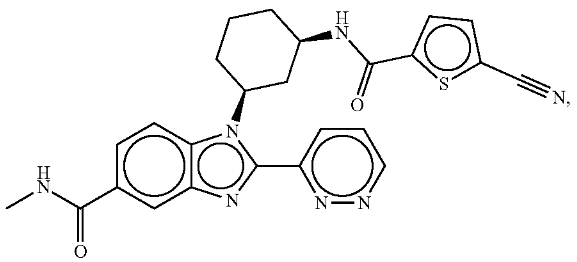
256
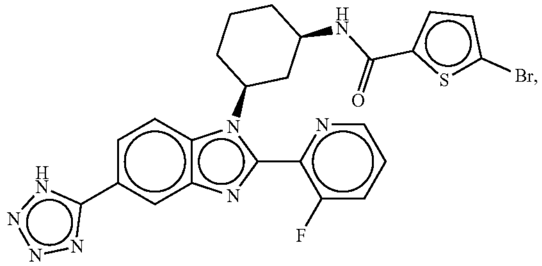
257
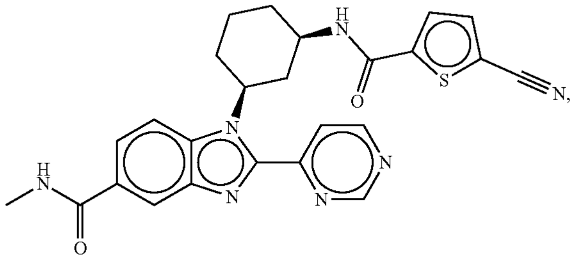
258
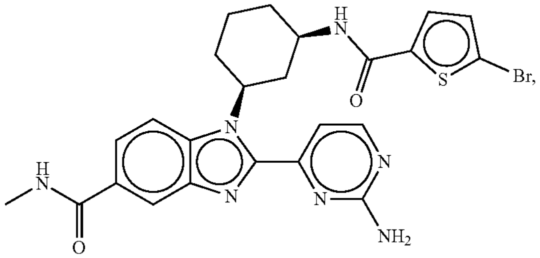
259
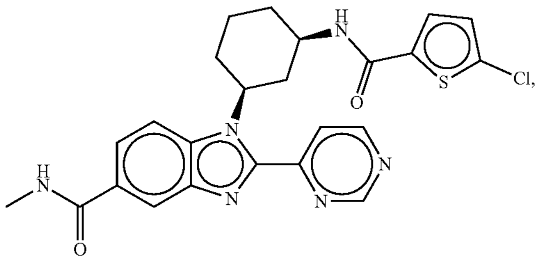
-continued
260
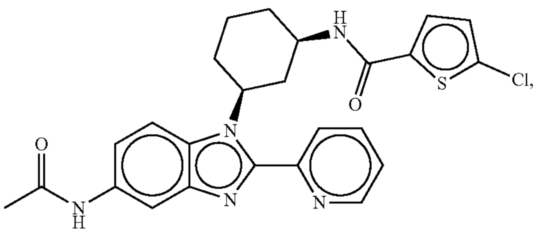
261
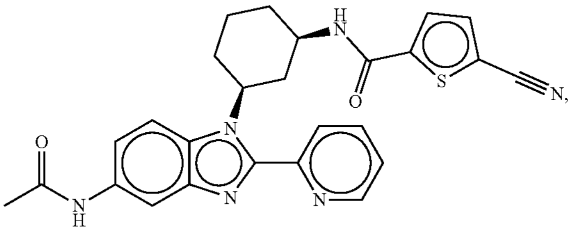
262
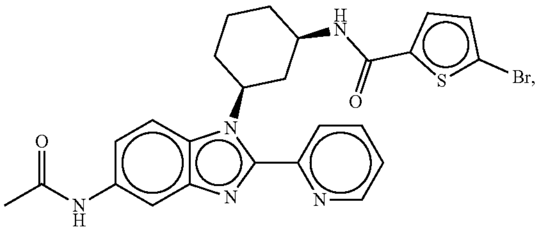
263
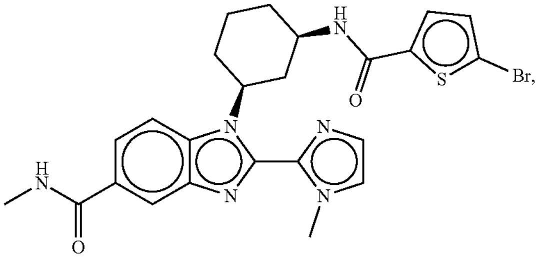
264
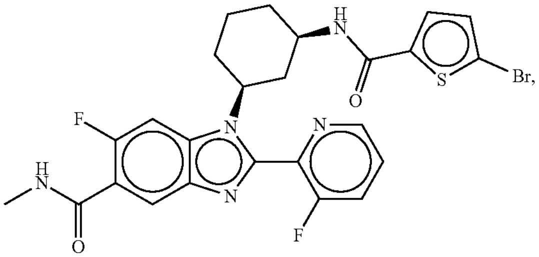
265
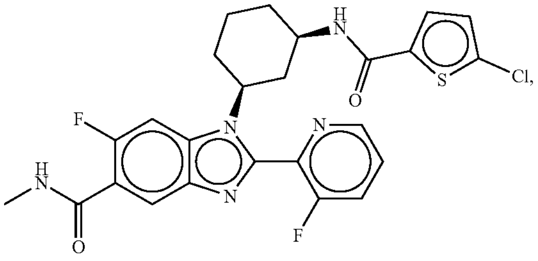

-continued
266
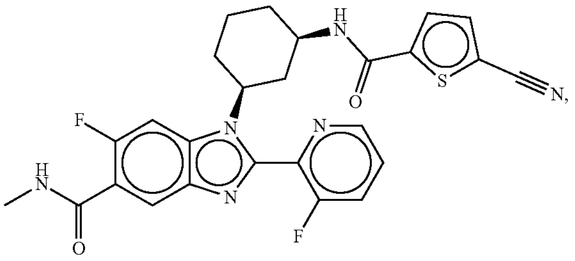
267
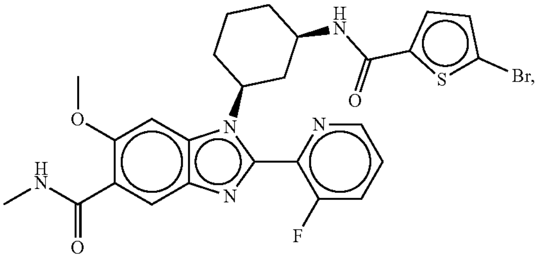
268
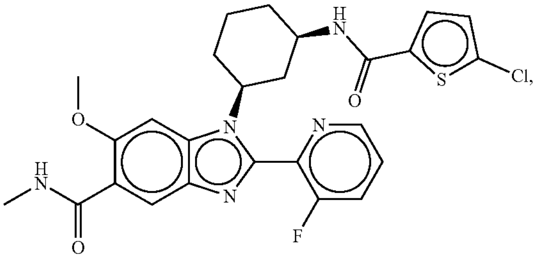
269
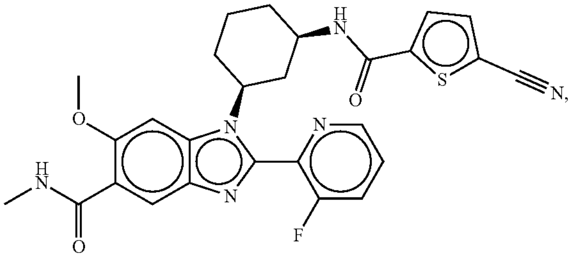
270
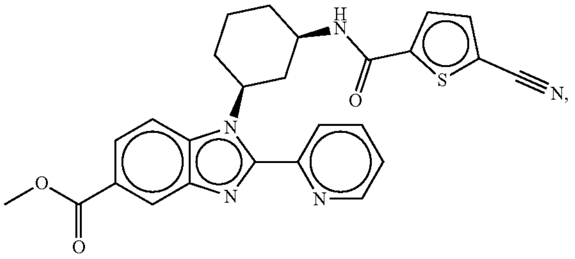
-continued
271
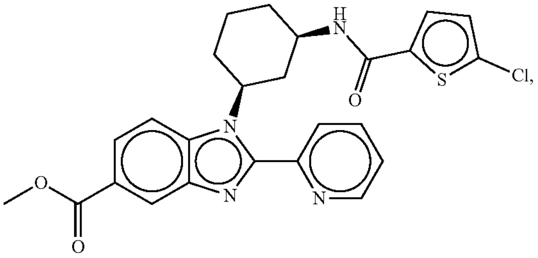
272
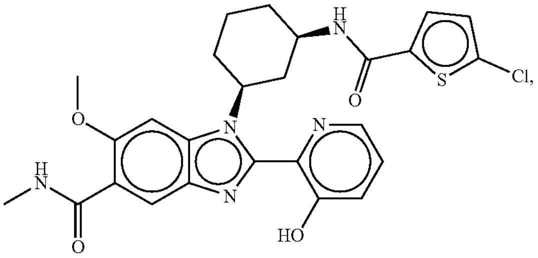
273
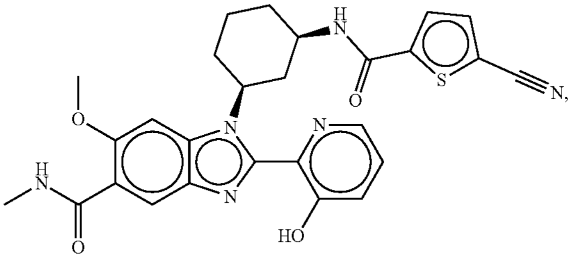
274
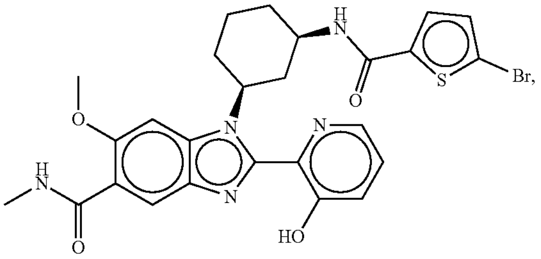
275
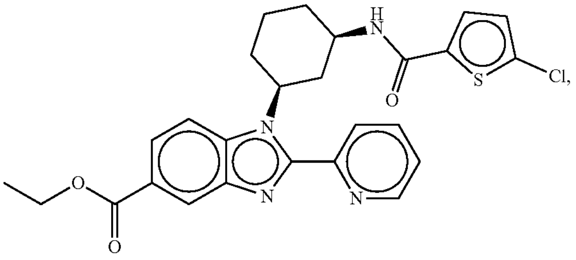

-continued
276
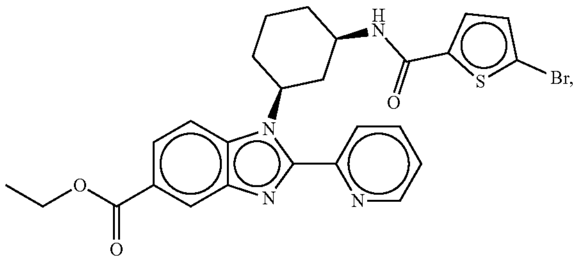
277
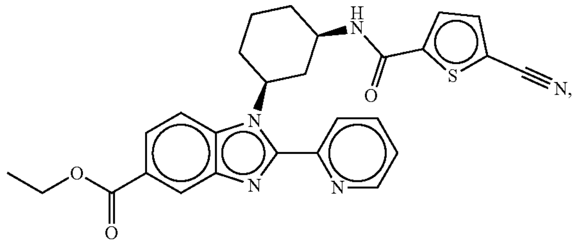
278
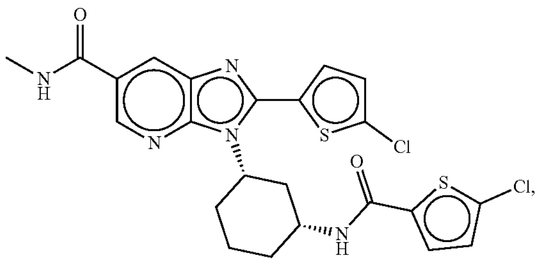
279
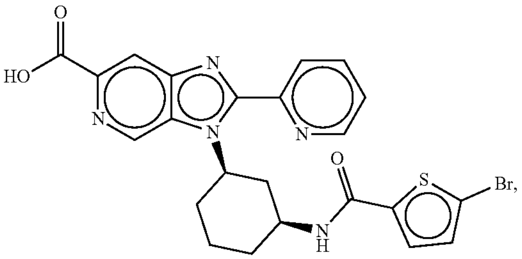
280
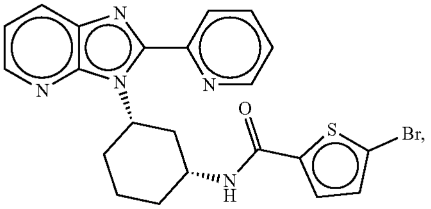
281
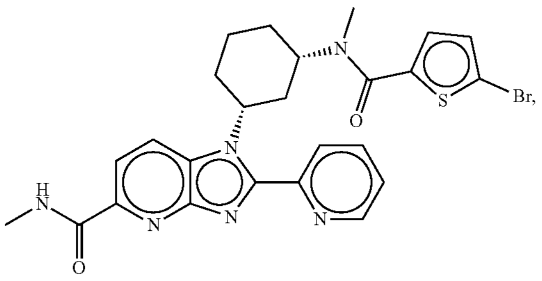
-continued
282
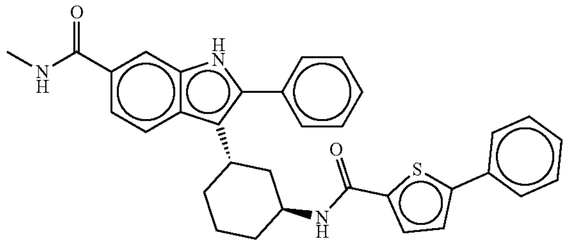
,
283
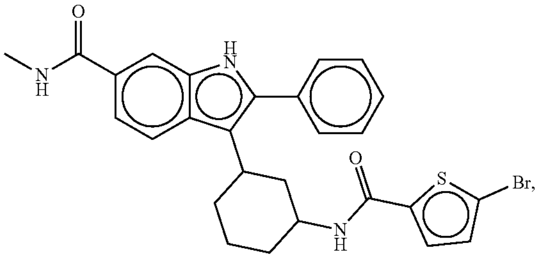
284
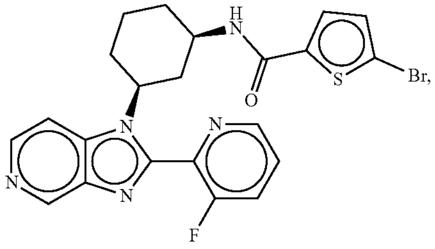
285
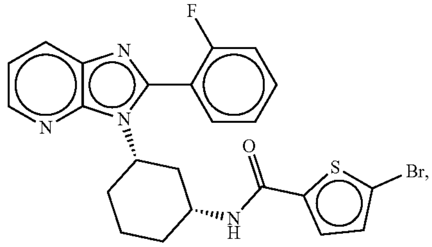
286
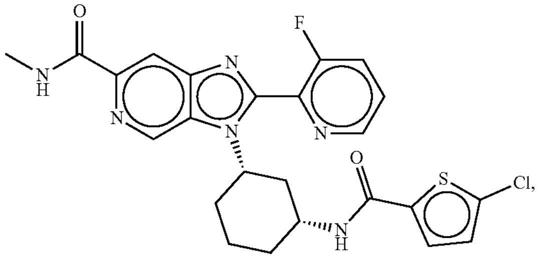
287
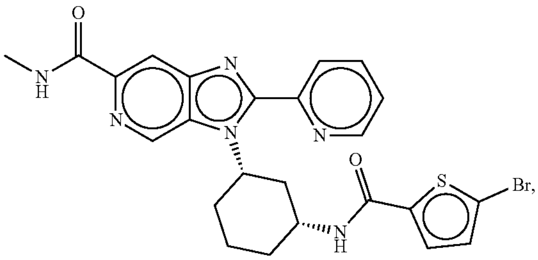

-continued
288
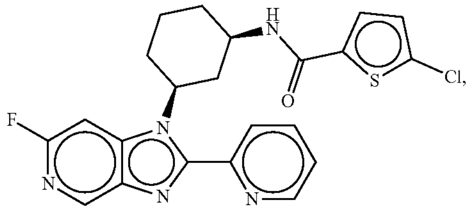
289
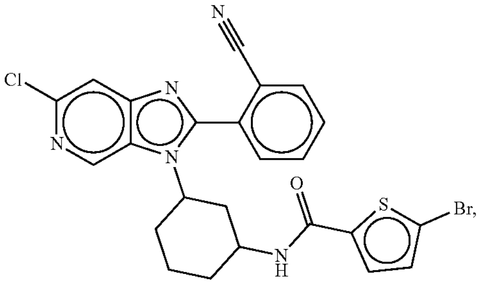
290
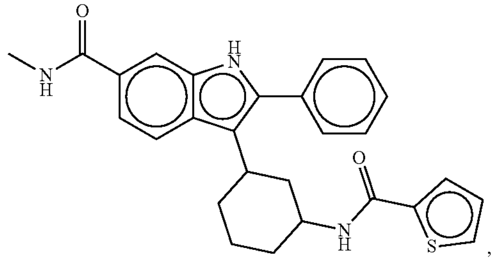
291
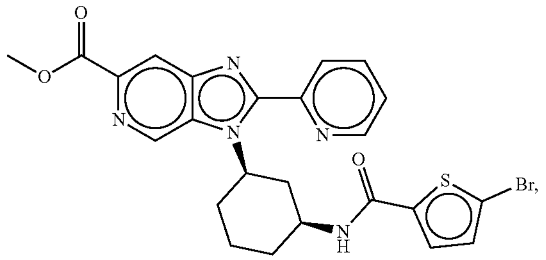
292
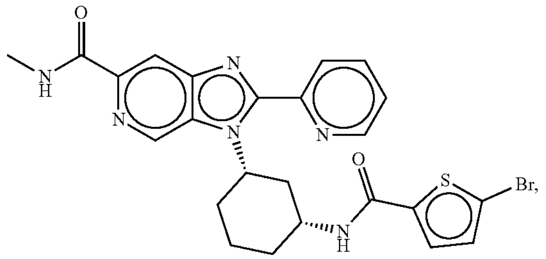
293
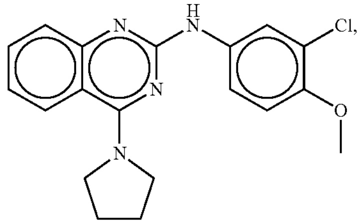
-continued
294
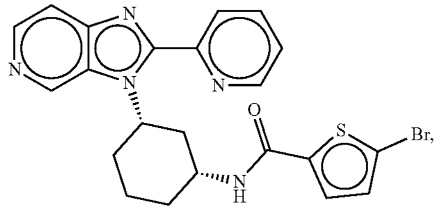
295
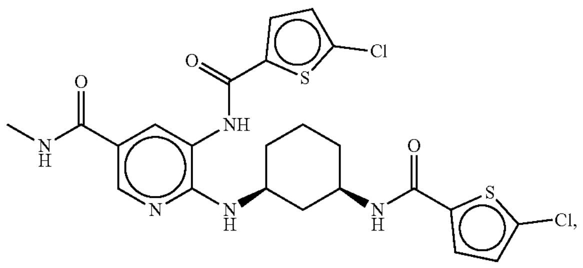
296
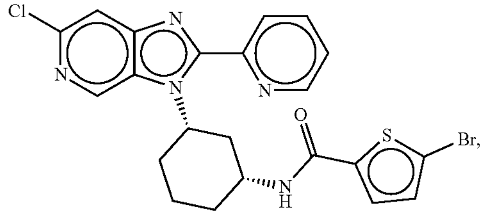
297
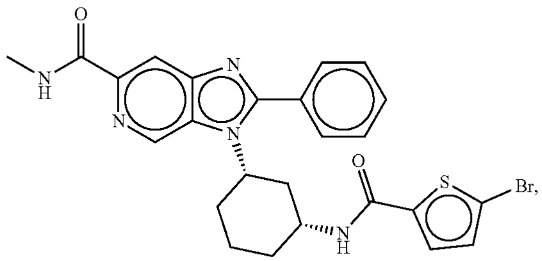
298
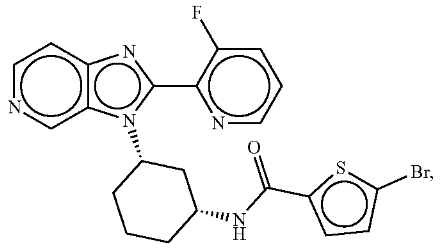
299
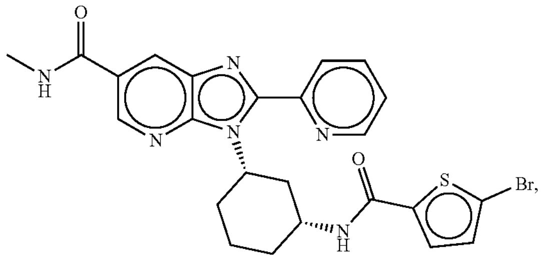

-continued

300

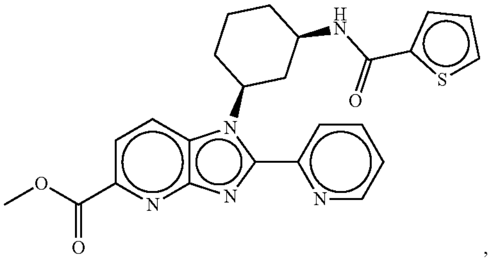

,

301

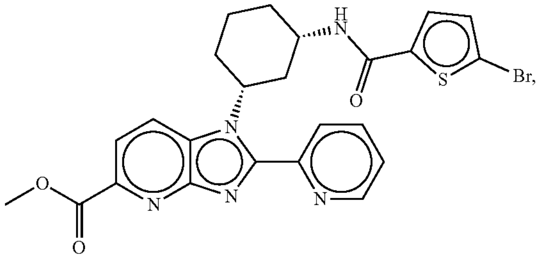

302

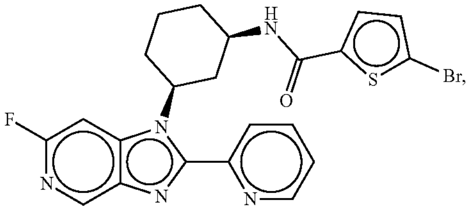

303

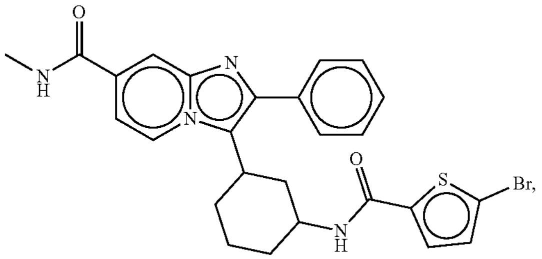

304

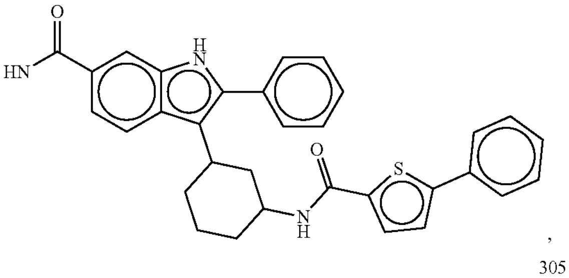

,

305

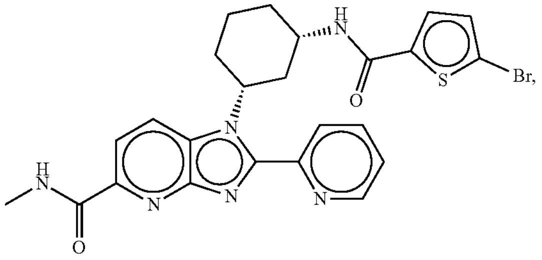

-continued

306

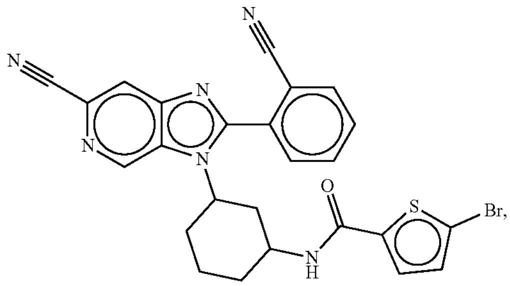

and pharmaceutically acceptable salts thereof.

In some embodiments, the compounds disclosed herein selectively inhibit BCAT2 as compared to BCAT1.

In some embodiments, the methods described herein reduce and/or ameliorate symptoms of the organic acidemia in the patient.

In some embodiments, the organic acidemia is selected from the group consisting of all forms of methylmalonic acidemia (MMA), all forms of propionic acidemia (PA), isovaleric acidemia, glutaric aciduria type 1 (GA1), beta-ketothiolase deficiency (BKT), 3-methylcrotonyl-CoA carboxylase deficiency (3-MCC), 3-hydroxy-3-methylglutaryl-CoA lyase deficiency (HMG), 3-Methylglutaconic acidemia or 3-Methylglutaconyl-CoA Hydratase Deficiency (MGA), D-2 Hydroxyglutaric Aciduria (D2-HGA), Isobutyryl-CoA Dehydrogenase Deficiency 3-Hydroxyisobutyric aciduria (ICBD), L-2-Hydroxy-glutaricaciduria (L2HGA), Malonyl-CoA Decarboxylase Deficiency aka Malonic Acidemia (MA), Multiple carboxylase deficiency (MCD, holocarboxylase synthetase), and 3-Hydroxyisobutyryl-CoA Hydrolase Deficiency (HIBCH).

In some embodiments, the methods described herein cause a decrease in toxic branched-chain amino acid (BCAA) metabolite levels. In some embodiments, the toxic metabolite is selected from propionic acid, 2-methylcitric acid, 3-hydroxypropionic acid, propionyl-CoA, methylmalonic acid, methylmalonyl-CoA and isovaleric acid. In some embodiments, the toxic metabolites allosterically inhibit enzymes.

In some embodiments, the methods described herein cause an increase in circulating branched-chain amino acid (BCAA) levels. In some embodiments, the branched-chain amino acid is selected from one or more of leucine, isoleucine, and valine.

In some embodiments, the methods described herein modulate metabolic flux through a BCAA pathway. In some embodiments, the decrease in metabolic flux occurs before and or after treatment. In some embodiments, the methods described herein inhibit and/or reduce BCAT2-mediated flux through a BCAA pathway.

In some embodiments, the reduction of BCAT2-mediated flux occurs as metabolism of leucine is reduced or inhibited. In some embodiments, the metabolism of leucine is reduced and/or inhibited at one or more enzymes in the BCAA metabolic pathway, selected from branched chain α-ketoacid dehydrogenase (BCKDH), isovaleryl CoA dehydrogenase (IVD), 3-methylcrotonyl-CoA carboxylase (3MCC), 3-methylglutaconic-CoA hydratase (3MGA), 3-hydroxy-3-methylglutaryl-CoA lyase (HMGL), acetyl-CoA carboxylase (AC), and malonyl-CoA decarboxylase (MA).

In some embodiments, the reduction of BCAT2-mediated flux occurs as metabolism of isoleucine is reduced and/or inhibited. In some embodiments, the metabolism of isoleucine is reduced and/or inhibited at one or more enzymes in the BCAA metabolic pathway, selected from BCKDH, methylbutyryl CoA dehydrogenase (SBCAD), Hydratase, 2-methyl-3-hydroxyisobutyric dehydrogenase (MHBD), acetoacetyl-CoA thiolase (T2), AC, MA, propionyl-CoA carboxylase (PCC), methylmalonyl-CoA mutase (MUT), and succinyl-CoA ligase (SUCLA).

In some embodiments, the reduction of BCAT2-mediated flux occurs as metabolism of valine is reduced and/or inhibited. In some embodiments, the metabolism of valine is reduced and/or inhibited at one or more enzymes in the BCAA metabolic pathway, selected from BCKDH, isobutyryl-CoA dehydrogenase (IBDH), Hydratase, 3-hydroxyisobutyryl-CoA deacylase (hydrolase)(HIBDA), 3-hydroxyisobutyrate dehydrogenase (HIBDH), methylmalonic semialdehyde dehydrogenase (MMSDH), PCC, MUT, and SUCLA.

In some embodiments, the methods described herein may further comprise administering an inhibitor of an amino acid transporter, optionally a SLC6A19 inhibitor. In some specific embodiments, the levels of branched chain amino acids are reduced compared to treatment without administration of the inhibitor of an amino acid transporter.

In yet another embodiment, described herein is a method for identifying a candidate compound for treatment of an organic acidemia, comprising:

(a) obtaining a test compound having the ability to directly or indirectly bind to BCAT2;
(b) assaying for functional modulation of BCAT2; and
(c) classifying the test compound as a candidate compound if reduced, low or substantially no activity of BCAT2 is detected.

In some embodiments, the functional modulation of BCAT2 is assayed using a cell-based assay. In some embodiments, the test compound is classified as a candidate compound if an increase in branch chain amino acids is measured. In some embodiments, the test compound is classified as a candidate compound if a decrease in propionyl-carnitine is measured.

In other embodiments, the functional modulation of BCAT2 is assayed using a cell-free assay. In some embodiments, the cell-free assay is an enzyme-coupled fluorescent assay. In some embodiments, the test compound is classified as a candidate compound if a decrease in L-glutamate is measured. In some embodiments, the test compound is classified as a candidate compound if a decrease in α-ketoglutarate is measured.

In another embodiment, provided herein is a method for making an agent for the treatment of an organic acidemia, comprising:

(a) identifying a candidate compound, comprising:
  (i) obtaining a test compound having the ability to directly or indirectly bind to BCAT2;
  (ii) assaying for functional modulation of BCAT2; and
  (iii) classifying the test compound as a candidate compound if reduced, low or substantially no activity of BCAT2 is detected; and
(b) formulating the candidate compound for the treatment of an organic acidemia.

In some embodiments, the functional modulation of BCAT2 is assayed using a cell-based assay. In some embodiments, the test compound is classified as a candidate compound if an increase in branch chain amino acids is measured. In some embodiments, the test compound is classified as a candidate compound if a decrease in propionyl-carnitine is measured.

In other embodiments, the functional modulation of BCAT2 is assayed using a cell-free assay. In some embodiments, the cell-free assay is an enzyme-coupled fluorescent assay. In some embodiments, the test compound is classified as a candidate compound if a decrease in L-glutamate is measured. In some embodiments, the test compound is classified as a candidate compound if a decrease in α-ketoglutarate is measured.

In some embodiments, the organic acidemia may be selected from the group consisting of all forms of methylmalonic acidemia (MMA), all forms of propionic acidemia (PA), isovaleric acidemia, glutaric aciduria type 1 (GA1), beta-ketothiolase deficiency (BKT), 3-methylcrotonyl-CoA carboxylase deficiency (3-MCC), 3-hydroxy-3-methylglutaryl-CoA lyase deficiency (HMG), 3-Methylglutaconic acidemia or 3-Methylglutaconyl-CoA Hydratase Deficiency (MGA), D-2 Hydroxyglutaric Aciduria (D2-HGA), Isobutyryl-CoA Dehydrogenase Deficiency 3-Hydroxyisobutyric aciduria (ICBD), L-2-Hydroxy-glutaricaciduria (L2HGA), Malonyl-CoA Decarboxylase Deficiency aka Malonic Acidemia (MA), Multiple carboxylase deficiency (MCD, holocarboxylase synthetase), and 3-Hydroxyisobutyryl-CoA Hydrolase Deficiency (HIBCH).

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs.

BRIEF DESCRIPTION OF THE FIGURES

In FIG. 2, the order of conditions is (left to right): vehicle, 30 mg/kg BCAT, 100 mg/kg BCAT, and 300 mg/kg BCAT.

FIG. 5A-B shows that overload of BCAAs from feeding with a precursor—enriched diet results in increased renal excretion of those amino acids. In each set of histograms, the left bar represents the normal diet and the right bar represents the precursor—enriched diet.

DETAILED DESCRIPTION

Figure 1:
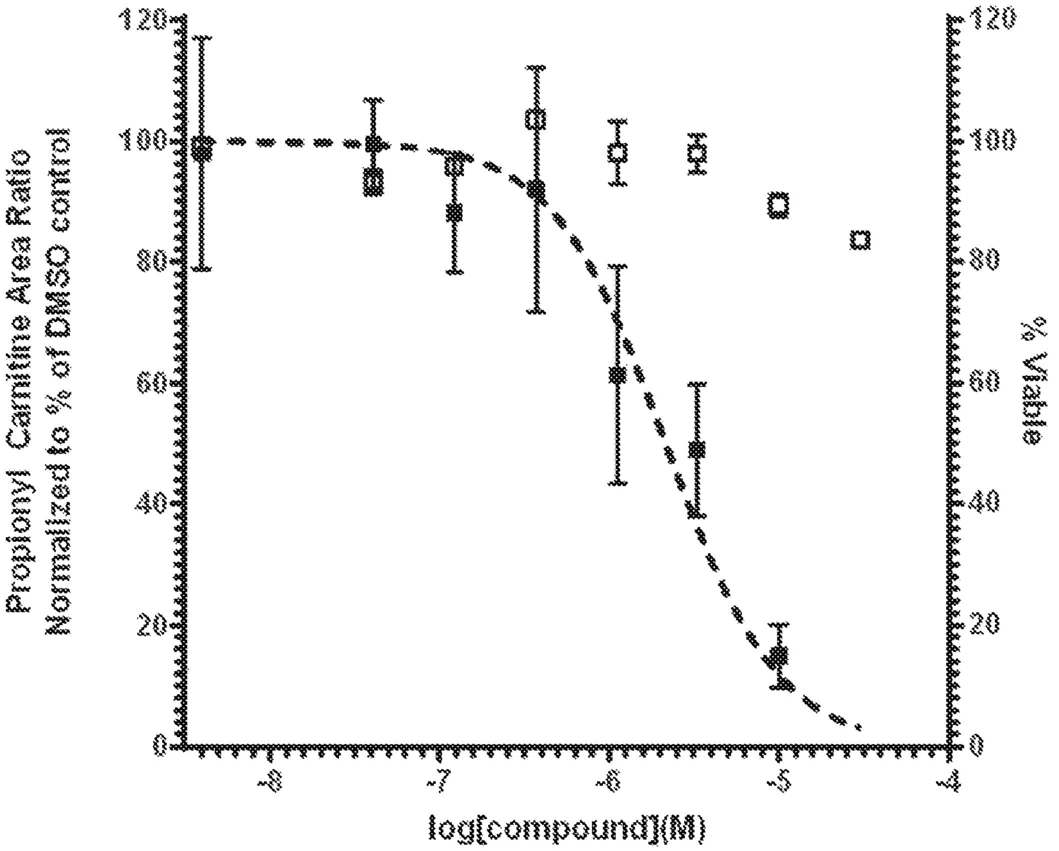
FIG. 1 depicts the effects of the BCAT2 inhibitor, a compound of Formula Ia, on flux through the BCAA pathway, and on a downstream metabolite, propionyl carnitine. The results show that propionyl carnitine levels are inhibited in the presence of increasing concentrations of the BCAT2 inhibitor compound with little impact on cell viability.

In some embodiments, provided herein are compounds of Formula (I), (Ia), (II), (III), (IV), (V), (VI), (VII), and additional compounds. The compounds disclosed herein are BCAT2 inhibitors.

The present disclosure is based, in part, on the discovery that inhibition of a target in the branched-chain amino acid (BCAA) metabolism pathway could be used to identify inhibitors that would be successful in reducing the substrate toxic load of a patient suffering from an organic acidemia. The present disclosure further provides for methods of treating an organic acidemia by reducing the levels of toxic metabolites and/or substrate molecules by administering a BCAT2 inhibitor compound disclosed herein to a patient in need thereof. The present disclosure provides, in part, methods for treating an organic acidemia by administering a BCAT2 inhibitor and an inhibitor of an amino acid transporter, inclusive of a SLC6A19 inhibitor to a patient in need thereof.

In some embodiments of the present disclosure, a patient receiving a BCAT inhibitor compound (e.g., a BCAT2 inhibitor compound) also receives an inhibitor of an amino acid transporter, inclusive of a SLC6A19 (e.g., amino acid transporter B0 ATI) inhibitor in order to treat and/or prevent hyperaminoacidemia. In various embodiments, administration of an inhibitor of an amino acid transporter, inclusive of a SLC6A19 inhibitor reduces the amino acid load of a patient undergoing treatment with a BCAT2 inhibitor compound.

In one aspect, the disclosure provides a method for identifying whether a candidate compound is useful for the treatment of an organic acidemia, comprising a candidate compound for treatment of an organic acidemia, comprising: (a) obtaining a test compound having the ability to directly or indirectly bind to a BCAT (e.g., BCAT2); (b) assaying for functional modulation of the BCAT (e.g., BCAT2); and (c) classifying the test compound as a candidate compound if reduced, low or substantially no activity of the BCAT (e.g., BCAT2) is detected.

In another aspect, the present disclosure provides a method for making an agent for the treatment of an organic acidemia, comprising: (a) identifying a candidate compound, comprising: (i) obtaining a test compound having the ability to directly or indirectly bind to a BCAT (e.g., BCAT2); (ii) assaying for functional modulation of the BCAT (e.g., BCAT2); and (iii) classifying the test compound as a candidate compound if reduced, low or substantially no activity of the BCAT (e.g., BCAT2) is detected; and (b) formulating the candidate compound for the treatment of an organic acidemia.

In another aspect, the present disclosure provides a method for treating or preventing an organic acidemia, comprising administering to a subject in need thereof an effective amount of a compound disclosed herein.

In another aspect, the present disclosure provides a method for treating or preventing an organic acidemia, comprising administering to a subject in need thereof an effective amount of a compound selected from Table 1.

In another aspect, the present disclosure provides a method for reducing toxic branched-chain amino acid (BCAA) metabolites, comprising administering to a subject in need thereof an effective amount of a compound disclosed herein.

In another aspect, the present disclosure provides a method for reducing toxic branched-chain amino acid (BCAA) metabolites, comprising administering to a subject in need thereof an effective amount of a compound selected from Table 1.

In another aspect, the present disclosure provides a method of reducing a toxic load burden in cells of a patient having organic acidemia, comprising administering to a subject in need thereof an effective amount of a compound disclosed herein.

In another aspect, the present disclosure provides a method of reducing a toxic load burden in cells of a patient having organic acidemia, comprising administering to a subject in need thereof an effective amount of a compound selected from Table 1.

TABLE 1

| Structure | IUPAC Name |
|---|---|
| 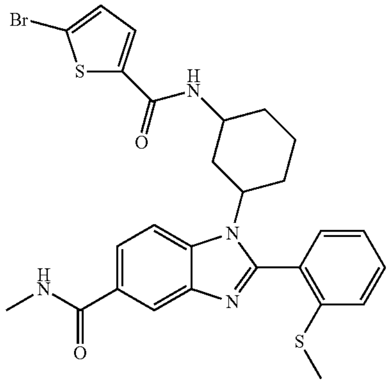 [SMILES: CNC(=O)c1ccc2c(c1)nc(-c1ccccc1SC)n2C1CCCC(NC(=O)c2ccc(Br)s2)C1] | 1-(3-(5-bromothiophene-2-carboxamido)cyclohexyl)-N-methyl-2-(2-(methylthio)phenyl)-1H-benzo[d]imidazole-5-carboxamide |
| 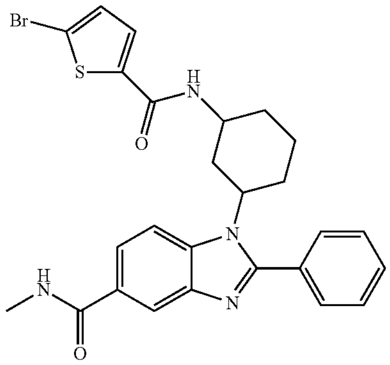 [SMILES: CNC(=O)c1ccc2c(c1)nc(-c1ccccc1)n2C1CCCC(NC(=O)c2ccc(Br)s2)C1] | 1-(3-(5-bromothiophene-2-carboxamido)cyclohexyl)-N-methyl-2-phenyl-1H-benzo[d]imidazole-5-carboxamide |
| 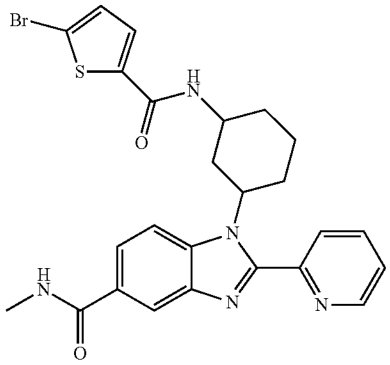 | 1-(3-(5-bromothiophene-2-carboxamido)cyclohexyl)-N-methyl-2-(pyridin-2-yl)-1H-benzo[d]imidazole-5-carboxamide |
| 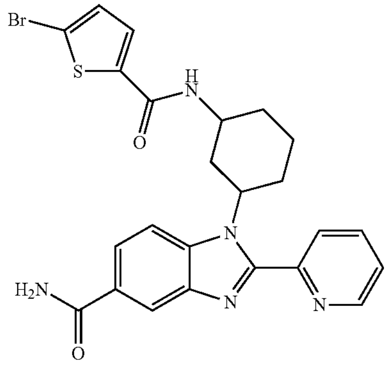 [SMILES: NC(=O)c1ccc2c(c1)nc(-c1ccccn1)n2C1CCCC(NC(=O)c2ccc(Br)s2)C1] | 1-(3-(5-bromothiophene-2-carboxamido)cyclohexyl)-2-(pyridin-2-yl)-1H-benzo[d]imidazole-5-carboxamide |

TABLE 1-continued

| Structure | IUPAC Name |
|---|---|
| 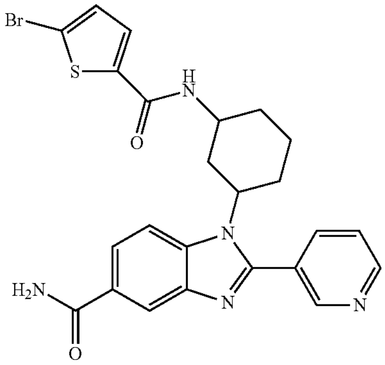 [SMILES: NC(=O)c1ccc2c(c1)nc(-c1cccnc1)n2C1CCCC(NC(=O)c2ccc(Br)s2)C1] | 1-(3-(5-bromothiophene-2-carboxamido)cyclohexyl)-2-(pyridin-3-yl)-1H-benzo[d]imidazole-5-carboxamide |
| 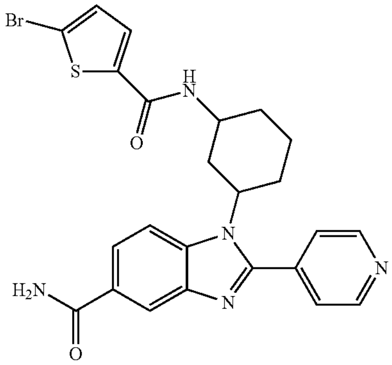 [SMILES: NC(=O)c1ccc2c(c1)nc(-c1ccncc1)n2C1CCCC(NC(=O)c2ccc(Br)s2)C1] | 1-(3-(5-bromothiophene-2-carboxamido)cyclohexyl)-2-(pyridin-4-yl)-1H-benzo[d]imidazole-5-carboxamide |
| 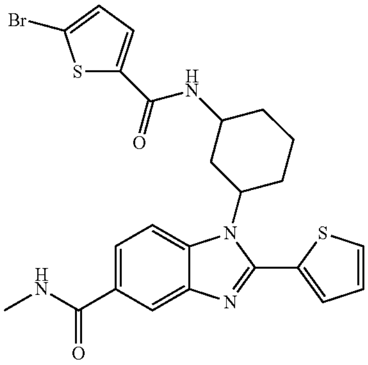 [SMILES: CNC(=O)c1ccc2c(c1)nc(-c1cccs1)n2C1CCCC(NC(=O)c2ccc(Br)s2)C1] | 1-(3-(5-bromothiophene-2-carboxamido)cyclohexyl)-N-methyl-2-(thiophen-2-yl)-1H-benzo[d]imidazole-5-carboxamide |
| 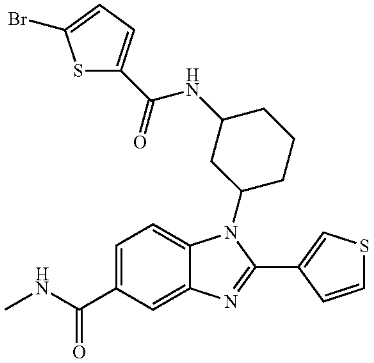 [SMILES: CNC(=O)c1ccc2c(c1)nc(-c1ccsc1)n2C1CCCC(NC(=O)c2ccc(Br)s2)C1] | 1-(3-(5-bromothiophene-2-carboxamido)cyclohexyl)-N-methyl.-2-(thiophen-3-yl)-1H-benzo[d]imidazole-5-carboxamide |

TABLE 1-continued

| Structure | IUPAC Name |
|---|---|
| 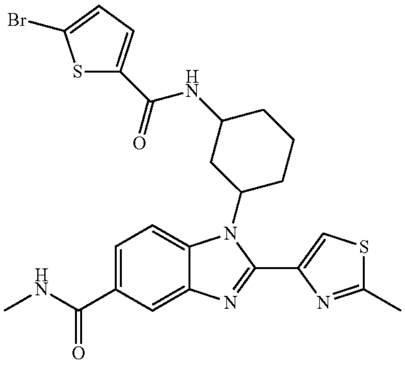 | 1-(3-(5-bromothiophene-2-carboxamido)cyclohexyl)-N-methyl-2-(2-methylthiazol-4-yl)-1H-benzo[d]imidazole-5-carboxamide |
| 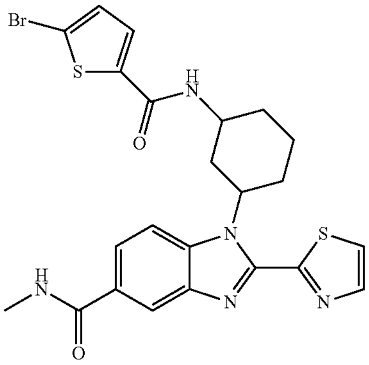 [SMILES: CNC(=O)c1ccc2c(c1)nc(-c1nccs1)n2C1CCCC(NC(=O)c2ccc(Br)s2)C1] | 1-(3-(5-bromothiophene-2-carboxamido)cyclohexyl)-N-methyl-2-(thiazol-2-yl)-1H-benzo[d]imidazole-5-carboxamide |
| 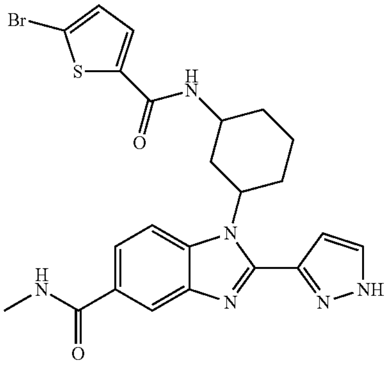 [SMILES: CNC(=O)c1ccc2c(c1)nc(-c1cc[nH]n1)n2C1CCCC(NC(=O)c2ccc(Br)s2)C1] | 1-(3-(5-bromothiophene-2-carboxamido)cyclohexyl)-N-methyl-2-(1H-pyrazol-3-yl)-1H-benzo[d]imidazole-5-carboxamide |
| 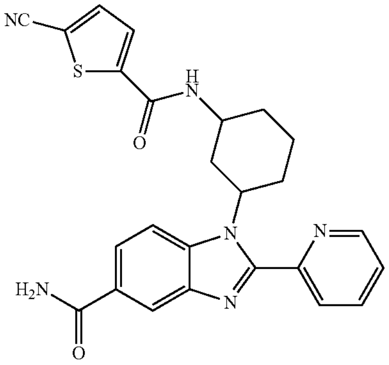 [SMILES: N#Cc1ccc(C(=O)NC2CCCC(n3c(-c4ccccn4)nc4cc(C(N)=O)ccc43)C2)s1] | 1-(3-(5-cyanothiophene-2-carboxamido)cyclohexyl)-2-(pyridin-2yl)-1H-benzo[d]imidazole-5-carboxamide |

TABLE 1-continued

| Structure | IUPAC Name |
| --- | --- |
| 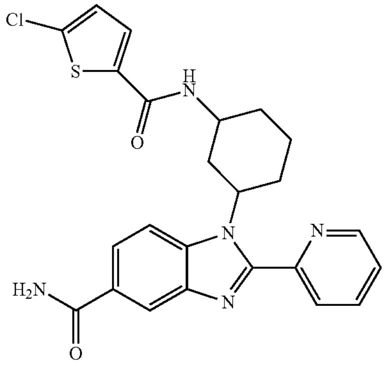 [SMILES: NC(=O)c1ccc2c(c1)nc(-c1ccccn1)n2C1CCCC(NC(=O)c2ccc(Cl)s2)C1] | 1-(3-(5-chlorothiophene-2-carboxamido)cyclohexyl)-2-(pyridin-2-yl)-1H-benzo[d]imidazole-5-carboxamide |
| 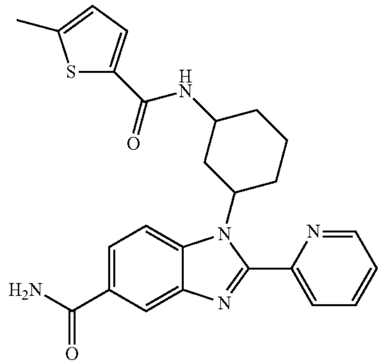 [SMILES: Cc1ccc(C(=O)NC2CCCC(n3c(-c4ccccn4)nc4cc(C(N)=O)ccc43)C2)s1] | 1-(3-(5-methylthiophene-2-carboxamido)cyclohexyl)-2-(pyridin-2-yl)-1H-benzo[d]imidazole-5-carboxamide |
| 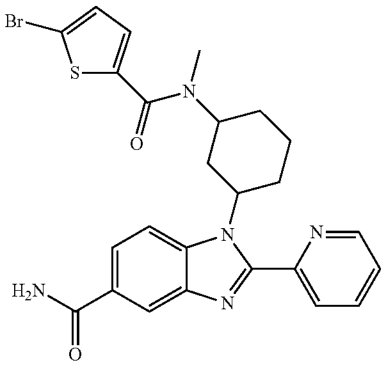 [SMILES: CN(C(=O)c1ccc(Br)s1)C1CCCC(n2c(-c3ccccn3)nc3cc(C(N)=O)ccc32)C1] | 1-(3-(5-bromo-N-methylthiophene-2-carboxamido)cyclohexyl)-2-(pyridin-2-yl)-1H-benzo[d]imidazole-5-carboxamide |
| 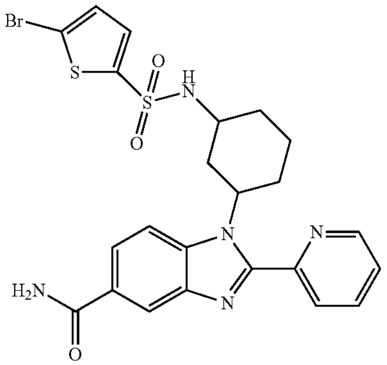 [SMILES: NC(=O)c1ccc2c(c1)nc(-c1ccccn1)n2C1CCCC(NS(=O)(=O)c2ccc(Br)s2)C1] | 1-(3-(5-bromothiophene)-2-sulfonamido)cyclohexyl)-2-(pyridin-2-yl)-1H-benzo[d]imidazole-5-carboxamide |

TABLE 1-continued

| Structure | IUPAC Name |
| --- | --- |
| 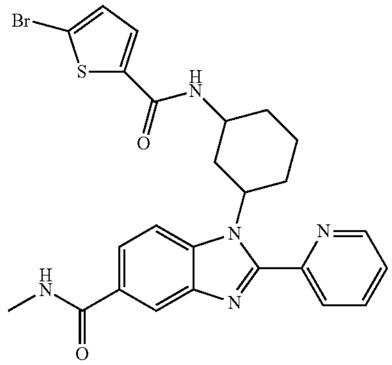 [SMILES: CNC(=O)c1ccc2c(c1)nc(-c1ccccn1)n2C1CCCC(NC(=O)c2ccc(Br)s2)C1] | 2-bromo-N-(3-(5-(methylcarbamoyl)-2-(pyridin-2-yl)-1H-benzo[d]imidazol-1-yl)cyclohexyl)thiazole-5-carboxamide |
| 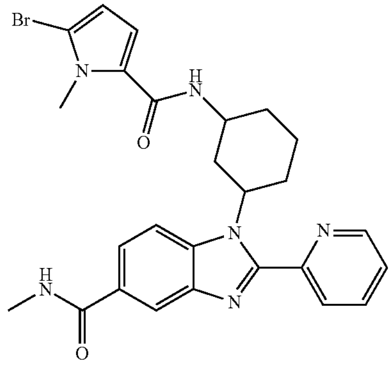 | 1-(3-(5-bromo-1-methyl-1H-pyrrole-2-carboxamido)cyclohexyl)-N-methyl-2-(pyridin-2-yl)-1H-benzo[d]imidazole-5-carboxamide |
| 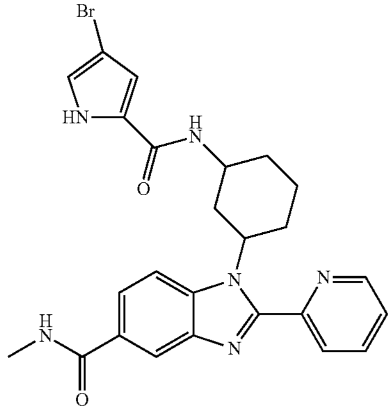 [SMILES: CNC(=O)c1ccc2c(c1)nc(-c1ccccn1)n2C1CCCC(NC(=O)c2cc(Br)c[nH]2)C1] | 1-(3-(4-bromo-1H-pyrrole-2-carboxamido)cyclohexyl)-N-methyl-2-(pyridin-2-yl)-1H-benzo[d]imidazole-5-carboxamide |
| 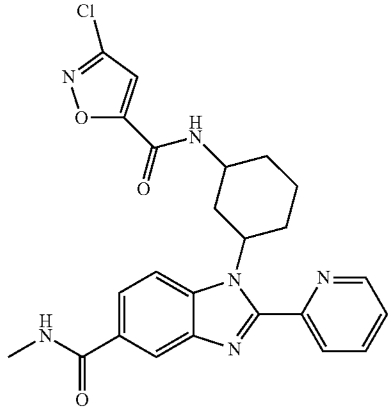 [SMILES: CNC(=O)c1ccc2c(c1)nc(-c1ccccn1)n2C1CCCC(NC(=O)c2cc(Cl)no2)C1] | 3-chloro-N-(3-(5-(methylcarbamoyl)-2-(pyridin-2-yl)-1H-benzo[d]imidazol-1-cyclohexyl)isoxazole-5-carboxamide |

TABLE 1-continued

| Structure | IUPAC Name |
|---|---|
| 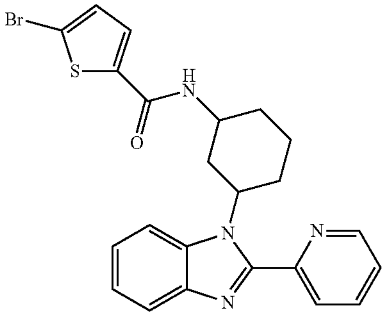 [SMILES: O=C(NC1CCCC(n2c(-c3ccccn3)nc3ccccc32)C1)c1ccc(Br)s1] | 5-bromo-N-(3-(2-(pyridin-2-yl)-1H-benzo[d]imidazol-1-yl)cyclohexyl)thiophene-2-carboxamide |
| 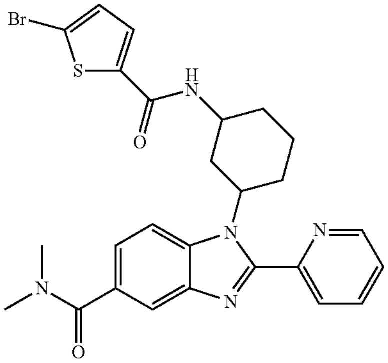 [SMILES: CN(C)C(=O)c1ccc2c(c1)nc(-c1ccccn1)n2C1CCCC(NC(=O)c2ccc(Br)s2)C1] | 1-(3-(5-bromothiophene-2-carboxamido)cyclohexyl)-N,N-dimethyl-2-(pyridin-2-yl)-1H-benzo[d]imidazole-5-carboxamide |
| 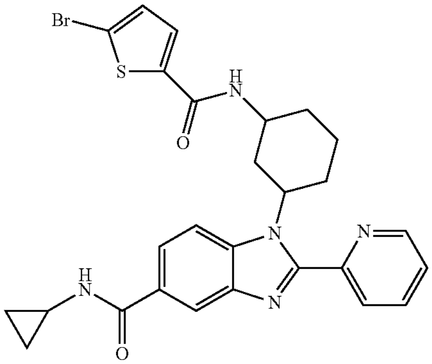 [SMILES: O=C(NC1CC1)c1ccc2c(c1)nc(-c1ccccn1)n2C1CCCC(NC(=O)c2ccc(Br)s2)C1] | 1-(3-(5-bromothiophene-2-carboxamido)cyclohexyl)-N-cyclopropyl-2-(pyridin-2-yl)-1H-benzo[d]imidazole-5-carboxamide |
| 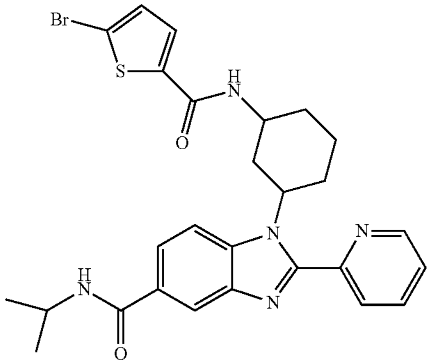 [SMILES: CC(C)NC(=O)c1ccc2c(c1)nc(-c1ccccn1)n2C1CCCC(NC(=O)c2ccc(Br)s2)C1] | 1-(3-(5-bromothiophene-2-carboxamido)cyclohexyl)-N-isopropyl-2-(pyridin-2-yl)-1H-benzo[d]imidazole-5-carboxamide |

In another aspect of the present disclosure, the compound may be selected from the group consisting of Compounds 106-306, and pharmaceutically acceptable salts, as provided above.

In some embodiments, the methods of the present disclosure further comprise administering an additional therapeutic agent. In various embodiments, the additional therapeutic agent is an inhibitor of an amino acid transporter, inclusive of an inhibitor of SLC6A19.

In other embodiments, the disclosure provides for the use of compounds of Formula (I), (II), (III), (IV), (V), (VI), (VII), or any compounds disclosed therein, or their pharmaceutically acceptable salts, alone or in combination with an additional therapeutic, in the manufacture of a medicament useful for the treatment or prevention of one or more organic acidemias.

Branched-Chain Amino Acid Metabolic Pathway

Without wishing to be bound by any one theory, it is presently thought that inhibiting the BCAT2 step in the BCAA pathway will result in the systemic accumulation of branched-chain amino acids in circulation, thereby preventing the formation of toxic metabolites that cannot be processed in patients with mutations in the BCAA pathway (e.g., patients having one or more organic acidemias). It is therefore postulated that substrate reduction therapy will cause a decrease in the toxic load burden in patient cells and have transformative effects in reducing their symptoms. Novel inhibitors could be developed as therapeutics for rare organic acidemia patients under the orphan drug program at the FDA.

The branched-chain amino acids (BCAA) are leucine, isoleucine, and valine. They share common membrane transport systems and enzymes for their transamination and irreversible oxidation. They can be glucogenic (valine), ketogenic (leucine and isoleucine) or both (isoleucine), since their end products, succinyl-CoA and/or acetyl-CoA can enter the Krebs cycle for energy generation and gluconeogenesis or act as precursors for lipogenesis and ketone body production through acetyl-CoA and acetoacetate. Leucine, in particular, plays a central role in metabolism and participates in numerous signaling pathways. It is a potent stimulator of the mammalian target of rapamycin complex 1 and downstream targets that enhance translation elongation and protein synthesis. In addition, leucine may act as an inhibitor of muscle protein breakdown, via interactions with the ubiquitin-proteasome and the autophagy-lysosome system. Furthermore, leucine stimulates insulin secretion from the pancreatic β-cell serving as metabolic fuel as well as an allosteric activator of glutamate dehydrogenase. Lastly, it also plays a role in central nervous system food intake regulatory circuits and feeding behavior.

The enzyme BCAT (e.g., mitochondrial BCAT isoenzyme, or "BCATm" or "BCAT2"; or cytosolic BCAT isoenzyme, or "BCATc" or "BCAT1") catalyzes the first step in the branched-chain amino acid catabolic pathway via a reversible transamination that is dependent on pyridoxal-phosphate. This first step is followed by the irreversible oxidative decarboxylation and coupled thioesterification of the respective ketoacids by the single mitochondrial branched chain α-ketoacid dehydrogenase (BCKDH) complex to form coenzymeA derivatives. The oxidation of BCAAs and branched chain α-ketoacids (BCKAs) is tightly regulated primarily at the BCKD step, which commits BCAAs to oxidative metabolism. The next step in the BCAA metabolic pathway is dehydrogenation of the activated ketoacid by either isovaleryl-CoA dehydrogenase (leucine metabolism) or the α-methyl-branched chain dehydrogenase (isoleucine and valine metabolism). After these first three steps, the metabolism of each of the BCAAs diverges and eventually yields acetyl-CoA and/or propionyl-CoA. Terminal valine metabolism is unique because a free acid, 3-hydroxyisobutyric acid forms after the hydrolysis of the corresponding thioester. 3-hydroxyisobutyric acid is dehydrogenated, then reacylated to complete metabolism.

In various embodiments, the present disclosure contemplates methods of administering a BCAT2 inhibitor compound to a patient in need thereof that cause a modulation of metabolic flux (e.g., before or after treatment) through a mitochondrial BCAA pathway. In various embodiments, the present disclosure contemplates methods of administering a BCAT2 inhibitor compound to a patient in need thereof that cause a decrease in metabolic flux (e.g., before or after treatment) through a mitochondrial BCAA pathway. In various embodiments, the present disclosure contemplates methods of administering a BCAT2 inhibitor compound to a patient in need thereof that cause a modulation of catabolic flux (e.g., before or after treatment) through a mitochondrial BCAA pathway. More specifically, it is contemplated in some embodiments, that methods of the disclosure inhibit and/or reduce BCAT2-mediated flux through a mitochondrial BCAA pathway.

For example, with respect to leucine, reduction of BCAT2-mediated flux can occur as metabolism of leucine is reduced and/or inhibited. In various embodiments, the metabolism of leucine is reduced and/or inhibited at one or more enzymes in the BCAA metabolic pathway, selected from branched chain α-ketoacid dehydrogenase (BCKDH), isovaleryl CoA dehydrogenase (IVD), 3-methylcrotonyl-CoA carboxylase (3MCC), 3-methylglutaconic-CoA hydratase (3MGA), 3-hydroxy-3-methylglutaryl-CoA lyase (HMGL), acetyl-CoA carboxylase (AC), and malonyl-CoA decarboxylase (MA).

In further embodiments, with respect to isoleucine, reduction of BCAT2-mediated flux occurs as metabolism of isoleucine is reduced and/or inhibited. In some embodiments, the metabolism of isoleucine is reduced and/or inhibited at one or more enzymes in the BCAA metabolic pathway, selected from BCKDH, methylbutyryl CoA dehydrogenase (SBCAD), Hydratase, 2-methyl-3-hydroxyisobutyric dehydrogenase (MHBD), acetoacetyl-CoA thiolase (T2), AC, MA, propionyl-CoA carboxylase (PCC), methylmalonyl-CoA mutase (MUT), and succinyl-CoA ligase (SUCLA).

In further embodiments, with respect to valine, reduction of BCAT2-mediated flux occurs as metabolism of valine is reduced and/or inhibited. In some embodiments, the metabolism of valine is reduced and/or inhibited at one or more enzymes in the BCAA metabolic pathway, selected from BCKDH, isobutyryl-CoA dehydrogenase (IBDH), Hydratase, 3-hydroxyisobutyryl-CoA deacylase (hydrolase) (HIBDA), 3-hydroxyisobutyrate dehydrogenase (HIBDH), methylmalonic semialdehyde dehydrogenase (MMSDH), PCC, MUT, and SUCLA.

Methods for Treatment of Organic Acidemias

In various aspects, the present disclosure provides a method for treating one or more organic acidemias. In these aspects, the "agent of the disclosure" comprises compounds useful for both monotherapy and combination therapy (e.g. as an additional therapeutic agent). In general, monotherapy comprises the use of compounds of Formula I, or their pharmaceutically acceptable salts, while combination therapy comprises compounds of Formula I, or their pharmaceutically acceptable salts in combination with an additional therapeutic agent, including, for example, an inhibitor of an amino acid transporter, inclusive of a SLC6A19 inhibitor.

The disclosure contemplates, in some embodiments, that administration of an additional therapeutic agent, such as an inhibitor of an amino acid transporter, inclusive of a SLC6A19 inhibitor, reduces elevated levels of branched-chain amino acids, as compared to treatment without administration of an inhibitor of an amino acid transporter, inclusive of a SLC6A19 inhibitor. In various embodiments, administration of an inhibitor of an amino acid transporter, inclusive of a SLC6A19 inhibitor (e.g., separately or in combination with a BCAT2 inhibitor compound described herein) can reduce hyperaminoacidemia caused by BCAT2 inhibition per the methods of the present disclosure.

As used herein, organic acidemias are characterized as a group of inheritable metabolic disorders which disrupt normal amino acid metabolism, particularly branched-chain amino acids, causing a buildup of acids which are usually not present.

In some embodiments, the organic acidemia is selected from the group consisting of all forms of methylmalonic acidemia (MMA), all forms of propionic acidemia (PA), isovaleric acidemia, glutaric aciduria type 1 (GA1), beta-ketothiolase deficiency (BKT), 3-methylcrotonyl-CoA carboxylase deficiency (3-MCC), 3-hydroxy-3-methylglutaryl-CoA lyase deficiency (HMG), 3-Methylglutaconic acidemia or 3-Methylglutaconyl-CoA Hydratase Deficiency (MGA), D-2 Hydroxyglutaric Aciduria (D2-HGA), Isobutyryl-CoA Dehydrogenase Deficiency 3-Hydroxyisobutyric aciduria (ICBD), L-2-Hydroxy-glutaricaciduria (L2HGA), Malonyl-CoA Decarboxylase Deficiency aka Malonic Acidemia (MA), Multiple carboxylase deficiency (MCD, holocarboxylase synthetase), and 3-Hydroxyisobutyryl-CoA Hydrolase Deficiency (HIBCH).

In various embodiments, the organic acidemia is methylmalonic acidemia or propionic acidemia.

Mutations to one or more components of the BCAA catabolic pathway can cause one or more organic acidemias. For example, various enzymes or components acting throughout the BCAA pathway can become mutated, resulting in manifestation of an organic acidemia. In some embodiments, the BCAA metabolic pathway for leucine includes enzymes or components that can become mutated, including one or more of branched chain α-ketoacid dehydrogenase (BCKDH), isovaleryl CoA dehydrogenase (IVD), 3-methylcrotonyl-CoA carboxylase (3MCC), 3-methylglutaconic-CoA hydratase (3MGA), 3-hydroxy-3-methylglutaryl-CoA lyase (HMGL), acetyl-CoA carboxylase (AC), and malonyl-CoA decarboxylase (MA). In some embodiments, the BCAA metabolic pathway for isoleucine includes enzymes or components that can become mutated, including one or more of BCKDH, methylbutyryl CoA dehydrogenase (SBCAD), Hydratase, 2-methyl-3-hydroxyisobutyric dehydrogenase (MHBD), acetoacetyl-CoA thiolase (T2), AC, MA, propionyl-CoA carboxylase (PCC), methylmalonyl-CoA mutase (MUT), and succinyl-CoA ligase (SUCLA). In further embodiments, the BCAA metabolic pathway for valine includes enzymes or components that can become mutated, including one or more of BCKDH, isobutyryl-CoA dehydrogenase (IBDH), Hydratase, 3-hydroxyisobutyryl-CoA deacylase (hydrolase)(HIBDA), 3-hydroxyisobutyrate dehydrogenase (HIBDH), methylmalonic semialdehyde dehydrogenase (MMSDH), PCC, MUT, and SUCLA.

Disorders of the branched chain amino acid metabolic pathway are further described in Manoli and Venditti, Disorders of branched chain amino acid metabolism, Translational Science of Rare Diseases 1 (2016) 91-110 and Schiff et al., J. M. Saudubray et al. (Eds.), Branched-chain Organic Acidurias Inborn Metabolic Diseases, Springer Verlag Berlin (279-294) 2016, both of which are hereby incorporated by reference in their entireties.

In some embodiments, the organic acidemia is selected from one or more of Maple syrup urine disease: Type Ia; Maple syrup urine disease: Type Ib; Maple syrup urine disease: Type II; Maple syrup urine disease: mild variant; Isovaleric acidemia; 3-Methylcrotonyl-CoA carboxylase deficiency; 3-Methylcrotonyl-CoA carboxylase 2 deficiency; 3-Methylglutaconic aciduria type I; 3-Methylglutaconic aciduria type II: Barth syndrome; 3-Methylglutaconic aciduria type III: Costeff Syndrome; 3-Methylglutaconic aciduria type IV: "unclassified"; 3-Methylglutaconic aciduria type V; 3-Methylglutaconic aciduria type VI: deafness, encephalopathy, Leigh-like syndrome; 3-Methylglutaconic aciduria type VII: cataracts, neurological involvement and neutropenia; 3-Hydroxy-3-methylglutaryl-CoA lyase deficiency; 2-Methyl-3-hydroxybutyryl-CoA Dehydrogenase Deficiency; Mitochondrial short-chain enoyl-CoA hydratase-1 deficiency; Methylbutyryl-CoA dehydrogenase deficiency; Mitochondrial acetoacetyl-CoA thiolase deficiency; Isobutyryl-CoA dehydrogenase deficiency; 3-Hydroxyisobutyryl-CoA deacylase deficiency; 3-Hydroxyisobutyric aciduria; Methylmalonic semialdehyde dehydrogenase deficiency; Propionic acidemia, Methylmalonic acidemia: Mut subtype; Methylmalonic acidemia: Cobalamin A; Methylmalonic acidemia: Cobalamin B; and Methylmalonic acidemia: Cobalamin D.

In various embodiments, methods of the present disclosure contemplate reducing levels of toxic substrate metabolites that result from the BCAA metabolic pathway. Toxic substrate metabolites can include, but are not limited to, propionic acid, 2-methylcitric acid, 3-hydroxypropionic acid, propionyl-CoA, methylmalonic acid, methylmalonyl-CoA and isovaleric acid.

Methymalonic Acidemia

Methylmalonic acidemia ("MMA") is an autosomal recessive disorder caused by defects in the mitochondrial localized enzyme methylmalonyl-CoA mutase (MUT). The estimated incidence of MMA is 1 in 25,000-48,000. MUT is an enzyme that catalyzes the conversion of L-methylmalonyl-CoA to succinyl-CoA. This reaction is one of several enzymatic reactions required to metabolize branch chain amino acids, odd chain fatty acids, cholesterol, and propionate produced by the gut flora. MUT deficiency, the most common cause of isolated MMA, is characterized by the accumulation of methylmalonic acid and other toxic metabolites. MMA is associated with metabolic instability, seizures, pancreatitis, strokes, and kidney failure, and it can be lethal, even when patients are being properly managed, underscoring the need for new therapies for this disease. Current MMA treatments include, but are not limited to, dietary restrictions, liver transplantation, combined liver and kidney transplantation, and liver-directed gene therapy.

The MUT enzyme requires adenosylcobalamin (Ado-Cbl) as a coenzyme. Therefore, methylmalonic acid metabolism is inevitably linked to vitamin B12 (cobalamin), its adequate intake and correct uptake, transport, and intracellular metabolism. The cblA, cblB, and variant 2 form of cblD complementation groups are linked to processes unique to Ado-Cbl synthesis. The cblC, cblD, cblF, cblJ complementation groups are associated with defective methyl-cobalamin synthesis, as well. Combined MMA and homocystinuria, cobalamin C (cblC) type, is the most common disorder of cobalamin metabolism. CblC typically presents in the neonatal period with neurological deterioration, failure to thrive, cytopenias, and multisystem pathology including renal and hepatic dysfunction.

Propionic Acidemia

The related disorder, propionic acidemia ("PA"), is an autosomal recessive disorder caused by defects in propionyl CoA carboxylase ("PCC") of either the propionyl CoA carboxylase alpha (PCCA) or beta subunits (PCCB). PCC is inactive in affected individuals with either PCCA or PCCB deficiency. Patients with PA cannot metabolize branch chain amino acids, odd chain fatty acids, cholesterol, and propionate produced by the gut flora. The condition leads to an abnormal buildup of particular acids known as organic acids such as propionic acid, 2-methylcitric acid, and 3-hydroxypropionic acid. As a result, a substance called propionyl-CoA and other potentially harmful compounds can accumulate to toxic levels in the body. This accumulation damages the brain, nervous system and heart, causing the serious health problems associated with PA. PA is associated with metabolic instability, seizures, pancreatitis, strokes, and a propensity to develop hyperammonemia. PA treatments include, but are not limited to, dietary restrictions, liver transplantation, and liver-directed gene therapy. Like MMA, PA can be lethal, even when patients are being properly managed.

Maple Syrup Urine Disease

Maple syrup urine disease ("MSUD"), is a rare genetic disorder characterized by deficiency of certain enzymes (e.g., branched-chain α-ketoacid dehydrogenase complex) required to break down (metabolize) the three branched-chain amino acids. In the classic, severe form of MSUD, the plasma concentrations of the BCAAs begin to rise within a few hours of birth. If untreated, symptoms begin to emerge, often within the first 24-48 hours of life. The classic form of MSUD is associated with lethargy and/or irritability, progressive encephalopathy, opisthotonus, and coma. Intermediate MSUD is associated with metabolic encephalopathy with stress, anorexia, and growth failure. Intermittent MSUD is associated with normal early development, episodic crises associated with stress. Type III, E3 deficient MSUD is associated with Leigh-type encephalopathy, lactic acidosis, and is often lethal.

Compounds of the Disclosure

In various aspects, the present disclosure provides for the identification and use of a candidate compound. In embodiments providing for identification and use of a candidate compound, the candidate compound may be a chemical, molecule, compound, biologic (e.g. an antibody or peptide), drug, pro-drug, cellular therapy, low molecular weight synthetic compound, or a small molecule drug. In some embodiments, the candidate compound is selected from a library of compounds known in the art. In some embodiments, the candidate compound is useful for treating an organic acidemia and/or preventing an organic acidemia.

In some embodiments, provided herein is a compound of Formula (I) or a pharmaceutically acceptable salt thereof:

(I)

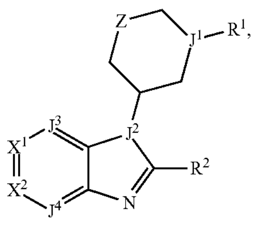

wherein

Z may be $CH_2$, $CF_2$, O, or a bond;

each of $J^1$, $J^2$, $J^3$, and $J^4$ may independently be CH or N;

$X^1$ may be N or $CR^{5A}$;

$X^2$ may be N or $CR^{5B}$;

$R^1$ may be $C_1$-$C_6$ alkyl, $—NR^3S(O)R^4$, $—NR^3SO_2R^4$, $—NR^3C(O)R^4$, $—C(O)(CH_2)_mNR^3R^4$, $C_6$-$C_{10}$ aryl, 5-10-membered heteroaryl, or (5-10-membered heteroaryl)-$C_1$-$C_6$ alkyl;

$R^2$ may be $—NR^6R^7$, $C_1$-$C_6$ alkyl, $C_3$-$C_8$ cycloalkyl, $C_6$-$C_{10}$ aryl, or 5-10 membered heteroaryl, wherein each aryl or heteroaryl is optionally substituted with one, two, or three substituents $R^{2'}$ independently selected from halo, —CN, $—NO_2$, $C_1$-$C_6$ alkyl, $C_1$-$C_6$ alkoxy, halo$C_1$-$C_6$ alkyl, halo$C_1$-$C_6$ alkoxy, $C_2$-$C_6$ alkenyl, $C_2$-$C_6$ alkynyl, $—C(O)NR^6R^7$, $—C(O)R^6$, $—NR^6R^7$, $—NR^6C(O)R^7$, —OH, —S-(halo$C_1$-$C_6$ alkyl), $C_6$-$C_{10}$ aryl, and 5-10 membered heterocyclyl; or two $R^{2'}$ substituents together with the atoms to which they are attached form a five-membered heterocyclyl or $C_3$-$C_8$ cycloalkyl, each optionally substituted with halo;

$R^3$ may be H or $C_1$-$C_6$ alkyl;

$R^4$ may be H, $C_1$-$C_6$ alkyl, $C_2$-$C_6$ alkenyl, $C_6$-$C_{10}$ aryl, or 5-10 membered heteroaryl, wherein each aryl or heteroaryl is optionally substituted with one, two, or three substituents $R^4$ independently selected from halo, —CN, $—NO_2$, $C_1$-$C_6$ alkyl, halo$C_1$-$C_6$ alkyl, $C_1$-$C_6$ alkoxy, $C_2$-$C_6$ alkenyl, $C_3$-$C_8$ cycloalkyl, $C_6$-$C_{10}$ aryl, $—(CH_2)_qNR^8C(O)R^9$, $—C(O)NR^8R^9$, $—C(O)OR^9$, $—C(O)R^9$, and 5-10 membered heterocyclyl;

$R^{5A}$ may be H, halo, —CN, $C_1$-$C_6$ alkyl, halo$C_1$-$C_6$ alkyl, $C_1$-$C_6$ alkoxy, $—(CH_2)_rOH$, $—C(O)NR^8R^9$, $—NR^8COR^9$, 5-10 membered heteroaryl, $—C(O)R^8$, or $—C(O)OR^8$;

$R^{5B}$ may be H, halo, —CN, $C_1$-$C_6$ alkyl, halo$C_1$-$C_6$ alkyl, $C_1$-$C_6$ alkoxy, $—(CH_2)_rOH$, $—C(O)NR^8R^9$, $—NR^8COR^9$, 5-10 membered heteroaryl, $—C(O)R^8$, or $—C(O)OR^8$;

or $R^{5A}$ and $R^{5B}$ together with the atoms to which they are attached may form a six-membered heterocyclyl ring optionally substituted with oxo;

$R^6$ and $R^7$ may independently be H, $C_1$-$C_6$ alkyl, or $C_3$-$C_8$ cycloalkyl;

each $R^8$ may independently be H, $C_1$-$C_6$ alkyl, or $C_3$-$C_8$ cycloalkyl;

each $R^9$ may independently be H, $C_1$-$C_6$ alkyl, $C_2$-$C_6$ alkenyl, or $C_3$-$C_8$ cycloalkyl;

m may be 0 or 1;

q may be 0 or 1; and r may 0 or 1.

In some embodiments, $R^{5A}$ is not be hydrogen.

In some embodiments, $R^{5B}$ is not be hydrogen or $—C(O)NR^8R^9$.

In some embodiments, $R^2$ is not be unsubstituted aryl or unsubstituted heteroaryl. In some embodiments, $R^2$ is not be aryl substituted with one $—S—C_1$-$C_6$ alkyl. In some embodiments, $R^2$ is not be 5-10 membered heteroaryl substituted with one $C_1$-$C_6$ alkyl.

In some embodiments, the compound of Formula (I) is not selected from the group consisting of:

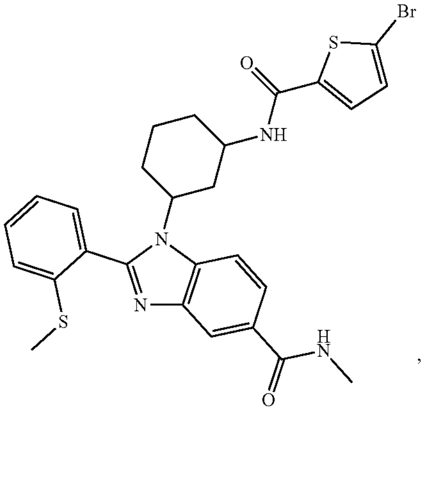

,

-continued
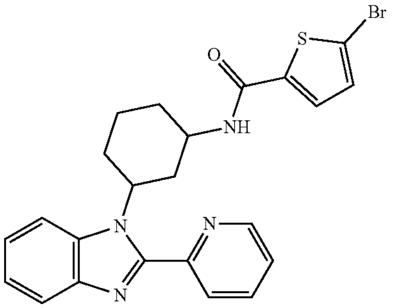
,
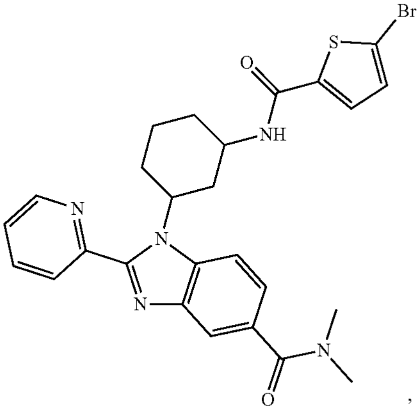
,
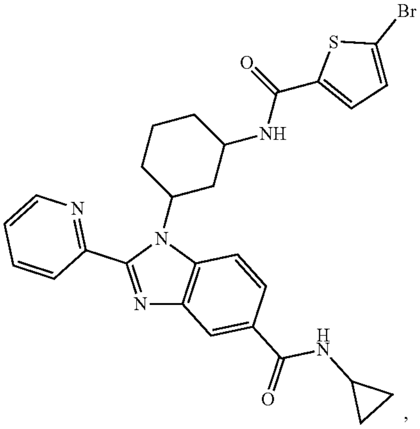
,
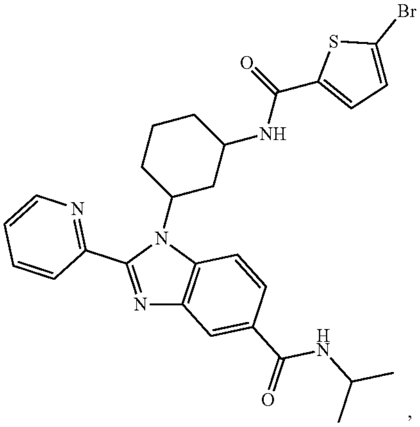
,
-continued
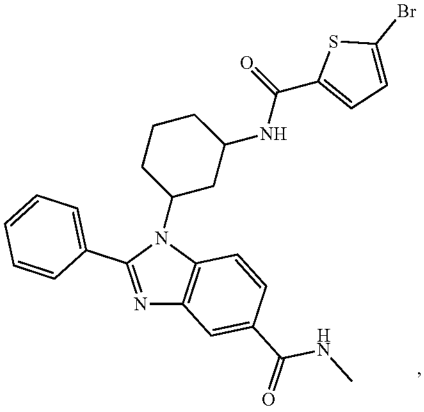
,
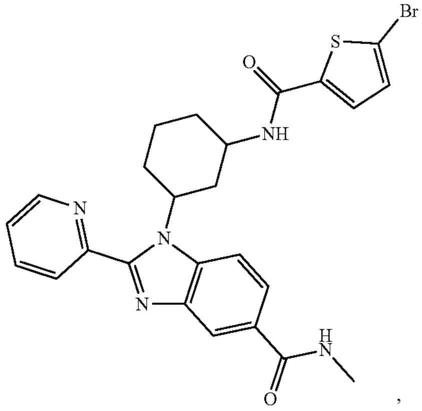
,
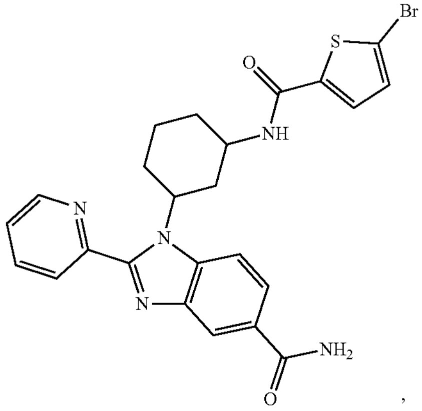
,
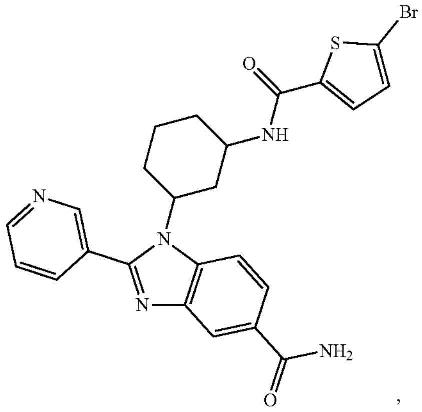
, -continued
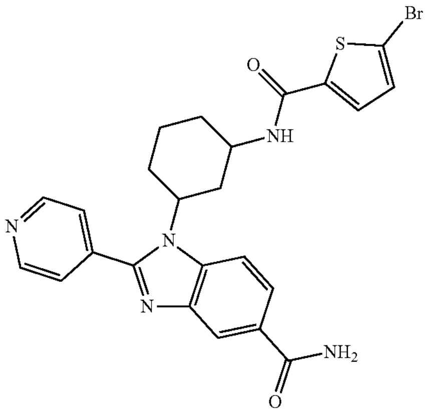
,
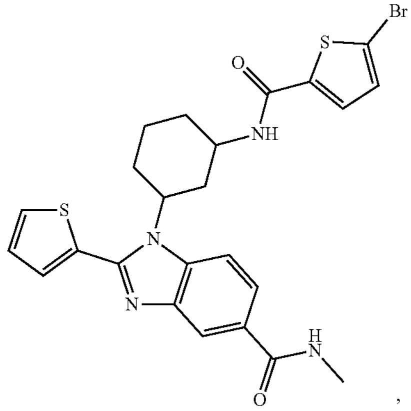
,
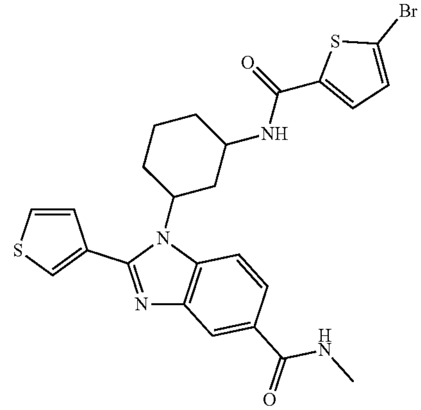
,
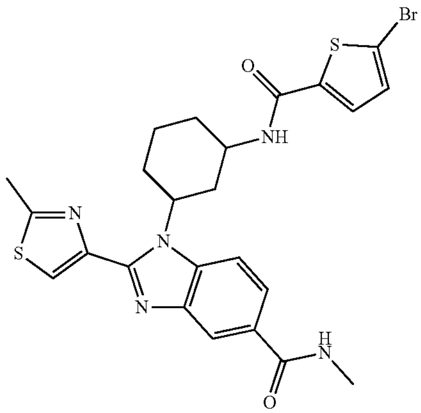
,
-continued
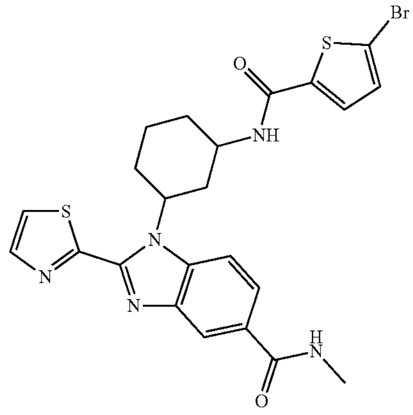
,
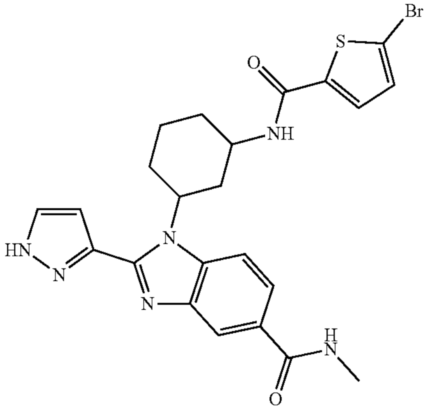
,
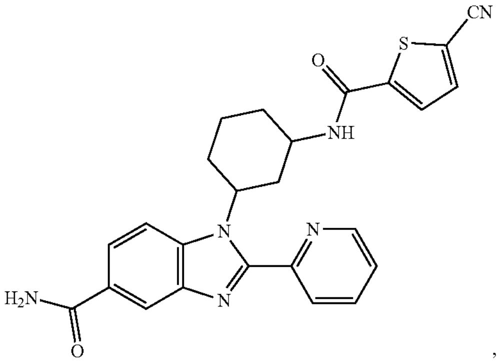
,
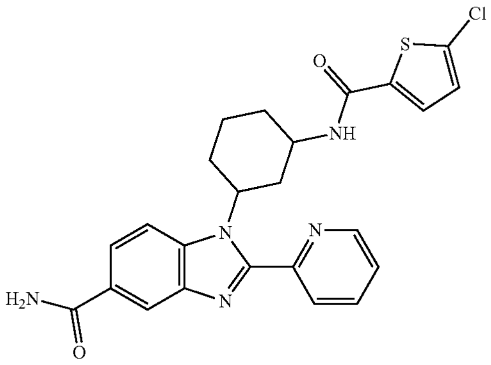
, -continued

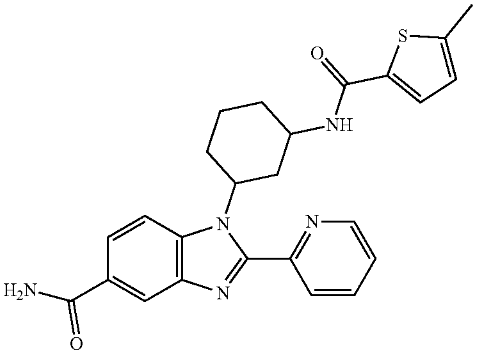

,

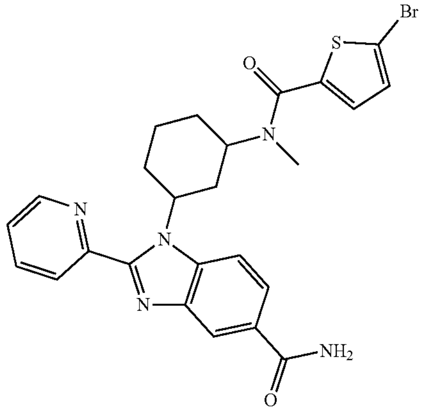

,

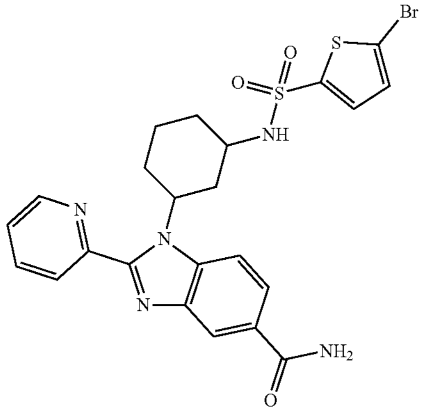

,

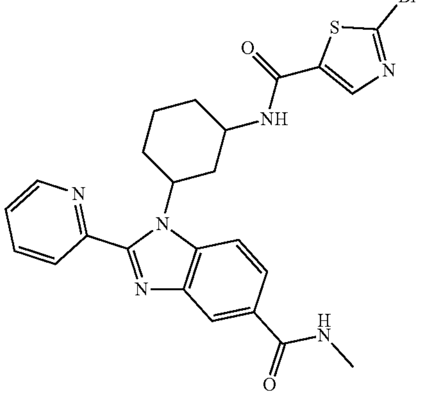

,

-continued

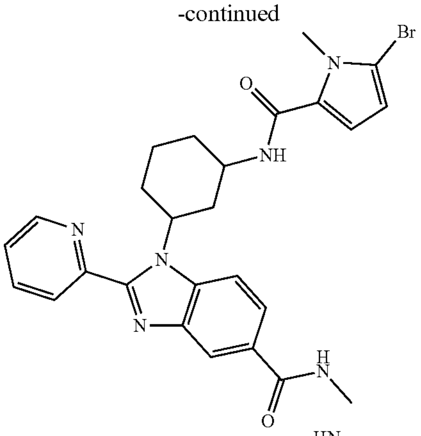

,

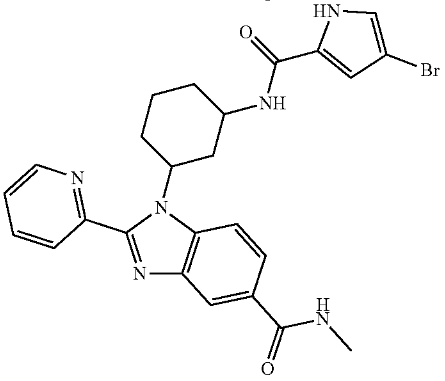

,

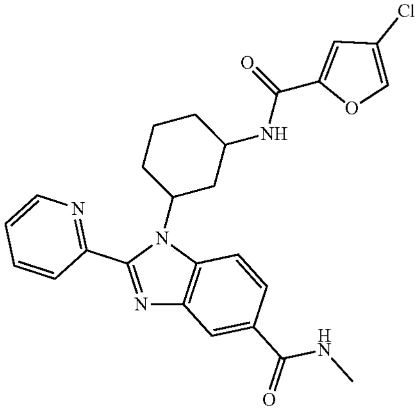

, and pharmaceutically acceptable salts and stereoisomers thereof.

In some embodiments, Z may be $CH_2$. In other embodiments, Z may be $CF_2$. In yet other embodiments, Z may be O. In still yet other embodiments, Z may be a bond.

In some embodiments, $J^1$ may be CH. In other embodiments, $J^1$ may be N.

In some embodiments, $J^2$ may be CH. In other embodiments, $J^2$ may be N.

In some embodiments, $J^3$ is CH. In other embodiments, $J^3$ may be N.

In some embodiments, $J^4$ may be CH. In other embodiments, $J^4$ may be N.

In some embodiments, $X^1$ may be N. In other embodiments, $X^1$ may be $CR^{5A}$.

In some embodiments, $X^2$ may be N. In other embodiments, $X^2$ may be $CR^{5B}$.

In some embodiments, $J^2$ may be N and $X^1$ may be N. In other embodiments, $J^2$ may be N and $J^3$ may be N. In yet other embodiments, $J^2$ may be N and $J^4$ may be N. In still yet other embodiments, $J^2$ may be N and $X^2$ may be N. In some embodiments, each of $J^2$, $J^3$, and $J^4$ may be CH; $X^1$ may be $CR^{5A}$; and $X^2$ may be $CR^{5B}$.

In some embodiments, $R^1$ may be $NR^3C(O)R^4$. In other embodiments, $R^1$ may be —$C(O)(CH_2)_mNR^3R^4$.

In some embodiments, $R^3$ may be hydrogen. In other embodiments, $R^1$ may be $C_{1-6}$ alkyl.

In some embodiments, $R^4$ may be $C_{6-10}$ aryl or 5-10 membered heteroaryl, each optionally substituted with one, two, or three substituents $R^4$. In some embodiments, $R^4$ may be selected from the phenyl, thiophene, oxazole, isoxazole, thiazole, furan, and pyrrole, each of which may be optionally substituted with one, two, or three substituents $R^{4'}$, wherein each $R^{4'}$ may be independently selected from the group consisting of —F, —Cl, —Br, —CN, —$NO_2$, —$CF_3$, —$CH_3$, —$CH(CH_3)_2$, —$C(O)CH_3$, —$C(O)OCH_3$, phenyl, cyclopropyl, and morpholinyl.

In some embodiments, m may be 0. In other embodiments, m may be 1.

In some embodiments, $R^2$ may be $C_{6-10}$ aryl or 5-10 membered heteroaryl, each optionally substituted with one, two, or three substituents $R^{2'}$. In some embodiments, $R^2$ may be selected from the group consisting of phenyl, pyridine, pyrimidine, pyridazine, pyrazine, imidazole, or thiophene, each of which may be optionally substituted with one, two, or three substituents $R^{2'}$, wherein each $R^{2'}$ may be independently selected from the group consisting of —F, —Cl, —Br, —CN, $NO_2$, —$CH_3$, —$CF_2H$, —CH≡CH, —C(O)H, —$CONH_2$, —$C(O)NHCH_3$, —OH, —$OCH_3$, —$OCF_3$, —$SCF_3$, —$NH_2$, —$NHC(O)CH_3$, and morpholine.

In some embodiments, $X^2$ may be $CR^{5B}$ and $R^{5B}$ may be —$C(O)NR^8R^9$. In other embodiments, $X^2$ may be $CR^{5B}$ and $R^{5B}$ may be halo, —CN, $C_1$-$C_6$ alkyl, halo$C_1$-$C_6$ alkyl, $C_1$-$C_6$ alkoxy, —$(CH_2)_rOH$, —$NR^8COR^9$, 5-10 membered heteroaryl, —$C(O)R^8$, or —$C(O)OR^8$. In yet other embodiments, $X^2$ may be $CR^{5B}$ and $R^{5B}$ may be —$NR^BCOR^9$. In some embodiments, $X^2$ may be $CR^{5B}$ and $R^{5B}$ may be —$C(O)OR^8$. In some embodiments, $X^2$ may be $CR^{5B}$ and $R^{5B}$ may be —CF %, —$COCH_3$, —$CH_2OH$, —CN, or tetrazole.

In some embodiments, $R^8$ may be hydrogen. In other embodiments, $R^8$ may be —$C_{1-6}$ alkyl.

In some embodiments, $R^9$ may be hydrogen. In other embodiments. $R^9$ may be —$C_{1-6}$ alkyl.

In some embodiments, provided herein is a compound of Formula (I) having the structure of Formula (Ia) or a pharmaceutically acceptable salt thereof:

(Ia)

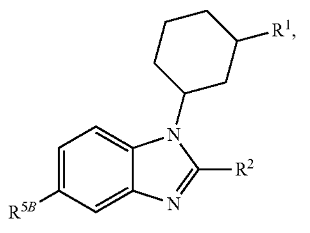

wherein $R^1$ may be $C_1$-$C_6$ alkyl, —$NR^3S(O)R^4$, —$NR^3SO_2R^4$, —$NR^3C(O)R^4$, —$C(O)(CH_2)_mNR^3R^4$, $C_6$-$C_{10}$ aryl, or 5-10-membered heteroaryl;

$R^2$ may be $C_1$-$C_6$ alkyl, $C_6$-$C_{10}$ aryl, or 5-10-membered heteroaryl;

$R^4$ may be $C_6$-$C_{10}$ aryl or 5-10-membered heteroaryl;

$R^{5B}$ may be —$C(O)NR^8R^9$; and $R^8$ and $R^9$ are independently H, $C_1$-$C_6$ alkyl, or $C_3$-$C_8$ cycloalkyl.

In some embodiments, provided herein is a compound of Formula (Ia) or a pharmaceutically acceptable salt thereof, wherein:

$R^1$ may be —$NR^3SO_2R^4$ or —$NR^3C(O)R^4$;

$R^1$ may be aryl or 5-10-membered heteroaryl;

$R^3$ may be H or $C_1$-$C_6$ alkyl;

$R^4$ may be $C_6$-$C_{10}$ aryl or 5-10-membered heteroaryl;

$R^{5B}$ may be —$C(O)NR^8R^9$; and $R^8$ and $R^9$ may independently be H or $C_1$-$C_6$ alkyl.

In some embodiments, provided herein is a compound of Formula (Ia) or a pharmaceutically acceptable salt thereof, wherein:

$R^1$ is —$NR_3C(O)R_4$;

$R^2$ is $C_6$-$C_{10}$ aryl or 5-10-membered heteroaryl;

$R^3$ is H or methyl;

$R^4$ is $C_6$-$C_{10}$ aryl or 5-10-membered heteroaryl;

$R^{5B}$ is —$C(O)NR^8R^9$; and $R^8$ and $R^9$ are independently H or $C_1$-$C_6$ alkyl.

In some embodiments, provided herein is a compound of Formula (Ia) or a pharmaceutically acceptable salt thereof, wherein:

$R_1$ is —$NR_3C(O)R_4$;

$R^2$ is $C_6$-$C_{10}$ aryl or 5-10-membered heteroaryl;

$R^3$ is H or methyl;

$R^4$ is $C_6$-$C_{10}$ aryl or 5-10-membered heteroaryl;

$R^5$ is —$C(O)NR^8R^9$; and $R^8$ and $R^9$ are independently H or methyl.

In some embodiments, the compound of the present disclosure may be 1-(3-(5-bromothiophene-2-carboxamido)cyclohexyl)-N-methyl-2-(2-(methylthio)phenyl)-1H-benzo[d]imidazole-5-carboxamide, 1-(3-(5-bromothiophene-2-carboxamido)cyclohexyl)-N-methyl-2-phenyl-1H-benzo[d]imidazole-5-carboxamide, 1-(3-(5-bromothiophene-2-carboxamido)cyclohexyl)-N-methyl-2-(pyridin-2-yl)-1H-benzo[d]imidazole-5-carboxamide, 1-(3-(5-bromothiophene-2-carboxamido)cyclohexyl)-2-(pyridin-2-yl)-1H-benzo[d]imidazole-5-carboxamide, 1-(3-(5-bromothiophene-2-carboxamido)cyclohexyl)-2-(pyridin-3-yl)-1H-benzo[d]imidazole-5-carboxamide, 1-(3-(5-bromothiophene-2-carboxamido)cyclohexyl)-2-(pyridin-4-yl)-1H-benzo[d]imidazole-5-carboxamide, 1-(3-(5-bromothiophene-2-carboxamido)cyclohexyl)-N-methyl-2-(thiophen-2-yl)-1H-benzo[d]imidazole-5-carboxamide, 1-(3-(5-bromothiophene-2-carboxamido)cyclohexyl)-N-methyl-2-(thiophen-3-yl)-1H-benzo[d]imidazole-5-carboxamide, 1-(3-(5-bromothiophene-2-carboxamido)cyclohexyl)-N-methyl-2-(2-methylthiazol-4-yl)-1H-benzo[d]imidazole-5-carboxamide, 1-(3-(5-bromothiophene-2-carboxamido)cyclohexyl)-N-methyl-2-(thiazol-2-yl)-1H-benzo[d]imidazole-5-carboxamide, 1-(3-(5-bromothiophene-2-carboxamido)cyclohexyl)-N-methyl-2-(1H-pyrazol-3-yl)-1H-benzo[d]imidazole-5-carboxamide, 1-(3-(5-cyanothiophene-2-carboxamido)cyclohexyl)-2-(pyridin-2-yl)-1H-benzo[d]imidazole-5-carboxamide, 1-(3-(5-chlorothiophene-2-carboxamido)cyclohexyl)-2-(pyridin-2-yl)-1H-benzo[d]imidazole-5-carboxamide, 1-(3-(5-methylthiophene-2-carboxamido)cyclohexyl)-2-(pyridin-2-yl)-1H-benzo[d]imidazole-5-carboxamide, 1-(3-(5-bromo-N-methylthiophene-2-carboxamido)cyclohexyl)-2-(pyridin-2-yl)-1H-benzo[d]imidazole-5-carboxamide, 1-(3-((5-bromothiophene)-2-sulfonamido)cyclohexyl)-2-(pyridin-2-yl)-1H-benzo[d]imidazole-5-carboxamide, 2-bromo-N-(3-(5-(methylcarbamoyl)-2-(pyridin-2-yl)-1H-benzo[d]imidazol-1-yl)cyclohexyl)thiazole-5-carboxamide, 1-(3-(5-bromo-1-methyl-1H-pyrrole-2-carboxamido)cyclohexyl)-N-methyl-2-(pyridin-2-yl)-1H-benzo[d]imidazole-5-carboxamide, 1-(3-(4-bromo-1H-pyrrole-2-carboxamido)cyclohexyl)-N-methyl-2-(pyridin-2-yl)-1H-benzo[d]imidazole-5-carboxamide, 3-chloro-N-(3-(5-(methylcarbamoyl)-2-(pyridin-2-yl)-1H-benzo[d]imidazol-1-yl)cyclohexyl)isoxazole-5-carboxamide, 5-bromo-N-(3-(2-(pyridin-2-yl)-1H-benzo[d]imidazol-1-yl)cyclohexyl)thiophene-2-carboxamide, 1-(3-(5-bromothiophene-2-carboxamido)cyclohexyl)-N,N-dimethyl-2-(pyridin-2-yl)-1H-benzo[d]imidazole-5-carboxamide, 1-(3-(5-bromothiophene-2-carboxamido)cyclohexyl)-N-cyclopropyl-2-(pyridin-2-yl)-1H-benzo[d]imidazole-5-carboxamide, and 1-(3-(5-bromothiophene-2-carboxamido)cyclohexyl)-N-isopropyl-2-(pyridin-2-yl)-1H-benzo[d]imidazole-5-carboxamide; or a pharmaceutical acceptable salt thereof.

In further embodiments, provided herein may be a compound of Formula (I) having the structure of Formula (II):

(II)

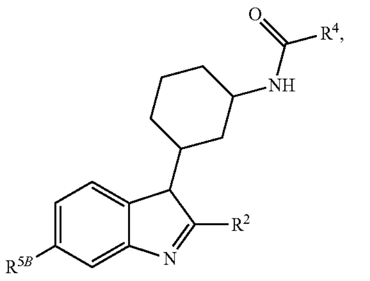

or a pharmaceutically acceptable salt thereof, wherein $R^2$ may be $C_6$-$C_{10}$ aryl or 5-10 membered heteroaryl, wherein each aryl or heteroaryl may be optionally substituted with one, two, or three substituents $R^{2'}$ independently selected from halo, —CN, —$NO_2$, $C_1$-$C_6$ alkyl, $C_1$-$C_6$ alkoxy, halo$C_1$-$C_6$ alkyl, halo$C_1$-$C_6$ alkoxy, $C_2$-$C_6$ alkenyl, $C_2$-$C_6$ alkynyl, —C(O)$NR^6R^7$, —C(O)$R^6$, —$NR^6R^7$, —$NR^6$C(O)$R^7$, —OH, —S-(halo$C_1$-$C_6$ alkyl), $C_6$-$C_{10}$ aryl, and 5-10 membered heterocyclyl; or two $R^{2'}$ substituents together with the atoms to which they are attached may form a five-membered heterocyclyl or $C_3$-$C_8$ cycloalkyl, each optionally substituted with halo;

$R^4$ may be 5-10 membered heteroaryl, optionally substituted with one, two, or three substituents $R^{4'}$ independently selected from halo, —CN, —$NO_2$, $C_1$-$C_6$ alkyl, halo$C_1$-$C_6$ alkyl, $C_1$-$C_6$ alkoxy, $C_2$-$C_6$ alkenyl, $C_3$-$C_8$ cycloalkyl, $C_6$-$C_{10}$ aryl, —$(CH_2)_q NR^8$C(O)$R^9$, —C(O)$NR^8R^9$, —C(O)$OR^9$, —C(O)$R^9$, and 5-10 membered heterocyclyl; and $R^{5B}$ may be —C(O)$NR^8R^9$.

In some embodiments, $R^2$ may be phenyl optionally substituted with one, two, or three substituents $R^{2'}$ independently selected from halo, —CN, —$NO_2$, and $C_1$-$C_6$ alkyl. In other embodiments, $R^2$ is 5-10 membered heteroaryl optionally substituted with one, two, or three substituents $R^{2'}$ independently selected from halo, —CN, —$NO_2$, and $C_1$-$C_6$ alkyl.

In some embodiments, $R^4$ may be thiophene optionally substituted with halo or phenyl.

In further embodiments, provided herein may be a compound of Formula (I) having the structure of Formula (III):

(III)

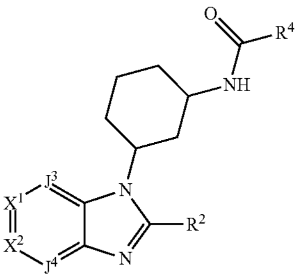

or a pharmaceutically acceptable salt thereof wherein each $J^3$ and $J^4$ is independently CH or N;

$X^1$ is N or $CR^{5A}$;

$X^2$ is N or $CR^{5B}$;

wherein one, two, three, or four of $J^3$, $J^4$, $X^1$, and $X^2$ is N;

$R^2$ is $C_6$-$C_{10}$ aryl or 5-10 membered heteroaryl, wherein each aryl or heteroaryl is optionally substituted with one, two, or three substituents $R^{2'}$ independently selected from halo, —CN, —$NO_2$, $C_1$-$C_6$ alkyl, $C_1$-$C_6$ alkoxy, halo$C_1$-$C_6$ alkyl, halo$C_1$-$C_6$ alkoxy, $C_2$-$C_6$ alkenyl, $C_2$-$C_6$ alkynyl, —C(O)$NR^6R^7$, —C(O)$R^6$, —$NR^6R^7$, —$NR^6$C(O)$R^7$, —OH, —S-(halo$C_1$-$C_6$ alkyl), $C_6$-$C_{10}$ aryl, and 5-10 membered heterocyclyl; or two $R^{2'}$ substituents together with the atoms to which they are attached form a five-membered heterocyclyl or $C_3$-$C_8$ cycloalkyl, each optionally substituted with halo; and $R^4$ is H, $C_1$-$C_6$ alkyl, $C_2$-$C_6$ alkenyl, $C_6$-$C_{10}$ aryl, or 5-10 membered heteroaryl, wherein each aryl or heteroaryl is optionally substituted with one, two, or three substituents $R^{4'}$ independently selected from halo, —CN, —$NO_2$, $C_1$-$C_6$ alkyl, halo$C_1$-$C_6$ alkyl, $C_1$-$C_6$ alkoxy, $C_2$-$C_6$ alkenyl, $C_3$-$C_8$ cycloalkyl, $C_6$-$C_{10}$ aryl, —$(CH_2)_q$ $NR^8$C(O)$R^9$, —C(O)$NR^8R^9$, —C(O)$OR^9$, —C(O)$R^9$, and 5-10 membered heterocyclyl.

In some embodiments, $R^2$ may be phenyl optionally substituted with one, two, or three substituents $R^{2'}$ independently selected from halo, —CN, —$NO_2$, and $C_1$-$C_6$ alkyl. In other embodiments, $R^2$ is 5-10 membered heteroaryl optionally substituted with one, two, or three substituents $R^{2'}$ independently selected from halo, —CN, —$NO_2$, and $C_1$-$C_6$ alkyl.

In some embodiments, R; may be thiophene optionally substituted with halo or phenyl.

In some embodiments, $X^2$ may be $CR^{5B}$; $R^{5B}$ may be selected from hydrogen, -halo, —C(O)$NR^8R^9$, —$NR^8COR^9$, or —C(O)$OR^B$; and $R^8$ and $R^9$ may each independently be H or $C_1$-$C_6$ alkyl.

In further embodiments, provided herein may be a compound of formula (I) having the structure of Formula (IV):

(IV)

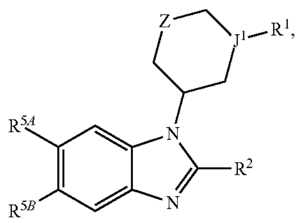

or a pharmaceutically acceptable salt thereof, wherein $R^1$ is $C_1$-$C_6$ alkyl, —$NR^3C(O)R^4$, —$C(O)(CH_2)_mNR^3R^4$, $C_6$-$C_{10}$ aryl, 5-10-membered heteroaryl, or (5-10-membered heteroaryl)-$C_1$-$C_6$ alkyl; and $R^2$ is —$NR^6R^7$, $C_1$-$C_6$ alkyl, $C_3$-$C_8$ cycloalkyl, $C_6$-$C_{10}$ aryl, or 5-10 membered heteroaryl, wherein each aryl or heteroaryl is substituted with one, two, or three substituents $R^{2'}$ independently selected from halo, —CN, —$NO_2$, $C_1$-$C_6$ alkoxy, halo$C_1$-$C_6$ alkyl, halo$C_1$-$C_6$ alkoxy, $C_2$-$C_6$ alkenyl, $C_2$-$C_6$ alkynyl, —C(O)$NR^6R^7$, —$C(O)R^6$, —$NR^6R^7$, —$NR^6C(O)R^7$, —OH, $C_6$-$C_{10}$ aryl, and 5-10 membered heterocyclyl; or two $R^{2'}$ substituents together with the atoms to which they are attached form a five-membered heterocyclyl or $C_3$-$C_8$ cycloalkyl, each optionally substituted with halo.

In yet further embodiments, provided herein may be a compound of Formula (I) having the structure of Formula (V):

(V)

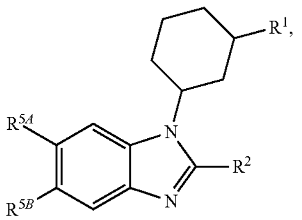

or a pharmaceutically acceptable salt thereof wherein $R^{5A}$ is halo, —CN, $C_1$-$C_6$ alkyl, halo$C_1$-$C_6$ alkyl, $C_1$-$C_6$ alkoxy, —$(CH_2)_rOH$, —$C(O)NR^8R^9$, —$NR^8COR^9$, 5-10 membered heteroaryl, —$C(O)R^8$, or —$C(O)OR^8$;

$R^{5B}$ is H, halo, —CN, $C_1$-$C_6$ alkyl, halo$C_1$-$C_6$ alkyl, $C_1$-$C_6$ alkoxy, —$(CH_2)_rOH$, —$C(O)NR^8R^9$, —$NR^8COR^9$, 5-10 membered heteroaryl, —$C(O)R^8$, or —$C(O)OR^8$; and or $R^{5A}$ and $R^{5B}$ together with the atoms to which they are attached form a six-membered heterocyclyl ring optionally substituted with oxo.

In still yet further embodiments, provided herein may be a compound of Formula (I) having the structure of Formula (VI):

(VI)

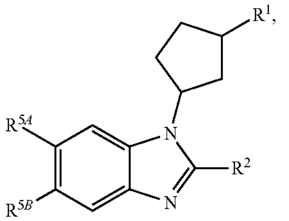

or a pharmaceutically acceptable salt thereof.

In still yet further embodiments, provided herein may be a compound of Formula (I) having the structure of Formula (VII), or a pharmaceutically acceptable salt thereof:

(VII)

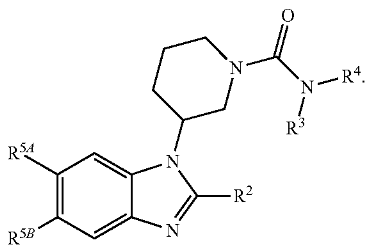

In still yet further embodiments, provided herein are compounds selected from the group consisting of Compounds 106-306, and pharmaceutically acceptable salts thereof, as described above.

The compounds of the present disclosure, which can be in the form of a free base, may be isolated from the reaction mixture in the form of a pharmaceutically acceptable salt. The pharmaceutically acceptable salts may also be obtained by treating the free base of the compounds disclosed herein with an organic or inorganic acid such as hydrogen chloride, hydrogen bromide, hydrogen iodide, sulfuric acid, phosphoric acid, acetic acid, propionic acid, glycolic acid, maleic acid, malonic acid, methanesulphonic acid, fumaric acid, succinic acid, tartaric acid, citric acid, benzoic acid, and ascorbic acid.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. The isotopes may be isotopes of carbon, chlorine, fluorine, hydrogen, iodine, nitrogen, oxygen, phosphorous, sulfur, and technetium, including $^{11}C$, $^{13}C$, $^{14}C$, $^{36}Cl$, $^{18}F$, $^{2}H$, $^{3}H$, $^{123}I$, $^{125}I$, $^{13}N$, $^{15}N$, $^{15}O$, $^{17}O$, $^{18}O$, $^{31}P$, $^{32}P$, $^{35}S$, and $^{99m}Tc$. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise Chemical Synthesis Methods The compounds included in the present disclosure can be prepared by methods well known in the art of organic chemistry. See, for example, March, Advanced Organic Chemistry, 4th Edition, John Wiley & Sons, 2001. During synthetic sequences it may be necessary and/or desirable to protect sensitive or reactive groups on any of the molecules concerned. This is achieved by means of conventional protecting groups, such as those described in Greene and Wutts, Protective Groups in Organic Synthesis, 3rd Edition, John Wiley & Sons, 1999. The protective groups are optionally removed at a convenient subsequent stage using methods well known in the art.

The products of the reactions are optionally isolated and purified, if desired, using conventional techniques, but not limited to, filtration, distillation, crystallization, chromatography and the like. Such materials are optionally characterized using conventional means, including the measurement of physical constants and spectral data.

The synthesis method of the compounds is represented by the general scheme below. Detailed synthesis method can be found in the Examples section.

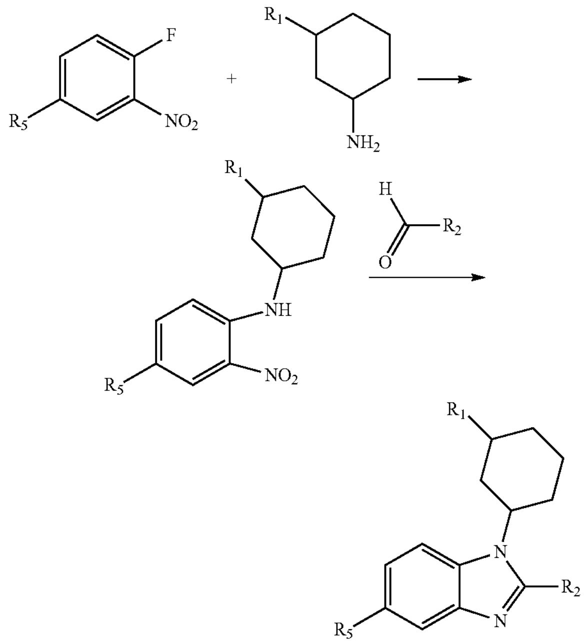

Additional synthesis methods of the compounds is represented by the general scheme below. Detailed synthesis method can be found in the Examples section.

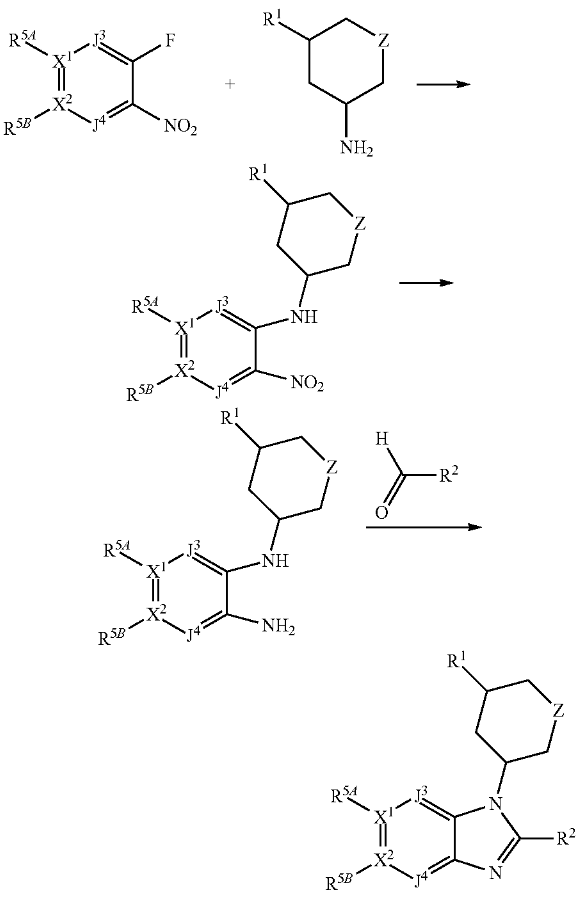

Methods of Identifying Candidate Compounds

The present disclosure provides, in part, methods for identifying whether a candidate compound is useful for the treatment of an organic acidemia, comprising a candidate compound for treatment of an organic acidemia, comprising: (a) obtaining a test compound having the ability to directly or indirectly bind to a BCAT (e.g., BCAT2); (b) assaying for functional modulation of the BCAT (e.g., BCAT2); and (c) classifying the test compound as a candidate compound if reduced, low or substantially no activity of the BCAT (e.g., BCAT2) is detected.

In various embodiments, the present disclosure contemplates the use of various assays for classifying candidate compounds for use in the functional modulation of BCAT2. For example, the functional modulation of BCAT2 can be assayed using a cell-based assay. In some embodiments, the test compound is classified as a candidate compound if an increase in branch-chain amino acids is measured. In some embodiments, the test compound is classified as a candidate compound if a decrease in propionyl-carnitine is measured.

In further embodiments, the the functional modulation of BCAT2 is assayed using a cell-free assay. In various embodiments, the cell-free assay is an enzyme-coupled fluorescent assay. For example, the disclosure contemplates use of an assay that monitors the production of L-glutamate from branch-chain amino acids and α-ketoglutarate through the coupling of hBCATm activity to two additional enzymes, L-Glutamate Oxidase (L-GOx) and Horseradish Peroxidase (HRP). Specifically, L-GOx catabolizes L-glutamate to generate α-ketoglutarate and HRP, the latter being utilized by HRP and leading to the formation of fluorescent resorufin from the redox-sensitive dye Amplex Red. In some embodiments, the test compound is classified as a candidate compound if a decrease in L-glutamate is measured. In further embodiments, the test compound is classified as a candidate compound if a decrease in α-ketoglutarate is measured.

Methods for Making Agents of the Disclosure

The present disclosure provides methods for making an agent for the treatment of an organic acidemia, comprising: (a) identifying a candidate compound, comprising: (i) obtaining a test compound having the ability to directly or indirectly bind to a BCAT (e.g., BCAT2); (ii) assaying for functional modulation of the BCAT (e.g., BCAT2); and (iii) classifying the test compound as a candidate compound if reduced, low or substantially no activity of the BCAT (e.g., BCAT2) is detected; and (b) formulating the candidate compound for the treatment of an organic acidemia.

Pharmaceutically Acceptable Salts and Excipients

Any agent described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in Journal of Pharmaceutical Science, 66, 2-19 (1977) and The Handbook of Pharmaceutical Salts; Properties, Selection, and Use. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term "pharmaceutically acceptable salt" also refers to a salt of the compounds of the present disclosure having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl) amine; N-methyl-D-glucamine; and amino acids such as arginine, lysine, and the like.

In some embodiments, an agent of the disclosure is in the form or a pharmaceutically acceptable salt. In some embodiments, the pharmaceutically acceptable salt is a sodium salt.

Further, any agent described herein can be administered to a subject as a component of a composition that comprises a pharmaceutically acceptable carrier or vehicle. Such compositions can optionally comprise a suitable amount of a pharmaceutically acceptable excipient so as to provide the form for proper administration.

Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents.

Formulations. Administration, and Dosing

Any agent described herein can be administered orally. Such agents can also be administered by any other convenient route, for example, by intravenous infusion or bolus injection, by absorption through epithelial or mucocutaneous linings (e.g., oral mucosa, rectal and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer.

In specific embodiments, it may be desirable to administer locally to the area in need of treatment.

In another embodiment, delivery can be in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989). In yet another embodiment, delivery can be in a controlled release system. In one embodiment, a slow release intra-ocular device may be used. In some embodiments, this device consists of a locally delivered erodible or non-erodable liquid, gel, polymer, etc.

In another embodiment, polymeric materials can be used (see *Medical Applications of Controlled Release*, Langer and Wise (eds.), CRC Pres., Boca Raton, Florida (1974); *Controlled Drug Bioavailability, Drug Product Design and Performance*, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105). In another embodiment, a controlled-release system can be placed in proximity of the target area to be treated, e.g., the retina, thus requiring only a fraction of the systemic dose (see, e.g., Goodson, in *Medical Applications of Controlled Release, supra*, vol. 2, pp. 115-138 (1984)). Other controlled-release systems discussed in the review by Langer, 1990, *Science* 249:1527-1533)$_{m}$ay be used.

Administration of any agent described herein can, independently, be one to four times daily or one to four times per month or one to six times per year or once every two, three, four or five years. Administration can be for the duration of one day or one month, two months, three months, six months, one year, two years, three years, and may even be for the life of the subject. Chronic, long-term administration will be indicated in many cases. The dosage may be administered as a single dose or divided into multiple doses. In general, the desired dosage should be administered at set intervals for a prolonged period, usually at least over several weeks or months, although longer periods of administration of several months or years or more may be needed.

The dosage regimen utilizing any agent described herein can be selected in accordance with a variety of factors including type, species, age, weight, sex and medical condition of the subject; the severity of the condition to be treated; the route of administration; the renal or hepatic function of the subject; the pharmacogenomic makeup of the individual; and the specific compound of the disclosure employed. Any agent described herein can be administered in a single daily dose, or the total daily dosage can be administered in divided doses of two, three or four times daily. Furthermore, any agent described herein can be administered continuously rather than intermittently throughout the dosage regimen.

Subjects and/or Animals

In some embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal, such, for example, a zebrafish. In some embodiments, the subject and/or animal may comprise fluorescently-tagged cells (with e.g. GFP). In some embodiments, the subject and/or animal is a transgenic animal comprising a fluorescent cell. In some embodiments, the subject and/or animal is a human. In some embodiments, the human is a pediatric human. In other embodiments, the human is an adult human. In other embodiments, the human is a geriatric human. In other embodiments, the human may be referred to as a patient.

In certain embodiments, the human has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In other embodiments, the subject is a non-human animal, and therefore the disclosure pertains to veterinary use. In a specific embodiment, the non-human animal is a household pet. In another specific embodiment, the non-human animal is a livestock animal.

Kits

The disclosure provides kits that can simplify the administration of any agent described herein. An exemplary kit of the disclosure comprises any agent described herein in unit dosage form. In one embodiment, the unit dosage form is a container, such as a pre-filled syringe, which can be sterile, containing any agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the ocular surface. The kit can also further comprise one or more additional agent described herein.

In one embodiment, the kit comprises a container containing an effective amount of an agent of the disclosure, including, for example, compound of Formula I, Ia, II, III, IV, V, VI, or VII or a pharmaceutically acceptable salt thereof, or any compound disclosed herein and an effective amount of another therapeutic agent, such those described herein.

Definitions

The following definitions are used in connection with the disclosure disclosed herein. Unless defined otherwise, all technical and scientific terms used herein have the same meaning as commonly understood to one of skill in the art to which this disclosure belongs.

An "effective amount," when used in connection with an agent of the disclosure, for example, a BCAT2 inhibitor (e.g., a compound of Formula I, Ia, II, III, IV, V, VI, or VII or a pharmaceutically acceptable salt thereof, or any compound disclosed herein), is an amount that is effective for reducing toxic load of BCAA metabolites and/or substrate molecules, as described herein.

An agent is "useful for the treatment of an organic acidemia" if the agent provides a measurable treatment, prevention, or reduction in the rate and/or symptoms of pathogenesis of an organic acidemia.

As used herein, "a," "an," or "the" can mean one or more than one. Further, the term "about" when used in connection with a referenced numeric indication means the referenced numeric indication plus or minus up to 10% of that referenced numeric indication. For example, the language "about 50" covers the range of 45 to 55.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the disclosure, the present disclosure, or embodiments thereof, may alternatively be described using alternative terms such as "consisting of" or "consisting essentially of."

"Solvate" refers to the compound formed by the interaction of a solvent and an EPI, a metabolite, or salt thereof. Suitable solvates are pharmaceutically acceptable solvates including hydrates.

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

"Alkyl" refers to a straight or branched hydrocarbon chain radical consisting solely of carbon and hydrogen atoms, containing no unsaturation, having from one to ten carbon atoms (e.g., $(C_{1-10})$alkyl or $C_{1-10}$ alkyl). Whenever it appears herein, a numerical range such as "1 to 10" refers to each integer in the given range—e.g., "1 to 10 carbon atoms" means that the alkyl group may consist of 1 carbon atom, 2 carbon atoms, 3 carbon atoms, etc., up to and including 10 carbon atoms, although the definition is also intended to cover the occurrence of the term "alkyl" where no numerical range is specifically designated. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl and decyl. The alkyl moiety may be attached to the rest of the molecule by a single bond, such as for example, methyl (Me), ethyl (Et), n-propyl (Pr), 1-methylethyl (isopropyl), n-butyl, n-pentyl, 1,1-dimethylethyl (t-butyl) and 3-methylhexyl. Unless stated otherwise specifically in the specification, an alkyl group is optionally substituted by one or more of substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —ORa, —SRa, —OC(O)—Ra, —N(Ra)2, —C(O)Ra, —C(O)ORa, —OC(O)N(Ra)2, —C(O)N(Ra)2, —N(Ra)C(O)ORa, —N(Ra)C(O)Ra, —N(Ra)C(O)N(Ra)2, N(Ra)C(NRa)N(Ra)2, —N(Ra)S(O)tRa (where t is 1 or 2), —S(O)tORa (where t is 1 or 2), —S(O)tN(Ra)2 (where t is 1 or 2), or PO3(Ra)2 where each Ra is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e. $(C_{3-10})$cycloalkyl or $C_{3-10}$ cycloalkyl). Whenever it appears herein, a numerical range such as "3 to 10" refers to each integer in the given range—e.g., "3 to 10 carbon atoms" means that the cycloalkyl group may consist of 3 carbon atoms, etc., up to and including 10 carbon atoms. Illustrative examples of cycloalkyl groups include, but are not limited to the following moieties: cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, =O, —ORa, —SRa, —OC(O)—Ra, —N(Ra)2, —C(O)Ra, —C(O)ORa, —OC(O)N(Ra)2, —C(O)N(Ra)2, —N(Ra)C(O)ORa, —N(Ra)C(O)Ra, —N(Ra)C(O)N(Ra)2, N(Ra)C(NRa)N(Ra)2, —N(Ra)S(O)tRa (where t is 1 or 2), —S(O)tORa (where t is 1 or 2), —S(O)tN(Ra)2 (where t is 1 or 2), or PO3(Ra)2, where each Ra is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

As used herein, "haloalkyl" refers to a straight- or branched-chain alkyl group having from 1 to 12 carbon atoms in the chain, substituting one or more hydrogens with halogens. Examples of haloalkyl groups include, but are not limited to, —$CF_3$, —$CHF_2$, —$CH_2F$, —$CH_2CF_3$, —$CH_2CHF_2$, —$CH_2CH_2F$, —$CH_2CH_2Cl$, —$CH_2CF_2CF_3$ and other groups that in light of the ordinary skill in the art and the teachings provided herein, would be considered equivalent to any one of the foregoing examples.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. In various embodiments, a heteroaryl contains from 1 to 4 heteroatoms, from 1 to 3 heteroatoms, from 1 to 2 heteroatoms, or 1 heteroatom. For example, in various embodiments, a heteroaryl contains 1 to 4 nitrogen atoms, 1 to 3 nitrogen atoms, 1 to 2 nitrogen atoms, 2 nitrogen atoms and 1 sulfur or oxygen atom, 1 nitrogen atom and 1 sulfur or oxygen atom, or 1 sulfur or oxygen atom. Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, a heteroaryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —ORa, —SRa, —OC(O)—Ra, —N(Ra)2, —C(O)Ra, —C(O)ORa, —OC(O)N(Ra)2, —C(O)N(Ra)2, —N(Ra)C(O)ORa, —N(Ra)C(O)Ra, —N(Ra)C(O)N(Ra)2, N(Ra)C(NRa)N(Ra)2, —N(Ra)S(O)tRa (where t is 1 or 2), —S(O)tORa (where t is 1 or 2), —S(O)tN(Ra)2 (where t is 1 or 2), or PO3(Ra)2, where each Ra is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

Substituted heteroaryl also includes ring systems substituted with one or more oxide O—) substituents, such as, for example, pyridinyl N-oxides.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atoms although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. In various embodiments, the heteroalkyl may have from 1 to 4 heteroatoms, from 1 to 3 heteroatoms, 1 or 2 heteroatoms, or 1 heteroatom. The heteroalkyl group of the compounds may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s)$_m$ay be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations.

In various embodiments, a heterocyclyl contains from 1 to 4 heteroatoms, from 1 to 3 heteroatoms, from 1 to 2 heteroatoms, or 1 heteroatom. For example, in various embodiments, a heterocyclyl contains 1 to 4 nitrogen atoms, 1 to 3 nitrogen atoms, 1 to 2 nitrogen atoms, 2 nitrogen atoms and 1 sulfur or oxygen atom, 1 nitrogen atom and 1 sulfur or oxygen atom, or 1 sulfur or oxygen atom. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3- dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to —C(S)R, wherein R is hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "sulfonyl" group refers to an "—$SO_2R$" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "S-sulfonamide" group refers to a "—$SO_2NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamide" group refers to a "—$N(R_A)SO_2R_B$" group in which $R_A$ and $R_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-carbamyl" group refers to a "—$OC(=O)NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "—$N(R_A)OC(=O)R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-thiocarbamyl" group refers to a "—$OC(=S)NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-thiocarbamyl" group refers to an "—$N(R_A)OC(=S)R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-amido" group refers to a "—$C(=O)NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-amido" group refers to a "—$N(R_A)C(=O)R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "aminoalkyl" group refers to an amino group connected via an alkylene group.

An "alkoxyalkyl" group refers to an alkoxy group connected via an alkylene group, such as a "$C_{2-4}$ alkoxyalkyl" and the like.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

When two R groups are said to form a ring (e.g., a carbocyclyl, heterocyclyl, aryl, or heteroaryl ring) "together with the atom to which they are attached," it is meant that the collective unit of the atom and the two R groups are the recited ring. The ring is not otherwise limited by the definition of each R group when taken individually. For example, when the following substructure is present:

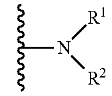

and $R^1$ and $R^2$ are defined as selected from the group consisting of hydrogen and alkyl, or $R^1$ and $R^2$ together with the nitrogen to which they are attached form a heterocyclyl, it is meant that $R^1$ and $R^2$ can be selected from hydrogen or alkyl, or alternatively, the substructure has structure:

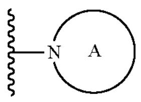

where ring A is a heterocyclyl ring containing the depicted nitrogen.

Similarly, when two "adjacent" R groups are said to form a ring "together with the atoms to which they are attached,"

it is meant that the collective unit of the atoms, intervening bonds, and the two R groups are the recited ring. For example, when the following substructure is present:

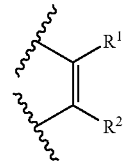

and $R^1$ and $R^2$ are defined as selected from the group consisting of hydrogen and alkyl, or $R^1$ and $R^2$ together with the atoms to which they are attached form an aryl or carbocyclyl, it is meant that $R^1$ and $R^2$ can be selected from hydrogen or alkyl, or alternatively, the substructure has structure:

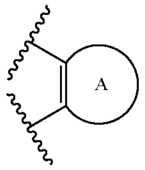

where A is an aryl ring or a carbocyclyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

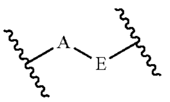

includes the substituent being oriented such that the A is attached at the leftmost attachment point of the molecule as well as the case in which A is attached at the rightmost attachment point of the molecule.

This disclosure is further illustrated by the following non-limiting examples.

EXAMPLES

Example 1: BCAT2 and BCAT1 Inhibition In Vitro

This Example evaluated whether a compound of the disclosure, a BCAT2 inhibitor compound of Formula (I), shown below:

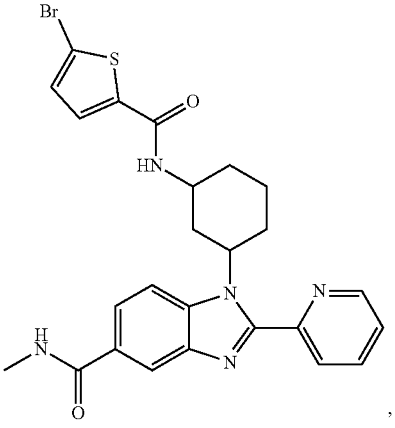 [SMILES: CNC(=O)c1ccc2c(c1)nc(-c1ccccn1)n2C1CCCC(NC(=O)c2ccc(Br)s2)C1]

, could inhibit levels of the downstream metabolite propionyl carnitine, which is found to be elevated in patients with propionic acidemia, by analyzing propionyl carnitine levels in conditioned media in human fibroblasts from a patient with propionic acidemia treated with a dose response of the compound of the disclosure.

Primary human fibroblasts from a patient with propionic acidemia (Coriell #GM00371) were plated in complete media (EMEM, 15% FBS) in a 96-well plate at 10,000 cells/well and incubated overnight at 37° C. at 5% $CO_2$. Compounds were serially diluted initially in DMSO then into serum-free EMEM media. The cells were then washed with D-PBS before addition of the media containing the diluted compound, and were then incubated at 37° C. at 5% $CO_2$ overnight.

The conditioned media was removed from cells after 24 hours of compound treatment and was diluted 2× with D3-propionyl carnitine internal standard diluted in MS-grade methanol. Plates were sealed and samples were frozen at −80DGC for more than 30 minutes, followed by thawing at room temperature and centrifugation for 10 minutes at 4000 rpm. The samples were then analyzed for propionyl carnitine by LC-LC/MS using TSQ Vantage using a Kinetex 2.6 μm Biphenyl 2.1×50 mm column with Mobile Phase A of 95% (0.1% Formic acid in Water)+5% Water and Mobile Phase B of 95% McOH+5% (0.1% Formic acid in Water).

Cell viability was also determined with cell Titer-Glo reagent (Promega) by addition of equal volumes of D-PBS and Cell Titer-Glo reagent to cell wells and following manufacturer's recommendations for detection of luminescence signal.

The results of the experiment are depicted in FIG. 1, showing the effect of the BCAT2 inhibitor, a compound of Formula Ia, shown below:

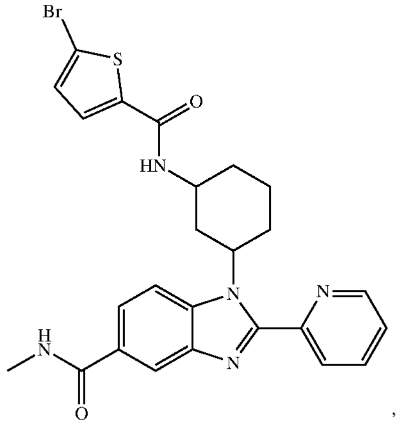 [SMILES: CNC(=O)c1ccc2c(c1)nc(-c1ccccn1)n2C1CCCC(NC(=O)c2ccc(Br)s2)C1]
, on flux through the BCAA pathway, and on a downstream metabolite, propionyl carnitine. The results show that propionyl carnitine levels are inhibited in the presence of increasing concentrations of the BCAT2 inhibitor with little impact on cell viability. This suggests that BCAT2 reduces flux through the BCAA pathways.

The BCAT1 inhibitory activity of selected compounds of the present disclosure were also evaluated. Compounds were prepared as up to 10 mM stock solutions generally using DMSO as the vehicle. 10-point dose response curves were generated using the Echo-550 (Labcyte) acoustic dispenser. Compound source plates (384-well, solid white assay plate, Corning #3570) were made by serially diluting compound stocks to create 1 mM, 0.1 mM, and 0.01 mM solutions in DMSO into Echo certified LDV plates. The Echo then serially spotted 100% DMSO stock solutions into source dose response plates to generate a semi-log fold dilution scheme. 100% DMSO was added to the spotted dose response plates to bring the final volume to 5 µL, creating a 333× stock plate. 120 nL of the dose response stock plate was then spotted into the assay plate. 10 µL of assay buffer (50 mM Tris with 0.05% TWEEN-20) was then added to the plates resulting in a 4× working concentration in the assay plate. Final assay test concentration range was 3 µM to 0.0001 µM with a final DMSO concentration of 0.3%.

BCAT1 enzyme stock was first diluted to a 4× working concentration of 0.24 µg/mL in assay buffer (final assay concentration is 0.06 ug/ml). 10 µL of the 4×BCAT1 solution was then added to the previously prepared assay plate containing test compound or controls, and incubated at room temperature, protected from light, for either 10 or 60 minutes. After the compound incubation period, 20 µL of assay buffer plus 2× substrate is added to all wells (Final assay concentration of substrates is 300 µM L-leucine and 250 µM alpha-ketoglutaric acid). Enzyme reaction was then incubated for 10 minutes at room temperature. After the 10 minute incubation, the enzymatic reaction was halted with the addition of 5 µL of 0.6N HCl and incubated for 1 min. 5 µL of 1M Tris (pH 8.0) was then added to neutralize pH. 12.5 µL of the quenched assay volume was then transferred to a white, 384 well plate and 12.5 µL of Glutamate detection reagent was added (detection reagent prepared per Promega Glutamate Glo kit instructions). Plates were then incubated for 30 minutes at room temperature, protected from light. After glutamate detection incubation period, luminescence was read on BMG Novostar and relative light units was measured and exported for analysis.

Compound modulation of BCAT1 enzymatic activity was determined as follows. $IC_{50}$ values were calculated in ActivityBase, using a 4-parameter fit equation. Data was normalized to maximum inhibition form the reference agent VS558CSA (at 10 µM). Relative light units were exported for analysis and % inhibition values for each well were calculated using the following formula:

$$\%\ \text{inhibition} = \frac{\mathit{RLU}\ \text{TEST AGENT} - \text{Plate Average}\ \mathit{RLU\ REF\ INHIB}}{\text{Plate Average}\ \mathit{RLU\ DMSO}\ \text{CONTROL} - \text{Plate Average}\ \mathit{RLU\ REF\ INHIB}} \times 100$$

BCAT2 inhibitory activity for additional compounds of the present disclosure are provided below, along with BCAT1 inhibitory data.

| Compound | BCAT2 ENZYME INHIBITION HUMAN $IC_{50}$ (µM) | BCAT1 ENZYME INHIBITION HUMAN $IC_{50}$ (µM) |
|---|---|---|
| 101 | D | D |
| 102 | B | D |
| 103 | B | N/D |
| 104 | D | N/D |
| 105 | A | C |
| 106 | D | N/D |
| 107 | C | N/D |
| 108 | D | N/D |
| 109 | B | D |
| 110 | D | N/D |
| 111 | D | N/D |
| 112 | B | D |
| 113 | A | N/D |
| 114 | B | N/D |
| 115 | D | N/D |
| 116 | D | N/D |
| 117 | D | N/D |
| 118 | D | N/D |
| 119 | B | N/D |
| 120 | D | N/D |
| 121 | D | N/D |
| 122 | D | N/D |
| 123 | A | N/D |
| 124 | A | N/D |
| 125 | D | N/D |
| 126 | A | N/D |
| 127 | C | N/D |
| 128 | C | N/D |
| 129 | B | N/D |
| 130 | C | N/D |
| 131 | C | N/D |
| 132 | B | N/D |
| 133 | B | N/D |
| 134 | A | D |
| 135 | A | D |
| 136 | A | B |
| 137 | A | A |
| 138 | A | C |
| 139 | A | B |
| 140 | B | N/D |
| 141 | A | N/D |
| 142 | A | N/D |
| 143 | A | D |
| 144 | C | N/D |
| 145 | A | B |
| 146 | D | N/D |
| 147 | A | D |
| 148 | A | N/D |
| 149 | B | D |
| 150 | D | N/D |
| 151 | A | C |
| 152 | A | N/D |
| 153 | C | N/D |
| 154 | A | D |

-continued

| Compound | BCAT2 ENZYME INHIBITION HUMAN $IC_{50}$ (μM) | BCAT1 ENZYME INHIBITION HUMAN $IC_{50}$ (μM) |
|---|---|---|
| 155 | A | B |
| 156 | A | B |
| 157 | A | A |
| 158 | D | N/D |
| 159 | B | N/D |
| 160 | D | N/D |
| 161 | A | B |
| 162 | D | N/D |
| 163 | A | D |
| 164 | B | N/D |
| 165 | D | N/D |
| 166 | A | C |
| 167 | D | N/D |
| 168 | C | N/D |
| 169 | A | D |
| 170 | C | N/D |
| 171 | B | N/D |
| 172 | A | N/D |
| 173 | D | D |
| 174 | A | N/D |
| 175 | A | N/D |
| 176 | A | N/D |
| 177 | A | N/D |
| 178 | A | N/D |
| 179 | B | N/D |
| 180 | A | C |
| 181 | A | N/D |
| 182 | D | N/D |
| 184 | A | B |
| 185 | A | N/D |
| 186 | B | N/D |
| 187 | D | N/D |
| 188 | A | N/D |
| 189 | A | N/D |
| 190 | B | N/D |
| 191 | D | N/D |
| 192 | A | N/D |
| 193 | A | C |
| 194 | A | D |
| 195 | A | D |
| 196 | A | D |
| 197 | A | A |
| 198 | A | B |
| 199 | A | A |
| 200 | A | B |
| 202 | D | D |
| 203 | D | D |
| 204 | B | D |
| 205 | A | B |
| 206 | A | A |
| 207 | A | A |
| 208 | A | B |
| 209 | A | N/D |
| 210 | A | N/D |
| 211 | A | N/D |
| 212 | A | N/D |
| 213 | A | N/D |
| 214 | A | N/D |
| 215 | A | N/D |
| 216 | A | N/D |
| 217 | D | D |
| 218 | D | D |
| 219 | D | D |
| 220 | D | D |
| 221 | A | B |
| 222 | A | B |
| 223 | A | A |
| 224 | A | B |
| 225 | A | D |
| 226 | A | B |
| 227 | D | D |
| 228 | D | D |
| 229 | D | D |
| 230 | A | C |
| 231 | A | D |
| 232 | A | D |
| 233 | A | C |
| 234 | A | B |
| 235 | C | D |
| 236 | B | D |
| 237 | B | D |
| 238 | B | D |
| 239 | B | D |
| 240 | A | C |
| 241 | A | D |
| 242 | D | D |
| 243 | B | D |
| 279 | B | 0 |
| 280 | B | D |
| 281 | D | N/D |
| 282 | D | N/D |
| 283 | D | N/D |
| 284 | A | B |
| 285 | A | C |
| 286 | A | A |
| 288 | B | D |
| 289 | A | N/D |
| 290 | D | N/D |
| 291 | A | B |
| 292 | A | B |
| 293 | D | N/D |
| 294 | B | D |
| 296 | A | N/D |
| 297 | A | N/D |
| 298 | A | C |
| 300 | D | N/D |
| 301 | B | N/D |
| 302 | A | C |
| 303 | B | D |
| 304 | D | N/D |
| 305 | D | N/D |
| 306 | A | D |

N/D: Not Determined
A: <100 nM;
100 nM ≤ B < 500 nm;
500 ≤ C < 1000 nm;
D ≥ 1000 nM Example 2: BCAT2 Inhibition In Vivo This Example evaluated the pharmacodynamics associated with acute and repetitive treatment with the BCAT2 inhibitor compound shown below:

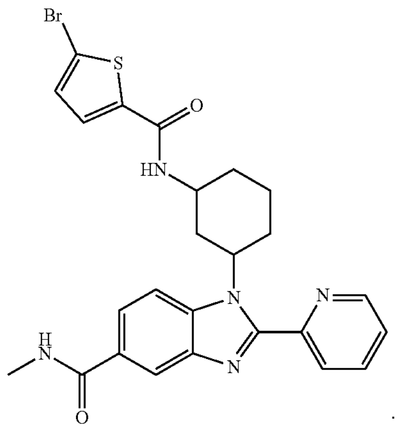 [SMILES: CNC(=O)c1ccc2c(c1)nc(-c1ccccn1)n2C1CCCC(NC(=O)c2ccc(Br)s2)C1]

.

Chemicals

A branched chain aminotransferases 2 (BCAT2) inhibitor compound was synthesized according to Example 3.

Hydroxypropyl methylcellulose (HPMC), branch chain amino acids L-Cysteine, L-Histidine, L-Isoleucine, L-Leucine, L-Lysine, L-Methionine, L-Phenylalanine, L-Threonine, L-Tryptophan, L-Tyrosine and L-Valine were purchased from Sigma-Aldrich (St. Louis, MO). All other reagents were obtained from common sources, and they were of reagent grade or better.

Animals

Male, C57Black/6J mice (6-7 weeks, Jackson Laboratories, Bar Harbor, ME) were used in all in vivo experiments. Animals were maintained on a 12 hour light/dark reverse cycle in a temperature- and humidity-controlled room with access to food and water ad libitum. Before the experiment, animals underwent a 7-day acclimation period. All procedures involving mice were approved by the Institutional Animal Care and Use Committee of the University of Arizona and were conducted in accordance with Principles of Laboratory Animal Care (National Institutes of Health Publication 85-23, revised in 1985).

Bioanalysis of Plasma, Urine, and Tissue Homogenate Extracts

All biological samples were stored in −80° C. until analysis. Branched chain amino acids (valine, leucine isoleucine) and serine in mice plasma and urine were extracted by a method based on protein precipitation using acetoniuile (ACN) containing D8-Valine as internal standard and analyzed by liquid chromatograph mass spectrometry (LC-MS/MS) on Agilent 1290 Infinite II separation HPLC coupled to a Agilent 6490 QQQ MS. In particular, 20 μL of mouse plasma were precipitated with 180 μL acetonitrile containing 5 μg/ml D8-Valine. Samples were vortexed vigorously and centrifuged to remove precipitated protein. 2 μL of supernatant was injected on a Phenomenex Gemini C18 column (4.6 mm×150 mm, 5 μm particle size) for separation under a linear gradient from 2% ACN to 50% ACN in 10 minutes followed by a 7 minute equilibration with 2% ACN. Amino acid transition was 132.1 to 86.1 for Leucine/Isoleucine, 106.1 to 60.1 for Serine, 118.1 to 72.1 for Valine.

Propionyl carnitine in mice plasma was extracted by a solid phase extraction $(SPE)_m$ethod and analyzed by LC-MS/MS on Thermo Scientific TSQ vantage. The samples were injected on a Kinetex Biphenyl column (2.1×50 mm, 2.6 $\mu m)_m$aintained at room temperature. Analytes were eluted with a linear gradient consisting 0.095% Formic acid in water (A) and 0.0005% formic acid in McOH (B).

Pharmacodmamic Studies: Acute Treatment with BCAT2 Inhibitor

Animals were fast overnight followed by oral administration with vehicle (0.5% HPMC K100+0.1 Tween 80, pH=10.0) or indicated doses of compound (30, 100, 300 mg/kg) as suspension for 6 hours. After the compound dosing, animals were able to access food and water freely. Then, each mouse received an oral feeding mix of amino acid 1.5 g/10 mL/Kg. The amino acid mix was prepared in 0.5% HPMC/0.1% Tween 80, pH 7 and compose of 114 mg L-Cysteine, 114 mg L-Histidine, 468 mg L-Isoleucine, 939 mg L-Leucine, 486 mg L-Lysine, 39 mg L-Methionine, 75 mg L-Phenylalanine, 264 mg L-Threonine, 15 mg L-Tryptophan, 21 mg L-Tyrosine and 468 mg L-Valine. One hour after amino acid challenge, blood samples were taken by intra-cardiac puncture using K2-EDTA coated tubes. Plasma was collected after centrifugation and stored at −80° C. until analysis.

Figure 2:
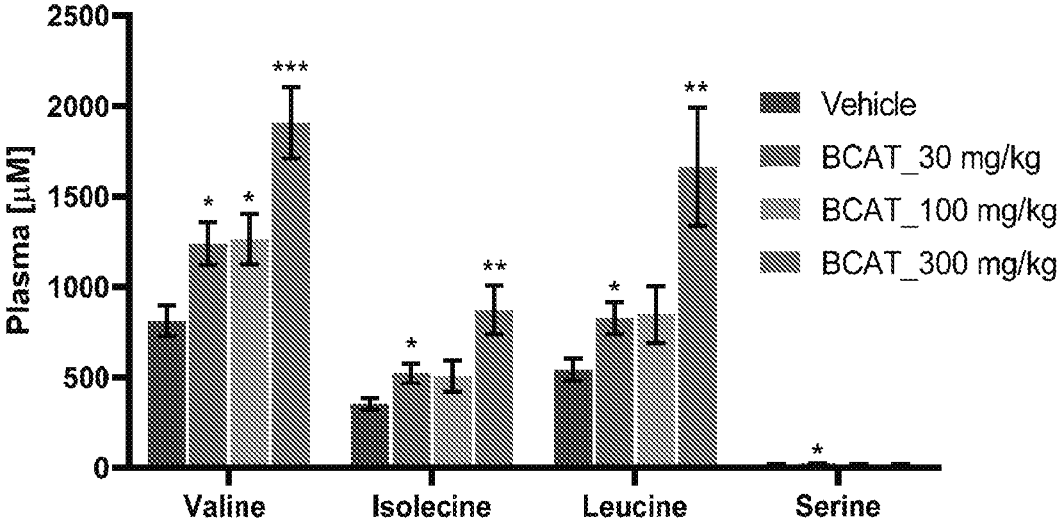
FIG. 2 depicts the amino acids level in plasma of mice treated with various doses of a BCAT2 inhibitor compound (30, 100, and 300 mg/kg, PO) for 6 hours and received an oral feeding of amino acid mixture 1 hour before plasma collection. Each bar represents the mean±S.E.M. (N=8-9 per group). *P<0.05, P<0.01, *P<0.001 compared with vehicle control. Within each set of histograms, the leftmost bar depicts the vehicle plasma level; the second from left bar depicts the BCAT2 inhibitor compound at 30 mg/kg plasma level; the third from left bar depicts the BCAT2 inhibitor compound at 100 mg/kg plasma level; and the rightmost bar depicts the BCAT2 inhibitor compound at 300 mg/kg plasma level.

The results depicted in FIG. 2 show that the BCAT2 inhibitor compound can block branched chain amino acids (BCAA) entering their catabolic pathways. As shown in FIG. 2, the BCAT2 inhibitor compound elevated levels of Valine (Val), Isoleucine (Ile) and Leucine (Leu) in plasma relative to vehicle controls in a dose-dependent manner. This experiment demonstrated that the BCAT2 inhibitor compound effectively raised the levels of BCAAs in an acute animal model.

Pharmacodynamic Studies: Repetitive Treatment with BCAT2 Inhibitor Compound

Animals were grouped based on pair matched body weight and received either vehicle (0.5% HPMC K100+0.1 Tween 80, pH=10.0) or a daily dose of compound (200 mg/kg, PO) for 9 days. From day 1 to day 5, all animals were provided with normal diet. On day 6, the diet was switched to a precursor enriched chow (700% isoleucine, valine and threonine enriched, TD. 140829; Envigo) for half of the animals; the other half were still fed with normal diet. On day 9, blood, bladder urine as well as tissue samples (liver, brain, heart, muscle and kidney) were harvested 4 hours after the last dose. Three mice in each treatment/diet group were retained for a 3-day recovery phase observation. On day 12, blood, bladder urine as well as tissue samples (liver, brain, heart, muscle and kidney) were harvested. During the entire study course (day 1 to day 12), mice were able to access food and water freely. Body weights were measured daily and any abnormal behavior for toxicity signs was recorded.

Figure 3:
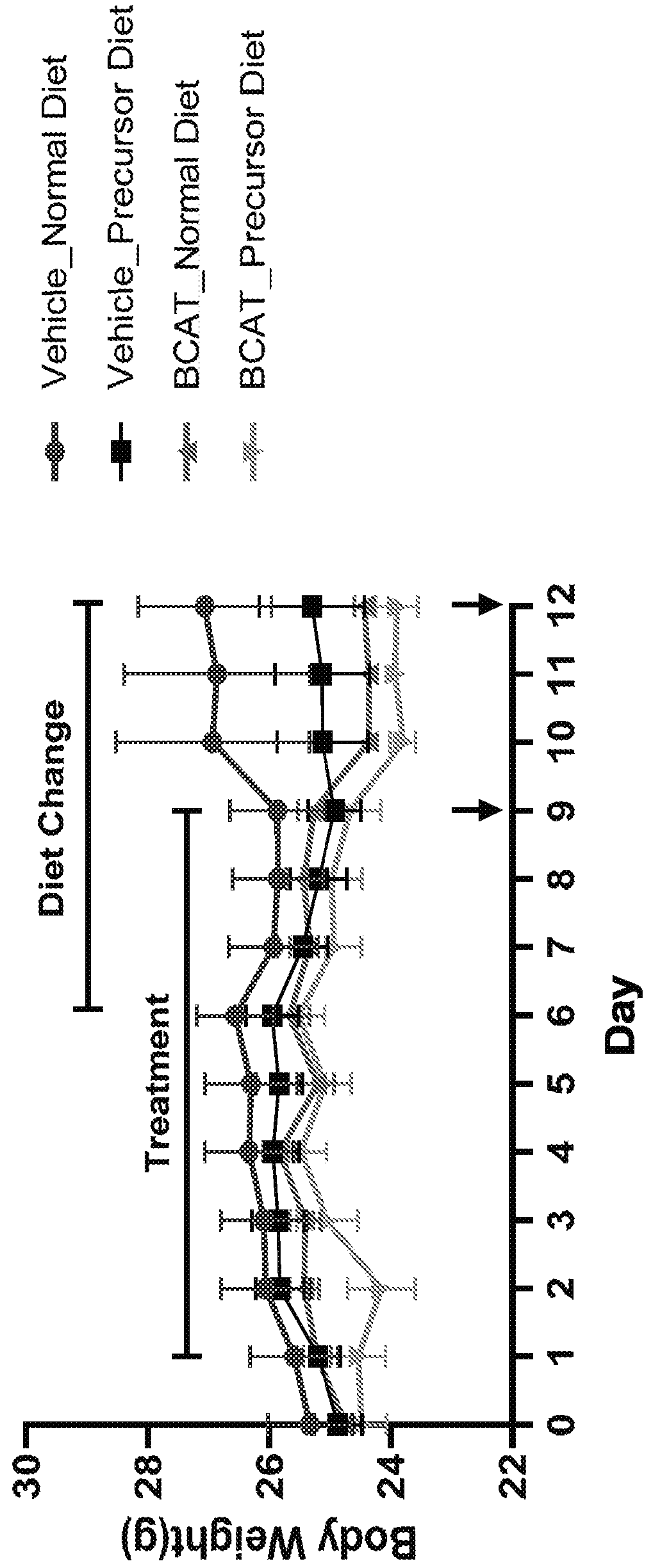
FIGS. 3A-D depicts (A) body weight monitoring during the 9-day BCAT2 inhibitor compound treatment (200 mg/kg, PO, once a day) and 3-day recovery phase. Mice were able to access the food and water freely during the study. Five days after the first dose, the diet was switched to a precursor enriched chow for half of the animals. Diet for the other half animals remained the same as normal diet. Body weight was measured at (B) day 0 (C) day 9 and (D) day 12. Each bar represents the mean±S.E.M. Dots represent individual values. For FIGS. 3B-D, in each set of histograms, the left bar represents the vehicle dosing and the right bar represents the BCAT2 inhibitor compound dosing.
Figure 3:
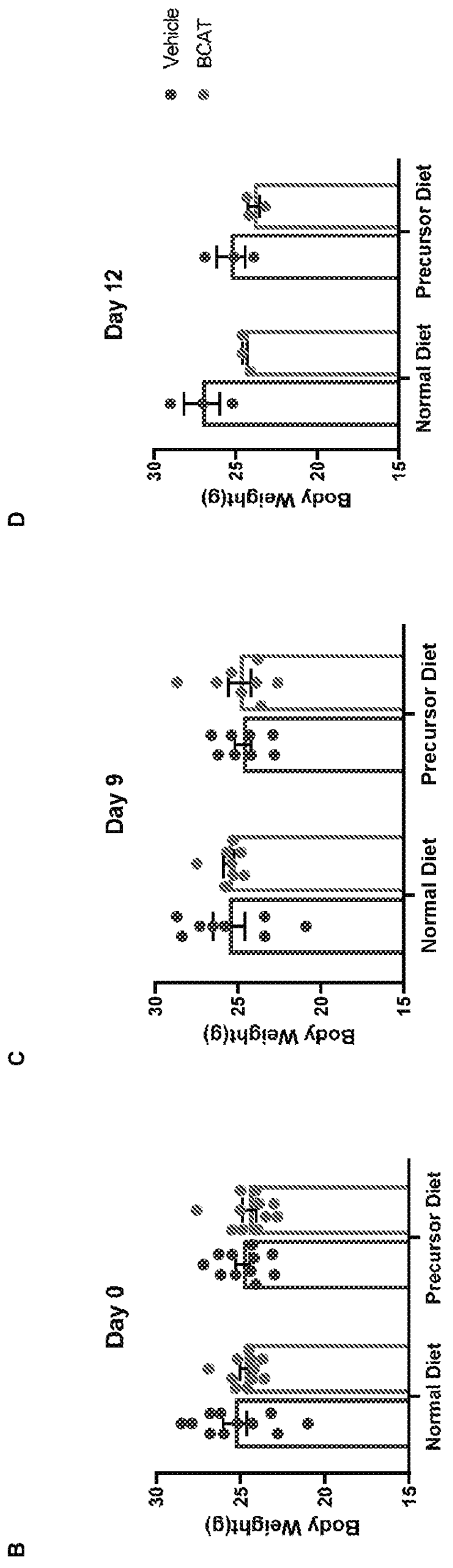

FIG. 3A-D shows the results of mouse body weight monitoring over the course of the study. Considering body weight could be a confounding factor to investigate the BCAA and PC levels in biological samples following repetitive dosing, mice were grouped based on pair matched body weight at day 0 and were monitored for the changes of body weight during the entire study course. FIG. 3A showed no significant loss of body weight was observed during the study. Body weight measured before the treatment (day 0) and measured at the two collection days (day 9 and 12) showed no significant difference between the groups (FIGS. 3B, 3C, and 3D). In addition, there were no obvious abnormal behaviors reflecting toxicities observed during the study. In each set of FIGS. 3B, 3C, and 3D, the left bar is vehicle and the right bar is BCAT.

Figure 4:
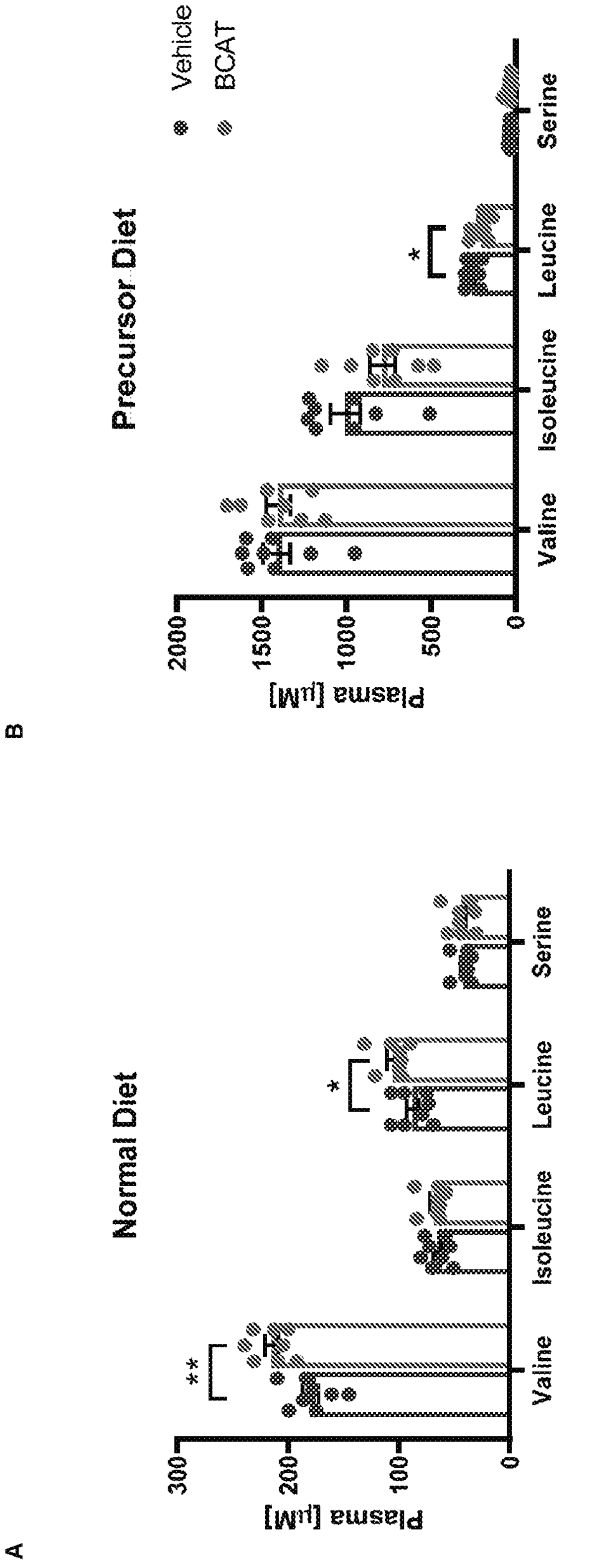
FIGS. 4A-B shows the Day 9 mice plasma levels of valine, isoleucine, leucine and serine. Mice were treated with vehicle or BCAT2 inhibitor compound (200 mg/kg, PO, once a day) for 9 days and were able to access the food and water freely during the study. Five days after the first dose, diet was switched to a precursor—enriched chow for half of the animals (B). Diet for the other half animals remained the same as normal diet (A). Each bar represents the mean±S.E.M. Dots represent individual values. N=8 per group. *$P<0.05$, **$P<0.01$ compared with vehicle control. For each set of histograms, the left bar represents the vehicle dosage and the right bar represents the BCAT2 inhibitor compound dosage.

FIG. 4A-B depicts the plasma levels of BCAAs following repetitive treatment with BCAT2 inhibitor compound in mice. As shown in FIG. 4A, repetitive dosing with BCAT2 inhibitor compound (200 mg/kg, PO) for 9 days significantly increased the plasma levels of Val and Leu but not Ile and Ser in mice fed with normal diet. In each set, the left bar is vehicle and the right bar is BCAT.

Changes in catabolic state or an augmented protein intake often result in an increased throughput of the propionate pathway in propionic acidemia patients. To replicate this state and test if BCAT2 inhibitor compound can block BCAAs entering the propionate pathway, a dietary challenge was used in the repetitive doing study. Mice were switched to a precursor—enriched diet comprised of increased levels of Isoleucine, Valine and threonine 5 days after the compound treatment. Data showed no significant changes on the levels of BCCAs between compound and vehicle treatment in mice plasma collected on Day 9 (FIG. 4B), except a slight but significant decrease of plasma level of leucine observed in Day 9 samples.

Figure 5:
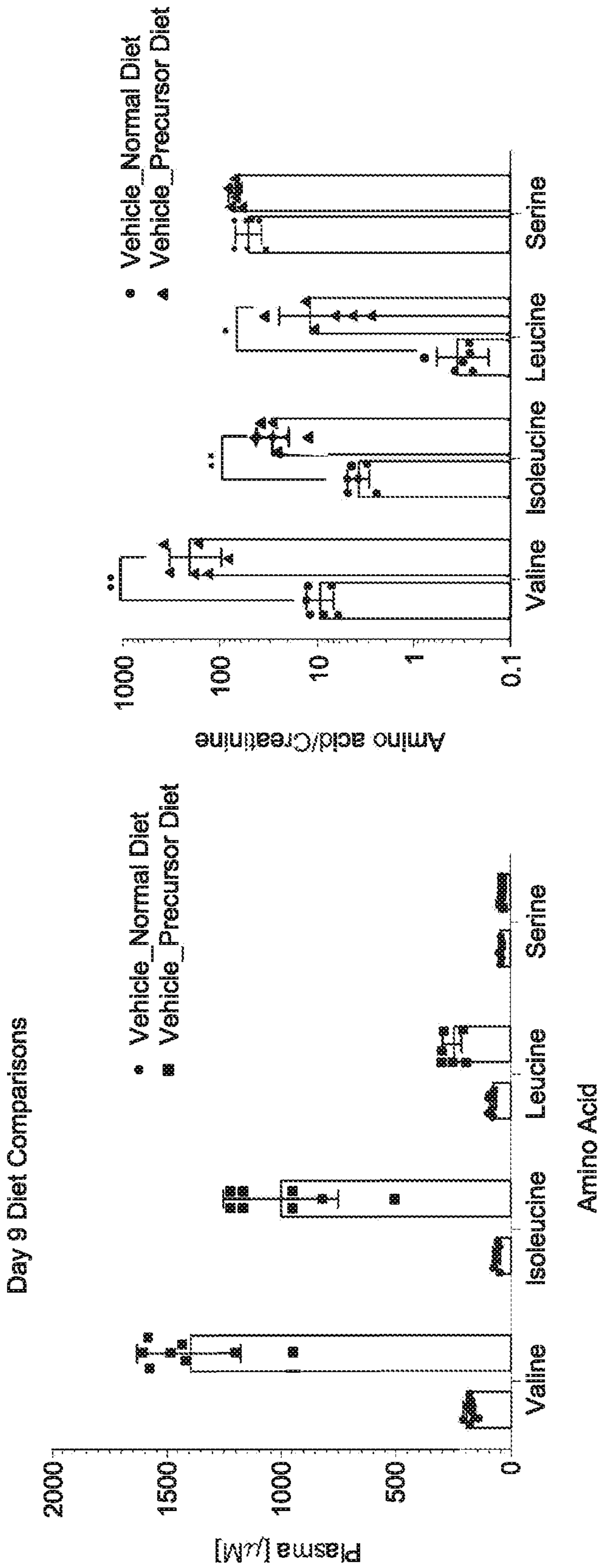
FIG. 5A-B depicts plasma (5A) and urine (5B) amino acid levels in Day 9 samples from mice given either normal or precursor—enriched diets.

FIG. 5A-B depicts plasma (5A) and urine (5B) amino acid levels in Day 9 samples from mice given either normal or precursor—enriched diets. FIG. 5A-B shows that overload of BCAAs from feeding with a precursor—enriched diet results in increased renal excretion of those amino acids.

Example 3: 3—HIB Assay In Vitro

Cell Plating: Cells (Coriell Institute GM00371 cells) were plated (96-well clear bottom sterile plate; Greiner 655098) at 10,000 cells/0.1 mL in Eagle's minimum essential medium (EMEM)/15% FBS (Gibco 16000-044) with a Combi dispenser in a cell culture hood and incubated at 37° C. and 5% $CO_2$ overnight.

Compound Dilution: Compound were prepared as 33.3× intermediate dilution in DMSO in 96 well round polystyrene plates. For 30 μM final maximum start with 30 μL of 10 mM in DMSO. 10-12 1:3 serial dilutions were prepared from left to right (20 μL+40 μL DMSO). A 10× secondary dilution was prepare in EMEM by taking 7.5 μL 33.3× and transfer to replicate 96 well round polystyrene plates and then adding 242.5 μL EMEM A 1× final dilution in EMEM was prepared by taking 50 μL 10× dilution and transferring to replicate 96 well polypropylene assay block (Costar 3956) and adding 450 μL EMEM A control was prepared for maximal compound inhibition by taking 20 μL 10 mM Reference Compound A and adding 40 μL DMSO for a concentration of 3.3 mM To 7.5 μL of the 3.3 mM Reference Compound A solution and added 242.5 μL EMEM to make a 100 μM solution. The subsequent Reference Compound A solution was diluted with EMEM to achieve a final concentration of 10 μM. The structure of Reference Compound A is:

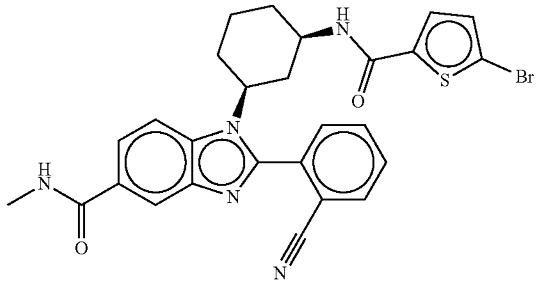

A control was prepared for maximal compound toxicity by taking 7.5 μL Reference Compound B and 242.5 μL EMEM to make 300 μM solution. 50 μL of that 100 μM Reference Compound B solution was combined with 450 μL EMEM to achieve a concentration of 30 μM. The structure of Reference Compound B is

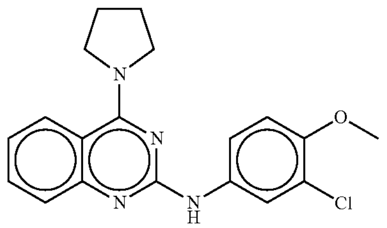

A DMSO Control was prepared by dilution 7.5 μL with 242.5 μL EMEM and taking 50 μL of the subsequent solution and diluting with 450 μL EMEM.

Compound Treatment: Media was aspirated from the cells and 100 μL of D-PBS (ThermoFisher 14190144) was added and then removed. 100 μL of diluted compound was added to the cells in the place and the cells were incubated at 37° C. and 5% $CO_2$ for 24 hours.

Collection of Conditioned Media: For 3HIB MS detection: 20 μL conditioned media was removed from the cells and was transferred to a labeled replicate 96 well polypropylene assay plate (VWR 62408-946). And the plate was heat sealed and stored at −80° C.

Viability Assay: To the cells remaining in the plate 25 μL D-PBS and 25 μL Cell titer glo reagent (Promega G7572). The plate was placed on a shaker for 2 minutes, incubated at room temperature in the dark and then read on a Clariostar microplate reader.

3HIB Derivatization (Generalized SOP): The media collected for 3HIB MS detection was derivatized under the following conditions. Buffer: 0.1M 1-Ethyl-3-(3-dimethylaminopropyl)carbodiimide (EDC) dissolved in 0.1 M 2-(N-morpholino)ethanesulfonic acid (1'IES) adjusted to pH 5.6. Buffer prep: weighed 10.6 g MES (Sigma #M-5287) per 500 mL HPLC grade $H_2O$. Stored at 4° C.; 0.1M EDC: Weighed 1.971 g EDC (#E-1769) per 100 mL MES. Adjusted pH to 5.6 with ~40 drops of 1N NaOH and stored at 4° C. Buffer has a short half-life should be used within two weeks.

Derivatization: To 20 μL sample was added 60 μL 5 uM 3HIB-4C13 internal standard followed by 20 μL EDC in MES and 100 μL MES. The plate was sealed and incubate at 50° C. for w hours then centrifuged at 4000 rpm at 6° C. for 10 minutes. LC-MS analysis was then conducted and the data was processed using standard methods.

| Compoound | 3HIB INHIBITION $IC_{50}$ (μM) MEAN GM00371 cells Direct MS Assay | 3HIB INHIBITION $IC_{50}$ (μM) MEAN GM00371 cells Viablility Assay |
|---|---|---|
| 102 | C | C |
| 105 | B | C |
| 106 | N/D | D |
| 107 | D | D |
| 108 | N/D | D |
| 109 | B | B |
| 110 | N/D | D |
| 111 | N/D | D |
| 112 | C | D |
| 113 | D | C |
| 115 | N/D | D |
| 116 | D | D |
| 117 | N/D | D |
| 118 | N/D | D |
| 120 | N/D | D |
| 121 | N/D | D |
| 122 | N/D | D |
| 123 | D | D |
| 124 | D | D |
| 126 | B | D |
| 127 | D | D |
| 128 | D | D |
| 129 | D | D |
| 131 | D | D |
| 132 | N/D | D |
| 133 | D | D |
| 134 | C | D |
| 135 | B | C |
| 136 | A | A |
| 137 | B | B |
| 138 | D | D |
| 139 | D | D |
| 140 | C | C |
| 141 | D | D |
| 142 | N/D | D |
| 143 | N/D | D |
| 144 | N/D | D |
| 145 | A | B |
| 146 | N/D | D |
| 151 | A | B |
| 152 | B | B |
| 154 | A | B |

-continued

| Compoound | 3HIB INHIBITION $IC_{50}$ (μM) MEAN GM00371 cells Direct MS Assay | 3HIB INHIBITION $IC_{50}$ (μM) MEAN GM00371 cells Viablility Assay |
|---|---|---|
| 155 | C | C |
| 157 | A | A |
| 161 | B | B |
| 163 | B | B |
| 166 | N/D | B |
| 169 | N/D | D |
| 172 | B | B |
| 174 | B | C |
| 175 | A | B |
| 176 | B | B |
| 177 | A | B |
| 178 | D | D |
| 181 | D | D |
| 184 | B | B |
| 185 | C | C |
| 188 | B | N/D |
| 189 | B | N/D |
| 192 | C | C |
| 193 | B | C |
| 196 | ND | D |
| 197 | A | N/D |
| 198 | ND | D |
| 199 | A | N/D |
| 200 | N/D | D |
| 205 | N/D | D |
| 206 | N/D | B |
| 207 | A | B |
| 208 | D | B |
| 209 | N/D | B |
| 210 | N/D | D |
| 211 | N/D | B |
| 212 | N/D | A |
| 213 | N/D | A |
| 214 | N/D | B |
| 215 | N/D | B |
| 216 | N/D | D |
| 221 | N/D | D |
| 222 | N/D | B |
| 223 | N/D | B |
| 224 | N/D | B |
| 225 | N/D | D |
| 226 | N/D | C |
| 230 | N/D | D |
| 234 | N/D | D |
| 239 | N/D | B |
| 279 | N/D | D |
| 283 | N/D | D |
| 284 | N/D | D |
| 285 | N/D | C |
| 289 | N/D | C |
| 290 | N/D | D |
| 291 | B | B |
| 292 | B | B |
| 296 | B | C |
| 297 | N/D | B |
| 304 | N/D | D |

N/D: Not determined
A: <100 nM;
100 nM ≤ B < 500 nm;
500 ≤ C < 1000 nm;
D ≥ 1000 nM

Example 3: Synthesis of a BCAT2 Inhibitor Compound

Compound Synthesis

All solvents and reagents were used as obtained from commercial sources. 1H NMR spectra were recorded on a Varian Mercury 400 Plus. Chemical shifts are expressed in parts per million (ppm, δ units). Coupling constants (J) are in units of hertz (Hz). Splitting patterns describe apparent multiplicities and are designated as s (singlet), d (doublet), t (triplet), q (quartet), dd (double doublet), dt (double triplet), m (multiplet), br (broad). Analytical purity for a final compound was ≥95% unless stated otherwise. The purity of final compounds was checked using an Agilent 1100 HPLC system coupled with a Thermo Finnigan LCQ Mass Spectrometer. All mass spectra were performed by electrospray ionization (ESI). Two different HPLC conditions were used to analyze compound purity: LC-MS method A: 10-98% AcCN—$H_2O$ (0.1°% TFA) in 2.7 min, hold at 98% AcCN for 0.38 min, with the flow rate of 0.9 mL/min on a Phenomenex Luna 3μ C8(2) 100 A 30×3.00 mm column. LC-MS method B: 10-95% AcCN— $H_2O$ (0.1% formic acid) in 3.0 min, with the flow rate of 0.5 mL/min on a Kinetex 2.6μ C18 100 A 30×2.10 mm column. High resolution mass spectrometry (HRMS) was completed on a Waters qTOF Premiere mass spectrometer operating in W mode positive ionization with a resolving power of approximately 15000. Flow injection was completed using a Waters Nanoacquity LC. HRMS acceptable error is 3 mDa or 5 ppm, although most analyses are observed within 0.5 mDa with isotope fits in good agreement with the proposed structures. Purification of final compounds for biological testing was performed on a Gilson GX-281 system with a Phenomenex Luna 5μ C8(2) 100×21.20 mm 100 A column running gradient of 5-95% MeCN/$H_2O$ (+0.1% TFA or 0.1% formic acid) over 15-20 minutes with flow rate of 22 mL/min.

Tert-butyl (3-((4-(methylcarbamoyl-2-nitrophenyl) amino)cyclohexyl)carbamate (3)

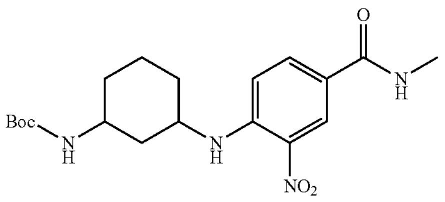 [SMILES: CNC(=O)c1ccc(NC2CCCC(NC(=O)OC(C)(C)C)C2)c([N+](=O)[O-])c1]

To a solution of 4-fluoro-3-nitrobenzoic acid (1.00 g, 5.40 mmol) in acetonitrile (40 mL) was added HATU (2.054 g, 5.40 mmol) and DIPEA (1.03 mL, 5.94 mmol). The reaction was stirred at room temperature for 15 min followed by addition of methanamine (HCl salt, 0.401 g, 5.94 mmol) and DIPEA (1.03 mL, 5.94 mmol). The reaction was continuously stirred for 3 h then was concentrated in vacuo. The residue was dissolved in water and extracted with ethyl acetate. The organic layer was washed with water, dried over $Na_2SO_4$, and condensed in vacuo to provide 4-fluoro-N-methyl-3-nitrobenzamide as a crude product. This crude product was dissolved in ethanol (40 mL) followed by addition of tert-butyl (3-aminocyclohexyl)carbamate (1.10 g, 5.13 mmol, racemic mixture of diastereomers) and DIPEA (1.03 mL, 5.94 mmol). The reaction was stirred at 85° C. for 6 h, then concentrated, and the residue was dissolved in ethyl acetate and washed with water. The organic layer was dried over $Na_2SO_4$ and condensed in vacuo to provide the title compound as a crude product with purity >95% (mixture of diatereomers). LC-MS (ESI) m/z $[M+1]^+$=392.7, Rt=2.13 min (HPLC method A).

Tert-butyl (3 (5-(methylcarbamoyl)-2-(2-(methylthio)phenyl-1H-benzo[d]imidazol-1-yl)cyclohexyl) carbamate (4)

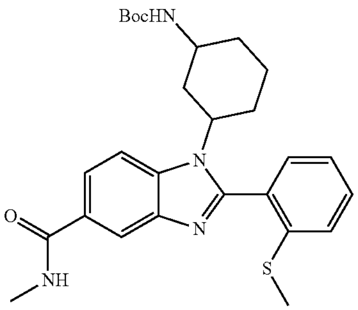 [SMILES: CNC(=O)c1ccc2c(c1)nc(-c1ccccc1SC)n2C1CCCC(NC(=O)OC(C)(C)C)C1]

To a solution of 4-fluoro-N-methyl-3-nitrobenzamide (69 mg, 0.35 mmol) in 1,4-Dioxane (4 mL) was added 1,1-dimethylethyl (3-aminocyclohexyl)carbamate (54 mg, 0.25 mmol) and DIPEA (87 μL, 0.5 mmol). The reaction was stirred at 80° C. for 24 h then was cooled to room temperature and added 2-(methylthio)benzaldehyde (38 mg, 0.25 mmol), sodium dithionite (131 mg, 0.75 mmol), and water (1.0 mL). The reaction was stirred at 80° C. for 24 h, then concentrated in vacuo. The residue was purified by preparative HPLC to afford the title compound 4 (48.9 mg, 39.5% yield). LC-MS (ESI) m/z $[M+1]^+$=495.2; Rt=1.97 min (HPLC method A).

cis 1-(3-(5-bromothiophene-2-carboxamido)cyclohexyl)-N-methyl-2-(pyridin-2-yl)-1H-benzo[d]imidazole-5-carboxamide (8b)

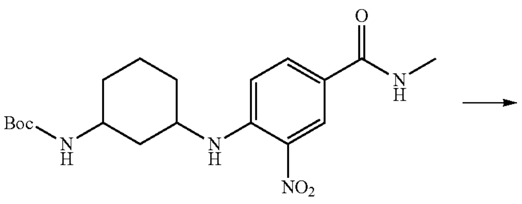

3

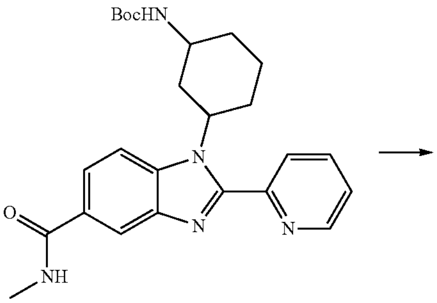

-continued

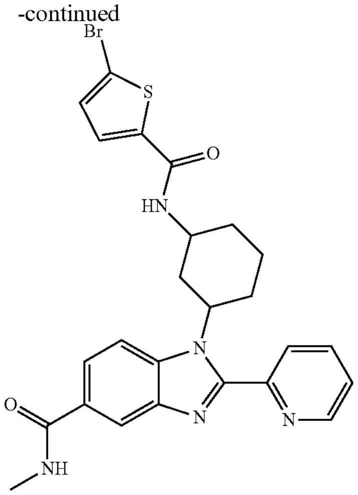

To a solution of the crude material 3 (5.4 mmol) in 1,4-dioxane (40 mL) was added picolinaldehyde (0.579 g, 5.40 mmol), sodium dithionite ($Na_2S_2O_4$)(5.64 g, 32.4 mmol) and water (10 mL). The reaction was stirred at 80° C. for 18 h, then concentrated in vacuo followed by extraction with ethyl acetate. The ethyl acetate layer was dried over $Na_2SO_4$ and condensed in vacua. The residue was purified by chromatography (silica gel column, UV detection at 298 nm, eluent system: 0-8% $CH_3OH$—$CH_2Cl_2$ over 40 min with flow rate of 60 mL/min) to yield intermediate tert-butyl (3-(5-(methylcarbamoyl)-2-(pyridin-2-yl)-1H-benzo[d]imidazol-1-yl)cyclohexyl)carbamate as a mixture of diastereomers (1.5 g, 62% yield for 3 steps from 4-fluoro-3-nitrobenzoid acid). LC-MS (ESI) m/z $[M+1]^+$=450.0; Rt=1.78 min (HPLC method A).

To the above intermediate (1.5 g, 3.34 mmol) in DCM (30 mL) was added dropwise TFA (2.57 mL, 33.4 mmol). The reaction was stirred at room temperature for 18 h. The reaction was condensed in vacuo and the resulting residue was dissolved in acetonitrile (30 mL) to provide solution A. In a separate vial, a reaction of 5-bromothiophene-2-carboxylic acid (0.691 g, 3.34 mmol), HATU (1.269 g, 3.34 mmol), and DIPEA (1.276 mL, 7.34 mmol) in acetonitrile (30 mL) was stirred at room temperature for 30 min. To this reaction was added the solution A. The resultant was stirred at room temperature for 4 h then was condensed in vacuo. The residue was participated between ethyl acetate and water. The aqueous layer was extracted twice by ethyl acetate and the combined ethyl acetate solution was washed with saturated $NaHCO_3$ solution followed by brine, then dried over $Na_2SO_4$ and concentrated to provide a crude product. The crude product was first purified by silica gel chromatography (ISCO system, detection at 298 nm, eluting with 0-8% $CH_3OH$—$CH_2Cl_2$ over 50 min at flow rate of 85 mL/min) to yield trans-isomer (800 mg) and a mixture of cis- and trans-isomers (857 mg). The combined yield for cis- and trans-isomers is 1.65 g (92% yield over 2 steps). The 857 mg of cis- and trans-mixture was further purified by preparative HPLC system (Column: Phenomenex Gemini C18 110A, Ax1A, 100×30.00 mm, 5μ column; flow rate: 40 mL/min; UV detection: 254 nm; gradient: 20-55% AcCN—$H_2O$ (0.2% formic acid as modifier) in 20 min) to yield pure cis-isomer product (8b, 305 mg). MS (ESI) m/z $[M+1]^+$=538.1 and 540.1; Rt=2.24 min (HPLC method B); $^1H$ NMR NMR (400 MHz, DMSO-$d_6$) δ 8.79-8.75 (m, 1H), 8.51-8.44 (m, 2H), 8.23 (s, 1H), 8.16 (dd, 1H, J=7.7, 1.4 Hz), 8.06-8.00 (m, 1H), 7.91-7.81 (m, 2H), 7.59-7.54 (m, 2H), 7.24 (dd, 1H, J=3.9, 0.8 Hz), 5.57-5.47 (m, 1H), 3.92-3.80 (m, 1H), 2.81 (d, 3H, J=4.3 Hz), 2.49-2.34 (m, 1H), 2.32-2.19 (m, 1H), 2.17-2.09 (m, 1H), 2.01-1.83 (m, 3H), 1.54-1.38 (m, 2H). HRMS $(M+H)^+$ calcd for $[C_{25}H_{24}BrN_5O_2S+H]$538.0812; found 538.0815. For the trans-isomer, LC-MS (ESI) m/z $[M+1]^+$=538.0 and 540.1; Rt=2.10 min (HPLC method B); $^1$H NMR NMR (400 MHz, DMSO-$d_6$) δ8.43-8.42 (m, 1H), 8.19 (d, 1H, J=4.0 Hz), 8.15 (s, 1H), 8.05-8.01 (m, 2H), 7.95 (d, 1H, J=9.2 Hz), 7.89 (dd, 1H, =8.0, 1.2 Hz), 7.75 (dd, 1H, J=8.8, 1.2 Hz), 7.67 (d, 1H, J=8.0 Hz), 7.38-7.35 (m, 1H), 7.28 (d, 1H, J=4.0 Hz), 5.55-5.49 (m, 1H), 4.26 (s, 1H), 2.76 (d, 3H, J=4.4), 2.44-2.42 (m, 1H), 2.38-2.28 (m, 2H), 1.93-1.92 (m, 2H), 1.90-1.83 (m, 1H), 1.77-1.74 (m, 1H), 1.67-1.63 (m, 1H). HRMS $(M+H)^+$ calcd for $[C_{25}H_{24}BrN_5O^2S+H]$ 538.0812; found 538.0814.

cis 1-(3-(5-bromothiophene-2-carboxamido)cyclohexyl)-N-methyl-2-(2-(methylthio)phenyl)-1H-benzo[d]imidazole-5-carboxamide (1)

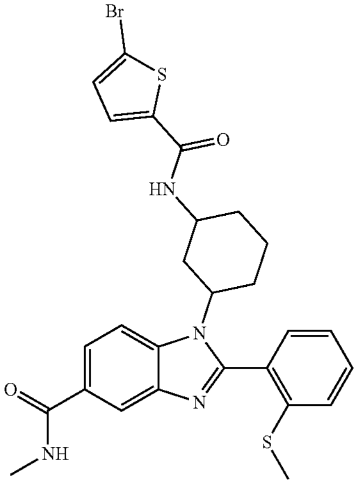 [SMILES: CNC(=O)c1ccc2c(c1)nc(-c1ccccc1SC)n2C1CCCC(NC(=O)c2ccc(Br)s2)C1]

Using 4 as a starting material, the title compound was prepared analogously to the synthesis of 8b as a white solid in 14% overall yield. LC-MS (ESI) m/z $[M+1]^+$=583.1; $^1$H NMR NMR (400 MHz, DMSO-$d_6$) δ 8.50-8.38 (m, 2H), 8.19 (s, 1H), 7.86-7.78 (m, 2H), 7.62-7.48 (m, 3H), 7.40 (d, 1H, J=7.1 Hz), 7.36-7.29 (m, 1H), 7.24 (dd, 1H, J=3.9, 0.7 Hz), 3.96-3.86 (m, 1H), 3.72-3.60 (m, 1H), 2.81 (d, 3H, J=4.3 Hz), 2.42 (s, 3H), 2.36-2.00 (m, 3H), 1.99-1.74 (m, 3H), 1.48-1.17 (m, 2H). HRMS $(M+H)^+$ calcd for $[C_{27}H_{27}BrN_4O_2S_2+H]$583.0837; found 583.0842.

cis 1-(3-(5-bromothiophene-2-carboxamido)cyclohexyl)-N-methyl-2 phenyl-1H-benzo[d]imidazole-5-carboxamide (8a)

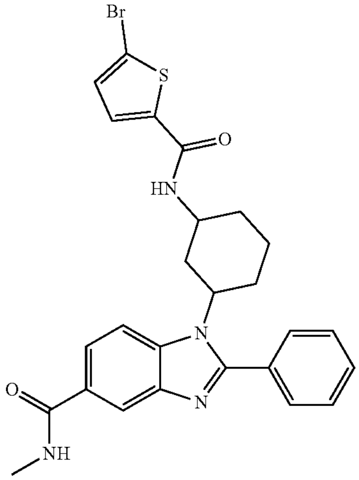 [SMILES: CNC(=O)c1ccc2c(c1)nc(-c1ccccc1)n2C1CCCC(NC(=O)c2ccc(Br)s2)C1]

The title compound was prepared analogously to the synthesis of 8b as a white solid in 12.5% overall yield. LC-MS (ESI) m/z $[M+1]^+$=537.3; $^1$H NMR NMR (400 MHz, CD OD) δ 8.27-8.25 (m, 1H), 8.14 (d, 1H, J=8.8 Hz), 8.03 (dd, 1H, J=8.8, 1.2 Hz), 7.83-7.71 (m, 5H), 7.48 (dd, 1H, J=3.9, 0.8 Hz), 7.13 (d, 1H, J=3.9 Hz), 4.70-4.60 (m, 1H), 3.97-3.88 (m, 1H), 2.98 (s, 3H), 2.52-2.33 (m, 3H), 2.17-1.99 (m, 3H), 1.64-1.45 (m, 2H). HRMS $(M+H)^+$ calcd for $[C_{26}H_{25}BrN_4O_2S+H]$ 537.0960; found 537.0961.

cis 1-(3-(5-bromothiophene-2-carboxamido)cyclohexyl)-(pyridin-2-yl)-1H-benzo[d]imidazole-5-carboxamide (8c)

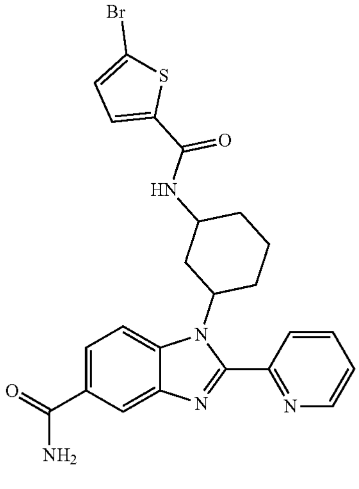 [SMILES: NC(=O)c1ccc2c(c1)nc(-c1ccccn1)n2C1CCCC(NC(=O)c2ccc(Br)s2)C1]

as shown below.

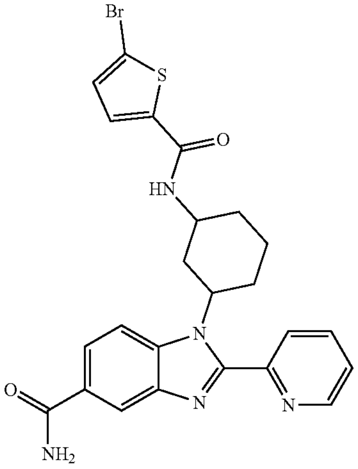 [SMILES: NC(=O)c1ccc2c(c1)nc(-c1ccccn1)n2C1CCCC(NC(=O)c2ccc(Br)s2)C1]

The title compound was prepared analogously to the synthesis of 8b as a white solid in 4.0% overall yield. LC-MS (ESI) m/z $[M+1]^+$=524.4 and 526.5; 1H NMR NMR (400 MHz, DMSO-d) δ 8.78 (dd, 1H, J=5.9, 0.8 Hz), 8.47 (d, 1H, J=7.8 Hz), 8.29 (s, 1H), 8.16 (d, 1H, J=7.8 Hz), 8.05-8.01 (m, 2H), 7.88 (s, 2H), 7.58-7.55 (m, 2H), 7.31 (s, 1H), 7.23 (d, 1H, J=4.3 Hz), 5.55-5.49 (m, 1H), 3.85-3.69 (m, 1H), 2.47-2.39 (m, 1H), 2.36-2.25 (m, 1H), 2.13-2.10 (m, 1H), 1.96-1.88 (m, 3H), 1.48-1.44 (m, 2H). HRMS $(M+H)^+$ calcd for $[C_{24}H_{22}BrN_5O_2S+H]$ 524.0756; found 524.0757.

as shown below.

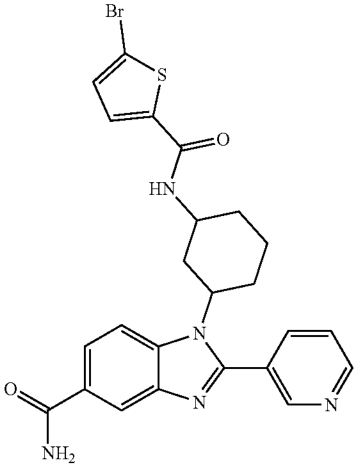 [SMILES: NC(=O)c1ccc2c(c1)nc(-c1cccnc1)n2C1CCCC(NC(=O)c2ccc(Br)s2)C1]

The title compound was prepared analogously to the synthesis of 8b as a white solid in 4.6% overall yield for 5 steps (from 4-fluoro-3-nitro-benzoid acid). LC-MS (ESI) m/z=524.6 and 526.1; $^1$H NMR NMR (400 MHz, DMSO-$d_6$) δ 8.88 (d, 1H, J=2.4 Hz), 8.79 (d, 1H, J=4.2 Hz), 8.45 (d, 1H, J=7.8 Hz), 8.29 (s, 1H), 8.12 (m, 1H), 8.03 (s, 1H), 7.88 (s, 2H), 7.66 (d, 1H, J=5.1 Hz), 7.64 (d, 1H, J=5.8 Hz), 7.55 (d, 1H, J=3.9 Hz), 7.32 (m, 1H), 7.24 (d, 1H, J=3.9 Hz), 4.38 (m, 1H), 3.82 (m, 1H), 1.98-1.95 (m, 1H), 2.38-2.35 (m, 1H), 2.48-2.42 (m, 1H), 1.90-1.83 (m, 2H), 1.42-1.44 (m, 2H). HRMS $(M+H)^+$ calcd for $[C_{24}H_{22}BrN_5O_2S+H]$ 524.0756; found 524.0753.

The title compound was prepared analogously to the synthesis of 8b as a white solid in 4.0% overall yield for 5 steps (from 4-fluoro-3-nitro-benzoid acid). LC-MS (ESI) m/z $[M+1]^+$=524.6 and 526.1; H NMR NMR (400 MHz, DMSO-$d_6$) δ8.82 (d, 2H, J=5.5 Hz), 8.45 (d, 1H, J=8.4 Hz), 8.30 (s, 1H), 8.03 (m, 1H), 7.88 (s, 2H), 7.74 (d, 2H, J=5.5 Hz), 7.55 (d, 1H, J=3.5 Hz), 7.33 (m, 1H), 7.24 (d, 1H, J=3.2 Hz), 4.44 (m, 1H), 3.88 (m, 1H), 2.42-2.39 (m, 1H), 2.36-2.33 (m, 1H), 2.22-2.12 (m, 1H), 1.99-1.96 (m, 1H), 1.99-1.96 (m, 2H), 1.43 (m, 2H). HRMS $(M+H)^+$ calcd for $[C_{24}H_{22}BrN_5O_2S+H]$ 524.0756; found 524.0757.

cis N-(3-aminocyclohexyl)-5-bromothiophene-2-carboxamide (6, TFA Salt)

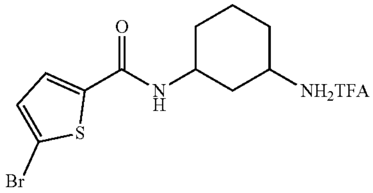

To a solution of 5-bromothiophene-2-carboxylic acid (19.27 g, 93 mmol) in DCM (200 mL) was added HOBt (16.29 g, 106 mmol), EDCI (20.40 g, 106 mmol) and triethylamine (29.7 mL, 213 mmol). The mixture was stirred at room temperature for 30 minutes. Then tert-butyl (3-aminocyclohexyl)carbamate (19.0 g, 89 mmol) was added. The reaction was stirred at room temperature overnight. The precipitate was filtered, washed with DCM to give the cis-compound cis-tert-butyl-3-(5-bromothiophene-2-carboxamido)cyclohexyl)carbamate (mixture of two cis-isomers, 12.0 g, 29.8 mmol, 33.6% yield) as a white solid (the filtrate contains mainly the trans isomers). LC-MS (ESI) m/z=405.0 $(M+H)^+$; $^1$H NMR (300 MHz, DMSO-$d_6$) δ 8.37 (d, J=7.78 Hz, 1H), 7.62 (d, J=3.99 Hz, 1H), 7.26 (d, J=3.99 Hz, 1H), 6.85 (d, J=7.78 Hz, 1H), 3.7 (m, 1H), 3.26 (m, 1H), 1.93 (d, J=11.58 Hz, 1H), 1.73 (m, 3H), 1.38 (br. s., 9H), 1.31-1.14 (m, 4H). To the above Boc protected intermediate cis-tert-butyl-3-(5-bromothiophene-2-carboxamido)cyclohexyl)carbamate (12.0 g, 29.8 mmol) in DCM (100 mL) was added TFA (22.10 mL, 298 mmol). The mixture was stirred at room temperature for 4 h then concentrated in vacuo to give a brown viscous oil. This oil was triturated with diisopropyl ether to give the title compound 6 (12.0 g, 97% yield) as a beige powder. LC-MS (ESI) m/z=304.9 $(M+H)^+$.

cis 5-bromo-N-3-((4-(methylcarbamoyl)-2-nitrophenyl)amino)cyclohexyl)thiophene-2-carboxamide (7)

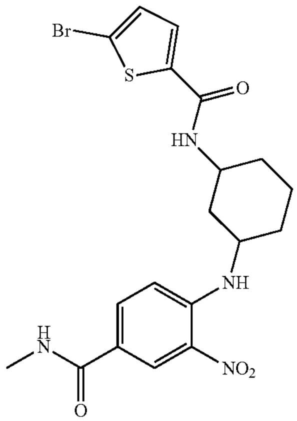 [SMILES: CNC(=O)c1ccc(NC2CCCC(NC(=O)c3ccc(Br)s3)C2)c([N+](=O)[O-])c1]

To a solution of 4-fluoro-N-methyl-3-nitrobenzamide (4.99 g, 25.2 mmol) in ethanol (100 mL), was added compound 6 (TFA salt, 10.0 g, 23.97 mmol) followed by DIEA (8.71 mL, 52.7 mmol). The resultant was heated at 85° C. for 6 h, then at room temperature overnight. The reaction was concentrated in vacuo, and the residue was treated with water and ethyl acetate (200 mL). The yellow solid formed was filtered and washed with diisopropyl ether to give, after drying, the title compound 7 (8.8 g, 76% yield) as a yellow powder. LC-MS: Rt=3.07 min, MS (ESI) m/z=482.8 (M+H)+; $^1$H NMR (300 MHz, DMSO-$d_6$) δ8.63 (s, 5H), 8.45 (m, 2H), 8.10 (d, J=7.78 Hz, 1H), 7.98 (d, J=8.73 Hz, 1H), 7.62 (d, J=3.80 Hz, 1H), 7.25 (m, 2H), 3.91 (m, 1H), 3.87 (m, 1), 2.77 (d, J=3.99 Hz, 3H), 2.22 (m, 1H), 2.02 (m, 1H), 1.9-1.79 (m, 2H), 1.47 (m, 2H), 1.31 (m, 2H).

cis 1-3-(5-bromothiophene-2-carboxamido)cyclohexyl)N-methyl-2-(thiophen-2-yl)-1H-benzo[d]imidazole-5-carboxamide (8f)

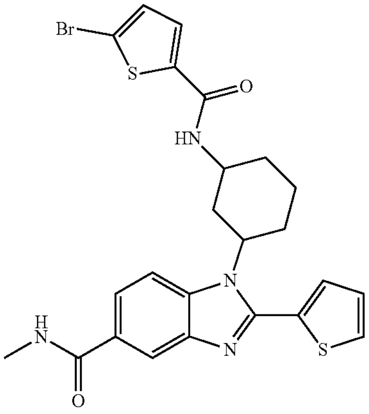 [SMILES: CNC(=O)c1ccc2c(c1)nc(-c1cccs1)n2C1CCCC(NC(=O)c2ccc(Br)s2)C1]

Compound 7 (241 mg, 0.5 mmol), thiophene-2-carbaldehyde (72.9 mg, 0.650 mmol), and sodium dithionite (0.261 g, 1.500 mmol) were mixed in 1,4-dioxane (4 mL) and $H_2O$ (2 mL). The reaction mixture was heated at 130° C. for 1 h under microwave irradiation. The reaction mixture was then concentrated in vacuo. Water was added to the residue and the aqueous phase was extracted with ethyl acetate (2×50 mL). The organic phase was washed with water, then dried over $Na_2SO_4$ and concentrated in vacuo. The residue was chromatographed on a silic gel column eluted with $CH_2Cl_2$/MeOH=94/6 (v/v) to afford the title compound 8f in 29.4% yield (80 mg) as a yellow solid. LC-MS (ESI) m/z 544.8 $(M+H)^+$; $^1$H NMR (300 MHz, DMSO-$d_6$) δ 8.49 (m, 2H), 8.19 (br s, 1H), 7.96-7.75 (m, 3H), 7.60 (br s, 2H), 7.3 (m, 2H), 4.79 (br s, 1H), 3.94 (br s, 1H), 2.83 (br s, 3H), 2.46-2.22 (m, 2H), 2.16 (m, 1H), 1.94 (m, 3H), 1.54 (m, 2H); HRMS $(M+H)^+$ calcd for $[C_{24}H_{23}BrN_4O_2S_2+H]$ 543.0524; found 543.0547.

cis 1-3-(5-bromothiophene-2-carboxamido)cyclohexyl)-N-methyl-2-(thiophen-3-yl)-1H-benzo[d]imidazole-5-carboxamide (8g)

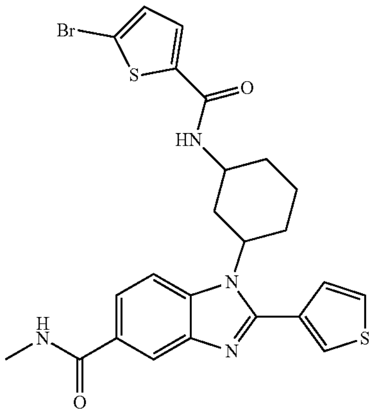 [SMILES: CNC(=O)c1ccc2c(c1)nc(-c1ccsc1)n2C1CCCC(NC(=O)c2ccc(Br)s2)C1]

The title compound was prepared analogously to the synthesis of 8f as a yellow solid in 33.1% yield. LC-MS (ESI) m/z=544.8 $(M+H)^+$; $^1$H NMR (300 MHz, DMSO-$d_6$) δ 8.49 (m, 2H), 8.20 (s, 1H), 8.05 (br s, 1H), 7.83 (br s, 3H), 7.59 (m, 1H), 7.50 (d, J=4.18 Hz, 1H), 7.26 (m, 1H), 4.59 (br s, 1H), 3.88 (br s, 1H) 2.83 (m, 3H), 2.43-2.26 (m, 2H), 2.12 (m, 1H), 2.05-1.80 (m, 3H), 1.48 (m, 2H); HRMS $(M+H)^+$ calcd for $[C_{24}H_{23}BrN_4O_2S_2+H]$ 543.0524; found 543.0543.

cis 1-3-(5-bromothiophene-2-carboxamido)cyclohexyl)-N-methyl-2-(2-methylthiazol-4-yl)-1H-benzo[d]imidazole-5-carboxamide (8h)

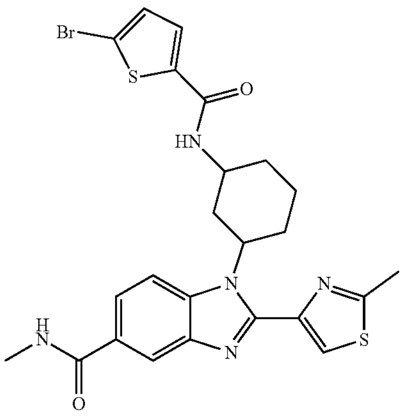

To a solution of compound 7 (241 mg, 0.5 mmol) in 1,4-dioxane (10 mL) and water (1 mL) was added 2-methylthiazole-4-carbaldehyde (95 mg, 0.750 mmol) and sodium dithionite (261 mg, 1.500 mmol). The resultant was heated at 85° C. for 24 h, then cooled to room temperature. The reaction was concentrated in vacuo, and the residue was treated with water and ethyl acetate (20 mL). The off-white solid formed was filtered off and washed with diisopropyl ether to give, after drying, the title compound 8h as a off white powder (160 mg, 57.3% yield). LC-MS $(ESI)_m$; z=559.8 $(M+H)^+$; $^1H$ NMR (300 MHz, DMSO-$d_6$) δ 8.48 (m, 2H), 8.26 (s, 1H), 8.19 (s, 1H), 7.83 (m, 2H), 7.6 (d, J=3.99 Hz, 1H), 7.27 (d, J=3.99 Hz, 1H), 5.47 (m, 1H), 3.91 (m, 1H), 2.82 (m, 6H), 2.47-2.17 (m, 2H), 2.10 (d, J=10.82 Hz, 1H), 1.94 (d, J=7.59 Hz, 3H), 1.5 (m, 2H).

cis 1-3-(5-bromothiophene-2-carboxamido)cyclohexyl)N-methyl-2-(thiazol-2-yl)-1H-benzo[d]imidazole-5-carboxamide (8i)

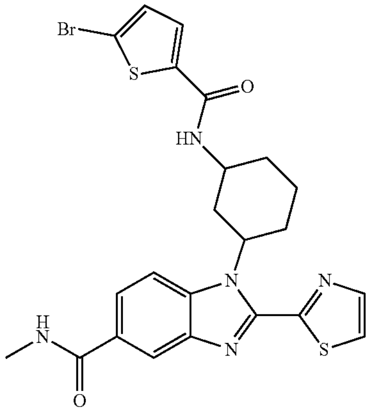 [SMILES: CNC(=O)c1ccc2c(c1)nc(-c1nccs1)n2C1CCCC(NC(=O)c2ccc(Br)s2)C1]

The title compound was prepared analogously to the synthesis of 8h as a cream powder in 25.7% yield. LC-MS (ESI) m/z=545.8 $(M+H)^+$; $^1H$ NMR (300 MHz, DMSO-$d_6$) δ8.52 (m, 2H), 8.25 (s, 1H), 8.17 (d, J=3.23 Hz, 1H), 8.04 (d, J=3.23 Hz, 1H), 7.89 (q, 0.1=8.73 Hz, 2H), 7.60 (d, J=3.99 Hz, 1H), 7.27 (d, J=3.99 Hz, 1H), 6.11 (br s, 1H), 3.97 (br s, 1H), 2.83 (d, J=4.37 Hz, 3H), 2.22-2.48 (m, 2H), 2.15 (d, J=11.58 Hz, 1H), 1.96 (d, J=8.54 Hz, 3H), 1.53 (m, 2H).

cis 1-3-(5-bromothiophene-2-carboxamido)cyclohexyl)-N-methyl-2-(1H-pyrazol-3-yl)-1H-benzo[d]imidazole-5-carboxamide (8j)

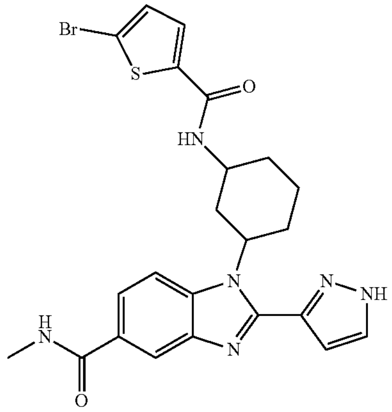 [SMILES: CNC(=O)c1ccc2c(c1)nc(-c1cc[nH]n1)n2C1CCCC(NC(=O)c2ccc(Br)s2)C1]

The title compound was prepared analogously to the synthesis of 8h as a yellow solid in 70.2% yield. LC-MS (ESI) m/z=528.9 $(M+H)^+$; $^1H$ NMR (300 MHz, DMSO-$d_6$) δ 8.55 (d, J=6.64 Hz, 2H), 8.21 (br s, 1H), 8.07 (br s, 1H), 7.98 (d, J=8.54 Hz, 1H), 7.88 (d, J=8.16 Hz, 1H), 7.60 (d, J=3.99 Hz, 1H), 7.27 (d, J=3.99 Hz, 1H), 7.04 (br s, 1H), 5.76 (br s, 1H), 3.95 (br s, 1H), 2.84 (d, J=3.99 Hz, 3H), 2.25-2.47 (m, 2H), 2.18 (m, 1H), 1.95 (m, 3H), 1.52 (m, 2H).

cis 1-3-(5-cyanothiophene-2-carboxamido)cyclohexyl)-2-(pyridin-2-yl)-1H-benzo[d]imidazole-5-carboxamide (9Aa)

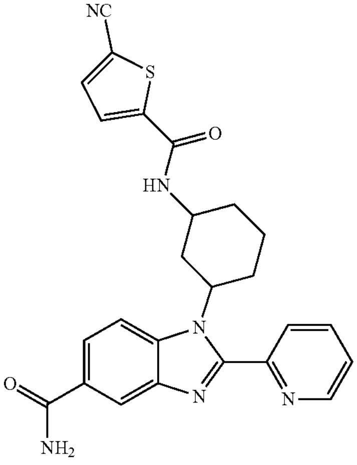

Using 5-cyanothiophene-2-carboxylic acid instead of 5-bromothiophene-2-carboxylic acid, the title compound was prepared analogously to the synthesis of 8b as a white solid. LC-MS (ESI) m/z $[M+1]^+$471.2; $^1H$ NMR (400 MHz, DMSO-$d_6$) δ 8.81-8.77 (m, 2H), 8.30 (s, 1H), 8.18 (d, 1H, J=6.8 Hz), 8.03 (m, 2H), 7.95 (d, 1H, J=4.0 Hz), 7.88 (s, 2H), 7.82 (d, 1H, J=3.6 Hz), 7.56 (m, 1H), 7.32 (m, 1H), 5.55 (m, 1H), 3.89 (m, 1H), 2.31 (m, 2H), 2.26 (m, 1H), 1.91 (m, 3H), 1.49 (m, 2H). HRMS $(M+H)^+$ calcd for $[C_{25}H_{22}N_6O_2S+H]$ 471.1603; found 471.1608.

cis 1-(3-(5-chlorothiophene-2-carboxamido)cyclohexyl)-2-(pyridin-2-yl)-1H-benzo[d]imidazole-5-carboxamide (9Ab)

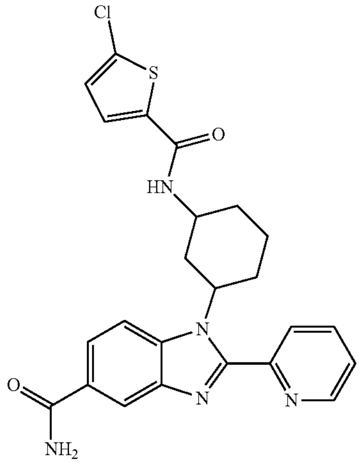 [SMILES: NC(=O)c1ccc2c(c1)nc(-c1ccccn1)n2C1CCCC(NC(=O)c2ccc(Cl)s2)C1]

Using 5-chlorothiophene-2-carboxylic acid instead of 5-bromothiophene-2-carboxylic acid, the title compound was prepared analogously to the synthesis of 8b as a white solid. LC-MS (ESI) m/z $[M+1]^+$=480.2 and 482.1; $^1H$ NMR (400 MHz, DMSO-$d_6$) δ 8.78 (d, 1H, J=4.4 Hz), 8.49 (d, 1H, J=8.0 Hz), 8.30 (s, 1H), 8.18 (d, 1H, J=7.6 Hz), 8.05-8.02 (m, 2H), 7.87 (s, 2H), 7.61 (d, 1H, J=3.6 Hz), 7.58-7.55 (m, 1H), 7.32 (br, 1H), 7.14 (d, 1H, J=4.0 Hz), 5.54 (m, 1H), 3.88 (m, 1H), 2.31 (m, 2H), 2.13 (m, 1H), 1.89-1.91 (m, 3H), 1.46 (m, 2H). HRMS $(M+H)^+$ calcd for $[C_{24}H_{22}ClN_5O_2S+H]$ 480.1261; found 480.1263.

cis 1-(3-(S-methylthiophene-2-carboxamido)cyclohexyl)-2-(pyridin-2 yl)-1H-benzo[d]imidazole-5-carboxamide (9Ac)

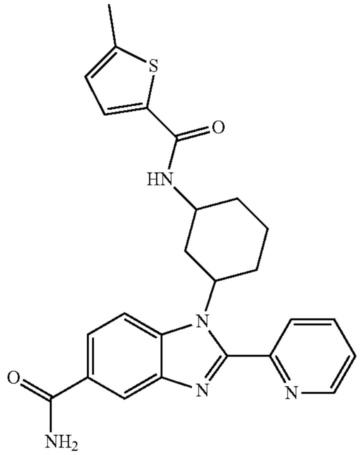 [SMILES: Cc1ccc(C(=O)NC2CCCC(n3c(-c4ccccn4)nc4cc(C(N)=O)ccc43)C2)s1]

Using 5-methylthiophene-2-carboxylic acid instead of 5-bromothiophene-2-carboxylic acid, the title compound was prepared analogously to the synthesis of 8b as a white solid. LC-MS (ESI) m/z $[M+1]^+$=460.2; $^1H$ NMR (400 MHz, DMSO-$d_6$) δ 8.78 (d, 1H, J=4.8 Hz), 8.30 (s, 1H), 8.25

(d, 1H, J=9.6 Hz), 8.17 (d, 1H, J=7.6 Hz), 8.04 (m, 2H), 7.89 (s, 2H), 7.60-7.57 (m, 1H), 7.52 (d, 1H, J=3.6 Hz), 7.34 (br, 1H), 6.80 (d, 1H, J=4.0 Hz), 5.52 (m, 1H), 3.86 (m, 1H), 2.30-2.21 (m, 2H), 2.13 (m, 1H), 1.96 (m, 1H), 1.89 (m, 2H), 1.46 (m, 2H). HRMS $(M+H)^+$ calcd for $[C_{25}H_{25}N_5O_2S+H]$ 460.1807; found 460.1808.

cis 1-(3-(5-bromo-N-methylthiophene-2-carboxamido)cyclohexyl)-2-(pyridin-2-yl)-1H-benzo[d]imidazole-5-carboxamide (9Ad)

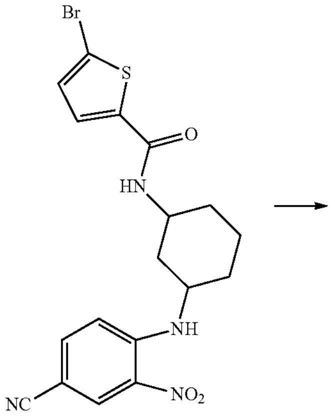

I

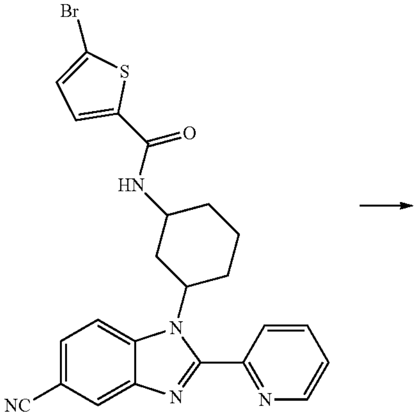

II

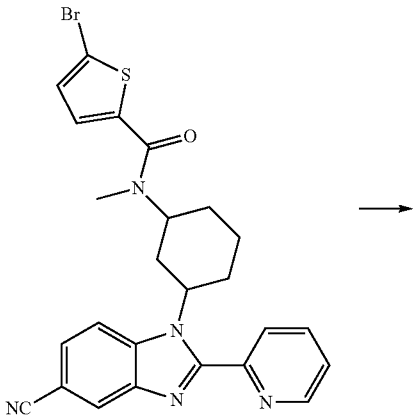

III

-continued

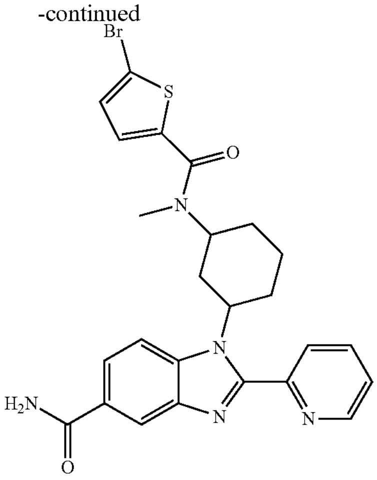

9Ad

To a solution of 4-fluoro-3-nitrobenzonitrile (0.717 g, 4.31 mmol) in ethanol (20 mL) was added cis N-(-3-aminocyclohexyl)-5-bromothiophene-2-carboxamide (TFA salt, 1.5 g, 3.60 mmol) and then DIEA (1.307 mL, 7.91 mmol). The reaction mixture was heated at 85° C. for 6 hours and then at room temperature overnight. Ethanol was removed in vacuo then water was added followed by ethyl acetate (200 mL). The yellow solid formed was collected and triturated with diisopropyl ether to afford compound i (mixture of cis-isomers)(1.25 g, 77% yield) as a yellow powder. LC-MS (ESI) m/z=448.8 $(M+H)^+$; $^1H$ NMR (300 MHz, DMSO-$d_6$) δ 8.52 (d, J=1.90 Hz, 1H), 8.43 (d, J=7.59 Hz, 1H), 8.23 (d, J=7.97 Hz, 1H), 7.85 (dd, J=9.11, 1.71 Hz, 1H), 7.62 (d, J=3.99 Hz, 1H), 7.22-7.39 (m, 2H), 3.90 (br s, 2H), 2.18 (m, 1H), 1.98 (d, J=9.87 Hz, 1H), 1.74-1.92 (m, 2H), 1.20-1.59 (m, 4H). Using compound i and picolinaldehyde as starting material, compound ii (mixture of cis-isomers) was prepared analogously to 8h as a cream solid in 43.4% yield. LC-MS (ESI) m/z=507.9 $(M+H)^+$; $^1H$ NMR (300 MHz, DMSO-$d_6$) δ 8.81 (d, J=4.18 Hz, 1H), 8.50 (d, J=7.78 Hz, 1H), 8.32 (d, J=1.14 Hz, 1H), 8.21 (d, J=7.97 Hz, 1H), 7.98-8.14 (m, 2H), 7.74 (dd, J=8.64, 1.42 Hz, 1H), 7.53-7.68 (m, 2H), 7.27 (d, J=3.99 Hz, 1H), 5.58 (t, J=12.24 Hz, 1H), 3.90 (br s, 1H), 2.40 (q, J=12.08 Hz, 1H), 2.27 (d, J=8.92 Hz, 1H), 2.16 (m, 1H), 1.82-2.08 (m, 3H), 1.35-1.61 (m, 2H). To a solution of compound ii (950 mg, 1.876 mmol) in DMF (20 mL) was added sodium hydride (90 mg, 3.75 mmol) and then iodomethane (293 mg, 2.064 mmol). The reaction mixture was stirred at room temperature for 4 h and then concentrated under reduced pressure. The residue was partitioned between water and ethyl acetate (20 mL). The organic layer was washed twice with water, then dried over anhydrous $Na_2SO_4$ and concentrated under reduced pressure. The residue was triturated with diisopropyl ether/ $CH_2Cl_2$, and the resulting precipitate was filtered and dried to give compound iii (mixture of cis-isomers) as a off-white solid (910 mg, 93% yield). LC-MS (ESI) m/z=521.9 $(M+H)^+$. A mixture of compound iii (894 mg, 1.718 mmol)

in sulfuric acid (2000 mg, 20.39 mmol) and water (37.1 mg, 2.061 mmol) was stirred at room temperature for 1 h and then diluted with water and ethyl acetate (20 mL). The mixture was neutralised with NaOH (1N). The organic layer was washed twice with water, then dried over anhydrous $Na_2SO_4$ and concentrated under reduced pressure. The residue was purified by chromatography on a silica gel column eluted with $CH_2Cl_{1-2}$/MeOH (95/5, v/v) to afford the desired compound 9Ad (mixture of cis-isomers)(200 mg, 21.62% yield) as a white solid. LC-MS (ESI) m/z=540.0 $(M+H)^+$; $^1H$ NMR (300 MHz, $CDCl_3$) δ 8.74 (d, J=4.36 Hz, 1H), 8.28 (m, 2H), 7.92 (m, 2H), 7.76 (d, J=8.54 Hz, 1H), 7.44 (ddd, J=7.54, 4.89, 1.04 Hz, 1H), 7.14 (d, J=3.80 Hz, 1H), 7.03 (d, J=3.80 Hz, 1H), 5.77 (m, 1H), 4.54 (br s, 1H), 3.15 (s, 3H), 2.60 (q, 0.1=12.08 Hz, 1H), 2.3 (m, 2H), 2.11 (m, 2H), 1.93 (m, 1H), 1.48-1.85 (m, 2H). HRMS $(M+H)^+$ calcd for $[C_{25}H_{24}BrN_5O_2S+H]$ 538.0912; found 538.0934.

cis 1,3-(5-bromothiophene-2-sulfonamido)cyclohexyl)-2-(pyridin-2-yl)-1H-benzo[d]imidazole-5-carboxamide (9Ae)

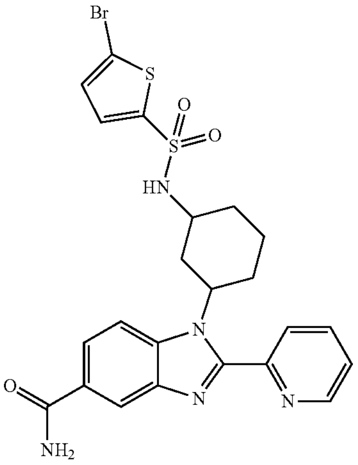 [SMILES: NC(=O)c1ccc2c(c1)nc(-c1ccccn1)n2C1CCCC(NS(=O)(=O)c2ccc(Br)s2)C1]

Using 5-bromothiophene-2-sulfonyl chloride instead of 5-bromothiophene-2-carboxylic acid, the title compound was prepared analogously to 8b in 43.3% yield (13.4 mg). LC-MS (ESI) m/z $[M+1]^+$=560.1 and 562.1; 1H NMR (400 MHz, DMSO-$d_6$) δ 8.72 (d, 1H, J=4.4 Hz), 8.29 (s, 1H), 8.19 (d, 1H, J=7.2 Hz), 8.16 (d, 1H, J=8.0 Hz), 8.04 (m, 2H), 7.85 (s, 2H), 7.58 (m, 1H), 7.45 (d, 1H, J=4.0 Hz), 7.33 (br, 1H), 7.30 (d, 1H, J=4.4), 5.34 (m, 1H), 3.23 (m, 1H). 2.26-2.21 (m, 2H), 2.03 (m, 1H), 1.83-1.79 (m, 3H), 1.41 (m, 2H). HRMS $(M+H)^+$ calcd for $[C_{23}H_{22}BrN_5O_3S_2+H]$ 560.0426; found 560.0423.

Using 5-bromothiophene-2-sulfonyl chloride instead of 5-bromothiophene-2-carboxylic acid, the title compound was prepared analogously to 8b in 43.3% yield (13.4 mg). LC-MS (ESI) m/z $[M+1]^+$=560.1 and 562.1; $^1H$ NMR (400 MHz, DMSO-$d_6$) δ8.72 (d, 1H, J=4.4 Hz), 8.29 (s, 1H), 8.19 (d, 1H, J=7.2 Hz), 8.16 (d, 114, J=8.0 Hz), 8.04 (m, 2H), 7.85 (s, 2H), 7.58 (m, 1H), 7.45 (d, 1H, J=4.0 Hz), 7.33 (br, 1H), 7.30 (d, 1H, J=4.4), 5.34 (m, 1H), 3.23 (m, 1H), 2.26-2.21 (m, 2H), 2.03 (m, 1H), 1.83-1.79 (m, 3H), 1.41 (m, 2H). HRMS $(M+H)^+$ calcd for $[C_{23}H_{22}BrN_5O_3S_2+H]$ 560.0426; found 560.0423.

cis-2-bromo-N-(3-(5-(methylcarbamoyl)-2-(pyridin-2-yl)-1H-benzo[d]imidazol-1-yl)cyclohexyl)thiazole-5-carboxamide (9Ba)

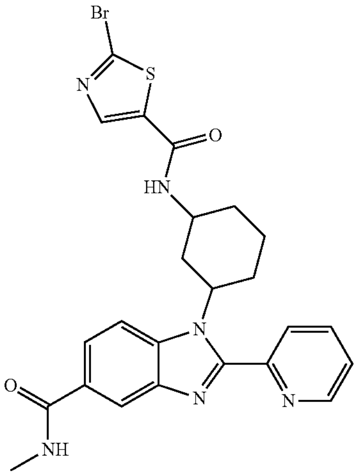 [SMILES: CNC(=O)c1ccc2c(c1)nc(-c1ccccn1)n2C1CCCC(NC(=O)c2cnc(Br)s2)C1]

Using 2-bromothiazole-5-carboxylic acid instead of 5-bromothiophene-2-carboxylic acid, the title compound was prepared analogously to 8b in 32% yield (63 mg). LC-MS (ESI) m/z=540.8 $(M+H)^+$; $^1H$ NMR (300 MHz, DMSO-$d_6$) δ 8.79 (d, J=4.18 Hz, 1H), 8.73 (d, J=7.78 Hz, 1H), 8.49 (d, J=4.55 Hz, 1H), 8.27 (s, 1H), 8.2 (m, 2H), 8.05 (td, J=7.73 Hz, 1.61 Hz, 1H), 7.87 (m, 2H), 7.58 (td, J=6.17, 0.95 Hz, 1H), 5.56 (t, J=12.15 Hz, 1H), 3.9 (m, 1H), 2.83 (d, J=4.37 Hz, 3H), 2.23-2.47 (m, 2H), 2.17 (d, J=11.20 Hz, 1H), 1.83-2.06 (m, 3H), 1.57 (m, 2H); HRMS $(M+H)^+$ calcd for $[C_{24}H_{23}BrN_6O_2S+H]$ 539.0865; found 539.0856.

cis 1-(3-(5-bromo-1-methyl-1H pyrrole-2-carboxamido)cyclohexyl)-N-methyl-2-(pyridin-2-yl)-1H-benzo[d]imidazole-5-carboxamide (9Bb)

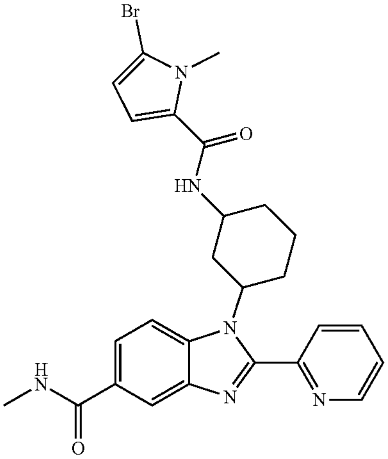 [SMILES: CNC(=O)c1ccc2c(c1)nc(-c1ccccn1)n2C1CCCC(NC(=O)c2ccc(Br)n2C)C1]

Using 5-bromo-1-methyl-1H-pyrrole-2-carboxylic acid instead of 5-bromothiophene-2-carboxylic acid, the title compound was prepared analogously to 8b as a cream solid in 30.7% yield. LC-MS (ESI) m/z=536.9 $(M+H)^+$; $^1H$ NMR (300 MHz, DMSO-$d_6$) δ 8.80 (d, J=4.18 Hz, 1H), 8.48 (d, J=4.36 Hz, 1H), 8.22 (m, 2H), 8.04 (m, 2H), 7.87 (m, 2H), 7.58 (m, 1H), 6.82 (d, J=3.99 Hz, 1H), 6.22 (d, J=3.99 Hz, 1H), 5.57 (br. s., 1H), 3.87 (m, 1H), 3.8 (s, 3H), 2.84 (d, J=4.18 Hz, 3H), 2.43 (m, 1H), 2.26 (d, J=10.06 Hz, 1H), 2.10 (d, J=11.20 Hz, 1H), 1.99-1.89 (m, 3H), 1.46 (m, 2H). HRMS $(M+H)^+$ calcd for $[C_{26}H_{27}BrN_6O_2+H]$, 535.1457; found 535.1448.

cis-1-(3-(4-bromo-1H-pyrrole-2-carboxamido)cyclohexyl)-N-methyl-2-(pyridin-2-yl)-1H-benzo[d]imidazole-5-carboxamide (9Bc)

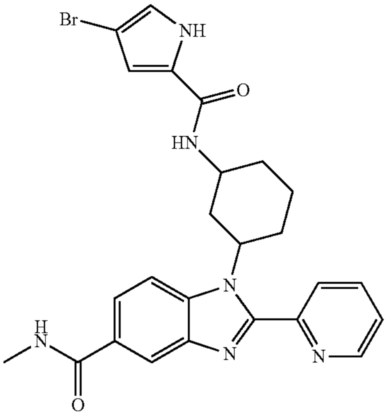 [SMILES: CNC(=O)c1ccc2c(c1)nc(-c1ccccn1)n2C1CCCC(NC(=O)c2cc(Br)c[nH]2)C1]

Using 4-bromo-1H-pyrrole-2-carboxylic acid instead of 5-bromothiophene-2-carboxylic acid, the title compound was prepared analogously to 8b as white solid in 7.4% yield. LC-MS (ESI) m/z=523.0 $(M+H)^+$; $^1H$ NMR (300 MHz, DMSO-$d_6$) δ 11.79 (br s, 1H), 8.80 (br s, 1H), 8.49 (br s, 1H), 8.26 (br s, 1H), 8.20 (d, J=7.78 Hz, 1H), 8.04 (m, 2H), 7.89 (m, 2H), 7.59 (br s, 1H), 6.95 (br s, 1H), 6.86 (br s, 1H), 5.55 (br s, 1H), 3.90 (br s, 1H), 2.84 (br s, 3H), 2.41-2.13 (m, 3H), 1.92 (m, 3H), 1.46 (m, 2H). HRMS $(M+H)^+$ calcd for $[C_2SH_{25}BrN_6O_2+H]$ 521.1301; found 521.1252.

cis-3-chloro-N-(3-(5-(methylcarbamoyl)-2-(pyridin-2-yl)-1H-benzo[d]imidazol-1-yl)cyclohexyl)isoxazole-5-carboxamide (9Bd)

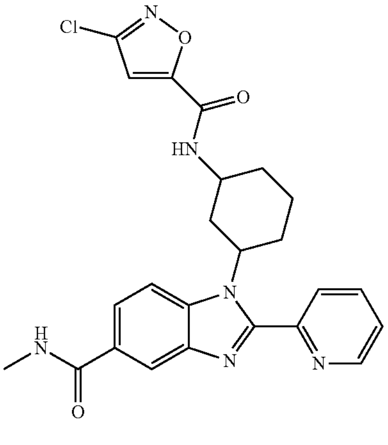 [SMILES: CNC(=O)c1ccc2c(c1)nc(-c1ccccn1)n2C1CCCC(NC(=O)c2cc(Cl)no2)C1]

Using 3-chloroisoxazole-5-carboxylic acid instead of 5-bromothiophene-2-carboxylic acid, the title compound was prepared analogously to 8b as white solid in 66.4% yield. LC-MS (ESI) to/z=479.1 $(M+H)^+$; $^1H$ NMR (300 MHz, DMSO-$d_6$) δ 9.07 (d, J=7.97 Hz, 1H), 8.79 (d, J=4.36 Hz, 1H), 8.48 (d, J=4.36 Hz, 1H), 8.27 (s, 1H), 8.20 (d, J=7.97 Hz, 1H), 8.04 (td, J=7.69, 1.52 Hz, 1H), 7.87 (m, 2H), 7.58 (dd, J=6.93, 5.41 Hz, 1H), 7.36 (s, 1H), 5.57 (t, J=11.96 Hz, 1H), 3.97 (br s, 1H), 2.84 (d, J=4.37 Hz, 3H), 2.56 (m, 1H), 2.19-2.36 (m, 1H), 2.15 (m, 1H), 1.99-1.9 (m, 3H), 1.38-1.65 (m, 2H). HRMS $(M+H)^+$ calcd for $[C_{24}H_{23}ClN_6O_3+H]$, 479.1598; found 479.1573.

cis 5-bromo-N-(3-(2-(pyridin-2-yl)-1H-benzo[d]imidazol-1-yl)cyclohexyl)thiophene-2-carboxamide (10a)

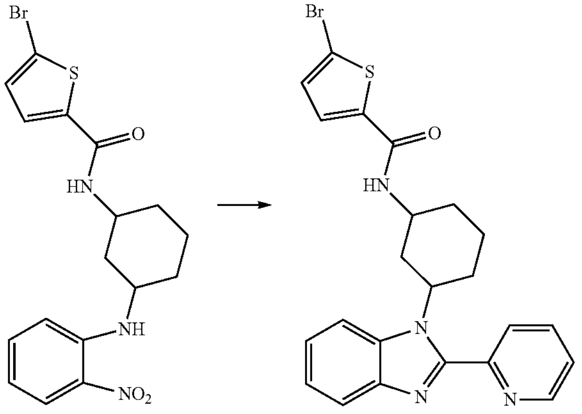 [SMILES: O=C(NC1CCCC(Nc2ccccc2[N+](=O)[O-])C1)c1ccc(Br)s1 ; O=C(NC1CCCC(n2c(-c3ccccn3)nc3ccccc32)C1)c1ccc(Br)s1]

Using cis 5-bromo-N-3-((2-nitrophenyl)amino)cyclohexyl)thiophene-2-carboxamide and picolinaldehyde as starting material, the title compound was prepared analogously to 8f in 16.6% yield (40 mg) as a yellow solid. LC-MS (ESI)=483.0 $(M+H)^+$; $^1H$ NMR (300 MHz, DMSO-$d_6$) δ 8.78 (d, J=4.37 Hz, 1H), 8.50 (d, J=7.78 Hz, 1H), 8.19 (d, J=7.78 Hz, 1H), 8.03 (t, J=7.02 Hz, 1H), 7.85 (d, J=7.78 Hz, 1H), 7.75 (d, J=7.40 Hz, 1H), 7.57 (m, 2H), 7.3 (m, 3H), 5.58 (m, 1H), 3.89 (br s, 1H), 2.38-2.47 (m, 1H), 2.30 (d, J=8.92 Hz, 1H), 2.12 (d, J=11.39 Hz, 1H), 1.94 (m, 3H), 1.48 (m, H). HRMS $(M+H)^+$ calcd for $[C_{23}H_{21}BrN_4OS+H]$ 481.0698; found 481.0633.

cis 1-(3-(5-bromothiophene-2-carboxamido)cyclohexyl)-N,N-dimethyl-2-(pyridin-2-yl)-1H-benzo[d]imidazole-5-carboxamide (10b)

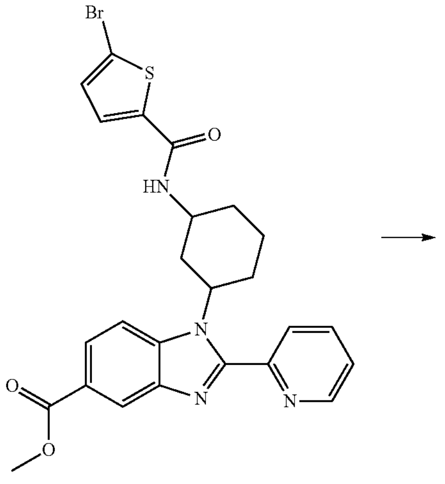

iv

-continued

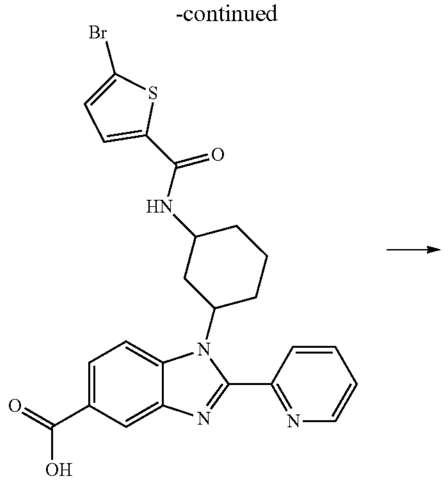

v

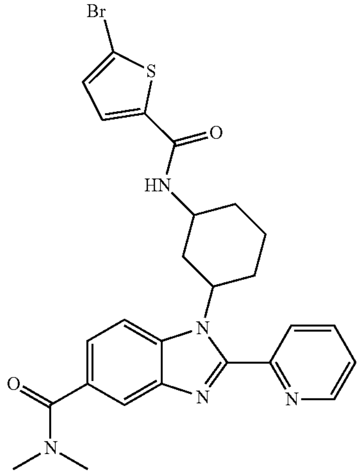

10b

Using methyl 4-fluoro-3-nitrobenzoate as a starting material (instead of 4-fluoro-N-methyl-3-nitrobenzamide converted from 4-fluoro-3-nitrobenzoic acid), the corresponding methyl ester (compound iv) was prepared analogously to 8b in 30% yield (400 mg). Saponification of the methyl ester afforded the corresponding acid v as a crude sample. MS (ESI) m/z $[M+1]^+$=524.9 and 526.9. The above crude acid (60 mg, 0.114 mmol) was added to a solution of HATU (43.4 mg, 0.114 mmol), DIEA (40 uL, 0.228 mmol), and dimethylamine (HCl salt, 13.97 mg, 0.171 mmol) in DMF (2 mL) and stirred at room temperature for 1 h. The reaction was condensed in vacuo and the residue was purified by HPLC to afford th title compound 10b (mixture of two cis-isomers) in 15.6% yield (11.9 mg). LC-MS (ESI) m/z [M+1]+=552.2 and 554.2; $^1H$ NMR (400 MHz, DMSO-$d_6$) δ 8.78 (d, 1H, J=4.4), 8.47 (d, 1H, J=8.0 Hz), 8.17 (d, 1H, J=8.0 Hz), 8.03 (t, 1H, J=7.2 Hz), 7.89 (d, 1H, J=8.2 Hz), 7.76 (s, 1H), 7.57 (m, 2H), 7.37 (d, 1H, J=8.0 Hz), 7.24 (d, 1H, J=4.0), 5.55 (m, 1H), 3.90-3.80 (m, 1H), 2.98 (s, 6H), 235-2.25 (m, 2H), 2.10-2.18 (m, 1H), 1.94-2.00 (m, 1H), 1.86-1.94 (m, 2H), 1.52-1.41 (m, 2H). HRMS $(M+H)^+$ calcd for $[C_{26}H_{26}BrN_5O_2S+H]$ 552.1069; found 552.1074.

cis 1-(3-(5-bromothiophene-2-carboxamido)cyclohexyl)-N-Cyclopropyl-2-(pyridin-2-yl)-1H-benzo[d]imidazole-5-carboxamide (10c)

as shown below.

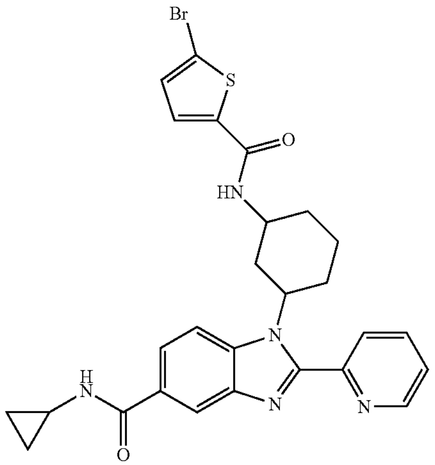 [SMILES: O=C(NC1CC1)c1ccc2c(c1)nc(-c1ccccn1)n2C1CCCC(NC(=O)c2ccc(Br)s2)C1]

Using cyclopropylamine instead of dimethylamine, the title compound was prepared analogously to 10b in 14.7% yield (12.7 mg). LC-MS (ESI) m/z [M+1]=564.3 and 566.3; 1H NMR (400 MHz, DMSO-$d_6$) δ 8.78 (d, 1H, J-5.2), 8.45-8.49 (m, 2H), 8.25 (s, 1H), 8.17 (d, 1H, J=8.0), 8.04 (t, 1H, J=7.2 Hz), 7.87 (d, 1H, J=8.4 Hz), 7.83-7.81 (m, 1H), 7.61-7.55 (m, 2H). 7.25 (d, 1H, J=4.4), 5.60-5.49 (m, 1H), 4.00-3.80 (m, 1H), 2.91-2.82 (m, 1H), 2.44-2.33 (m, 1H), 2.32-2.20 (m, 1H), 2.18-2.08 (m, 1H), 2.00-1.82 (m, 3H), 1.53-1.40 (m, 2H), 0.73-0.66 (m, 2H), 0.64-0.55 (m, 2H). HRMS $(M+H)^+$ calcd for $[C_{27}H_{26}BrN_5O_2S+H]$ 564.1069; found 564.1071.

cis 1-(3-(5-bromothiophene-2-carboxamido)cyclohexyl)N-isopropyl (pyridin-2-yl)-1H-benzo[d]imidazole-5-carboxamide (10d)

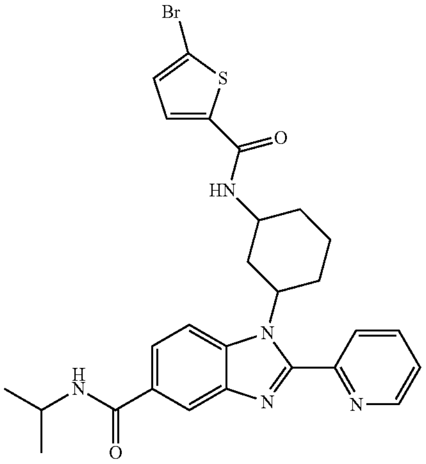 [SMILES: CC(C)NC(=O)c1ccc2c(c1)nc(-c1ccccn1)n2C1CCCC(NC(=O)c2ccc(Br)s2)C1]

Using isoproylamine instead of dimethylamine, the title compound was prepared analogously to 10b in 15.7% yield (12.2 mg). LC-MS (ESI) m/z $[M+1]^+$=568.2; $^1$H NMR (400 MHz, DMSO-$d_6$) δ 8.79 (d, 1H, J=4.7), 8.50 (d, 1H, J=3.9), 8.31 (s, 1H), 8.26 (d, 1H, J=7.9), 8.17 (d, 1H, J=7.9), 8.10-8.02 (m, 1H), 7.91-7.82 (m, 2H), 7.60-7.54 (m, 2H), 7.26 (d, 1H, J=4.3), 5.60-5.49 (m, 1H), 4.17-4.05 (m, 1H), 3.90-3.75 (m, 1H), 2.48-2.35 (m, 1H), 2.34-2.20 (m, 1H), 2.18-2.09 (m, 1H), 2.00-1.84 (m, 3H), 1.54-1.40 (m, 2H), 1.18 (d, 6H, J=6.6). HRMS $(M+H)^+$ calcd for $[C_{27}H_{28}BrN_5O_2S+H]$ 566.1225; found 566.1229.

3-((1S,3R)-3-(5-chlorothiophene-2-carboxamido)cyclohexyl)-2-(3 fluoropyridin-2-yl)-N-methyl-3H-imidazo[4,5-c]pyridine-6-carboxamide Step 1: Synthesis of 4-fluoro-N-methyl-3-nitrobenzamide

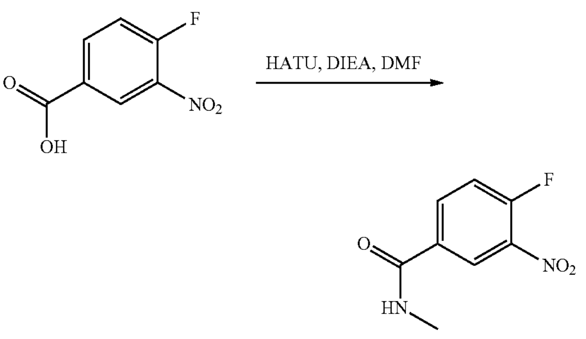

To a solution of 4-fluoro-3-nitrobenzoic acid (3.0 g, 16.21 mmol, 1.0 equiv.) and 1-(3-dimethylaminopropyl)-3-ethylcarbodiimide hydrochloride (3.74 g, 19.51 mmol, 1.2 equiv.) cooled in an ice-water bath was added methylamine solution (12.15 ml of a 2.0M solution in THF, 24.31 mmol, 1.5 equiv.). The reaction was warmed to room temperature and stirred for 18 hours. The solvents were evaporated in vacuo and the residue diluted with ethyl acetate (200 ml). The organic layer was washed with sat sodium bicarbonate solution (2×150 ml), 0.5 N hydrochloric acid solution (150 ml) and brine (150 ml), dried over magnesium sulfate and the solvents evaporated in vacuo to give 4-Fluoro-N-methyl-3-nitrobenzamide (2.10 g, 65% yield) as a yellow solid. 1H NMR (300 MHz, DMSO-$d_6$) δ 8.80 (d (broad), 0.1=4.5 Hz, 1H), 8.61 (dd, J=7.5, 2.3 Hz, 1H), 8.25 (m, 1H), 7.71 (dd, J=11.1, 8.7 Hz, 1H), 2.81 (d, J=4.5, 3H).

Step 2: Synthesis of Benzyl tert-butyl-cis-cyclohexane-1,3-diyl)dicarbamate

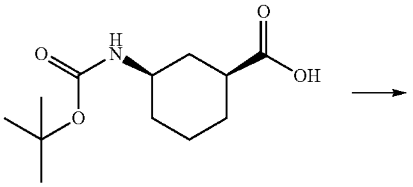

-continued

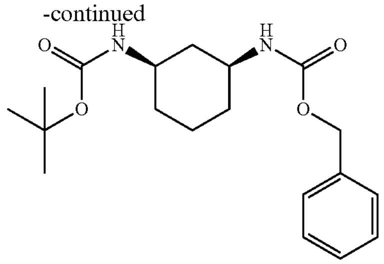

To a solution of Boc-cis-3-aminocyclohexane carboxylic acid (8.77 g, 36.05 mmol, 1.0 equiv.) and triethylamine (5.53 ml, 39.65 mmol, 1.1 equiv.) in toluene (150 ml) was added diphenylphosphoryl azide (7.79 ml, 36.05 mmol, 1.0 equiv.). The reaction mixture was heated at reflux for 3 h. and then the temperature was cooled to 80° C. Benzyl alcohol (4.69 ml, 45.06 mmol, 1.25 equiv.) and triethylamine (5.53 ml, 39.65 mmol, 1.1 equiv.) were added and the reaction stirred at 80° C. for 20 hours. The reaction was cooled to room temperature and diluted with water (100 ml). The aqueous layer was extracted with ethyl acetate (3×100 ml), the combined organic layers were washed with brine (100 ml), dried over magnesium sulfate and the solvents evaporated in vacuo. Trituration of the crude product with hexanes gave benzyl Teri-butyl-cis-cyclohexane-1,3-diyl)dicarbamate (7.81 g, 62% yield) as a colourless solid. $^1$H NMR (300 MHz, $CDCl_3$) δ 7.28-7.40 (m, 5H), 5.08 (s, 2H), 4.60 (s (broad), 1H), 4.36 (s (broad), 1H), 3.53 (m (broad), 2H), 2.28 (m, 1H), 1.97 (m, 2H), 1.76 (m, 1H), 1.64 (m, 1H), 1.43 (s, 9H), 0.97 (m, 3H).

Step 3: Synthesis of tert-butyl-cis-3-aminocyclohexyl)carbamate

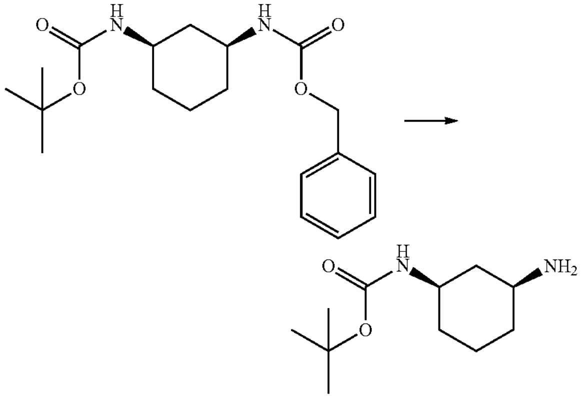

To a suspension of Palladium on carbon (10 wt. %, 1.19 g, 1.12 mmol, 0.05 equiv.) in ethanol (50 ml) in a Parr hydrogenation flask was slowly added tert-butyl N-[cis-3-(benzyloxycarbonylamino) cyclohexyl]carbamate (2)(7.81 g, 22.4 mmol, 1.0 equiv.) in ethanol (200 mL). The reaction mixture was hydrogenated under 30 psi pressure of hydrogen for 3 h. The reaction mixture was filtered through celite and the solvents evaporated in vacuo to give tert-butyl-cis-3-aminocyclohexyl)carbamate (4.70 g, 97% yield) as a colourless solid. 1H NMR (300 MHz, $CD_3OD$) δ 3.36 (m (broad), 1H), 2.76 (m (broad), 1H), 2.08 (m (broad), 1H), 1.74-1.91 (m, 3H), 1.44 (s, 9H), 1.36 (m, 1H), 1.06 (m, 3H).

Step 4: Synthesis of tert-butyl-cis-3-(((4-(methylcarbamoyl)-2-nitrophenyl)amino)cyclohexyl) carbamate

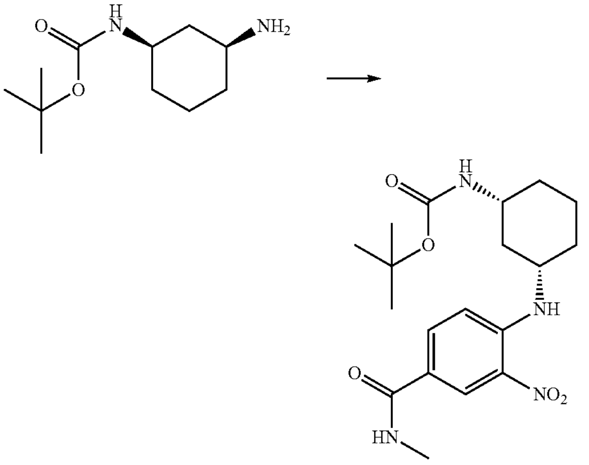

To a solution of tert-butyl N-[cis-3-aminocyclohexyl] carbamate (2.27 g, 10.59 mmol, 1.0 equiv.) and N,N-diisopropylethylamine (2.28 ml, 12.71 mmol, 1.2 equiv.) in ethanol (30 ml) was added 4-fluoro-N-methyl-3-nitro-benzamide (2.10 g, 10.59 mmol, 1.0 equiv.) in ethanol (20 ml). The reaction was refluxed for 20 hours. The solvents were evaporated in vacuo and the residue diluted with water (250 ml). The aqueous layer was extracted with ethyl acetate (4×250 ml), dried over magnesium sulfate and the solvents evaporated in vacuo to give tert-Butyl-cis-3-(((4-(methylcarbamoyl)-2-nitrophenyl)amino)cyclohexyl)carbamate (4.24 g, 100% yield) as a yellow solid. 1H NMR (600 MHz, DMSO-$d_6$) δ 8.62 (d, J=2.1 Hz, 1H), 8.47 (q, J=4.3 Hz, 1H), 8.07 (d, J=7.9 Hz, 1H), 7.97 (dd, J=9.1, 2.1 Hz, 1H), 7.22 (d, J=9.1, 1H), 6.87 (d, J=7.9, 1H), 3.77 (m, 1H), 3.43 (m, 1H), 2.77 (d, J=4.3, 3H), 2.12 (m, 1H), 1.96 (m, 1H), 1.80 (m, 1H), 1.75 (m, 1H), 1.42 (m, 1H), 1.39 (s, 9H), 1.24 (m, 1H), 1.11 (m, 1H).

Step 5: Synthesis of tert-butyl-(cis-3-((2-amino-4-(methylcarbamoyl)phenyl)amino)cyclohexyl) carbamate

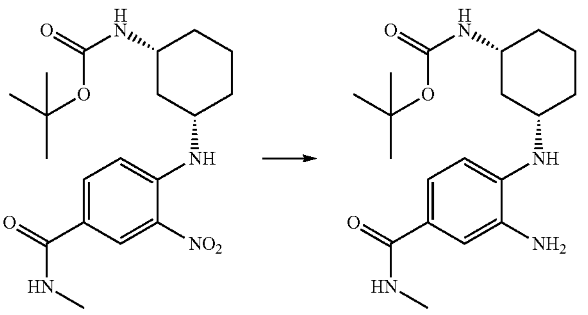 [SMILES: CNC(=O)c1ccc(N[C@H]2CCC[C@@H](NC(=O)OC(C)(C)C)C2)c([N+](=O)[O-])c1 ; CNC(=O)c1ccc(N[C@H]2CCC[C@@H](NC(=O)OC(C)(C)C)C2)c(N)c1]

To a suspension of Palladium on carbon (10 wt. %, 1.15 g, 10.8 mmol, 1.0 equiv.) in ethanol (50 ml) in a Parr hydrogenation flask was slowly added Teri-butyl-N-[cis-3-(benzyloxycarbonylamino) cyclohexyl]carbamate (7.81 g, 10.8 mmol, 1.0 equiv.) in ethanol (200 mL). The reaction mixture was hydrogenated under 40 psi pressure of hydrogen for 1 hour. The reaction mixture was filtered through celite and the solvents evaporated in vacuo to give ten-butyl-(cis-3-((2-amino-4-(methylcarbamoyl)phenyl)amino)cyclohexyl)carbamate (3.92 g, 100% yield) as a colourless solid. 1H NMR (300 MHz, $CDCl_3$) δ 7.32 (d, J=1.7 Hz, 1H), 7.17 (dd, J=8.4, 1.7 Hz, 1H), 6.66 (d, J=8.4 Hz, 1H), 6.29 (s (broad), 1H), 4.55 (s (broad), 1H), 3.55 (s (broad), 1H), 3.37 (m, 1H), 3.00 (m, 1H), 2.97 (d, J=4.5 Hz, 3H), 2.41 (m (broad), 1H), 2.04 (m (broad), 2H), 1.84 (m (broad), 1H), 1.45 (s, 9H), 1.09 (m, 3H).

Step 6: Synthesis of tert-butyl (cis-3-(5-(methylcarbamoyl)-2-(pyridin-2-yl)-1H-benzo[d]imidazol-1-yl) cyclohexyl)carbamate

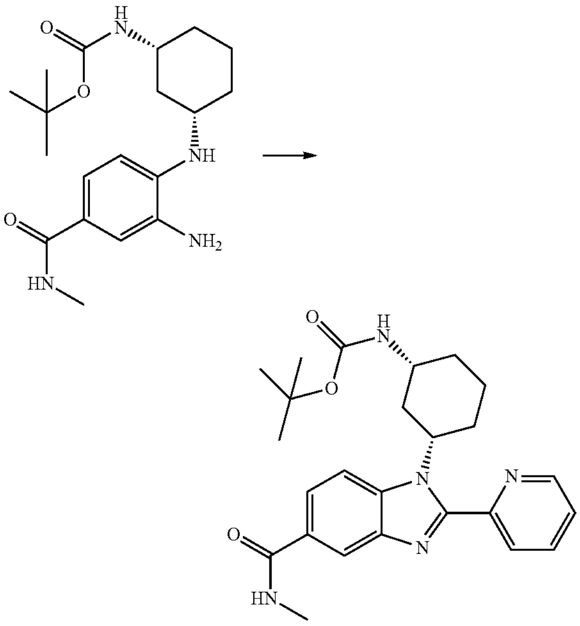

To a solution of tert-butyl-N-[cis-3-[2-amino-4-(methylcarbamoyl)anilino]cyclohexyl]carbamate (3.92 g, 10.8 mmol, 1.0 equiv.) and 2-pyridinecarboxaldehyde (1.24 ml, 12.96 mmol, 1.2 equiv.) in N,N-dimethylformamide (70 ml) and water (3 ml) was added potassium peroxomonosulfate (4.32 g, 7.02 mmol, 0.65 equiv.). The reaction was stirred for 3 hours. Water (30 ml) was added to the reaction mixture and the pH adjusted to 9 with 1N sodium hydroxide solution and stirred for 30 minutes. The mixture was extracted with ethyl acetate (4×100 ml), washed with brine (150 ml), dried over magnesium sulfate and the solvents evaporated in vacuo. The crude material was purified by silica chromatography eluting with 0 to 5% methanol in dichloromethane to give tert-butyl-(cis-3-(5-(methylcarbamoyl)-2-(pyridin-2-yl)-1H-benzo[d]imidazol-1-yl)cyclohexyl)carbamate (4.46 g, 92% yield) as a colourless solid. 1H NMR (300 MHz, $CDCl_3$) δ 8.73 (d, J=4.9 Hz, 1H), 8.29 (d, J=8.1 Hz, 1H), 8.21 (s, 1H), 7.90 (m, 2H), 7.69 (d, J=8.5 Hz, 1H), 7.43 (dd, J=7.2, 4.9 Hz, 1H), 6.43 (d (broad), J=4.9 Hz, 1H), 5.69 m (broad), 1H), 4.65 (s (broad), 1H), 3.63 (m (broad), 1H), 3.06 (d, J=4.9 Hz, 3H), 2.39 m (broad), 1H), 1.94-2.26 (m, 5H), 1.56 9 m, 1H), 1.42 (s, 9H), 1.29 (m, 1H).

Step 7: Synthesis of 1-(cis-3-(5-bromothiophene-2-carboxamido)cyclohexyl)-N-methyl-2-(pyridin-2-yl)-1H-benzo[d]imidazole-5-carboxamide

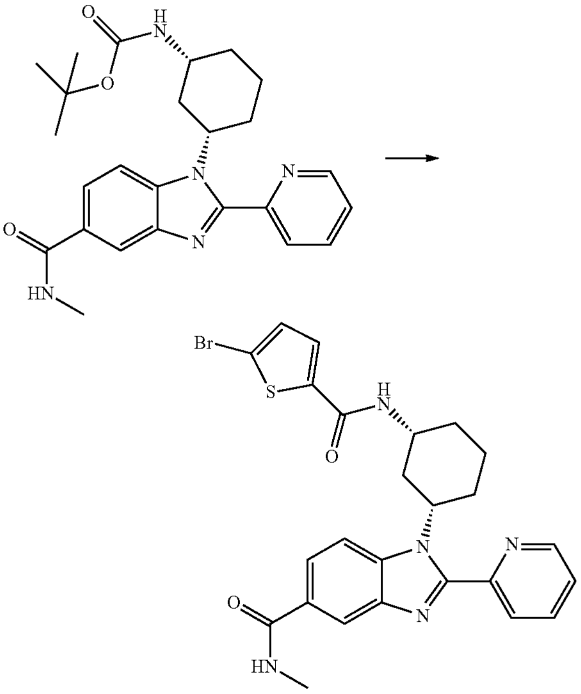

To a solution of tert-butyl-(cis-3-(5-(methylcarbamoyl)-2-(pyridin-2-yl)-1H-benzo[d]imidazol-1-yl)cyclohexyl)carbamate (6)(4.46 g, 9.92 mmol, 1.0 equiv.) in dichloromethane (80 ml) was added trifluoroacetic acid (7.59 mL, 99.21 mmol, 10.0 equiv.). The reaction was stirred for 2 hours. The solvents were evaporated in vacuo to give N-methyl-2-(2-pyridyl)-1-[cis-3-aminocyclohexyl]benzimidazole-5-carboxamide trifluoroacetic acid salt which was used directly. 5-Bromothiophene-2-carboxylic acid (3.08 g, 14.88 mmol, 1.5 equiv.) in N,N-dimethylformamide (100 ml) was cooled to 0° C. in an ice bath. (1-[Bis(di methylamino)methylene]-1H-1,2,3-triazolo[4,5-b]pyridinium 3-oxide hexafluorophosphate (5.66 g, 14.88 mmol, 1.5 equiv.) and N,N-diisopropylethylamine (10.69 ml, 59.53 mmol, 6.0 equiv.) was added and stirred for 30 minutes. N-methyl-2-(2-pyridyl)-1-[cis-3-aminocyclohexyl]benzimidazole-5-carboxamide trifluoroacetic acid salt (4.60 g, 9.92 mmol) in N,N-dimethylformamide (50 ml) was added. The reaction was warmed to room temperature and stirred for 20 hours. The reaction mixture was poured into saturated sodium bicarbonate solution (200 ml). The mixture was extracted with ethyl acetate (4×100 ml), washed with brine (200 ml), dried over magnesium sulfate and the solvents evaporated in vacuo. The crude material was purified by silica chromatography eluting with 0 to 5% methanol in dichloromethane to give 1-(cis-3-(5-bromothiophene-2-carboxamido)cyclohexyl)-N-methyl-2-(pyridin-2-yl)-1H-benzo[d]imidazole-5-carboxamide (3.68 g, 69% yield) as an off-white solid. 1H NMR (600 MHz, DMSO-$d_6$) δ 8.80 (d, J=4.6 Hz, 1H), 8.52 (d, J=7.8 Hz, 1H), 8.49 (q, 0.1=4.4 Hz, 1H), 8.26 (s, 1H), 8.21 (d, J=7.8 Hz, 1H), 8.05 (dd, J=7.8, 1.2 Hz, 1H), 7.91 (d, J=8.5 Hz, 1H), 7.85 (d, J=8.5 Hz, 1H), 7.59 (m, 2H), 7.27 (d, J=4.0 Hz, 1H), 5.56 (m, 1H), 3.89 (m, 1H), 2.84 (d, J=4.4

Hz, 3H), 2.43 (m, 1H), 2.29 (m, 1H), 2.14 (m, 1H), 1.98 (m, 1H), 1.93 (m, 2H), 1.48 (m, 2H).

1-(5-(5-bromothiophene-2-carboxamido)tetrahydro-2H-pyran-3-yl)-6-fluoro-N-methyl-2-(pyridin-2-yl)-1H-benzo[d]imidazole-5-carboxamide (234)

Preparation of 5-ethoxy-2H-pyran-3(6H)-one

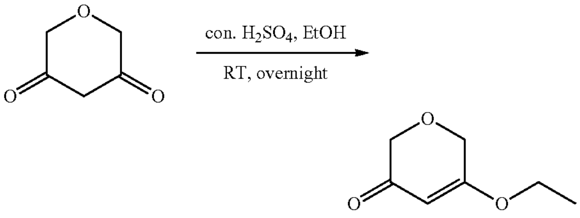

Into a 1000 ml round bottom flask, was placed oxane-3,5-dione (10.00 g, 87.64 mmol, 1.00 equiv) and 0.28 mL of con.$H_2SO_4$ in 300 mL of ethanol. This was stirred for 2 h at room temperature. Desired product could be detected by LC-MS. The crude product was used for next step directly without further purification.

Preparation of 5-amino-2H pyran-3(6H)-one

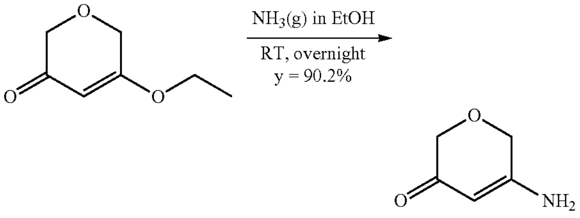

Into a 1000 mL round bottom flask, was placed about 5-ethoxy-2,6-dihydropyran-3-one (9.20 g, 64.72 mmol, 1.00 equiv) in 300 mL of ethanol, the $NH_3$ gas was introduce in slowly for 3 h at 0 degree C. Desired product could be detected by LC-MS ($[M+H]^+$: 114.1). This was concentrated and the residue was purified onto silica gel column with 40% of ethyl acetate in petroleum ether to afford 5-amino-2,6-dihydropyran-3-one (6.6 g, 90.2%) as a white solid.

Preparation of 5-aminotetrahydro-2H pyran-3-ol

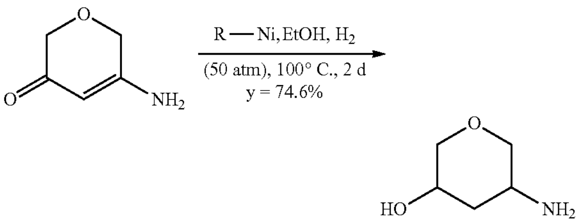

Into a 500 ml pressure tank, was placed 5-amino-2,6-dihydropyran-3-one (6.60 g, 58.35 mmol, 1.00 equiv), Raney Ni (8.00 g) in 250 mL of ethanol, The mixture was purged with nitrogen for 3 times and then was stirred under 50 atm. with $H_2$ gas for 2 days at 100 degree C. Desired product could be detected by LCMS. The reaction mixture was cooled to room temperature. After filtration and the filtrate was concentrated under vacuum and to afford 5-aminooxan-3-ol (5.1 g, 74.6%) as a colorless oil. LC-MS: ($[M+H]^+$): 118.1.

Preparation of Benzyl 5-hydroxytetrahydro-2H pyran-3-carboxylate

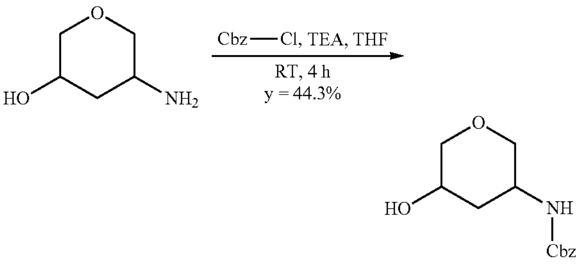

Into a 100 mL round bottom flask, was placed 5-aminooxan-3-ol (4.00 g, 34.15 mmol, 1.00 equiv), benzylcarbonochloridate (6.99 g, 40.97 mmol, 1.20 equiv), triethylamine (10.37 g, 102.44 mmol, 3.00 equiv) in 40 mL of tetrahydrofuran, this was stirred for 4 h at room temperature. Desired product could be detected by LC-MS. The solution was concentrated under reduced pressure. This was concentrated and the residue was purified onto silica gel column with 40% of ethyl acetate in petroleum ether to afford benzyl N-(5-hydroxyoxan-3-yl) carbamate (3.8 g, 44.3%) as a colorless oil. LC-MS: ($[M+H]^+$): 252.1.

Preparation of Benzyl 5-oxotetrahydro-2H-pyran-3-carboxylate

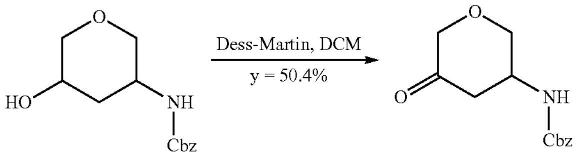 [SMILES: O=C(NC1COCC(O)C1)OCc1ccccc1 ; O=C1COCC(NC(=O)OCc2ccccc2)C1]

Into a 100 ml round bottom flask, was placed benzyl N-(5-hydroxyoxan-3-yl) carbamate (3.80 g, 15.12 mmol, 1.00 equiv), Dess-Martin periodinane (19.24 g, 45.37 mmol, 3.00 equiv) in 40 mL of dichloromethane. The reaction mixture was stirred for 2 h at room temperature, desired product could be detected by LCMS. The residue was diluted with 100 mL of $NaHCO_3$ solution and extracted with 3×100 mL of dichloromethane and the combined organic layers were dried over anhydrous $Na_2SO_4$ and filtered and concentrated and the crude product was purified onto silica gel column with 50% of ethyl acetate in petroleum ether to afford benzyl N-(5-oxooxan-3-yl) carbamate (1.9 g, 50.4%) as a colorless oil. LC-MS: ($[M+H]^+$): 250.1.

Preparation of Benzyl 5-oxotetrahydro-2H-pyran-3-carboxylate

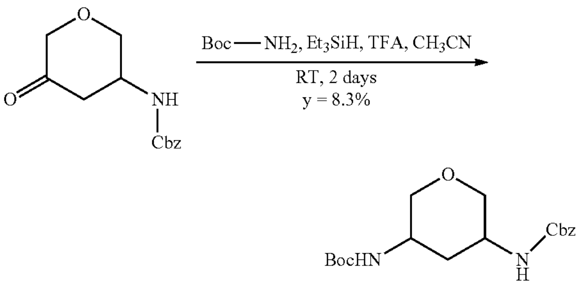

Into a 100 ml round bottom flask, was placed benzyl N-(5-oxooxan-3-yl) carbamate (1.80 g, 7.22 mmol, 1.00 equiv), tert-butyl carbamate (2.54 g, 21.66 mmol, 3.00 equiv), triethylsilane (2.519 g, 21.66 mmol, 3.00 equiv), 2,2,2-trifluoroacetic acid (1.647 g, 14.44 mmol, 2.00 equiv) in 50 mL of acetonitrile. The reaction mixture was stirred for 2 days at 38 degree C. under $N_2$ and desired product could be detected by LC-MS. The solids were filtrated out by filtration and the filtrate was concentrated under reduced pressure. The mixture was concentrated and purified by reverse phase chromatography eluting with 70% of acetonitrile in water (0.1% $NH_4HCO_3$) to afford benzyl N-[5-[(tert-butoxycarbonyl)amino]oxan-3-yl]carbamate (210 mg, 8.3%) as a white solid. This chiral-HPLC data indicates that the structure is a cis-trans mixture and the ratio is 1:1. LC-MS: ([M+H]$^+$): 368.2.

Preparation of Benzyl 5-oxotetrahydro-2H-pyran-3-carboxylate

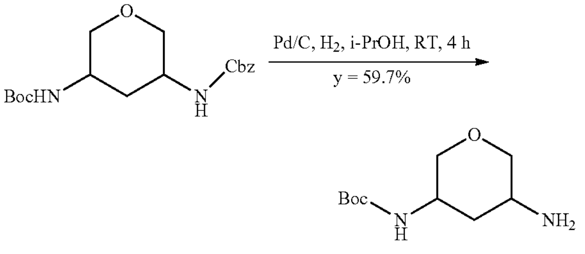

Into a 50 mL round bottom flask, benzyl N-[5-[(tert-butoxycarbonyl) amino]oxan-3-yl]carbamate (160.0 mg, 0.46 mmol, 1.00 equiv), Pd/C (9.72 mg, 0.09 mmol, 0.20 equiv) in 15 mL of isopropanol, this was stirred for 4 h at room temperature under $H_2$ atmosphere. After filtration and the filtrate was concentrated under vacuum and to afford tert-butyl N-(5-aminooxan-3-yl) carbamate (59 mg, 59.7%) as a white solid. $^1$H-NMR-PH-ICA-002-015-7: 1H NMR (300 MHz, DMSO-d$_6$) δ 6.86 (d, J=8.1 Hz, 1H), 3.67-3.65 (m, 2H), 2.88-2.60 (m, 3H), 2.07-1.58 (m, 3H), 1.38 (s, 9H), 1.18-0.74 (m, 2H). LC-MS: [M+H]$^+$: 217.2.

Preparation of 1-(5-(5-bromothiophene-2-carboxamido)tetrahydro-2H-pyran-3-yl)-6-fluoro-N-methyl-2-(pyridin-2-yl)-1H-benzo[d]imidazole-5-carboxamide 1-(5-(5-bromothiophene-2-carboxamido)tetrahydro-2H-pyran-3-yl)-6-fluoro-N-methyl-2-(pyridin-2-yl)-1H-benzo [d]imidazole-5-carboxamide (243)$_m$ay be prepared from benzyl 5-oxotetrahydro-2H-pyran-3-carboxylate in a manner analagous to that described for compounds 286 and 287.

3-(3-(5-bromothiophene-2-carboxamido)cyclohexyl)-N-methyl-2 phenyl-1H-indole-6-carboxamide (283)

Preparation of Benzyl (3-(6-(methylcarbamoyl)-1H-indol-3-yl)cyclohexyl)carbamate

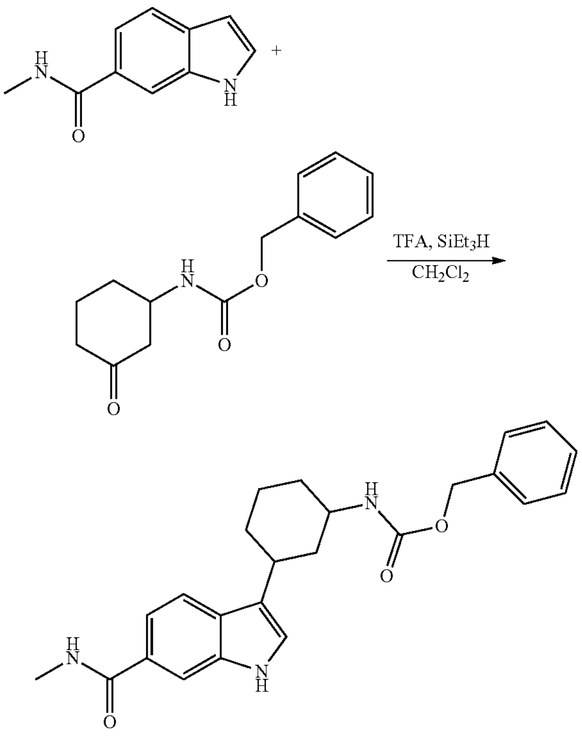

Benzyl (3-oxocyclohexyl)carbamate (1030.38 mg, 4.17 mmol) was added to a solution of N-methyl-1H-indole-6-carboxamide (500 mg, 2.87 mmol) in DCM (10 mL). The solution was cooled to 10° C. then trifluoroacetic acid (0.66 mL, 8.61 mmol) was added dropwise followed by triethylsilane (1.83 mL, 11.48 mmol). The reaction mixture was allowed to warm up to room temperature and kept stirring. The mixture was poured into a saturated solution of $NaHCO_3$ and extracted 3 time with ethyl acetate (AcOEt). The combined organic phases were washed with brine, dried over $MgSO_4$ and evaporated. The crude was purified on silica gel using AcOEt/Hexanes 50/50 as eluent and yielded 1 g of desired product (86%). MS: 406.34 [M+H]$^+$.

Preparation of Benzyl (3-(2-bromo-6-(methylcarbamoyl)-1H-indol-3-yl)cyclohexyl)carbamate and benzyl (3-(2-bromo-1-hydroxy-6-(methylcarbamoyl)-1H-indol-3-yl)cyclohexyl)carbamate

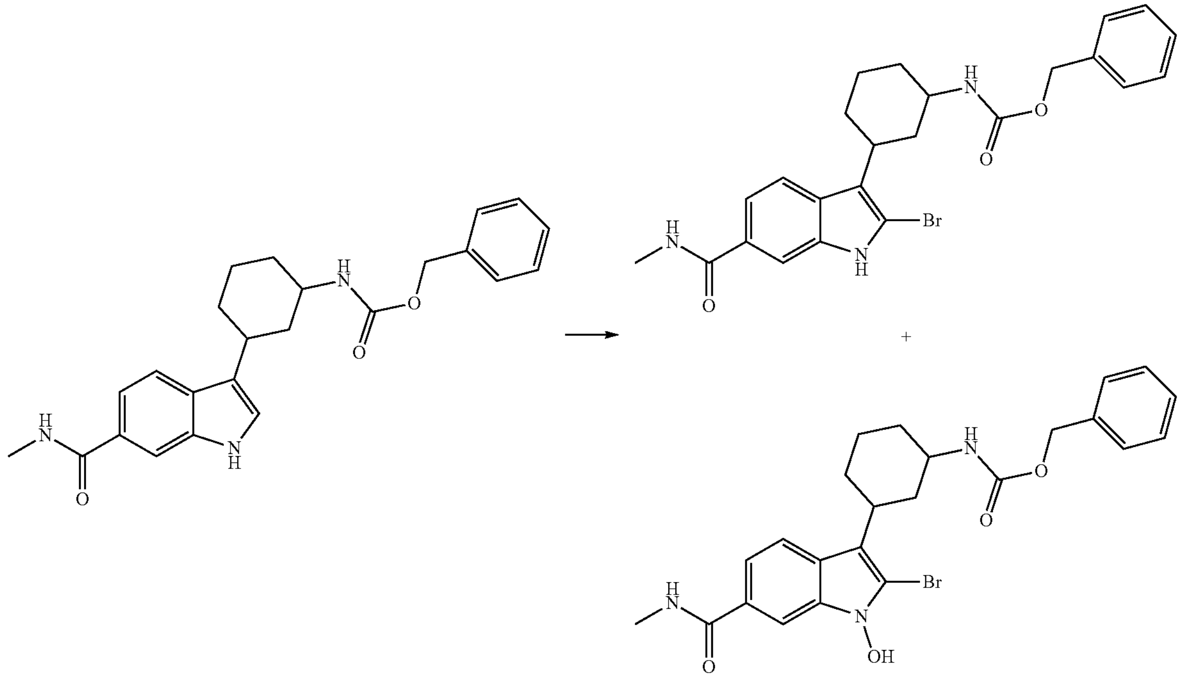 [SMILES: CNC(=O)c1ccc2c(C3CCCC(NC(=O)OCc4ccccc4)C3)c[nH]c2c1 ; CNC(=O)c1ccc2c(C3CCCC(NC(=O)OCc4ccccc4)C3)c(Br)[nH]c2c1 ; CNC(=O)c1ccc2c(C3CCCC(NC(=O)OCc4ccccc4)C3)c(Br)n(O)c2c1]

Pyridinium tribromide (1025.34 mg, 3.21 mmol) was added at once to a cool solution (ice bath) of benzyl N-[3-[6-(methylcarbamoyl)-1H-indol-3-yl]cyclohexyl]carbamate (1000. mg, 2.47 mmol) in THF (5 mL)/chloroform (5 mL) solution. The bath was removed and the reaction kept 2 hrs at room temperature. The mixture was 10 mL of 1M solution of $NaHSO_3$, 10 ml of 1N HCl, water, dried over $MgSO_4$ and evaporated. UPLC showed the expected product together with a side-product of MW 500, presumably an oxidized derivative of the expected compound. The 2 compounds were purified by HPLC using acetonitrile/water (0.1% formic acid) as eluent yielding: 390 mg of benzyl (3-(2-bromo-6-(methylcarbamoyl)-1H-indol-3-yl)cyclohexyl)carbamate (33%) and 209 mg of benzyl (3-(2-bromo-1-hydroxy-6-(methylcarbamoyl)-1H-indol-3-yl)cyclohexyl) carbamate (17%)

Preparation of Benzyl (3-(6-(methylcarbamoyl)-2 phenyl-1H-indol-3-yl)cyclohexyl)carbamate

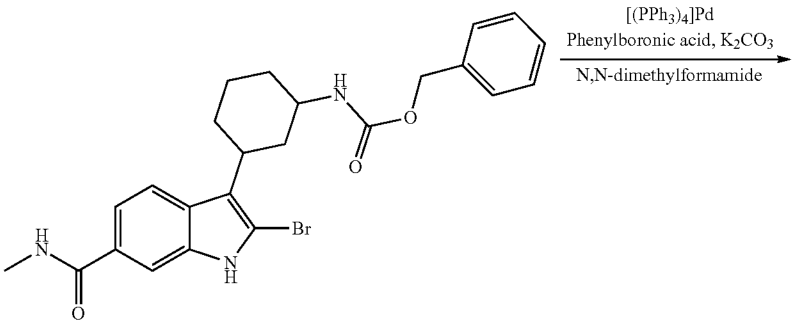

-continued

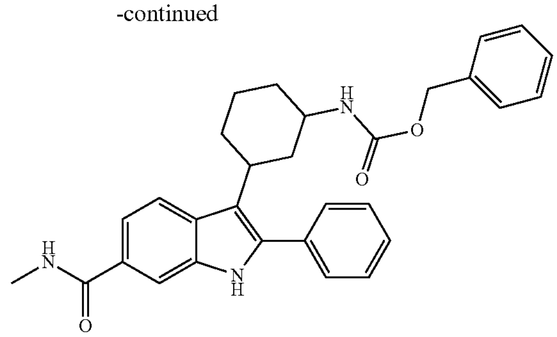

To a solution of benzyl N-[3-[2-bromo-6-(methylcarbamoyl)-1H-indol-3-yl]cyclohexyl]carbamate (145 mg, 0.3000 mmol), phenylboronic acid (43.8 mg, 0.3600 mmol), tetrakis (triphenylphosphine)palladium(0)(34.59 mg, 0.0300 mmol) in DMF (1 mL) was added and potassium carbonate (124.12 mg, 0.9000 mmol) in water (0.1000 mL). The mixture was degassed and put under Argon. Reaction was allowed to proceed overnight at 80° C. The mixture was poured in saturated solution of sodium chloride and extracted 3 time with ethyl acetate. The combined organic phases were washed with water, dried over $MgSO_4$ and evaporated. The crude was purified on silica gel using $CH_3OH/CH_2Cl_2$ 0 to 5% as eluent yielding 162 mg of desired product (112%). The product was not pure but used as is for next step. MS: 482.41 [M+H]+

Preparation of 3-(3-aminocyclohexyl)-N-methyl-2-phenyl-1H-indole-6-carboxamide

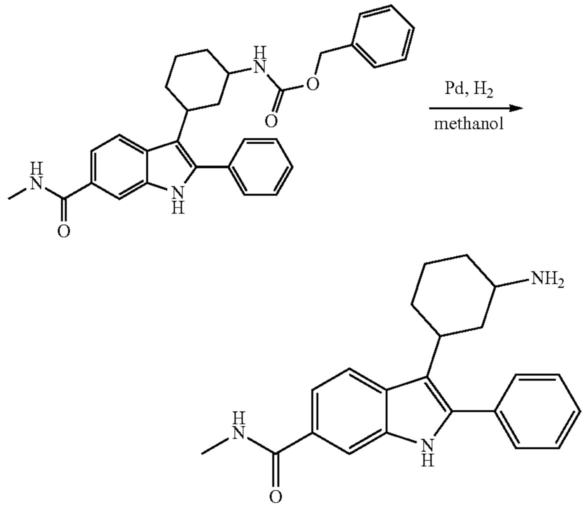

To benzyl N-[3-[6-(methylcarbamoyl)-2-phenyl-1H-indol-3-yl]cyclohexyl]carbamate (46. mg, 0.1000 mmol) in methanol (10 mL) was added palladium (16.94 mg, 0.1000 mmol). The mixture was hydrogenated in Parr instrument under 50 psi $H_2$ atmosphere for 2 h at RT. The mixture was filtered over $MgSO_4$ and evaporated yielding 37 mgs of white solid (111%)(2 peaks with same mass in UPLC: 90/10). MS: 348.38

Preparation of 3-(3-(5-bromothiophene-2-carboxamido)cyclohexyl)-N-methyl phenyl-1H-indole-6-carboxamide (283)

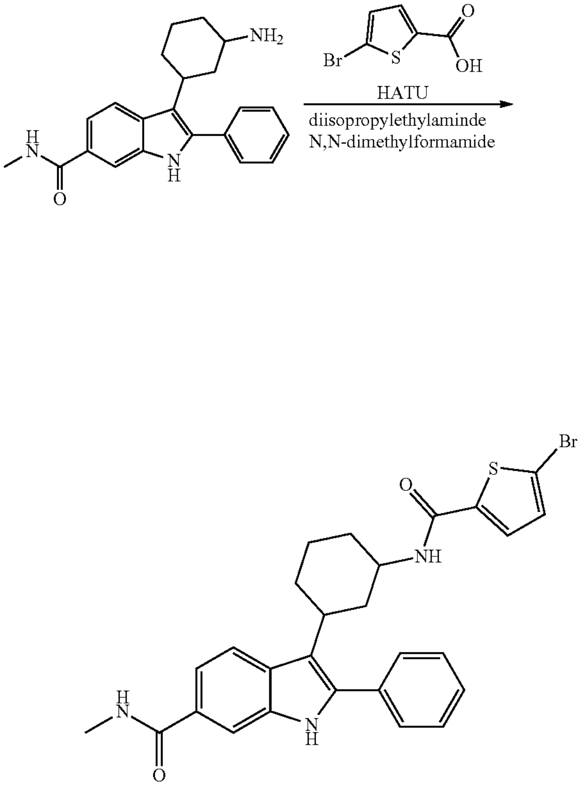

3-(3-aminocyclohexyl)-N-methyl-2-phenyl-1H-indole-6-carboxamide (37. mg, 0.1100 mmol) 5-bromothiophene-2-carboxylic acid (33.07 mg, 0.1600 mmol) HATU (80.98 mg, 0.2100 mmol), N,N-diisopropylethylamine (0.06 mL, 0.3200 mmol) and DMF (2 mL) were combined and allowed to stir for 5 hours at room temperature. The mixture was poured into a saturated solution of sodium bicarbonate and extracted 3 time with ethyl acetate. The combined organic phases are washed with water, dried over $MgSO_4$ and evaporated. The crude was purified on HPLC using acetonitrile/water (formic acid 0.1%) 20 to 100% yielding 30 mg of desired product (53%). MS: 538.28 [M+H]+.

Compounds 290 and 304 were prepared in a manner analogous to compound 283.

3-((1S,3R)-3-(S-chlorothiophene-2-carboxamido) cyclohexyl)-2-(3 fluoropyridin-2-yl)-N-methyl-3H-imidazo[4,5-c]pyridine-6-carboxamide (286)

Preparation of Tert-butyl ((1R,3S)-3-(6-chloro-2-(3 fluoropyridin-2-yl)-3H-imidazo[4,5-c]pyridin-3-yl) cyclohexyl)carbamate

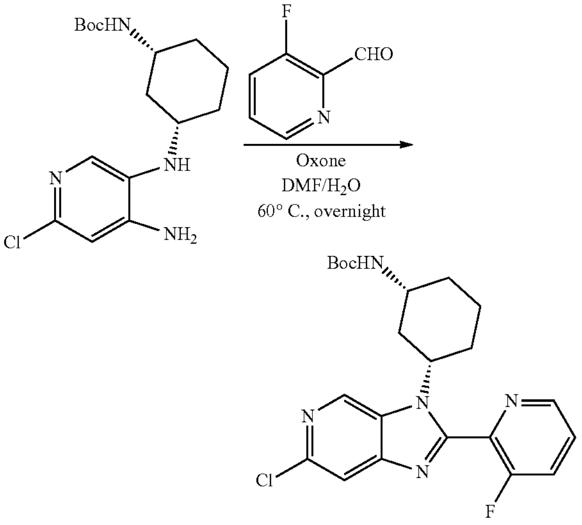

A mixture of tert-butyl N-[rac-(1R,3S)-3-[(3-amino-2-chloro-4-pyridyl)amino]cyclohexyl]carbamate (507 mg, 1.49 mmol), 3-fluoro-2-formylpyridine (186.08 mg, 1.49 mmol), and oxone (594.38 mg, 0.97 mmol) in DMF/water (10 ml/1 ml) was heated at 60° C. for 16 hrs. The reaction mixture was cooled to rt, and then diluted with ethyl acetate (30 ml), washed with water (10 ml) and brine (10 ml). The organic layer was dried over sodium sulfate, evaporated in vacuo to obtain the crude product. The crude product was purified with silica gel chromatography (eluent, 0-100% ethyl acetate/hexanes) to afford tert-butyl ((1R,3S)-3-(6-chloro-2-(3-fluoropyridin-2-yl)-3H-imidazo[4,5-c]pyridin-3-yl)cyclohexyl)carbamate (529 mg, 79.7%)

Preparation of Tert-bury ((1R,3S)-3-(6-cyano-2-(3-fluoropyridin-2-yl)-3H-imidazo[4,5-c]pyridin-3-yl) cyclohexyl)carbamate

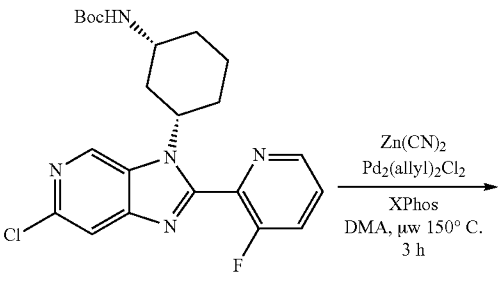

-continued

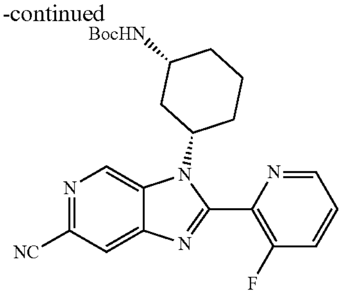

A mixture of tert-butyl N-[rac-(1R,3S)-3-[6-chloro-2-(3-fluoro-2-pyridyl)imidazo[4,5-c]pyridin-3-yl]cyclohexyl] carbamate (529 mg, 1.19 mmol), zinc cyanide (696.42 mg, 5.93 mmol), allylpalladium chloride dimer (43.41 mg, 0.12 mmol), and 2-dicyclohexylphosphino-2,4,6-triisopropylbiphenyl (XPhos)(113.11 mg, 0.24 mmol) and in DMA (7 ml) was heated at 150° C. under microwave irradiation for 200 mins. The reaction solution was cooled to the room temperature, diluted with diethyl acetate (50 ml), washed with saturated sodium bicarbonate (50 ml). The aqueous solution was extracted with ethyl acetate (20 ml×2). The combined organic layer was washed with brine (30 ml), dried over sodium sulfate, filtered, and evaporated in vacuo to get the crude product (contained DMA). The crude product was purified with silica gel (12 g, eluent, 0-100% ethyl acetate in hexanes) to afford the desired product tert-butyl N-[rac-(1R, 3S)-3-[6-cyano-2-(3-fluoro-2-pyridyl)imidazo[4,5-c]pyridin-3-yl]cyclohexyl]carbamate (190 mg, 0.4353 mmol, 36.7% yield).

Preparation of 5-chloro-N-((1R,3S)-3-(6-cyano-2-(3-fluoropyridin-2-yl)-3H-imidazo[4,5-c]pyridin-3-yl)cyclohexyl)thiophene-2-carboxamide

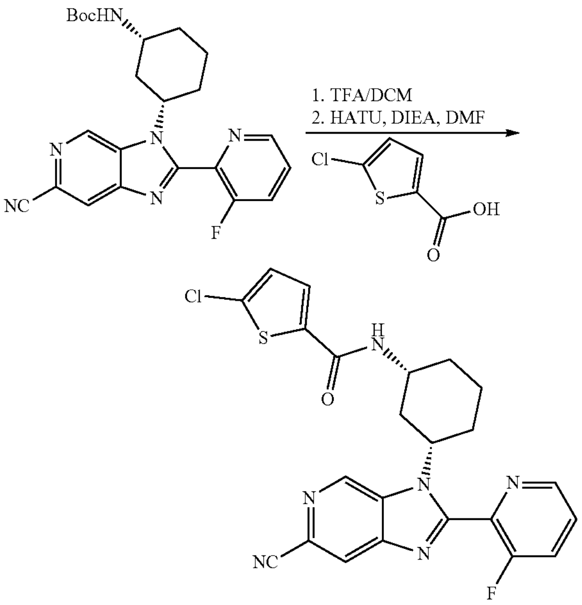

A mixture of tert-butyl N-[rac-(1R,3S)-3-[6-cyano-2-(3-fluoro-2-pyridyl)imidazo[4,5-c]pyridin-3-yl]cyclohexyl] carbamate (190 mg, 0.44 mmol) and 2,2,2-trifluoroacetic acid (1 mL, 13.07 mmol) in DCM (3 mL) was shaken at rt for 1 hr. The reaction solvent was removed by reduced pressure evaporation and high vacuum pump. The crude product 2-(3-fluoro-2-pyridyl)-3-[rac-(1S,3R)-3-aminocyclohexyl]imidazo[4,5-c]pyridine-6-carbonitrile (140 mg, 0.4162 mmol, 95.6% yield) was used for the next step without further purification.

A mixture of 2-(3-fluoro-2-pyridyl)-3-[rac-(1S,3R)-3-aminocyclohexyl]imidazo[4,5-c]pyridine-6-carbonitrile (140 mg, 0.4200 mmol), 5-chlorothiophene-2-carboxylic acid (81.21 mg, 0.5 mmol), HATU (237.38 mg, 0.62 mmol) and DIEA (0.23 mL, 1.25 mmol) in DMF (2 mL) was stirred at rt for 4 hrs. The reaction solution was diluted with ethyl acetate (10 ml), washed with saturated sodium bicarbonate (5 ml). The aqueous solution was extracted with ethyl acetate (10 ml). The combined organic layer was extracted with brine (5 ml), dried over sodium sulfate, filtered, and evaporated in vacuo to get the crude product. The crude product was purified with silica gel chromatography (12 g, 0-100% EA/Hex) to obtain the desired product 5-chloro-N-[rac-(1R,3S)-3-[6-cyano-2-(3-fluoro-2-pyridyl)imidazo[4,5-c]pyridin-3-yl]cyclohexyl]thiophene-2-carboxamide (126 mg, 0.2620 mmol, 62.9% yield).

Preparation of 3-((1 S,3R)-3-(5-chlorothiophene-2-carboxamido)cyclohexyl)-2-(3-fluoropyridin-2-yl)-3H-imidazo[4,5-c]pyridine-6-carboxylic Acid

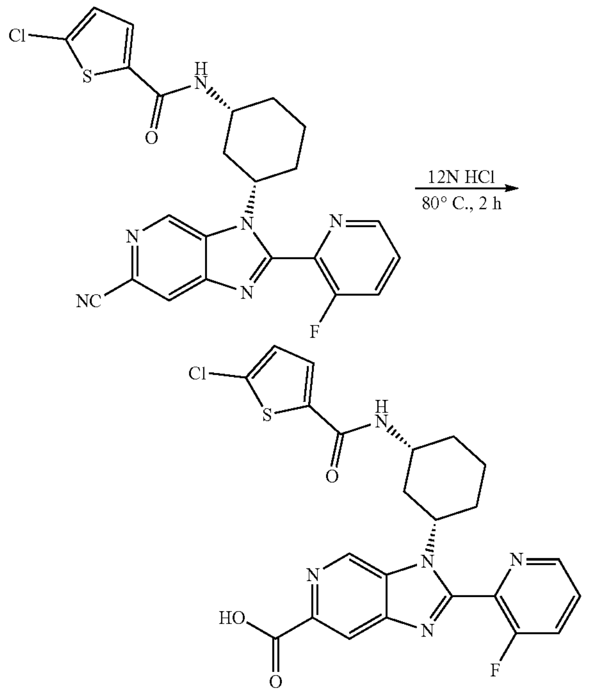

A solution of 5-chloro-N-[rac-(1R,3S)-3-[6-cyano-2-(3-fluoro-2-pyridyl)imidazo[4,5-c]pyridin-3-yl]cyclohexyl]thiophene-2-carboxamide (126 mg, 0.26 mmol) in 12N HCl (3 ml) was heated at 80° C. for 4 hrs. The reaction solution was cooled to rt, excessive amount potassium carbonate was slowly added to neutralize the solution. Ethyl acetate was then added to extract the solution for several times. The organic layer was dried over sodium sulfate, evaporated in vacuo to obtain the desired product 2-(3-fluoro-2-pyridyl)-3-[rac-(1S,3R)-3-[(5-chlorothiophene-2-carbonyl)amino]cyclohexyl]imidazo[4,5-c]pyridine-6-carboxylic acid (7, 85 mg, 0.17 mmol, 64.9% yield) without further purification.

Preparation of 3-((1S,3R)-3-(5-chlorothiophene-2-carboxamido)cyclohexyl)-2-(3-fluoropyridin-2-yl)-N-methyl-3H-imidazo[4,5-c]pyridine-6-carboxamide (286)

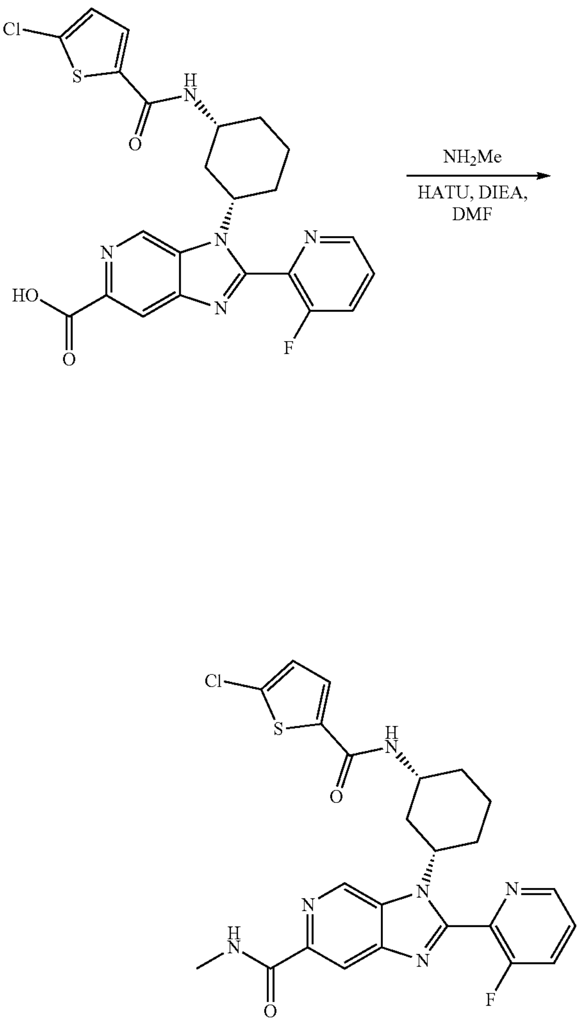

286

A mixture of 2-(3-fluoro-2-pyridyl)-3-[rac-(1S,3R)-3-[(5-chlorothiophene-2-carbonyl)amino]cyclohexyl]imidazo[4,5-c]pyridine-6-carboxylic acid (85 mg, 0.17 mmol), HATU (96.97 mg, 0.2600 mmol), DIEA (0.05 mL, 0.2600 mmol), and methylamine (0.17 mL, 0.34 mmol, 2.0M in THF) in DMF (2 ml) was stirred at rt for 3 hrs. The crude product was purified with prep-HPLC (30-100% ACN) to afford the desired product 2-(3-fluoro-2-pyridyl)-N-methyl-3-[rac-(1S,3R)-3-[(5-chlorothiophene-2-carbonyl)amino]cyclohexyl]imidazo[4,5-c]pyridine-6-carboxamide 286 (41 mg, 0.0799 mmol, 47% yield). 3-((1R,3S)-3-(5-bromothiophene-2-carboxamido)cyclohexyl)-N-methyl-2-(pyridin-2-yl-3H-imidazo[4,5-c]pyridine-6-carboxamide (287)

Step 1: Synthesis of Compound 287a

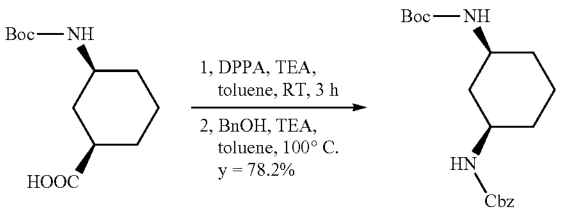

287a

Into a 250 mL 3-necked round bottom flask, was placed cis-3-[(tert-butoxycarbonyl)amino]cyclohexanecarboxylic acid (10.0 g, 41.1 mmol), triethylamine (9.0 mL, 64.50 mmol) and diphenylphosphoryl azide (10.0 mL, 46.35 mmol) in 250 mL of toluene, the resulting mixture was stirred for 3 h at room temperature. To this was added Benzyl alcohol (8.50 mL, 82.00 mmol) and the mixture was stirred for 4 h at 100° C., Desired product was detected by LCMS and starting material acid was consumed. The reaction mixture was cooled then concentrated and the residue was purified onto silica gel with 30% of ethyl acetate in petroleum ether to afford benzyl tert-butyl ((1R,3S)-cyclohexane-1,3-diyl)dicarbamate (287a)(11.2 g, 78.2%) as a white solid. LC-MS m/z: $[M-100+H]^+$: 249.2.

Step 2: Synthesis of Compound 287b

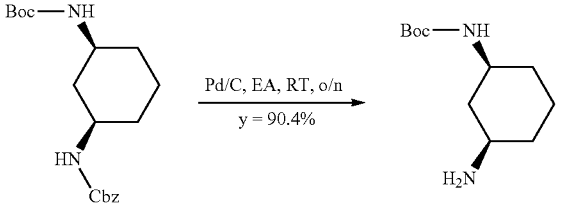

287a

287b

Into a 250 mL round bottom flask, was placed benzyl tert-butyl ((1R,3S)-cyclohexane-1,3-diyl)dicarbamate (8.0 g, 233.78 mmol, 1.00 equiv), Pd/C (800.0 mg) in 200 mL of ethyl acetate, this was stirred for overnight at room temperature under 1-1.2 atmosphere, monitored by TLC. After filtration and the filtrate was concentrated under vacuum and to afford tert-butyl ((1S,3R)-3-aminocyclohexyl) carbamate (287b)(4.45 g, 90.4%) as a light yellow oil.

Step 3: Synthesis of Compound 287c

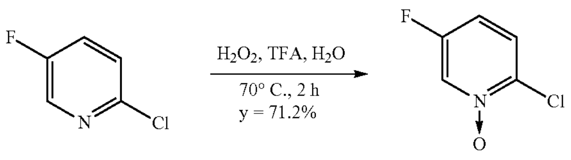

287c

Into a 500 ml 3-necked round bottom flask, was placed 2-chloro-5-fluoropyridine (10.00 g, 76.00 mmol, 1.00 equiv)

and 25 mL of 50% hydrogen peroxide in 200 mL of 2,2,2-trifluoroacetic acid. The resulted mixture was stirred at 70° C. until TLC showed starting material consumed. The reaction mixture was concentrated under vacuum and co-evaporated with 2×40 mL of toluene. The residue was diluted with 40 mL of water and 200 mL of dichloromethane and the pH value of the solution were adjusted to 8 with 28% ammonium hydroxide solution. The aqueous layer was extracted with 3×200 mL of dichloromethane and the combined organic layers were dried over anhydrous $Na_2SO_4$ and filtered and concentrated and the crude product was purified onto silica gel column with 10% of methanol in dichloromethane to afford 2-Chloro-5-fluoropyridine-1-oxide (287c)(8.10 g, 71.2%) as a yellow solid.

Step 4: Synthesis of Compound 287d

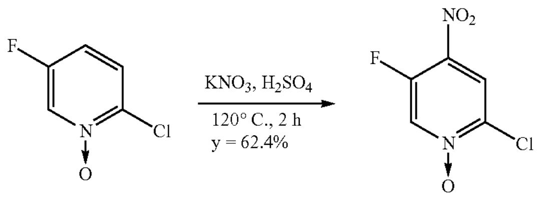

287c

287d

Into a 500 ml 3-necked round bottom flask, was placed 2-chloro-5-fluoropyridine 1-oxide (8.10 g, 54.90 mmol, 1.00 equiv) in 110 mL of con.$H_2SO_4$. Then to this was added 23.90 g of potassium nitrate in several batches at 0° C. The reaction mixture was stirred for 2 h at 120° C., monitor by TLC, the TLC showed the starting material was consumed. The reaction mixture was then quenched with 400 mL of water/ice. The pH value of the solution was adjusted to 8 with 28% ammonium hydroxide solution while the temperature was maintained below 15° C. in an ice bath. The light yellow crystals precipitated were collected by filtration and washed with 2×50 mL of water and dried to afford 2-chloro-5-fluoro-4-nitropyridine 1-oxide (287d) (6.60 g, 62.4%) as a light yellow solid. The crude product was used for next step directly without further purification.

Step 5: Synthesis of Compound 287e

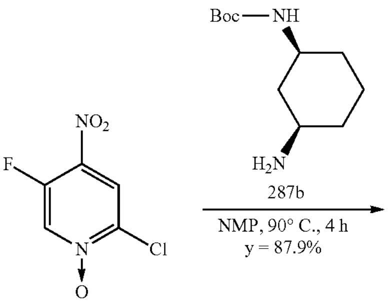

287d

-continued

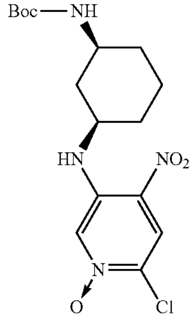

287e

Into a 100 ml 3-necked round bottom flask, was placed 2-chloro-5-fluoro-4-nitropyridine 1-oxide (287d)(6.60 g, 34.28 mmol, 1.00 equiv), tert-butyl ((1S,3R)-3-aminocyclohexyl) carbamate (287b)(7.36 g, 34.28 mmol, 1.00 equiv) in 20 mL of 1-methylpyrrolidin-2-one. The reaction mixture was stirred for 4 h at 90° C., the solution was cooled then quenched with 100 mL of ice/water. The yellow crystals precipitated were collected by filtration and washed with 2×50 mL of ice/water and dried to afford 5-(((1R,3S)-3-((tert-butoxycarbonyl)amino)cyclohexyl)amino)-2-chloro-4-nitropyridine 1-oxide (287e) (11.65 g, 87.9%) as a yellow solid. LC-MS (ESI) m/z $[M+H]^+$: 387.2, 389.2.

Step 6: Synthesis of Compound 287f

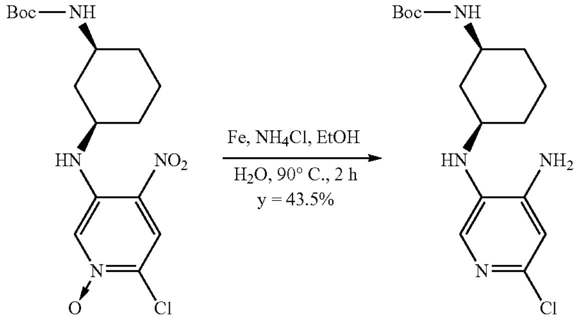

287e 287f

Into a 100 ml 3-necked round bottom flask, was placed 5-(((1R,3S)-3-((tert-butoxycarbonyl)amino) cyclohexyl) amino)-2-chloro-4-nitropyridine 1-oxide (287e)(11.60 g, 29.99 mmol, 1.00 equiv), Fe (5.02 g, 89.96 mmol, 3.00 equiv), $NH_4Cl$ (4.81 g, 89.96 mmol, 3.00 equiv) in 20 mL of ethanol and 20 mL of water. The reaction mixture was stirred for 2 h at 90° C. under $N_2$. The solids were filtrated out by filtration and the filtrate was concentrated under reduced pressure. The mixture was concentrated and purified by reverse phase chromatography eluting with 65% of acetonitrile in water (0.1% formic acid) to afford tert-butyl N-[(1S,3R)-3-[(4-amino-6-chloropyridin-3-yl)amino]cyclohexyl]carbamate (2870 (4.45 g, 43.5%) as a light yellow solid. $^1H$ NMR (300 MHz, DMSO-$d_6$) δ 7.45 (s, 1H), 7.12 (s, 1H), 6.86 (d, J=8.0 Hz, 1H), 6.66 (s, 1H), 5.06 (s, 1H), 3.33 (d, J=13.9 Hz, 2H), 2.07 (d, J=9.7 Hz, 1H), 1.93 (d, J=12.2 Hz, 1H), 1.74 (t, J=14.8 Hz, 2H), 1.38 (s, 9H), 1.05 (m, 3H). LC-MS (ESI) m/z $[M+H]^+$: 341.2, 343.2.

Step 7: Synthesis of Compound 287g

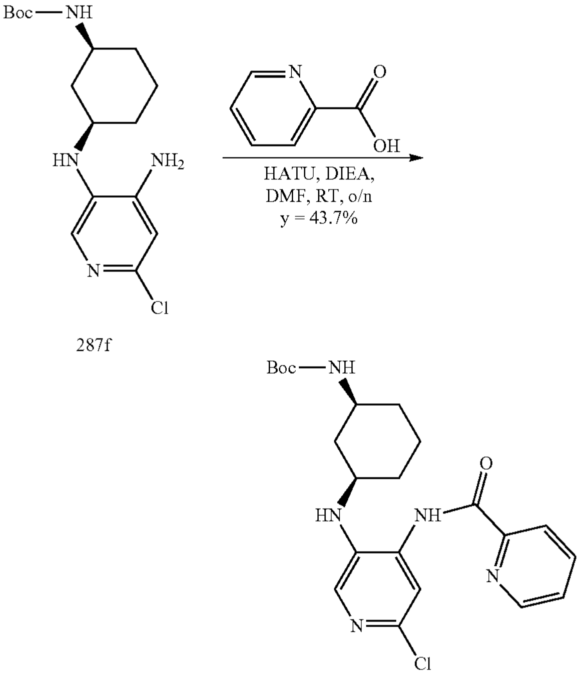

287f

287g

Into a 50 ml round bottom flask, was placed tert-butyl N-[(1S,3R)-3-[(4-amino-6-chloropyridin-3-yl)amino]cyclohexyl]carbamate (2.45 g, 7.19 mmol, 1.00 equiv), picolinic acid (0.88 g, 7.19 mmol, 1.00 equiv), N-ethyl-N-isopropylpropan-2-amine (2.79 g, 21.56 mmol, 3.00 equiv) in 15 mL of N,N-dimethylformamide, to this was added O-(7-azabenzotriazol-1-yl)-N,N,N',N'-tetramethyluronium hexafluorophosphate (3.28 g, 8.63 mmol, 1.20 equiv) at 0 degree C. and was stirred for overnight at room temperature. The solution was concentrated under reduced pressure and purified by reverse phase chromatography eluting with 60% of acetonitrile in water (0.1% formic acid) to afford tert-butyl N-[(1S, 3R)-3-[[6-chloro-4-(pyridine-2-amido)pyridin-3-yl]amino] cyclohexyl]carbamate (1.40 g, 43.7%) as a purple solid. LC-MS (ESI) m/z $[M+H]^+$: 446.2, 448.2.

Step 8: Synthesis of Compound 287h

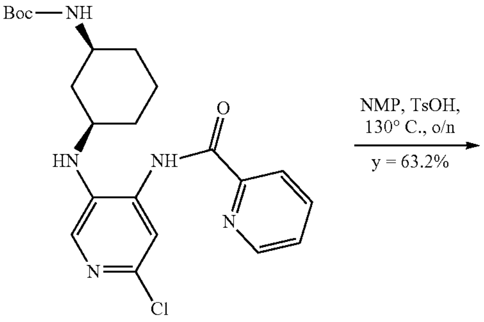

287g

-continued

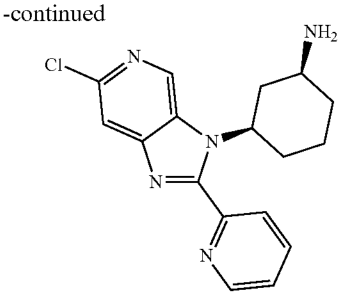

287h

Into a 50 ml round bottom flask, was placed tert-butyl N-[(1S,3R)-3-[[6-chloro-4-(pyridine-2-amido) pyridin-3-yl] amino]cyclohexyl]carbamate (1.40 g, 3.14 mmol, 1.00 equiv), 4-methylbenzenesulfonic acid (5.41 g, 31.39 mmol, 10 equiv) in 12 mL of 1-methylpyrrolidin-2-one, this was stirred for overnight at 130 degree C. The mixture was concentrated and purified by reverse phase chromatography eluting with 55% of acetonitrile in water (0.1% formic acid) to afford (1S,3R)-3-[6-chloro-2-(pyridin-2-yl)imidazo[4,5-c]pyridin-3-yl]cyclohexan-1-amine (287h)(650 mg, 63.2%) as a light yellow solid. LC-MS (ESI) m/z $[M+H]^+$: 328.1, 330.1.

Step 9: Synthesis of Compound 287i

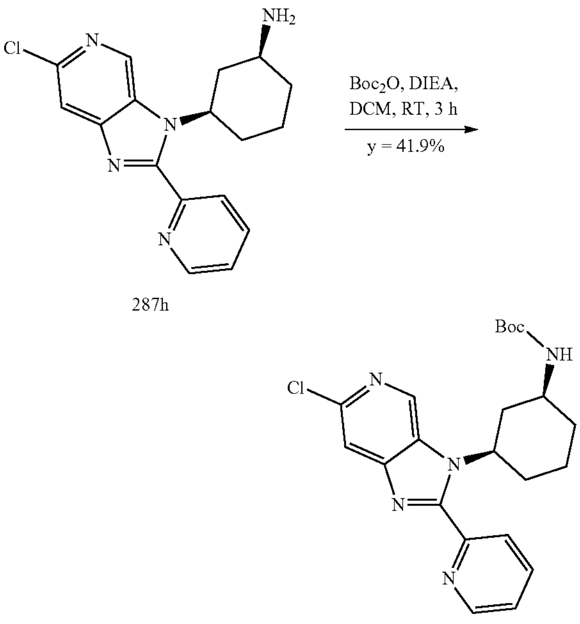

287h

287i

Into a 50 ml round bottom flask, was placed (1S,3R)-3-[6-chloro-2-(pyridin-2-yl)imidazo[4,5-c]pyridin-3-yl]cyclohexan-1-amine (650.0 mg, 1.98 mmol, 1.00 equiv), di-tert-butyl dicarbonate (519.3 mg, 2.38 mmol, 1.20 equiv), N-ethyl-N-isopropylpropan-2-amine (768.8 mg, 5.95 mmol, 3.00 equiv) in 10 mL of dichloromethane, this was stirred for 3 h at room temperature. The solution was concentrated under vacuum. The resulted residue was purified by reverse phase chromatography eluting with 60% of acetonitrile in water (0.1% formic acid) to afford tert-butyl ((1S,3R)-3-(6-chloro-2-(pyridin-2-yl)-3H-imidazo[4,5-c]pyridin-3-yl)cyclohexyl)carbamate (287i)(356 mg, 41.9%) as a yellow solid. LC-MS (ESI) m/z $[M+H]^+$: 428.1, 430.1.

Step 10: Synthesis of Compound 287j

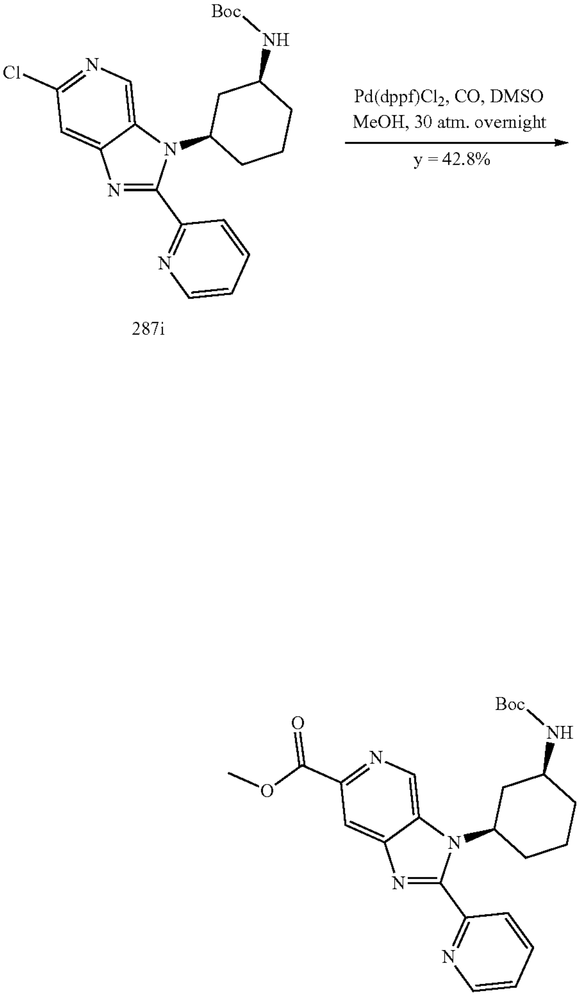

287i

287j

Into a 30 ml pressure tank, was placed tert-butyl N-[(1S,3R)-3-[6-chloro-2-(pyridin-2-yl)imidazo[4,5-c]pyridin-3-yl]cyclohexyl]-carbamate (350.00 mg, 0.82 mmol, 1.00 equiv), $Pd(dppf)Cl_2$ (777.99 mg, 1.06 mmol, 1.30 equiv), trimethylamine (248.29 mg, 2.45 mmol, 3.00 equiv) in 8 mL of methanol and 4 mL of (methylsulfinyl)methane, The mixture was purged with nitrogen for 3 times and then was pressurized to 30 atm. with carbon monoxide for overnight at 100 degree C. The reaction mixture was cooled to room temperature. The mixture was concentrated and purified by reverse phase chromatography eluting with 58% of acetonitrile in water (0.1% formic acid) to afford methyl 3-[(1R,3S)-3-[(tert-butoxycarbonyl)amino]cyclohexyl]-2-(pyridin-2-yl)imidazo[4,5-c]pyridine-6-carboxylate (158 mg, 42.8%) as a yellow solid. LC-MS (ESI) m/z $[M+H]^+$: 452.2, RT=0.70 min, Step 11: Synthesis of Compound 287k

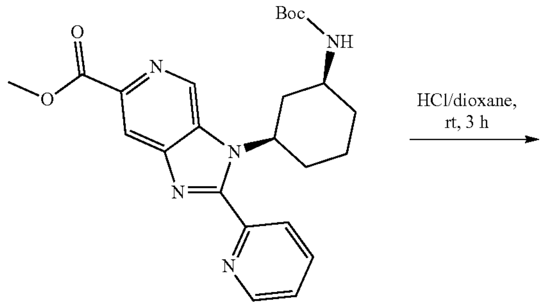

287j

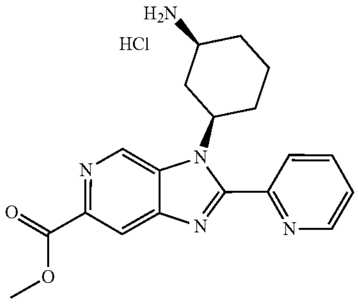

287k

Into a 50 ml round bottom flask, was placed methyl 3-[(1R,3S')-3-[(tert-butoxycarbonyl)amino]cyclohexyl]-2-(pyridin-2-yl)imidazo[4,5-c]pyridine-6-carboxylate (158.00 mg, 0.35 mmol, 1.00 equiv) in 20 mL of 4M HCl(g) in 1,4-dioxane solution. This was stirred for 3 h at room temperature. The solution was concentrated to afford 120 mg yellow solid. The crude product was used for next step directly without further purification. LC-MS (ESI) m/z $[M+H]^+$: 352.2.

Step 12: Synthesis of Compound 287l

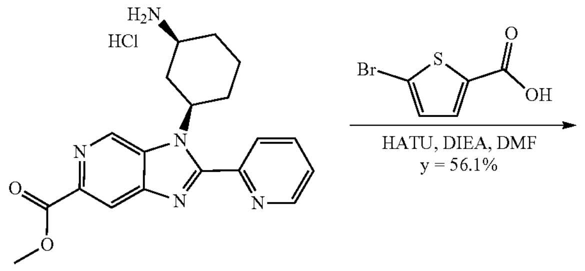

287k

-continued

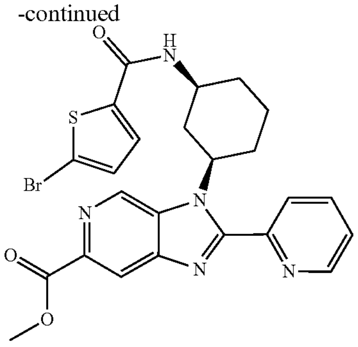

287l

Into a 25 ml round bottom flask, was placed 5-bromothiophene-2-carboxylic acid (120.0 mg, 0.58 mmol, 1.20 equiv), methyl 3-[(1R,3S)aminocyclohexyl]2(pyridinyl)imidazo[4,5c]pyridine6carboxyl at (169.7 mg, 0.48 mmol, 1.00 equiv), N-ethyl-N-isopropylpropan-2-amine (187.3 mg, 1.45 mmol, 3.00 equiv) in mL of N,N-dimethylformamide, to this was added O-(7-azabenzotriazol-1-yl)-N,N,N',N'-tetramethyluroniumhexafluorophosphate (220.4 mg, 0.58 mmol, 1.20 equiv) in 5.00 mL of N,N-dimethylformamide dropwise at 0 degree C., this was stirred for 4 h at room temperature. The mixture purified by reverse phase chromatography eluting with 52% of acetonitrile in water (0.1% formic acid) to afford methyl 3-[(1R,3S)-3-(5-bromothiophene-2-amido)cyclohexyl]-2-(pyridin-2-yl)imidazo[4,5-c]pyridine-6carboxylate 287l (103.3 mg, 56.1%) as a white solid. $^1H$ NMR (300 MHz, DMSO-$d_6$) δ 9.37 (d, J=1.0 Hz, 1H), 8.85-8.84 (m, 1H), 8.52 (d, J=7.8 Hz, 1H), 8.43 (d, J=0.9 Hz, 1H), 8.28-8.13 (m, 1H), 8.11-8.08 (m, 1H), 7.68-7.64 (m, 1H), 7.60 (d, J=4.0 Hz, 1H), 7.28 (d, J=4.0 Hz, 1H), 5.62 (t, J=12.4 Hz, 1H), 3.92 (s, 4H), 2.37 (d, J=11.8 Hz, 2H), 2.08 (d, J=12.0 Hz, 2H), 1.94 (d, J=12.3 Hz, 2H), 1.54 (t, J=9.5 Hz, 2H). LC-MS (ESI) m/z $[M+H]^+$: 542.0.

Step 13: Synthesis of Compound 287m

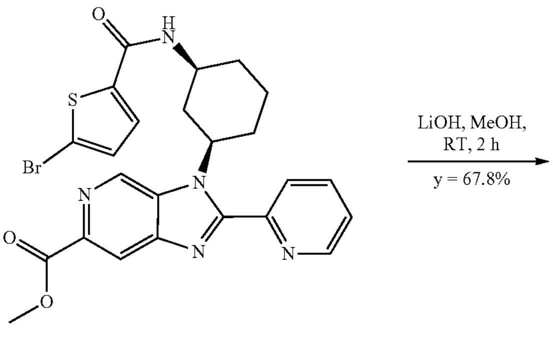

287l

-continued

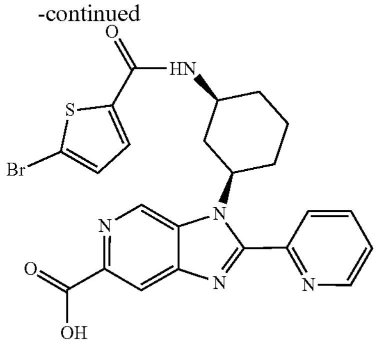

287m

Into a 50 ml round bottom flask, was placed methyl 3-[(1R,3S)-3-(5-bromothiophene-2-amido)cyclohexyl]-2-(pyridin-2-yl)imidazo[4,5-c]pyridine-6-carboxylate (90.0 mg, 0.17 mmol, 1.00 equiv), $LiOH.H_2O$ (34.9 mg, 084 mmol, 5.00 equiv) in 5 mL of methanol and 5 mL of water, this was stirred for 2 h at room temperature. The mixture was concentrated and purified by reverse phase chromatography eluting with 60% of acetonitrile in water (0.1% formic acid) to afford 3-[(1R,3S)-3-(5-bromothiophene-2-amido)cyclohexyl]-2-(pyridin-2-yl)imidazo[4,5-c]pyridine-6-carboxylic acid 287 m (59.4 mg, 67.8%) as a white solid. $^1$H NMR (300 MHz, DMSO-$d_6$) δ 9.35 (d, J=1.0 Hz, 1H), 8.85-8.84 (m, 1H), 8.51 (d, J=7.8 Hz, 1H), 8.40 (d, J=0.8 Hz, 1H), 8.26-8.13 (m, 1H), 8.10-8.07 (m, 1H), 7.68-7.64 (m, 1H), 7.59 (d, J=4.0 Hz, 1H), 7.28 (d, J=4.0 Hz, 1H), 5.63 (s, 1H), 3.92 (s, 1H), 2.77-2.71 (m, 1H), 2.42-2.26 (m, 2H), 2.08 (d, J=11.9 Hz, 1H), 1.94 (d, J=10.3 Hz, 2H), 1.52 (d, J=9.5 Hz, 2H). LC-MS (ESI) m/z $[M+H]^+$: 528.2.

Step 14: Synthesis of Compound 287

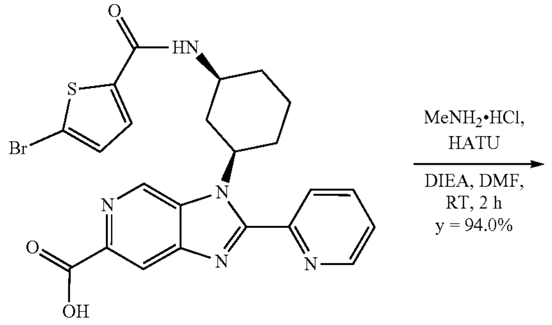

287m

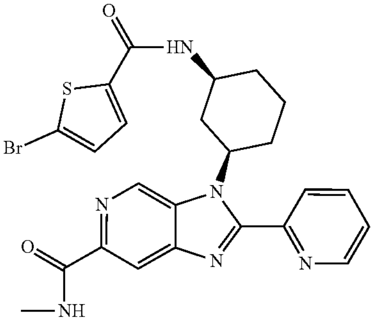

287

Into a 50 ml round bottom flask, was placed 3-[(1R,3S)-3-(5-bromothiophene-2-amido)cyclohexyl]-2-(pyridin-2-yl)imidazo[4,5-c]pyridine-6-carboxylic acid (55.0 mg, 0.11 mmol, 1.00 equiv), methylamine hydrochloride (6.9 mg, 0.095 mmol, 1.00 equiv), O-(7-azabenzotriazol-1-yl)-N,N,N',N'-tetramethyluroniumhexafluoro phosphate (43.3 mg, 0.11 mmol, 1.2 equiv), N-ethyl-N-isopropylpropan-2-amine (36.8 mg, 0.29 mmol, 3.00 equiv) in 3 mL of N,N-dimethylformamide. The reaction mixture was stirred for 2 h at room temperature and purified by reverse phase chromatography eluting with 60% of acetonitrile in water (0.1% formic acid) to afford methyl 3-[(1R,3S)-3-(5-bromothiophene-2-amido)cyclohexyl]-N-methyl-2-(pyridin-2-yl)imidazo[4,5-c]pyridine-6-carboxamide 287 (53.2 mg, 94.0%) as a white solid. $^1$H NMR (300 MHz, DMSO-$d_6$) δ 9.24 (s, 1H), 8.89-8.79 (m, 1H), 8.68 (d, J=5.1 Hz, 1H), 8.51 (d, J=7.8 Hz, 1H), 8.34 (s, 1H), 8.27 (d, J=7.9 Hz, 1H), 8.13-8.07 (m, 1H), 7.68-7.63 (m, 1H), 7.59 (d, J=4.0 Hz, 1H), 7.28 (d, J=4.0 Hz, 1H), 5.60 (d, J=12.4 Hz, 1H), 3.90 (s, 2H), 2.97-2.81 (m, 3H), 2.27 (d, J=3.7 Hz, 2H), 2.09 (d, J=11.7 Hz, 1H), 1.94 (d, J=9.3 Hz, 2H), 1.51 (d, J=7.7 Hz, 2H). LC-MS (ESI) m/z $[M+H]^+$: 541.1.

Additional Compounds

Additional compounds disclosed herein were prepared in a manner analogous to the procedures described above. The table below provides mass spectroscopy data for selected compounds disclosed herein.

| Compound No. | $[M+H]^+$ | Compound No. | $[M+H]^+$ | Compound No. | $[M+H]^+$ |
|---|---|---|---|---|---|
| 101 | 538.1<br>540.1 | 102 | 537.9<br>539.9 | 104 | 537.9<br>539.9 |
| 105 | 537.9<br>539.9 | 106 | 404.6 | 107 | 505.5 |
| 108 | 543.3 | 112 | 485.5 | 114 | 532.3<br>534.3 |
| 115 | 454.1 | 116 | 532.3<br>534.3 | 120 | 523.2<br>525.2 |
| 121 | 501.9 | 122 | 518.0 | 123 | 538.3<br>540.3 |
| 124 | 513.9 | 125 | 521.9<br>523.9 | 126 | 566.9<br>568.9 |
| 127 | 583.9 | 128 | 636.9<br>638.9 | 129 | 594.4<br>596.3 |
| 134 | 498.2 | 135 | 551.1<br>553.1 | 136 | 562.1<br>564.1 |
| 137 | 561.9<br>563.9 | 138 | 509.2 | 139 | 508.9 |
| 141 | 494.5<br>496.4 | 142 | 527.5 | 143 | 580.4<br>582.5 |
| 145 | 555.3<br>557.3 | 146 | 502.5 | 147 | 538.9<br>540.9 |
| 148 | 551.9<br>553.9 | 149 | 538.9<br>540.9 | 150 | 567.9<br>569.9 |
| 151 | 560.9<br>562.9 | 152 | 553.9<br>556.0 | 154 | 555.0<br>557.0 |
| 155 | 555.8<br>557.8 | 161 | 565.4<br>567.4 | 205 | 525.3<br>527.3 |
| 206 | 529.3<br>531.3 | 207 | 573.2<br>575.2 | 208 | 569.2<br>571.2 |
| 103 | 538.1<br>540.2 | 119 | 511.1<br>513.1 | 153 | 551.9<br>553.9 |
| 109 | 539.1<br>541.1 | 130 | 541.4 | 156 | 556.2<br>558.2 |
| 110 | 529.5 | 131 | 471.2 | 157 | 579.9<br>581.9 |
| 111 | 536.5 | 132 | 523.9<br>525.9 | 158 | 596.9<br>598.9 |
| 113 | 528.5 | 133 | 458.1 | 159 | 622.0<br>624.1 |
| 117 | 461.4 | 140 | 548.9<br>550.9 | 160 | 616.9<br>619.0 |

-continued

| Compound No. | [M + H]$^+$ | Compound No. | [M + H]$^+$ | Compound No. | [M + H]$^+$ |
|---|---|---|---|---|---|
| 118 | 433.4 | 144 | 500.6 | 162 | 561.9<br>563.9 |
| 163 | 570.9<br>572.9 | 171 | 556.9<br>558.9 | 179 | 535.1<br>537.1 |
| 164 | 570.9<br>572.9 | 172 | 518.5 | 180 | 589.1<br>591.1 |
| 165 | 561.0<br>564.0 | 173 | 501.7 | 181 | 490.2 |
| 166 | 620.9<br>622.9 | 174 | 520.7<br>522.2 | 182 | 601.2 |
| 167 | 560.9<br>562.9 | 175 | 573.1<br>575.1 | 183 | 534.6<br>536.2 |
| 168 | 596.9<br>598.9 | 176 | 573.1<br>575.1 | 184 | 571.1<br>573.2 |
| 169 | 556.9<br>558.9 | 177 | 527.4<br>529.4 | 185 | 563.3<br>565.3 |
| 170 | 550.9<br>552.9 | 178 | 510.6 | 186 | 554.2<br>556.2 |
| 187 | 544.4<br>546.4 | 195 | 462.6<br>464.1 | 202 | 472.7 |
| 188 | 518.4 | 196 | 523.3<br>525.4 | 203 | 478.4 |
| 189 | 499.3<br>501.3 | 197 | 512.4<br>514.4 | 204 | 566.2<br>568.2 |
| 190 | 543.3<br>545.2 | 198 | 503.7 | 209 | 589.3<br>591.3 |
| 191 | 510.4<br>512.1 | 199 | 556.2<br>558.1 | 210 | 575.3<br>577.3 |
| 192 | 519.7<br>521.6 | 200 | 529.3 | 211 | 568.1<br>570.1 |
| 193 | 543.2<br>545.2 | 201 | 499.4 | 212 | 541.2<br>543.2 |
| 194 | 506.5<br>508.6 | 202 | 471.5 | 213 | 585.2<br>587.2 |
| 214 | 524.3<br>526.3 | 222 | 542.8<br>544.9 | 230 | 534.8<br>536.7 |
| 215 | 573.2<br>575.2 | 223 | 586.6<br>588.6 | 231 | 563.3<br>565.3 |
| 216 | 556.2<br>558.2 | 224 | 529.3<br>531.3 | 232 | 554.3 |
| 217 | 489.7<br>491.7 | 225 | 513.0 | 233 | 606.7<br>608.6 |
| 218 | 455.8 | 226 | 513.1 | 234 | 557.8<br>559.7 |
| 219 | 494.4 | 227 | 506.3<br>508.4 | 235 | 528.2<br>530.2 |
| 220 | 489.7<br>491.7 | 228 | 478.3 | 236 | 546.1<br>548.2 |
| 221 | 534.0 | 229 | 555.8<br>557.8 | 237 | 590.0<br>591.9 |

-continued

| Compound No. | [M + H]$^+$ | Compound No. | [M + H]$^+$ | Compound No. | [M + H]$^+$ |
|---|---|---|---|---|---|
| 238 | 571.9<br>574.0 | 246 | 551.7<br>553.7 | 255 | 486.3 |
| 239 | 574.1<br>576.1 | 247 | 507.8<br>509.9 | 256 | 567.1<br>569.1 |
| 240 | 510.3<br>512.4 | 248 | 499.3 | 257 | 486.2 |
| 241 | 556.2<br>558.2 | 249 | 499.3<br>501.3 | 258 | 554.2<br>556.2 |
| 242 | 528.3<br>529.2<br>530.2<br>531.1 | 250 | 490.3 | 259 | 495.2<br>497.2 |
| 243 | 524.4<br>526.4 | 251 | 543.2<br>545.2 | 260 | 494.3<br>496.4 |
| 244 | 549.2<br>551.1 | 253 | 495.2<br>497.3 | 261 | 485.3 |
| 245 | 496.3 | 254 | 539.2<br>541.2 | 262 | 538.4<br>540.3 |
| 263 | 541.3<br>543.2 | 271 | 495.0<br>497.0 | 279 | 525.8<br>527.8 |
| 264 | 573.8<br>575.7 | 272 | 540.5<br>542.4 | 280 | 482.2<br>484.3 |
| 265 | 530.0<br>532.0 | 273 | 531.3 | 281 | 553.0<br>554.8 |
| 266 | 521.2 | 274 | 584.4<br>586.4 | 282 | 534.0 |
| 267 | 585.8<br>587.7 | 275 | 509.0 | 283 | 535.9<br>537.9 |
| 268 | 542.0<br>544.0 | 276 | 552.8<br>554.8 | 283 | 536.1<br>538.1 |
| 269 | 533.2 | 277 | 499.9 | 284 | 500.2<br>502.2 |
| 270 | 486.3 | 278 | 534.2<br>536.2 | 285 | 499.2<br>501.2 |
| 286 | 513.3<br>515.3 | 293 | 462.0<br>464.0 | 299 | 539.5<br>541.5 |
| 288 | 456.2 | 294 | 482.3<br>484.3 | 300 | 462.0 |
| 289 | 540.4<br>542.4 | 295 | 552.5<br>554.5 | 301 | 539.3<br>541.9 |
| 290 | 458.3 | 296 | 516.3<br>518.4 | 302 | 500.2<br>502.2 |
| 291 | 539.9<br>541.9 | 297 | 538.5<br>540.5 | 303 | 537.3<br>539.3 |
| 292 | 539.2<br>541.2 | 298 | 500.4<br>502.3 | 304 | 534.3 |
| 305 | 538.9<br>540.8 | 306 | 531.0<br>533.1 | | |

The table below provides $^1$H-NMR data for selected compounds disclosed herein.

| Compound No. | Peak list |
|---|---|
| 101 | $^1$H NMR (600 MHz, DMSO-$d_6$) δ = 8.48 (q, J = 4.5 Hz, 1H), 8.26-8.21 (m, 2H), 8.15-8.09 (m, 2H), 7.99 (d, J = 8.7 Hz, 1H), 7.96 (dt, J = 1.9, 7.7 Hz, 1H), 7.81 (dd, J = 1.7, 8.5 Hz, 1H), 7.77 (d, J = 3.8 Hz, 1H), 7.41 (ddd, J = 1.1, 4.9, 7.6 Hz, 1H), 7.36 (d, J = 3.8 Hz, 1H), 5.66-5.59 (m, 1H), 4.37-4.29 (m, 1H), 2.83 (d, J = 4.5 Hz, 3H), 2.50-2.34 (m, 3H), 2.04-1.94 (m, 1H), 1.91-1.78 (m, 3H), 1.76-1.69 (m, 1H) |
| 102 | $^1$H NMR (600 MHz, DMSO-$d_6$) δ = 8.80 (br d, J = 4.5 Hz, 1H), 8.54-8.47 (m, 2H), 8.27 (s, 1H), 8.20 (d, J = 7.6 Hz, 1H), 8.06 (dt, J = 1.7, 7.8 Hz, 1H), 7.93-7.88 (m, 1H), 7.88-7.84 (m, 1H), 7.60 (br d, J = 4.2 Hz, 2H), 7.27 (d, J = 3.8 Hz, 1H), 5.57 (br t, J = 12.3 Hz, 1H), 3.93-3.85 (m, 1H), 2.84 (d, J = 4.5 Hz, 3H), 2.44 (q, J = 12.0 Hz, 1H), 2.39-2.26 (m, 1H), 2.14 (br d, J = 11.7 Hz, 1H), 1.98 (br d, J = 11.3 Hz, 1H), 1.93 (br d, J = 7.2 Hz, 2H), 1.54-1.43 (m, 2H) |
| 102 | $^1$H NMR (300 MHz, DMSO-$d_6$) δ = 8.81-8.76 (m, 1H), 8.54-8.44 (m, 2H), 8.27-8.17 (m, 2H), 8.04 (t, J = 7.5 Hz, 1H), 7.87 (q, J = 8.5 Hz, 2H), 7.62-7.55 (m, 2H), 7.26 (d, J = 4.0 Hz, 1H), 5.61-5.49 (m, 1H), 3.94-3.81 (m, 1H), 2.82 (d, J = 4.3 Hz, 3H), 2.47-2.21 (m, 2H), 2.13 (br d, J = 12.2 Hz, 1H), 2.02-1.84 (m, 3H), 1.56-1.38 (m, 2H) |

-continued

| Compound No. | Peak list |
|---|---|
| 102 | $^1$H NMR (600 MHz, DMSO-$d_6$) δ = 8.81 (br d, J = 3.8 Hz, 1H), 8.48-8.36 (m, 2H), 8.27 (s, 1H), 8.21 (br d, J = 7.9 Hz, 1H), 8.06 (t, J = 7.9 Hz, 1H), 7.94-7.83 (m, 2H), 7.59 (br d, J = 4.2 Hz, 2H), 7.26 (d, J = 4.2 Hz, 1H), 5.59-5.52 (m, 1H), 3.90 (br dd, J = 3.6, 7.7 Hz, 1H), 2.85 (d, J = 4.2 Hz, 3H), 2.49-2.39 (m, 1H), 2.35-2.22 (m, 1H), 2.17 (br d, J = 11.7 Hz, 1H), 1.98-1.91 (m, 3H), 1.56-1.43 (m, 2H) |
| 102 | $^1$H NMR (600 MHz, DMSO-$d_6$) δ = 8.80 (s, 1H), 8.55 (d, J = 7.9 Hz, 1H), 8.52-8.48 (m, 1H), 8.27 (d, J = 1.5 Hz, 1H), 8.20 (d, J = 8.0 Hz, 1H), 8.06 (dt, J = 1.5, 7.7 Hz, 1H), 7.91 (d, J = 8.7 Hz, 1H), 7.85 (dd, J = 1.5, 8.7 Hz, 1H), 7.61 (d, J = 3.8 Hz, 1H), 7.61-7.58 (m, 1H), 7.27 (d, J = 3.8 Hz, 1H), 5.56 (br s, 1H), 3.96-3.83 (m, 1H), 2.84 (d, J = 4.5 Hz, 3H), 2.45 (d, J = 12.5 Hz, 1H), 2.28 (br s, 1H), 2.17-2.12 (m, 1H), 1.98 (br d, J = 11.3 Hz, 1H), 1.92 (br d, J = 9.8 Hz, 2H), 1.49 (br d, J = 10.2 Hz, 2H) |
| 103 | $^1$H NMR (600 MHz, DMSO-$d_6$) δ = 8.80 (br d, J = 4.5 Hz, 1H), 8.54-8.47 (m, 2H), 8.27 (s, 1H), 8.20 (d, J = 7.6 Hz, 1H), 8.06 (dt, J = 1.7, 7.8 Hz, 1H), 7.93-7.88 (m, 1H), 7.88-7.84 (m, 1H), 7.60 (br d, J = 4.2 Hz, 2H), 7.27 (d, J = 3.8 Hz, 1H), 5.57 (br t, J = 12.3 Hz, 1H), 3.93-3.85 (m, 1H), 2.84 (d, J = 4.5 Hz, 3H), 2.44 (q, J = 12.0 Hz, 1H), 2.39-2.26 (m, 1H), 2.14 (br d, J = 11.7 Hz, 1H), 1.98 (br d, J = 11.3 Hz, 1H), 1.93 (br d, J = 7.2 Hz, 2H), 1.54-1.43 (m, 2H) |
| 104 | $^1$H NMR (600 MHz, DMSO-$d_6$) δ = 8.80 (s, 1H), 8.54-8.46 (m, 2H), 8.27 (d, J = 1.1 Hz, 1H), 8.20 (d, J = 7.9 Hz, 1H), 8.05 (dt, J = 1.9, 7.7 Hz, 1H), 7.91 (d, J = 8.7 Hz, 1H), 7.86 (dd, J = 1.5, 8.7 Hz, 1H), 7.62-7.57 (m, 2H), 7.27 (d, J = 3.8 Hz, 1H), 5.61-5.51 (m, 1H), 3.93-3.85 (m, 1H), 2.84 (d, J = 4.5 Hz, 3H), 2.49-2.41 (m, 1H), 2.39-2.25 (m, 1H), 2.15 (br d, J = 11.7 Hz, 1H), 2.02-1.95 (m, 1H), 1.93 (br d, J = 7.6 Hz, 2H), 1.54-1.43 (m, 2H) |
| 105 | $^1$H NMR (300 MHz, CHLOROFORM-d) δ = 8.70 (d, J = 4.6 Hz, 1H), 8.17-8.09 (m, 2H), 7.83 (dt, J = 1.4, 7.9 Hz, 1H), 7.75-7.63 (m, 2H), 7.51-7.39 (m, 2H), 7.04-6.86 (m, 3H), 5.58-5.47 (m, 1H), 4.16-3.98 (m, 1H), 3.01 (d, J = 4.5 Hz, 3H), 2.34-1.95 (m, 6H), 1.59-1.38 (m, 4H) |
| 105 | $^1$H NMR (600 MHz, DMSO-$d_6$) δ = 8.80 (d, J = 5.1 Hz, 1H), 8.55-8.48 (m, 2H), 8.27 (d, J = 1.5 Hz, 1H), 8.20 (d, J = 8.0 Hz, 1H), 8.05 (dt, J = 1.7, 7.8 Hz, 1H), 7.91 (d, J = 8.7 Hz, 1H), 7.86 (dd, J = 1.7, 8.5 Hz, 1H), 7.62-7.57 (m, 2H), 7.27 (d, J = 4.2 Hz, 1H), 5.61-5.53 (m, 1H), 3.93-3.85 (m, 1H), 2.84 (d, J = 4.5 Hz, 3H), 2.44 (q, J = 12.1 Hz, 1H), 2.34-2.24 (m, 1H), 2.14 (br d, J = 11.7 Hz, 1H), 1.98 (br d, J = 11.0 Hz, 1H), 1.95-1.89 (m, 2H), 1.54-1.43 (m, 2H) |
| 105 | $^1$H NMR (600 MHz, DMSO-$d_6$) δ = 8.80 (d, J = 5.1 Hz, 1H), 8.54-8.46 (m, 2H), 8.27 (d, J = 1.5 Hz, 1H), 8.20 (d, J = 7.9 Hz, 1H), 8.06 (dt, J = 1.5, 7.7 Hz, 1H), 7.91 (d, J = 8.7 Hz, 1H), 7.85 (dd, J = 1.5, 8.7 Hz, 1H), 7.62-7.57 (m, 2H), 7.27 (d, J = 4.2 Hz, 1H), 5.60-5.53 (m, 1H), 3.93-3.85 (m, 1H), 2.84 (d, J = 4.5 Hz, 3H), 2.49-2.40 (m, 1H), 2.34-2.25 (m, 1H), 2.15 (br d, J = 11.7 Hz, 1H), 1.98 (br d, J = 11.3 Hz, 1H), 1.93 (br d, J = 7.6 Hz, 2H), 1.54-1.43 (m, 2H) |
| 301 | $^1$H NMR (600 MHz, DMSO-$d_6$) δ = 8.84 (d, J = 4.2 Hz, 1H), 8.53 (d, J = 7.6 Hz, 1H), 8.47 (d, J = 8.7 Hz, 1H), 8.27 (d, J = 7.9 Hz, 1H), 8.12 (dt, J = 1.5, 7.7 Hz, 1H), 8.08 (d, J = 8.7 Hz, 1H), 7.65 (t, J = 6.3 Hz, 1H), 7.60 (d, J = 4.2 Hz, 1H), 7.27 (d, J = 4.2 Hz, 1H), 5.64 (tt, J = 3.8, 12.4 Hz, 1H), 3.94 (s, 3H), 3.92-3.85 (m, 1H), 2.39-2.32 (m, 1H), 2.29-2.19 (m, 2H), 2.04 (br d, J = 11.7 Hz, 1H), 1.97-1.89 (m, 2H), 1.54-1.44 (m, 2H) |
| 106 | $^1$H NMR (600 MHz, DMSO-$d_6$) δ = 8.85-8.73 (m, 1H), 8.30 (br s, 1H), 8.26 (s, 1H), 8.20 (br d, J = 7.9 Hz, 1H), 8.04 (t, J = 8.4 Hz, 1H), 7.95 (br d, J = 6.4 Hz, 1H), 7.91-7.80 (m, 2H), 7.62-7.52 (m, 1H), 6.19 (br dd, J = 10.2, 17.0 Hz, 1H), 6.07 (br d, J = 17.0 Hz, 1H), 5.55 (br d, J = 9.8 Hz, 2H), 3.92-3.69 (m, 1H), 2.86 (br d, J = 4.5 Hz, 3H), 2.37-2.21 (m, 2H), 2.19-2.06 (m, 1H), 1.98 (br d, J = 11.0 Hz, 1H), 1.92 (br d, J = 10.6 Hz, 2H), 1.53-1.36 (m, 2H) |
| 107 | $^1$H NMR (600 MHz, DMSO-$d_6$) δ = 8.95 (d, J = 7.9 Hz, 1H), 8.82-8.78 (m, 1H), 8.50 (q, J = 4.3 Hz, 1H), 8.27 (s, 1H), 8.21 (d, J = 7.9 Hz, 1H), 8.14 (d, J = 4.5 Hz, 1H), 8.06 (dt, J = 1.9, 7.7 Hz, 1H), 7.92 (d, J = 8.8 Hz, 1H), 7.86 (dd, J = 1.9, 8.7 Hz, 1H), 7.82 (d, J = 4.5 Hz, 1H), 7.59 (ddd, J = 1.1, 4.9, 7.6 Hz, 1H), 5.63-5.52 (m, 1H), 3.98-3.89 (m, 1H), 2.84 (d, J = 4.5 Hz, 3H), 2.50-2.41 (m, 1H), 2.39-2.25 (m, 1H), 2.18 (br d, J = 11.7 Hz, 1H), 2.02-1.89 (m, 3H), 1.58-1.41 (m, 2H) |
| 108 | $^1$H NMR (600 MHz, DMSO-$d_6$) δ = 8.82-8.79 (m, 1H), 8.77 (t, J = 6.0 Hz, 1H), 8.54-8.47 (m, 1H), 8.46 (s, 1H), 8.37 (d, J = 7.9 Hz, 1H), 8.20 (d, J = 7.9 Hz, 1H), 8.05 (dt, J = 1.9, 7.7 Hz, 1H), 7.92-7.84 (m, 2H), 7.61-7.56 (m, 2H), 6.97 (d, J = 3.8 Hz, 1H), 6.28-6.19 (m, 1H), 6.17-6.11 (m, 1H), 5.64 (dd, J = 1.9, 10.2 Hz, 1H), 5.61-5.53 (m, 1H), 4.48 (d, J = 5.7 Hz, 2H), 3.94-3.85 (m, 1H), 2.84 (d, J = 4.5 Hz, 3H), 2.49-2.43 (m, 1H), 2.32-2.22 (m, 1H), 2.12 (br d, J = 12.1 Hz, 1H), 1.98 (br d, J = 11.7 Hz, 1H), 1.91 (br d, J = 9.8 Hz, 2H), 1.54-1.41 (m, 2H) |
| 282 | $^1$H NMR (600 MHz, DMSO-$d_6$) δ = 11.37 (s, 1H), 8.39-8.30 (m, 1H), 8.10 (d, J = 6.0 Hz, 1H), 7.96 (d, J = 4.2 Hz, 1H), 7.88 (d, J = 1.1 Hz, 1H), 7.85-7.74 (m, 3H), 7.63 (d, J = 3.8 Hz, 1H), 7.53-7.44 (m, 5H), 7.42-7.37 (m, 1H), 7.33-7.24 (m, 1H), 7.23-7.17 (m, 2H), 7.16-7.08 (m, 1H), 4.37-4.27 (m, 1H), 2.81 (d, J = 4.5 Hz, 3H), 2.34-2.25 (m, 1H), 2.24-2.07 (m, 2H), 1.95 (br dd, J = 3.8, 13.2 Hz, 1H), 1.89-1.76 (m, 2H), 1.76-1.61 (m, 2H) |

-continued

| Compound No. | Peak list |
|---|---|
| 283 | $^1$H NMR (600 MHz, DMSO-$d_6$) δ = 11.35 (s, 1H), 8.69 (br d, J = 3.8 Hz, 2H), 8.48 (d, J = 8.3 Hz, 2H), 8.34 (br d, J = 4.5 Hz, 1H), 8.15 (br d, J = 6.0 Hz, 1H), 7.88 (s, 1H), 7.83-7.78 (m, 2H), 7.56-7.41 (m, 6H), 7.38-7.28 (m, 4H), 7.26-7.14 (m, 2H), 4.27 (br s, 1H), 3.31-3.25 (m, 4H), 2.81 (br d, J = 4.2 Hz, 3H), 2.37-2.21 (m, 1H), 2.20-2.08 (m, 2H), 1.91 (br s, 1H), 1.82 (br s, 2H), 1.75-1.59 (m, 2H) |
| 283 | $^1$H NMR (600 MHz, DMSO-$d_6$) δ = 11.35 (s, 1H), 8.34 (q, J = 4.4 Hz, 1H), 8.15 (d, J = 6.0 Hz, 1H), 7.88 (s, 1H), 7.83-7.76 (m, 2H), 7.49 (dd, J = 1.3, 8.5 Hz, 1H), 7.44 (d, J = 7.2 Hz, 2H), 7.36 (d, J = 3.8 Hz, 1H), 7.32 (t, J = 7.7 Hz, 1H), 7.24-7.12 (m, 2H), 4.29-4.24 (m, 1H), 2.81 (d, J = 4.5 Hz, 3H), 2.46 (td, J = 1.8, 14.5 Hz, 1H), 2.31-2.21 (m, 1H), 2.20-2.05 (m, 2H), 2.01-1.86 (m, 1H), 1.82 (br s, 2H), 1.75-1.58 (m, 2H) |
| 109 | $^1$H NMR (600 MHz, DMSO-$d_6$) δ = 8.81 (br d, J = 4.5 Hz, 1H), 8.53 (br d, J = 7.6 Hz, 1H), 8.34 (s, 1H), 8.21 (br d, J = 7.9 Hz, 1H), 8.07 (br t, J = 7.7 Hz, 1H), 8.02-7.91 (m, 2H), 7.67-7.54 (m, 2H), 7.27 (d, J = 3.8 Hz, 1H), 5.56 (br t, J = 11.9 Hz, 1H), 3.91 (s, 4H), 2.48-2.36 (m, 1H), 2.35-2.23 (m, 1H), 2.17 (br d, J = 11.0 Hz, 1H), 2.07-1.96 (m, 1H), 1.96-1.89 (m, 2H), 1.49 (br s, 2H) |
| 119 | $^1$H NMR (600 MHz, DMSO-$d_6$) δ = 8.78 (br d, J = 4.2 Hz, 1H), 8.51 (d, J = 7.6 Hz, 1H), 8.19 (d, J = 7.9 Hz, 1H), 8.03 (dt, J = 1.5, 7.7 Hz, 1H), 7.80 (d, J = 8.3 Hz, 1H), 7.67 (s, 1H), 7.60 (d, J = 3.8 Hz, 1H), 7.62-7.54 (m, 1H), 7.30 (dd, J = 1.5, 8.7 Hz, 1H), 7.28 (d, J = 3.8 Hz, 1H), 5.62-5.52 (m, 1H), 5.33-5.10 (m, 1H), 4.63 (s, 2H), 3.97-3.83 (m, 1H), 2.49-2.42 (m, 1H), 2.33-2.19 (m, 1H), 2.12 (br d, J = 11.7 Hz, 1H), 2.01-1.87 (m, 3H), 1.55-1.41 (m, 2H) |
| 120 | $^1$H NMR (300 MHz, METHANOL-$d_4$) δ = 8.81 (br d, J = 4.1 Hz, 1H), 8.46-8.41 (m, 1H), 8.24-8.21 (m, 1H), 8.14-7.96 (m, 3H), 7.89-7.83 (m, 1H), 7.61-7.55 (m, 1H), 5.49-5.37 (m, 1H), 4.08-3.97 (m, 1H), 2.97 (s, 3H), 2.61-2.48 (m, 1H), 2.42-2.33 (m, 1H), 2.33-2.24 (m, 1H), 2.14-1.95 (m, 3H), 1.66-1.48 (m, 2H) |
| 121 | $^1$H NMR (600 MHz, DMSO-$d_6$) δ = 8.86-8.75 (m, 1H), 8.69 (d, J = 7.9 Hz, 1H), 8.50 (q, J = 4.3 Hz, 1H), 8.27 (d, J = 1.5 Hz, 1H), 8.21 (d, J = 7.9 Hz, 1H), 8.06 (dt, J = 1.9, 7.7 Hz, 1H), 7.96-7.89 (m, 2H), 7.88-7.83 (m, 1H), 7.81 (d, J = 4.2 Hz, 1H), 7.59 (ddd, J = 0.9, 4.7, 7.6 Hz, 1H), 5.63-5.53 (m, 1H), 3.99-3.88 (m, 1H), 2.84 (d, J = 4.2 Hz, 3H), 2.55 (s, 3H), 2.48 (br d, J = 12.1 Hz, 1H), 2.35-2.25 (m, 1H), 2.16 (br d, J = 11.7 Hz, 1H), 2.03-1.91 (m, 3H), 1.58-1.43 (m, 2H) |
| 122 | $^1$H NMR (600 MHz, DMSO-$d_6$) δ = 8.84-8.77 (m, 1H), 8.72 (d, J = 7.9 Hz, 1H), 8.50 (q, J = 4.4 Hz, 1H), 8.27 (d, J = 1.5 Hz, 1H), 8.20 (d, J = 8.4 Hz, 1H), 8.06 (dt, J = 1.9, 7.7 Hz, 1H), 7.91 (d, J = 8.7 Hz, 1H), 7.86 (dd, J = 1.7, 8.5 Hz, 1H), 7.80 (s, 2H), 7.60 (ddd, J = 1.1, 4.7, 7.7 Hz, 1H), 5.58 (br s, 1H), 3.93 (td, J = 3.8, 7.6 Hz, 1H), 3.84 (s, 3H), 2.84 (d, J = 4.5 Hz, 3H), 2.49-2.43 (m, 1H), 2.30 (br dd, J = 3.6, 12.3 Hz, 1H), 2.16 (br d, J = 12.1 Hz, 1H), 1.99 (br d, J = 11.3 Hz, 1H), 1.96-1.90 (m, 2H), 1.56-1.44 (m, 2H) |
| 124 | $^1$H NMR (600 MHz, DMSO-$d_6$) δ = 8.67 (br d, J = 7.2 Hz, 1H), 8.32 (br d, J = 3.8 Hz, 1H), 8.20 (s, 1H), 7.94 (d, J = 4.2 Hz, 1H), 7.85-7.72 (m, 3H), 7.61 (dt, J = 1.5, 7.9 Hz, 1H), 7.47 (dd, J = 1.5, 7.6 Hz, 1H), 7.27 (d, J = 8.7 Hz, 1H), 7.20-7.12 (m, 1H), 4.04 (tt, J = 3.9, 12.3 Hz, 1H), 3.81 (br d, J = 5.3 Hz, 1H), 2.85 (d, J = 4.5 Hz, 3H), 2.33 (q, J = 11.5 Hz, 1H), 2.26-2.16 (m, 1H), 1.89 (br d, J = 11.3 Hz, 3H), 1.59-1.45 (m, 1H), 1.43-1.26 (m, 1H) |
| 125 | $^1$H NMR (600 MHz, DMSO-$d_6$) δ = 8.80 (ddd, J = 0.9, 1.8, 4.8 Hz, 1H), 8.58-8.47 (m, 1H), 8.40 (d, J = 7.9 Hz, 1H), 8.27 (d, J = 1.5 Hz, 1H), 8.21 (td, J = 0.9, 7.9 Hz, 1H), 8.06 (dt, J = 1.5, 7.7 Hz, 1H), 7.91-7.84 (m, 2H), 7.59 (ddd, J = 1.1, 4.8, 7.6 Hz, 1H), 7.12 (d, J = 3.4 Hz, 1H), 6.74 (d, J = 3.4 Hz, 1H), 5.60-5.53 (m, 1H), 3.98-3.88 (m, 1H), 2.84 (d, J = 4.5 Hz, 3H), 2.60-2.54 (m, 1H), 2.24 (br dd, J = 3.4, 12.5 Hz, 1H), 2.13-2.04 (m, 1H), 1.97 (br d, J = 9.8 Hz, 1H), 1.94-1.85 (m, 2H), 1.57-1.42 (m, 2H) |
| 127 | $^1$H NMR (600 MHz, DMSO-$d_6$) δ = 8.67 (br d, J = 7.6 Hz, 1H), 8.37 (br d, J = 3.8 Hz, 1H), 8.25 (s, 1H), 8.02-7.97 (m, 1H), 7.94 (d, J = 4.2 Hz, 1H), 7.91-7.86 (m, 2H), 7.84-7.79 (m, 3H), 7.78-7.74 (m, 1H), 4.09 (tt, J = 3.8, 12.4 Hz, 1H), 3.80 (tdt, J = 3.8, 7.7, 11.6 Hz, 1H), 2.85 (d, J = 4.5 Hz, 3H), 2.43-2.34 (m, 1H), 2.24 (dq, J = 3.2, 12.5 Hz, 1H), 2.12 (br d, J = 12.1 Hz, 1H), 1.96-1.84 (m, 3H), 1.53-1.42 (m, 1H), 1.40-1.30 (m, 1H) |
| 129 | $^1$H NMR (600 MHz, DMSO-$d_6$) δ = 9.78 (s, 1H), 8.52-8.44 (m, 2H), 8.23 (s, 1H), 7.89-7.76 (m, 3H), 7.57 (br dd, J = 1.3, 15.3 Hz, 1H), 7.49-7.43 (m, 1H), 7.38-7.31 (m, 1H), 7.27 (d, J = 4.2 Hz, 1H), 4.12 (tt, J = 3.9, 12.3 Hz, 1H), 3.76-3.61 (m, 1H), 2.83 (d, J = 4.5 Hz, 3H), 2.40-2.30 (m, 1H), 2.29-2.18 (m, 1H), 2.09 (br d, J = 12.1 Hz, 1H), 2.00-1.93 (m, 1H), 1.90 (s, 3H), 1.86 (br dd, J = 3.6, 7.0 Hz, 2H), 1.49-1.40 (m, 1H), 1.33-1.22 (m, 1H) |
| 130 | $^1$H NMR (600 MHz, DMSO-$d_6$) δ = 9.78 (s, 1H), 8.80 (d, J = 7.9 Hz, 1H), 8.47 (q, J = 4.4 Hz, 1H), 8.23 (d, J = 1.1 Hz, 1H), 7.97 (d, J= 3.8 Hz, 1H), 7.90-7.74 (m, 4H), 7.63-7.53 (m, 1H), 7.50-7.42 (m, 1H), 7.39-7.30 (m, 1H), 4.15 (br d, J = 9.1 Hz, 1H), 3.81-3.67 (m, 1H), 2.83 (d, J = 4.5 Hz, 3H), 2.41-2.33 (m, 1H), 2.31-2.21 (m, 1H), 2.12 (br d, J = 11.7 Hz, 1H), 2.00-1.93 (m, 1H), 1.90-1.85 (m, 5H), 1.52-1.42 (m, 1H), 1.35-1.26 (m, 1H) |
| 131 | $^1$H NMR (600 MHz, DMSO-$d_6$) δ = 9.07 (d, J = 7.6 Hz, 1H), 8.85-8.77 (m, 1H), 8.51 (q, J = 4.3 Hz, 1H), 8.29 (s, 1H), 8.21 (d, J = 7.9 Hz, 1H), 8.09-8.00 (m, 2H), 7.92 (d, J = 4.2 Hz, 1H), 7.87 (s, 2H), 7.58 (ddd, J = 1.1, 4.9, 7.6 Hz, 1H), 6.11-6.02 (m, 1H), 4.44-4.34 (m, 1H), 2.84 (d, J = 4.5 Hz, 3H), 2.50-2.38 (m, 3H), 2.28-2.07 (m, 3H) |

-continued

| Compound No. | Peak list |
|---|---|
| 132 | $^1$H NMR (600 MHz, DMSO-$d_6$) δ = 8.81 (br d, J = 4.2 Hz, 1H), 8.78-8.71 (m, 1H), 8.51 (br d, J = 4.5 Hz, 1H), 8.29 (s, 1H), 8.25-8.17 (m, 1H), 8.05 (dt, J = 1.5, 7.7 Hz, 1H), 7.96-7.80 (m, 2H), 7.67 (d, J = 3.8 Hz, 1H), 7.58 (br dd, J = 5.1, 6.6 Hz, 1H), 7.33 (d, J = 3.8 Hz, 1H), 6.11-6.02 (m, 1H), 4.36 (br d, J = 8.7 Hz, 1H), 2.84 (d, J = 4.5 Hz, 3H), 2.50-2.37 (m, 3H), 2.29-2.04 (m, 3H) |
| 134 | $^1$H NMR (600 MHz, DMSO-$d_6$) δ = 8.82 (d, J = 7.9 Hz, 1H), 8.48 (q, J = 4.4 Hz, 1H), 8.23 (d, J = 1.5 Hz, 1H), 7.98 (d, J = 3.8 Hz, 1H), 7.89-7.82 (m, 3H), 7.55-7.50 (m, 1H), 7.49-7.45 (m, 1H), 7.44-7.37 (m, 2H), 4.10-3.98 (m, 1H), 3.80-3.71 (m, 1H), 2.83 (d, J = 4.5 Hz, 3H), 2.34 (q, J = 11.6 Hz, 1H), 2.18 (s, 4H), 2.12-2.02 (m, 1H), 1.85 (br d, J = 11.0 Hz, 3H), 1.52-1.40 (m, 1H), 1.38-1.26 (m, 1H) |
| 135 | $^1$H NMR (600 MHz, DMSO-$d_6$) δ = 8.52-8.46 (m, 2H), 8.23 (s, 1H), 7.89-7.83 (m, 2H), 7.58 (d, J = 4.2 Hz, 1H), 7.54-7.49 (m, 1H), 7.48-7.44 (m, 1H), 7.44-7.37 (m, 2H), 7.27 (d, J = 4.2 Hz, 1H), 4.06-3.98 (m, 1H), 3.71 (dtd, J = 4.2, 7.7, 15.5 Hz, 2H), 2.83 (d, J = 4.2 Hz, 3H), 2.33 (q, J = 11.5 Hz, 1H), 2.18 (s, 3H), 2.04 (br s, 1H), 1.90-1.79 (m, 3H), 1.48-1.38 (m, 1H), 1.34-1.24 (m, 1H) |
| 136 | $^1$H NMR (600 MHz, DMSO-$d_6$) δ = 8.53 (q, J = 4.4 Hz, 1H), 8.48 (d, J = 7.9 Hz, 1H), 8.29 (d, J = 1.5 Hz, 1H), 8.16-8.11 (m, 1H), 7.98-7.92 (m, 2H), 7.91-7.88 (m, 1H), 7.87-7.81 (m, 2H), 7.58 (d, J = 3.8 Hz, 1H), 7.27 (d, J = 4.2 Hz, 1H), 4.19 (tt, J = 4.2, 12.3 Hz, 1H), 3.87-3.76 (m, 1H), 2.84 (d, J = 4.5 Hz, 3H), 2.35 (q, J = 12.1 Hz, 1H), 2.27-2.16 (m, 1H), 2.14-2.07 (m, 1H), 1.97 (br d, J = 11.7 Hz, 1H), 1.89-1.80 (m, 2H), 1.47-1.33 (m, 2H) |
| 137 | $^1$H NMR (600 MHz, DMSO-$d_6$) δ = 8.53 (q, J = 4.5 Hz, 1H), 8.49 (d, J = 7.9 Hz, 1H), 8.29 (d, J = 1.1 Hz, 1H), 8.13 (dd, J = 1.1, 7.9 Hz, 1H), 7.97-7.92 (m, 2H), 7.92-7.88 (m, 1H), 7.84 (dtd, J = 1.3, 3.9, 7.8 Hz, 2H), 7.58 (d, J = 4.2 Hz, 1H), 7.27 (d, J = 3.8 Hz, 1H), 4.19 (tt, J = 3.9, 12.4 Hz, 1H), 3.81 (dtd, J = 4.0, 7.5, 11.3 Hz, 1H), 2.84 (d, J = 4.5 Hz, 3H), 2.35 (q, J = 12.2 Hz, 1H), 2.27-2.17 (m, 1H), 2.15-2.06 (m, 1H), 1.97 (br d, J = 11.3 Hz, 1H), 1.89-1.79 (m, 2H), 1.48-1.33 (m, 2H) |
| 138 | $^1$H NMR (600 MHz, DMSO-$d_6$) δ = 8.81 (d, J = 7.9 Hz, 1H), 8.53 (q, J = 4.4 Hz, 1H), 8.29 (d, J = 1.5 Hz, 1H), 8.13 (dd, J = 0.9, 8.1 Hz, 1H), 7.98 (d, J = 4.2 Hz, 1H), 7.97-7.93 (m, 2H), 7.92-7.89 (m, 1H), 7.87-7.82 (m, 3H), 4.21 (tt, J = 3.7, 12.3 Hz, 1H), 3.90-3.82 (m, 1H), 2.84 (d, J = 4.5 Hz, 3H), 2.39-2.32 (m, 1H), 2.28-2.18 (m, 1H), 2.13 (br d, J = 12.1 Hz, 1H), 1.98 (br d, J = 11.7 Hz, 1H), 1.91-1.81 (m, 2H), 1.49-1.36 (m, 2H) |
| 139 | $^1$H NMR (600 MHz, DMSO-$d_6$) δ = 8.82 (d, J = 7.9 Hz, 1H), 8.53 (q, J = 4.5 Hz, 1H), 8.29 (d, J = 1.5 Hz, 1H), 8.13 (dd, J = 0.9, 8.1 Hz, 1H), 7.98 (d, J = 4.2 Hz, 1H), 7.96-7.93 (m, 2H), 7.92-7.89 (m, 1H), 7.87-7.81 (m, 3H), 4.21 (tt, J = 3.8, 12.4 Hz, 1H), 3.90-3.81 (m, 1H), 2.84 (d, J = 4.5 Hz, 3H), 2.36 (q, J = 12.2 Hz, 1H), 2.28-2.18 (m, 1H), 2.13 (br d, J = 12.1 Hz, 1H), 1.98 (br d, J = 11.0 Hz, 1H), 1.92-1.80 (m, 2H), 1.50-1.38 (m, 2H) |
| 296 | $^1$H NMR (600 MHz, DMSO-$d_6$) δ = 9.10 (d, J = 0.8 Hz, 1H), 8.84 (qd, J = 0.9, 4.9 Hz, 1H), 8.49 (d, J = 7.9 Hz, 1H), 8.28-8.20 (m, 1H), 8.10 (dt, J = 1.5, 7.7 Hz, 1H), 7.89 (s, 1H), 7.66 (ddd, J = 1.1, 4.8, 7.6 Hz, 1H), 7.59 (d, J = 3.8 Hz, 1H), 7.28 (d, J = 4.2 Hz, 1H), 5.61 (tt, J = 3.8, 12.4 Hz, 1H), 3.97-3.84 (m, 1H), 2.40-2.32 (m, 1H), 2.31-2.17 (m, 2H), 2.05 (br d, J = 11.0 Hz, 1H), 1.92 (br d, J = 10.2 Hz, 2H), 1.59-1.40 (m, 2H) |
| 140 | $^1$H NMR (300 MHz, METHANOL-$d_4$) δ = 8.83 (td, J = 1.3, 4.9 Hz, 1H), 8.19-8.12 (m, 1H), 8.12-8.03 (m, 3H), 7.69-7.56 (m, 2H), 7.50 (d, J = 4.1 Hz, 1H), 7.14 (d, J = 4.0 Hz, 1H), 5.49 (tt, J = 3.7, 12.3 Hz, 1H), 4.10-3.94 (m, 1H), 2.49 (q, J = 11.9 Hz, 1H), 2.41-2.30 (m, 2H), 2.20-1.95 (m, 4H), 1.68-1.48 (m, 2H) |
| 141 | $^1$H NMR (600 MHz, DMSO-$d_6$) δ = 8.83-8.76 (m, 1H), 8.54 (d, J = 7.9 Hz, 1H), 8.50 (q, J = 4.4 Hz, 1H), 8.26 (d, J = 1.5 Hz, 1H), 8.20 (d, J = 7.6 Hz, 1H), 8.06 (dt, J = 1.9, 7.7 Hz, 1H), 7.94-7.89 (m, 1H), 7.85 (dd, J = 1.5, 8.7 Hz, 1H), 7.65 (d, J = 3.8 Hz, 1H), 7.59 (ddd, J = 1.1, 4.9, 7.6 Hz, 1H), 7.17 (d, J = 4.2 Hz, 1H), 5.63-5.50 (m, 1H), 3.95-3.83 (m, 1H), 2.84 (d, J = 4.5 Hz, 3H), 2.44 (q, J = 12.1 Hz, 1H), 2.34-2.25 (m, 1H), 2.14 (br d, J = 11.7 Hz, 1H), 1.98 (br d, J = 11.7 Hz, 1H), 1.93 (br d, J = 9.1 Hz, 2H), 1.55-1.41 (m, 2H) |
| 142 | $^1$H NMR (600 MHz, DMSO-$d_6$) δ = 8.65 (br d, J = 1.6 Hz, 1H), 8.37 (br s, 1H), 8.19 (s, 1H), 8.03-7.94 (m, 1H), 7.93 (d, J = 4.2 Hz, 1H), 7.89 (br s, 3H), 7.81 (d, J = 4.2 Hz, 1H), 7.76-7.69 (m, 2H), 7.63 (br d, J = 6.8 Hz, 1H), 7.26 (br s, 1H), 4.09 (tt, J = 3.9, 12.4 Hz, 1H), 3.76 (tdt, J = 3.8, 7.7, 11.6 Hz, 1H), 2.86 (d, J = 4.5 Hz, 3H), 2.32 (q, J = 12.1 Hz, 1H), 2.25-2.13 (m, 2H), 2.05-1.97 (m, 1H), 1.93-1.81 (m, 2H), 1.47 (dq, J = 3.8, 12.6 Hz, 1H), 1.39-1.28 (m, 1H) |
| 143 | $^1$H NMR (600 MHz, DMSO-$d_6$) δ = 8.43 (br d, J = 7.9 Hz, 2H), 8.17 (s, 1H), 8.05 (br s, 1H), 7.90-7.76 (m, 3H), 7.74-7.64 (m, 2H), 7.61-7.55 (m, 2H), 7.32 (br s, 1H), 7.26 (d, J = 4.2 Hz, 1H), 4.09-3.96 (m, 1H), 3.78-3.65 (m, 1H), 2.84 (d, J = 4.5 Hz, 3H), 2.30 (q, J = 12.0 Hz, 1H), 2.22-2.06 (m, 2H), 2.05-1.95 (m, 1H), 1.84 (br d, J = 11.0 Hz, 2H), 1.49-1.38 (m, 1H), 1.37-1.24 (m, 1H) |
| 144 | $^1$H NMR (600 MHz, DMSO-$d_6$) δ = 8.83-8.79 (m, 1H), 8.50 (q, J = 4.4 Hz, 1H), 8.32-8.26 (m, 2H), 8.20 (td, J = 0.9, 7.9 Hz, 1H), 8.06 (dt, J = 1.5, 7.7 Hz, 1H), 7.92-7.88 (m, 1H), 7.88-7.83 (m, 1H), 7.59 (ddd, J = 1.3, 4.6, 7.6 Hz, 1H), 7.54 (d, J = 3.8 Hz, 1H), 6.84-6.78 (m, 1H), 5.60-5.52 (m, 1H), 3.93-3.83 (m, 1H), 2.84 (d, J = 4.5 Hz, 3H), 2.45 (q, J = 12.2 Hz, 1H), 2.32-2.23 (m, 1H), 2.18-2.08 (m, 2H), 1.98 (br d, J = 11.3 Hz, 1H), 1.94-1.88 (m, 2H), 1.54-1.40 (m, 2H), 1.07-1.00 (m, 2H), 0.72-0.65 (m, 2H) |

-continued

| Compound No. | Peak list |
|---|---|
| 145 | $^1$H NMR (600 MHz, DMSO-$d_6$) δ = 8.53-8.46 (m, 2H), 8.25 (d, J = 1.1 Hz, 1H), 7.92-7.84 (m, 2H), 7.74-7.65 (m, 2H), 7.58 (d, J = 4.2 Hz, 1H), 7.49 (t, J = 9.1 Hz, 1H), 7.47-7.41 (m, 1H), 7.27 (d, J = 4.2 Hz, 1H), 4.22-4.12 (m, 1H), 3.85-3.76 (m, 1H), 2.84 (d, J = 4.2 Hz, 3H), 2.34 (q, J = 12.1 Hz, 1H), 2.26-2.17 (m, 1H), 2.04 (br d, J = 11.7 Hz, 1H), 1.94-1.82 (m, 3H), 1.51-1.33 (m, 2H) |
| 146 | $^1$H NMR (600 MHz, DMSO-$d_6$) δ = 8.83-8.78 (m, 1H), 8.50 (q, J = 4.4 Hz, 1H), 8.31 (d, J = 7.9 Hz, 1H), 8.27 (d, J = 1.5 Hz, 1H), 8.21 (d, J = 7.9 Hz, 1H), 8.06 (dt, J = 1.9, 7.7 Hz, 1H), 7.92-7.89 (m, 1H), 7.87-7.84 (m, 1H), 7.62-7.55 (m, 2H), 6.90-6.86 (m, 1H), 5.62-5.53 (m, 1H), 3.95-3.85 (m, 1H), 3.14 (td, J = 6.8, 13.3 Hz, 1H)m 2.84 (d, J = 4.5 Hz, 3H), 2.47 (br d, J = 12.1 Hz, 1H), 2.33-2.23 (m, 1H), 2.16-2.08 (m, 1H), 1.98 (br d, J = 11.7 Hz, 1H), 1.92 (br d, J = 9.8 Hz, 2H), 1.53-1.43 (m, 2H), 1.26 (d, J = 6.8 Hz, 6H) |
| 291 | $^1$H NMR (600 MHz, DMSO-$d_6$) δ = 9.29 (s, 1H), 8.80-8.74 (m, 1H), 8.44 (d, J = 7.9 Hz, 1H), 8.35 (s, 1H), 8.19 (d, J = 7.9 Hz, 1H), 8.03 (dt, J = 1.7, 7.8 Hz, 1H), 7.59 (ddd, J = 1.1, 4.7, 7.7 Hz, 1H), 7.52 (d, J = 4.2 Hz, 1H), 7.20 (d, J = 4.2 Hz, 1H), 5.55 (tt, J = 3.8, 12.4 Hz, 1H), 3.92-3.78 (m, 4H), 2.38-2.29 (m, 1H), 2.27-2.14 (m, 2H), 2.01 (br d, J = 11.0 Hz, 1H), 1.92-1.83 (m, 2H), 1.54-1.37 (m, 2H) |
| 279 | $^1$H NMR (600 MHz, DMSO-$d_6$) δ = 9.35 (s, 1H), 8.91-8.80 (m, 1H), 8.51 (d, J = 7.9 Hz, 1H), 8.41 (d, J = 0.8 Hz, 1H), 8.31-8.23 (m, 1H), 8.11 (dt, J = 1.9, 7.7 Hz, 1H), 7.66 (ddd, J = 1.1, 4.9, 7.6 Hz, 1H), 7.60 (d, J = 4.2 Hz, 1H), 7.28 (d, J = 3.8 Hz, 1H), 5.63 (tt, J = 3.9, 12.5 Hz, 1H), 3.97-3.85 (m, 1H), 2.46-2.39 (m, 1H), 2.36-2.21 (m, 2H), 2.09 (br d, J = 9.8 Hz, 1H), 1.99-1.89 (m, 2H), 1.61-1.43 (m, 2H) |
| 149 | $^1$H NMR (600 MHz, DMSO-$d_6$) δ = 9.38 (d, J = 1.1 Hz, 1H), 8.87 (dd, J = 1.7, 2.5 Hz, 1H), 8.83 (d, J = 2.6 Hz, 1H), 8.57-8.50 (m, 2H), 8.32 (d, J = 1.1 Hz, 1H), 7.98-7.92 (m, 1H), 7.91-7.85 (m, 1H), 7.60 (d, J = 4.2 Hz, 1H), 7.27 (d, J = 3.8 Hz, 1H), 5.47-5.36 (m, 1H), 3.97-3.84 (m, 1H), 2.84 (d, J = 4.5 Hz, 3H), 2.47-2.40 (m, 1H), 2.34-2.23 (m, 1H), 2.16 (br d, J = 11.7 Hz, 1H), 2.00 (br d, J = 12.1 Hz, 1H), 1.96-1.88 (m, 2H), 1.49 (br t, J = 10.6 Hz, 2H) |
| 150 | $^1$H NMR (600 MHz, DMSO-$d_6$) δ = 8.55-8.48 (m, 2H), 8.26 (d, J = 1.1 Hz, 1H), 7.96 (dd, J = 7.2, 8.3 Hz, 1H), 7.93-7.90 (m, 1H), 7.88-7.85 (m, 1H), 7.83 (d, J = 6.8 Hz, 1H), 7.60 (d, J = 3.8 Hz, 1H), 7.27 (d, J = 4.2 Hz, 1H), 7.07-7.02 (m, 1H), 5.69 (tt, J = 4.0, 12.4 Hz, 1H), 4.01 (s, 3H), 3.99-3.92 (m, 1H), 2.84 (d, J = 4.5 Hz, 3H), 2.45-2.30 (m, 2H), 2.24 (br d, J = 11.7 Hz, 1H), 2.02 (br d, J = 10.2 Hz, 1H), 1.97-1.88 (m, 2H), 1.61-1.46 (m, 2H) |
| 151 | $^1$H NMR (600 MHz, DMSO-$d_6$) δ = 8.38 (br s, 1H), 8.32 (br d, J = 6.8 Hz, 1H), 8.25 (s, 1H), 7.95-7.86 (m, 2H), 7.76 (d, J = 7.2 Hz, 1H), 7.71-7.62 (m, 3H), 7.56 (d, J = 4.2 Hz, 1H), 7.24 (d, J = 3.8 Hz, 1H), 4.17-4.07 (m, 2H), 3.83-3.71 (m, 1H), 2.86 (d, J = 4.2 Hz, 3H), 2.32 (q, J = 12.0 Hz, 1H), 2.23-2.11 (m, 2H), 2.03-1.93 (m, 1H), 1.86 (br d, J = 11.0 Hz, 2H), 1.51-1.39 (m, 1H), 1.38-1.27 (m, 1H) |
| 152 | $^1$H NMR (600 MHz, DMSO-$d_6$) δ = 13.41-13.12 (m, 1H), 8.61-8.52 (m, 2H), 8.38-8.28 (m, 2H), 7.99 (d, J = 8.7 Hz, 1H), 7.92 (dd, J = 1.9, 8.7 Hz, 1H), 7.62 (d, J = 4.2 Hz, 1H), 7.57-7.54 (m, 1H), 7.53-7.49 (m, 1H), 7.29 (d, J = 4.2 Hz, 1H), 6.36-6.23 (m, 1H), 4.02-3.91 (m, 1H), 2.86 (d, J = 4.5 Hz, 3H), 2.51-2.45 (m, 1H), 2.39-2.30 (m, 1H), 2.21-2.15 (m, 1H), 2.04-1.94 (m, 3H), 1.60-1.49 (m, 2H) |
| 154 | $^1$H NMR (600 MHz, DMSO-$d_6$) δ = 8.56-8.45 (m, 2H), 8.23 (d, J = 1.1 Hz, 1H), 7.92-7.79 (m, 2H), 7.66 (dt, J = 6.0, 7.9 Hz, 1H), 7.58 (d, J = 3.8 Hz, 1H), 7.56-7.50 (m, 2H), 7.47 (dt, J = 2.3, 8.7 Hz, 1H), 7.27 (d, J = 3.8 Hz, 1H), 4.41 (tt, J = 4.0, 12.5 Hz, 1H), 3.88-3.76 (m, 1H), 2.82 (d, J = 4.5 Hz, 3H), 2.43-2.34 (m, 1H), 2.31-2.19 (m, 1H), 2.12 (br d, J = 12.1 Hz, 1H), 1.98 (br d, J = 11.3 Hz, 1H), 1.86 (br d, J = 10.2 Hz, 2H), 1.51-1.35 (m, 2H) |
| 155 | $^1$H NMR (600 MHz, DMSO-$d_6$) δ = 8.80 (td, J = 1.1, 4.2 Hz, 1H), 8.48 (d, J = 7.9 Hz, 1H), 8.24 (br dd, J = 2.8, 4.3 Hz, 1H), 8.18 (d, J = 7.9 Hz, 1H), 8.05 (dt, J = 1.9, 7.7 Hz, 1H), 7.97 (d, J = 6.8 Hz, 1H), 7.78 (d, J = 11.3 Hz, 1H), 7.62-7.56 (m, 2H), 7.28 (d, J = 3.8 Hz, 1H), 5.53 (br t, J = 11.9 Hz, 1H), 3.95-3.82 (m, 1H), 2.82 (d, J = 4.5 Hz, 3H), 2.39 (q, J = 12.1 Hz, 1H), 2.28 (dq, J = 3.2, 12.3 Hz, 1H), 2.11 (br d, J = 11.7 Hz, 1H), 1.99-1.84 (m, 3H), 1.60-1.40 (m, 2H) |
| 155 | $^1$H NMR (600 MHz, DMSO-$d_6$) δ = 8.80 (td, J = 1.2, 4.1 Hz, 1H), 8.49 (d, J = 7.9 Hz, 1H), 8.28-8.22 (m, 1H), 8.18 (d, J = 7.9 Hz, 1H), 8.05 (dt, J = 1.5, 7.7 Hz, 1H), 7.97 (d, J = 6.4 Hz, 1H), 7.78 (d, J = 11.3 Hz, 1H), 7.59 (br dd, J = 1.1, 4.9 Hz, 1H), 7.28 (d, J = 4.2 Hz, 1H), 5.57-5.48 (m, 1H), 3.94-3.83 (m, 1H), 2.82 (d, J = 4.5 Hz, 3H), 2.45-2.34 (m, 1H), 2.33-2.22 (m, 1H), 2.11 (br d, J = 11.7 Hz, 1H), 1.99-1.85 (m, 3H), 1.63-1.41 (m, 2H) |
| 155 | $^1$H NMR (600 MHz, DMSO-$d_6$) δ = 8.83-8.76 (m, 1H), 8.48 (d, J = 7.9 Hz, 1H), 8.24 (br dd, J = 2.8, 4.3 Hz, 1H), 8.18 (d, J = 7.9 Hz, 1H), 8.06 (dt, J = 1.5, 7.7 Hz, 1H), 7.98 (d, J = 6.8 Hz, 1H), 7.79 (d, J = 11.3 Hz, 1H), 7.63-7.56 (m, 2H), 7.28 (d, J = 3.8 Hz, 1H), 5.52 (br t, J = 12.1 Hz, 1H), 3.89 (tdd, J = 3.6, 7.5, 15.1 Hz, 2H), 2.83 (d, J = 4.5 Hz, 3H), 2.44-2.35 (m, 1H), 2.28 (dq, J = 3.2, 12.4 Hz, 1H), 2.15-2.09 (m, 1H), 1.96 (br d, J = 11.0 Hz, 1H), 1.93-1.86 (m, 2H), 1.59-1.39 (m, 2H) |

-continued

| Compound No. | Peak list |
|---|---|
| 155 | $^1$H NMR (600 MHz, DMSO-$d_6$) δ = 8.80 (td, J = 1.2, 4.1 Hz, 1H), 8.49 (d, J = 7.9 Hz, 1H), 8.27-8.21 (m, 1H), 8.18 (d, J = 7.9 Hz, 1H), 8.05 (dt, J = 1.5, 7.7 Hz, 1H), 7.97 (d, J = 6.4 Hz, 1H), 7.78 (d, J = 11.3 Hz, 1H), 7.59 (br dd, J = 1.1, 4.9 Hz, 1H), 7.28 (d, J = 4.2 Hz, 1H), 5.57-5.47 (m, 1H), 3.93-3.83 (m, 1H), 2.82 (d, J = 4.5 Hz, 3H), 2.44-2.34 (m, 1H), 2.33-2.22 (m, 1H), 2.11 (br d, J = 11.7 Hz, 1H), 1.99-1.84 (m, 3H), 1.59-1.40 (m, 2H) |
| 161 | $^1$H NMR (600 MHz, DMSO-$d_6$) δ = 9.92-9.86 (m, 1H), 8.53-8.45 (m, 2H), 8.23 (d, J = 1.1 Hz, 1H), 8.11 (dd, J = 1.3, 7.7 Hz, 1H), 7.93-7.82 (m, 4H), 7.72 (dd, J = 0.9, 7.4 Hz, 1H), 7.58 (d, J = 4.2 Hz, 1H), 7.27 (d, J = 3.8 Hz, 1H), 4.19 (tt, J = 4.1, 12.3 Hz, 1H), 3.75 (dtd, J = 4.0, 7.7, 15.3 Hz, 1H), 2.83 (d, J = 4.5 Hz, 3H), 2.35 (q, J = 12.2 Hz, 1H), 2.26-2.16 (m, 1H), 2.11 (br d, J = 12.1 Hz, 1H), 1.96 (br d, J = 10.2 Hz, 1H), 1.83 (br d, J = 11.0 Hz, 2H), 1.49-1.28 (m, 2H) |
| 194 | $^1$H NMR (600 MHz, DMSO-$d_6$) δ = 8.82 (d, J = 4.2 Hz, 1H), 8.50 (d, J = 7.9 Hz, 1H), 8.33 (d, J = 1.5 Hz, 1H), 8.21 (d, J = 7.9 Hz, 1H), 8.12-8.03 (m, 2H), 7.75 (dd, J = 1.5, 8.7 Hz, 1H), 7.60 (d, J = 3.8 Hz, 1H), 7.27 (d, J = 4.2 Hz, 1H), 5.68-5.47 (m, 1H), 3.95-3.84 (m, 1H), 2.41 (q, J = 11.7 Hz, 1H), 2.31-2.23 (m, 1H), 2.17 (br d, J = 11.7 Hz, 1H), 2.00 (br d, J = 12.1 Hz, 1H), 1.95-1.86 (m, 2H), 1.55-1.39 (m, 2H) |
| 195 | $^1$H NMR (600 MHz, DMSO-$d_6$) δ = 8.83-8.80 (m, 1H), 8.52 (d, J = 7.9 Hz, 1H), 8.33 (d, J = 1.5 Hz, 1H), 8.21 (d, J = 7.9 Hz, 1H), 8.11-8.05 (m, 2H), 7.75 (dd, J = 1.7, 8.5 Hz, 1H), 7.66-7.59 (m, 2H), 7.17 (d, J = 3.8 Hz, 1H), 5.63-5.52 (m, 1H), 3.92-3.86 (m, 1H), 2.41 (q, J = 11.7 Hz, 1H), 2.32-2.21 (m, 1H), 2.20-2.14 (m, 1H), 2.00 (br d, J = 12.5 Hz, 1H), 1.96-1.89 (m, 2H), 1.55-1.41 (m, 2H) |
| 292 | $^1$H NMR (600 MHz, DMSO-$d_6$) δ = 9.25 (s, 1H), 8.84 (dd, J = 0.9, 4.0 Hz, 1H), 8.66 (q, J = 4.8 Hz, 1H), 8.49 (d, J = 7.9 Hz, 1H), 8.34 (s, 1H), 8.27 (d, J = 7.6 Hz, 1H), 8.10 (dt, J = 1.9, 7.7 Hz, 1H), 7.66 (ddd, J = 1.1, 4.7, 7.7 Hz, 1H), 7.59 (d, J = 4.2 Hz, 1H), 7.28 (d, J = 4.2 Hz, 1H), 5.62 (tt, J = 3.8, 12.4 Hz, 1H), 3.92 (td, J = 3.6, 7.5 Hz, 1H), 2.90 (d, J = 4.9 Hz, 3H), 2.47-2.40 (m, 1H), 2.33-2.21 (m, 2H), 2.09 (br d, J = 10.6 Hz, 1H), 1.95 (br d, J = 9.8 Hz, 2H), 1.62-1.44 (m, 2H) |
| 287 | $^1$H NMR (600 MHz, DMSO-$d_6$) δ = 9.24 (s, 1H), 8.89-8.79 (m, 1H), 8.65 (q, J = 4.8 Hz, 1H), 8.50 (d, J = 7.9 Hz, 1H), 8.34 (s, 1H), 8.27 (d, J = 7.9 Hz, 1H), 8.10 (dt, J = 1.9, 7.7 Hz, 1H), 7.65 (ddd, J = 1.1, 4.8, 7.6 Hz, 1H), 7.59 (d, J = 4.2 Hz, 1H), 7.28 (d, J = 4.2 Hz, 1H), 5.62 (br s, 1H), 3.97-3.86 (m, 1H), 2.90 (d, J = 4.9 Hz, 3H), 2.43 (br d, J = 12.1 Hz, 1H), 2.26 (br s, 2H), 2.14-2.05 (m, 1H), 2.00-1.88 (m, 2H), 1.61-1.43 (m, 2H) |
| 196 | $^1$H NMR (600 MHz, DMSO-$d_6$) δ = 8.82 (d, J = 4.2 Hz, 1H), 8.53 (d, J = 7.6 Hz, 1H), 8.43 (d, J = 1.1 Hz, 1H), 8.22-8.21 (m, 1H), 8.08 (dt, J = 1.9, 7.7 Hz, 1H), 7.99-7.93 (m, 2H), 7.63-7.58 (m, 2H), 7.27 (d, J = 4.2 Hz, 1H), 5.58 (br s, 2H), 3.98-3.86 (m, 4H), 2.43 (q, J = 12.1 Hz, 1H), 2.29 (br d, J = 12.5 Hz, 1H), 2.17 (br d, J = 11.7 Hz, 1H), 2.00 (br d, J = 11.7 Hz, 1H), 1.96-1.89 (m, 2H), 1.55-1.43 (m, 2H) |
| 197 | $^1$H NMR (600 MHz, DMSO-$d_6$) δ = 8.70-8.67 (m, 1H), 8.55-8.47 (m, 2H), 8.28 (d, J = 1.1 Hz, 1H), 8.05 (dt, J = 1.1, 9.3 Hz, 1H), 7.96-7.93 (m, 1H), 7.93-7.89 (m, 1H), 7.77 (td, J = 4.3, 8.7 Hz, 1H), 7.64 (d, J = 4.2 Hz, 1H), 7.17 (d, J = 4.2 Hz, 1H), 4.62 (tt, J = 4.1, 12.4 Hz, 1H), 3.90-3.81 (m, 1H), 2.84 (d, J = 4.5 Hz, 3H), 2.34 (q, J = 11.8 Hz, 1H), 2.24-2.14 (m, 1H), 2.14-2.09 (m, 1H), 1.94 (br d, J = 12.1 Hz, 1H), 1.91-1.83 (m, 2H), 1.48-1.36 (m, 2H) |
| 198 | $^1$H NMR (600 MHz, DMSO-$d_6$) δ = 8.81 (d, J = 7.9 Hz, 1H), 8.70-8.67 (m, 1H), 8.52 (q, J = 4.4 Hz, 1H), 8.28 (d, J = 1.1 Hz, 1H), 8.07-8.03 (m, 1H), 7.99-7.94 (m, 2H), 7.93-7.88 (m, 1H), 7.85 (d, J = 3.8 Hz, 1H), 7.77 (td, J = 4.3, 8.7 Hz, 1H), 4.64 (tdd, J = 4.1, 8.3, 16.5 Hz, 4H), 3.90 (td, J = 3.6, 7.5 Hz, 2H), 2.84 (d, J = 4.2 Hz, 3H), 2.35 (q, J = 12.0 Hz, 1H), 2.25-2.10 (m, 2H), 1.95 (br d, J = 12.5 Hz, 1H), 1.92-1.83 (m, 2H), 1.49-1.40 (m, 2H) |
| 199 | $^1$H NMR (600 MHz, DMSO-$d_6$) δ = 8.69-8.67 (m, 1H), 8.52 (q, J = 4.4 Hz, 1H), 8.48 (d, J = 7.9 Hz, 1H), 8.28 (d, J = 1.1 Hz, 1H), 8.07-8.02 (m, 1H), 7.96-7.92 (m, 1H), 7.92-7.88 (m, 1H), 7.77 (td, J = 4.3, 8.7 Hz, 1H), 7.59 (d, J = 4.2 Hz, 1H), 7.27 (d, J = 4.2 Hz, 1H), 4.62 (tt, J = 3.8, 12.4 Hz, 2H), 3.89-3.81 (m, 1H), 2.84 (d, J = 4.5 Hz, 3H), 2.34 (q, J = 11.8 Hz, 1H), 2.23-2.14 (m, 1H), 2.13-2.09 (m, 1H), 1.94 (br d, J = 12.1 Hz, 1H), 1.86 (br dd, J = 3.2, 7.0 Hz, 2H), 1.47-1.37 (m, 2H) |
| 200 | $^1$H NMR (600 MHz, DMSO-$d_6$) δ = 8.80 (d, J = 7.9 Hz, 1H), 8.50 (q, J = 4.4 Hz, 1H), 8.31 (dd, J = 1.1, 8.3 Hz, 1H), 8.19 (d, J = 1.1 Hz, 1H), 8.02-7.91 (m, 4H), 7.90-7.86 (m, 2H), 7.84 (d, J = 4.2 Hz, 1H), 4.23 (tt, J = 4.2, 12.3 Hz, 2H), 3.85 (ttd, J = 3.9, 7.7, 11.6 Hz, 1H), 2.83 (d, J = 4.5 Hz, 3H), 2.42-2.34 (m, 1H), 2.29-2.19 (m, 1H), 2.14 (br d, J = 10.2 Hz, 1H), 2.01-1.94 (m, 1H), 1.91-1.80 (m, 2H), 1.49-1.33 (m, 2H) |
| 205 | $^1$H NMR (600 MHz, DMSO-$d_6$) δ = 8.48 (d, J = 7.9 Hz, 1H), 8.25-8.20 (m, 1H), 7.93 (d, J = 6.8 Hz, 1H), 7.76 (d, J = 11.0 Hz, 1H), 7.63 (d, J = 4.2 Hz, 1H), 7.54-7.48 (m, 1H), 7.47-7.44 (m, 1H), 7.42-7.38 (m, 2H), 7.17 (d, J = 4.2 Hz, 1H), 4.05-3.96 (m, 1H), 3.76-3.67 (m, 1H), 2.82 (d, J = 4.5 Hz, 3H), 2.32-2.22 (m, 1H), 2.21-2.12 (m, 5H), 2.02 (br s, 1H), 1.88-1.75 (m, 3H), 1.51-1.39 (m, 1H), 1.35-1.22 (m, 1H) |

-continued

| Compound No. | Peak list |
|---|---|
| 206 | $^1$H NMR (600 MHz, DMSO-$d_6$) δ = 8.48 (d, J = 7.9 Hz, 1H), 8.27-8.22 (m, 1H), 7.96 (d, J = 6.8 Hz, 1H), 7.79 (d, J = 11.3 Hz, 1H), 7.75-7.65 (m, 2H), 7.63 (d, J = 4.2 Hz, 1H), 7.49 (t, J = 9.1 Hz, 1H), 7.44 (dt, J = 0.9, 7.5 Hz, 1H), 7.17 (d, J = 4.2 Hz, 1H), 4.20-4.12 (m, 1H), 3.81 (tdt, J = 4.0, 7.6, 11.5 Hz, 1H), 2.83 (d, J = 4.5 Hz, 4H), 2.28 (q, J = 12.1 Hz, 1H), 2.24-2.15 (m, 1H), 2.02 (br d, J = 11.7 Hz, 1H), 1.90-1.79 (m, 3H), 1.53-1.43 (m, 1H), 1.43-1.34 (m, 1H) |
| 207 | $^1$H NMR (600 MHz, DMSO-$d_6$) δ = 8.47 (d, J = 7.9 Hz, 1H), 8.24 (br dd, J = 3.0, 4.2 Hz, 1H), 7.96 (d, J = 6.8 Hz, 1H), 7.79 (d, J = 11.3 Hz, 1H), 7.73-7.65 (m, 2H), 7.59 (d, J = 3.8 Hz, 1H), 7.49 (t, J = 9.3 Hz, 1H), 7.46-7.42 (m, 1H), 7.27 (d, J = 4.2 Hz, 1H), 4.19-4.11 (m, 1H), 3.81 (tdt, J = 4.0, 7.6, 11.5 Hz, 1H), 2.83 (d, J = 4.5 Hz, 4H), 2.29 (q, J = 12.1 Hz, 1H), 2.24-2.13 (m, 1H), 2.02 (br d, J = 11.7 Hz, 1H), 1.84 (br dd, J = 3.4, 6.0 Hz, 3H), 1.53-1.43 (m, 1H), 1.43-1.33 (m, 1H) |
| 208 | $^1$H NMR (600 MHz, DMSO-$d_6$) δ = 8.47 (d, J = 7.6 Hz, 1H), 8.22 (br dd, J = 3.0, 4.2 Hz, 1H), 7.93 (d, J = 6.4 Hz, 1H), 7.75 (d, J = 11.3 Hz, 1H), 7.59 (d, J = 3.8 Hz, 1H), 7.54-7.49 (m, 1H), 7.48-7.44 (m, 1H), 7.43-7.34 (m, 2H), 7.27 (d, J = 4.2 Hz, 1H), 4.05-3.96 (m, 1H), 3.70 (dtd, J = 4.0, 7.8, 15.2 Hz, 2H), 2.82 (d, J = 4.5 Hz, 4H), 2.31-2.22 (m, 1H), 2.16 (s, 3H), 2.02 (br s, 1H), 1.88-1.75 (m, 3H), 1.51-1.39 (m, 1H), 1.35-1.22 (m, 1H) |
| 212 | $^1$H NMR (600 MHz, DMSO-$d_6$) δ = 8.48 (d, J = 7.9 Hz, 1H), 8.25 (d, J = 4.5 Hz, 1H), 8.10 (s, 1H), 7.75-7.68 (m, 2H), 7.64 (d, J = 4.2 Hz, 1H), 7.51 (t, J = 9.3 Hz, 1H), 7.46 (t, J = 7.6 Hz, 1H), 7.36 (s, 1H), 7.18 (d, J = 3.8 Hz, 1H), 4.29-4.22 (m, 3H), 4.05 (s, 3H), 3.88-3.81 (m, 1H), 2.85 (d, J = 4.5 Hz, 3H), 2.25-2.13 (m, 2H), 2.10-2.05 (m, 1H), 1.94-1.82 (m, 3H), 1.48-1.37 (m, 2H) |
| 216 | $^1$H NMR (600 MHz, DMSO-$d_6$) δ = 8.56-8.49 (m, 2H), 8.31-8.22 (m, 2H), 8.16 (dd, J = 1.9, 7.2 Hz, 1H), 7.94-7.89 (m, 1H), 7.88-7.83 (m, 1H), 7.60 (d, J = 4.2 Hz, 1H), 7.42 (dd, J = 2.3, 8.3 Hz, 1H), 7.27 (d, J = 3.8 Hz, 1H), 5.42 (ddd, J = 3.8, 8.8, 12.4 Hz, 1H), 3.96-3.87 (m, 1H), 2.84 (d, J = 4.5 Hz, 3H), 2.44 (q, J = 11.7 Hz, 1H), 2.35-2.24 (m, 1H), 2.14 (br d, J = 11.7 Hz, 1H), 2.01 (br d, J = 11.7 Hz, 1H), 1.97-1.90 (m, 2H), 1.55-1.44 (m, 2H) |
| 217 | $^1$H NMR (600 MHz, DMSO-$d_6$) δ = 8.74 (s, 1H), 8.64 (d, J = 4.5 Hz, 1H), 8.53 (q, J = 4.4 Hz, 1H), 8.28 (d, J = 1.5 Hz, 1H), 8.24 (d, J = 7.9 Hz, 1H), 8.13 (d, J = 8.7 Hz, 1H), 8.05 (dt, J = 1.5, 7.7 Hz, 1H), 7.86 (dd, J = 1.5, 8.7 Hz, 1H), 7.62 (t, J = 2.1 Hz, 1H), 7.55 (ddd, J = 1.1, 5.5, 7.0 Hz, 1H), 7.37 (dd, J = 1.5, 7.9 Hz, 1H), 7.25 (t, J = 8.1 Hz, 1H), 6.98 (dd, J = 1.9, 7.9 Hz, 1H), 5.54-5.43 (m, 1H), 4.38 (br dd, J = 4.3, 12.7 Hz, 1H), 4.20 (br d, J = 12.8 Hz, 1H), 3.77 (t, J = 12.1 Hz, 3H), 3.12-3.06 (m, 1H), 2.84 (d, J = 4.5 Hz, 3H), 2.18-2.12 (m, 1H), 1.90 (br d, J = 13.2 Hz, 1H), 1.61 (td, J = 3.8, 13.1 Hz, 1H) |
| 218 | $^1$H NMR (600 MHz, DMSO-$d_6$) δ = 8.64 (d, J = 4.2 Hz, 1H), 8.58-8.51 (m, 2H), 8.28 (d, J = 1.5 Hz, 1H), 8.24 (d, J = 7.9 Hz, 1H), 8.13 (d, J = 8.7 Hz, 1H), 8.05 (dt, J = 1.7, 7.8 Hz, 1H), 7.86 (dd, J = 1.7, 8.5 Hz, 1H), 7.54 (ddd, J = 1.1, 4.9, 7.6 Hz, 1H), 7.42 (dd, J = 1.1, 8.7 Hz, 2H), 7.24-7.20 (m, 2H), 6.95-6.92 (m, 1H), 5.55-5.45 (m, 1H), 4.39 (br dd, J = 4.2, 12.5 Hz, 3H), 4.20 (br d, J = 13.2 Hz, 2H), 3.76 (t, J = 12.1 Hz, 2H), 3.11-3.04 (m, 1H), 2.84 (d, J = 4.5 Hz, 3H), 2.14 (br d, J = 10.6 Hz, 1H), 1.89 (br d, J = 13.2 Hz, 1H), 1.61 (td, J = 3.8, 13.1 Hz, 1H) |
| 297 | $^1$H NMR (600 MHz, DMSO-$d_6$) δ = 9.20 (s, 1H), 8.65 (q, J = 4.8 Hz, 1H), 8.53 (d, J = 7.9 Hz, 1H), 8.31-8.29 (m, 1H), 7.78-7.72 (m, 2H), 7.69-7.62 (m, 3H), 7.59 (d, J = 4.2 Hz, 1H), 7.28 (d, J = 4.2 Hz, 1H), 4.51 (tt, J = 4.0, 12.5 Hz, 1H), 3.87-3.79 (m, 1H), 2.90 (d, J = 4.9 Hz, 3H), 2.40 (q, J = 12.2 Hz, 1H), 2.28 (dq, J = 3.2, 12.7 Hz, 1H), 2.24-2.18 (m, 1H), 2.07 (br d, J = 12.1 Hz, 1H), 1.90 (td, J = 3.5, 6.6 Hz, 2H), 1.57-1.48 (m, 1H), 1.48-1.39 (m, 1H) |
| 220 | $^1$H NMR (600 MHz, DMSO-$d_6$) δ = 8.74-8.71 (m, 1H), 8.54 (q, J = 4.4 Hz, 1H), 8.30 (s, 1H), 8.28 (d, J = 1.5 Hz, 1H), 8.25-8.21 (m, 1H), 8.15 (d, J = 8.7 Hz, 1H), 8.06 (dt, J = 1.9, 7.7 Hz, 1H), 7.86 (dd, J = 1.9, 8.7 Hz, 1H), 7.59 (ddd, J = 1.1, 4.9, 7.6 Hz, 1H), 7.42 (ddd, J = 1.5, 4.1, 8.0 Hz, 2H), 7.27 (dt, J = 1.3, 7.6 Hz, 1H), 7.14 (dt, J = 1.7, 7.6 Hz, 1H), 5.53 (ddd, J = 4.2, 11.9, 16.1 Hz, 1H), 4.31 (br dd, J = 4.3, 12.7 Hz, 1H), 4.16 (br d, J = 12.5 Hz, 1H), 3.83 (t, J = 12.1 Hz, 1H), 3.17-3.10 (m, 1H), 2.84 (d, J = 4.5 Hz, 3H), 2.55 (br dd, J = 4.2, 12.5 Hz, 1H), 2.24-2.18 (m, 1H), 1.93-1.87 (m, 1H), 1.65 (tq, J = 4.1, 13.0 Hz, 1H) |
| 227 | $^1$H NMR (600 MHz, DMSO-$d_6$) δ = 8.56 (q, J = 4.3 Hz, 1H), 8.37 (s, 1H), 8.26 (d, J = 1.5 Hz, 1H), 8.17 (d, J = 8.7 Hz, 1H), 7.88 (dd, J = 1.5, 8.7 Hz, 1H), 7.65-7.59 (m, 3H), 7.51-7.46 (m, 1H), 7.44 (dd, J =1.5, 7.9 Hz, 1H), 7.36 (dd, J = 1.7, 8.1 Hz, 1H), 7.28 (dt, J = 1.5, 7.7 Hz, 1H), 7.16 (dt, J = 1.7, 7.6 Hz, 1H), 4.44 (tt, J = 4.2, 11.9 Hz, 1H), 4.38-4.32 (m, 1H), 4.10 (br d, J = 13.2 Hz, 3H), 3.77 (br t, J = 12.3 Hz, 2H), 3.18 (br t, J = 12.3 Hz, 1H), 2.84 (d, J = 4.5 Hz, 3H), 2.55 (dd, J = 4.2, 12.5 Hz, 1H), 2.15 (br d, J = 11.3 Hz, 1H), 1.85 (br d, J = 13.2 Hz, 1H), 1.61-1.52 (m, 1H) |
| 228 | $^1$H NMR (600 MHz, DMSO-$d_6$) δ = 9.72 (s, 1H), 8.55 (q, J = 4.4 Hz, 1H), 8.26 (d, J = 1.5 Hz, 1H), 8.14 (d, J = 8.7 Hz, 1H), 7.87 (dd, J = 1.5, 8.7 Hz, 1H), 7.65-7.59 (m, 3H), 7.48-7.44 (m, 1H), 6.83-6.81 (m, 1H), 6.79-6.77 (m, 1H), 6.60 (dd, J = 1.5, 3.8 Hz, 1H), 4.41 (br dd, J = 4.0, 12.7 Hz, 1H), 4.38-4.32 (m, 1H), 4.12 (br d, J = 13.2 Hz, 1H), 3.76-3.68 (m, 5H), 3.19-3.11 (m, 1H), 2.84 (d, J = 4.5 Hz, 3H), 2.12-2.06 (m, 1H), 1.87-1.82 (m, 1H), 1.50 (tq, J = 3.8, 13.1 Hz, 1H) |

-continued

| Compound No. | Peak list |
|---|---|
| 234 | $^1$H NMR (600 MHz, DMSO-$d_6$) δ = 8.83-8.81 (m, 1H), 8.50 (d, J = 7.6 Hz, 1H), 8.27 (br dd, J = 2.8, 4.3 Hz, 1H), 8.24-8.19 (m, 1H), 8.07 (dt, J = 1.9, 7.7 Hz, 1H), 7.99 (d, J = 6.8 Hz, 1H), 7.89 (d, J = 11.3 Hz, 1H), 7.62-7.59 (m, 2H), 7.31 (d, J = 3.8 Hz, 1H), 5.82-5.74 (m, 1H), 4.18-4.13 (m, 2H), 4.10-4.00 (m, 2H), 4.00-3.84 (m, 3H), 3.44 (t, J = 10.8 Hz, 2H), 2.83 (d, J = 4.9 Hz, 3H), 2.68 (q, J = 12.1 Hz, 1H), 2.31-2.25 (m, 1H) |
| 285 | $^1$H NMR (600 MHz, DMSO-$d_6$) δ = 8.58 (d, J = 7.9 Hz, 1H), 8.45 (dd, J = 1.5, 4.9 Hz, 1H), 8.16 (dd, J = 1.5, 8.3 Hz, 1H), 7.75-7.70 (m, 2H), 7.62 (d, J = 3.8 Hz, 1H), 7.54-7.50 (m, 1H), 7.50-7.45 (m, 1H), 7.38 (dd, J = 4.7, 8.1 Hz, 1H), 7.26 (d, J = 4.2 Hz, 1H), 4.13 (br t, J = 12.1 Hz, 2H), 3.84-3.78 (m, 4H), 2.84 (q, J = 12.1 Hz, 1H), 2.67-2.59 (m, 1H), 2.01 (br d, J = 11.7 Hz, 1H), 1.89-1.81 (m, 3H), 1.45-1.33 (m, 2H) |
| 280 | $^1$H NMR (600 MHz, DMSO-$d_6$) δ = 8.82 (d, J = 4.5 Hz, 1H), 8.61 (d, J = 7.9 Hz, 1H), 8.44 (dd, J = 1.3, 4.7 Hz, 1H), 8.24 (d, J = 7.9 Hz, 1H), 8.17 (dd, J = 1.3, 8.1 Hz, 1H), 8.07 (dt, J = 1.7, 7.8 Hz, 1H), 7.65-7.60 (m, 2H), 7.37 (dd, J = 4.5, 7.9 Hz, 1H), 7.26 (d, J = 4.2 Hz, 1H), 5.60 (tt, J = 3.6, 12.2 Hz, 1H), 2.95 (q, J = 12.1 Hz, 2H), 2.75-2.61 (m, 2H), 2.14-2.07 (m, 1H), 1.97-1.87 (m, 3H), 1.45 (br t, J = 10.6 Hz, 2H) |
| 235 | $^1$H NMR (600 MHz, DMSO-$d_6$) δ = 8.83-8.77 (m, 1H), 8.55 (d, J = 7.9 Hz, 1H), 8.35 (q, J = 4.7 Hz, 1H), 8.19 (d, J = 7.9 Hz, 1H), 8.06 (dt, J = 1.9, 7.7 Hz, 1H), 7.95 (s, 1H), 7.78 (s, 1H), 7.65 (d, J = 4.2 Hz, 1H), 7.60 (ddd, J = 1.1, 4.9, 7.6 Hz, 1H), 7.18 (d, J = 3.8 Hz, 1H), 5.54 (br t, J = 12.5 Hz, 1H), 3.95-3.84 (m, 1H), 2.80 (d, J = 4.9 Hz, 3H), 2.38 (q, J = 12.0 Hz, 1H), 2.31-2.21 (m, 1H), 2.13 (br d, J = 11.7 Hz, 1H), 2.00-1.86 (m, 3H), 1.58-1.41 (m, 2H) |
| 236 | $^1$H NMR (600 MHz, DMSO-$d_6$) δ = 8.68 (d, J = 4.5 Hz, 1H), 8.51 (d, J = 7.9 Hz, 1H), 8.36 (q, J = 4.5 Hz, 1H), 8.07-8.02 (m, 1H), 8.02-7.99 (m, 1H), 7.80 (s, 1H), 7.79-7.75 (m, 1H), 7.64 (d, J = 4.2 Hz, 1H), 7.18 (d, J = 4.2 Hz, 1H), 4.62 (tt, J = 3.8, 12.5 Hz, 1H), 2.80 (d, J = 4.5 Hz, 3H), 2.26 (q, J = 12.1 Hz, 1H), 2.18-2.06 (m, 3H), 1.91 (br d, J = 11.7 Hz, 1H), 1.89-1.81 (m, 2H), 1.47-1.37 (m, 2H) |
| 237 | $^1$H NMR (600 MHz, DMSO-$d_6$) δ = 8.68 (td, J = 1.3, 4.5 Hz, 1H), 8.49 (d, J = 7.9 Hz, 1H), 8.36 (q, J = 4.5 Hz, 1H), 8.04 (dt, J = 1.3, 9.2 Hz, 1H), 8.01-8.00 (m, 1H), 7.80 (s, 1H), 7.77 (td, J = 4.3, 8.7 Hz, 1H), 7.59 (d, J = 3.8 Hz, 1H), 7.28 (d, J = 3.8 Hz, 1H), 4.62 (tt, J = 3.8, 12.4 Hz, 1H), 3.86 (br dd, J = 4.0, 7.0 Hz, 1H), 2.80 (d, J = 4.9 Hz, 3H), 2.30-2.22 (m, 1H), 2.18-2.03 (m, 3H), 1.91 (br d, J = 11.7 Hz, 1H), 1.88-1.80 (m, 2H), 1.47-1.37 (m, 2H) |
| 238 | $^1$H NMR (600 MHz, DMSO-$d_6$) δ = 8.80 (d, J = 5.2 Hz, 1H), 8.53 (d, J = 7.9 Hz, 1H), 8.35 (q, J = 4.8 Hz, 1H), 8.19 (d, J = 7.9 Hz, 1H), 8.06 (dt, J = 1.7, 7.8 Hz, 1H), 7.95 (s, 1H), 7.78 (s, 1H), 7.62-7.59 (m, 2H), 7.28 (d, J = 4.2 Hz, 1H), 5.54 (br s, 1H), 3.93-3.86 (m, 1H), 2.80 (d, J = 4.5 Hz, 3H), 2.43-2.34 (m, 1H), 2.26 (br dd, J = 3.6, 12.3 Hz, 1H), 2.13 (br d, J = 12.1 Hz, 1H), 1.98-1.88 (m, 3H), 1.55-1.43 (m, 2H) |
| 284 | $^1$H NMR (600 MHz, DMSO-$d_6$) δ = 9.66 (s, 1H), 8.78-8.72 (m, 2H), 8.54 (d, J = 6.8 Hz, 1H), 8.51 (br d, J = 7.9 Hz, 1H), 8.14 (t, J = 9.2 Hz, 1H), 7.96 (s, 1H), 7.87 (td, J = 4.3, 8.7 Hz, 1H), 7.60 (d, J = 4.2 Hz, 1H), 7.28 (d, J = 4.2 Hz, 1H), 4.92-4.84 (m, 1H), 3.89 (br dd, J = 3.6, 7.0 Hz, 1H), 2.29-2.17 (m, 2H), 2.14 (br d, J = 11.3 Hz, 1H), 2.03 (br d, J = 11.0 Hz, 1H), 1.88 (br d, J = 9.4 Hz, 2H), 1.52-1.41 (m, 2H) |
| 298 | 1H NMR (600 MHz, DMSO-$d_6$) δ = 9.74 (s, 1H), 8.75 (s, 1H), 8.69 (d, J = 6.4 Hz, 1H), 8.49 (d, J = 7.6 Hz, 1H), 8.30 (d, J = 6.0 Hz, 1H), 8.14 (t, J = 9.2 Hz, 1H), 7.88 (td, J = 4.4, 8.5 Hz, 1H), 7.61 (d, J = 4.2 Hz, 1H), 7.28 (d, J = 4.2 Hz, 1H), 4.93-4.85 (m, 1H), 3.88 (br dd, J = 3.4, 7.2 Hz, 2H), 2.31-2.18 (m, 2H), 2.15 (br s, 1H), 2.05 (br d, J = 12.1 Hz, 1H), 1.93-1.83 (m, 2H), 1.53-1.43 (m, 2H) |
| 294 | $^1$H NMR (600 MHz, DMSO-$d_6$) δ = 9.71 (s, 1H), 8.90 (d, J = 5.0 Hz, 1H), 8.67 (d, J = 6.4 Hz, 1H), 8.52 (d, J = 7.6 Hz, 1H), 8.36-8.29 (m, 2H), 8.17 (dt, J = 1.5, 7.7 Hz, 1H), 7.74 (ddd, J = 1.1, 4.9, 7.6 Hz, 1H), 7.62 (d, J = 4.2 Hz, 1H), 7.28 (d, J = 4.2 Hz, 1H), 5.72-5.65 (m, 1H), 3.94-3.87 (m, 3H), 2.38-2.27 (m, 3H), 2.10 (br dd, J = 3.4, 8.7 Hz, 1H), 1.98-1.90 (m, 2H), 1.62-1.49 (m, 2H) |
| 288 | $^1$H NMR (600 MHz, DMSO-$d_6$) δ = 9.28 (s, 1H), 8.72-8.66 (m, 2H), 8.48 (d, J = 7.6 Hz, 1H), 8.35 (s, 1H), 8.08 (t, J = 9.1 Hz, 1H), 7.81 (td, J = 4.3, 8.7 Hz, 1H), 7.64 (d, J = 4.2 Hz, 1H), 7.18 (d, J = 4.2 Hz, 1H), 4.75 (tt, J = 4.0, 12.4 Hz, 1H), 3.92-3.85 (m, 1H), 2.91 (d, J = 4.9 Hz, 3H), 2.34 (q, J = 11.8 Hz, 1H), 2.23-2.13 (m, 2H), 2.04 (br d, J = 12.5 Hz, 1H), 1.93-1.84 (m, 2H), 1.46 (br t, J = 10.6 Hz, 2H) |
| 241 | $^1$H NMR (600 MHz, DMSO-$d_6$) δ = 8.81 (td, J = 1.1, 4.2 Hz, 1H), 8.50 (q, J = 4.3 Hz, 1H), 8.27 (d, J = 1.5 Hz, 1H), 8.20 (d, J = 7.9 Hz, 1H), 8.07 (dt, J = 1.9, 7.7 Hz, 1H), 7.94 (d, J = 8.7 Hz, 1H), 7.89 (dd, J = 2.3, 8.3 Hz, 1H), 7.86 (dd, J = 1.9, 8.7 Hz, 1H), 7.60 (ddd, J = 1.1, 4.9, 7.6 Hz, 1H), 7.41 (s, 1H), 5.54 (ddd, J = 4.0, 8.5, 12.5 Hz, 1H), 3.98-3.89 (m, 1H), 2.84 (d, J = 4.5 Hz, 3H), 2.64-2.53 (m, 1H), 2.30-2.17 (m, 1H), 2.16-2.06 (m, 1H), 1.99-1.85 (m, 3H), 1.64-1.54 (m, 1H), 1.52-1.38 (m, 1H) |

-continued

| Compound No. | Peak list |
|---|---|
| 242 | $^1$H NMR (600 MHz, DMSO-$d_6$) δ = 8.82 (s, 1H), 8.51 (q, J = 4.4 Hz, 1H), 8.35 (d, J = 7.9 Hz, 1H), 8.27 (d, J = 1.5 Hz, 1H), 8.21 (d, J = 7.9 Hz, 1H), 8.08 (dt, J = 1.5, 7.7 Hz, 1H), 7.92 (d, J = 8.7 Hz, 1H), 7.87 (dd, J = 1.9, 8.7 Hz, 1H), 7.61 (ddd, J = 1.1, 4.9, 7.6 Hz, 1H), 7.33 (s, 1H), 5.59-5.51 (m, 1H), 3.92-3.85 (m, 3H), 2.84 (d, J = 4.5 Hz, 3H), 2.48-2.37 (m, 1H), 2.33-2.22 (m, 1H), 2.15 (br d, J = 12.1 Hz, 1H), 1.99 (br d, J = 11.7 Hz, 1H), 1.92 (br d, J = 8.7 Hz, 2H), 1.48 (br t, J = 10.0 Hz, 2H) |
| 243 | $^1$H NMR (600 MHz, DMSO-$d_6$) δ = 8.81 (s, 1H), 8.51 (q, J = 4.3 Hz, 1H), 8.26 (d, J = 1.5 Hz, 1H), 8.20 (d, J = 7.9 Hz, 1H), 8.09-8.03 (m, 2H), 7.85 (dd, J = 1.5, 8.7 Hz, 1H), 7.61 (ddd, J = 1.1, 4.9, 7.6 Hz, 1H), 7.31 (s, 1H), 7.31 (br s, 1H), 7.29 (d, J = 8.3 Hz, 1H), 5.53 (tt, J = 3.7, 12.3 Hz, 1H), 3.97 (s, 3H), 3.95-3.88 (m, 4H), 2.84 (d, J = 4.5 Hz, 3H), 2.32-2.22 (m, 1H), 2.20-2.13 (m, 1H), 1.99-1.86 (m, 3H), 1.67-1.56 (m, 1H), 1.52-1.40 (m, 1H) |
| 298 | $^1$H NMR (600 MHz, DMSO-$d_6$) δ = 8.82 (d, J = 4.2 Hz, 1H), 8.70 (s, 1H), 8.46 (d, J = 7.6 Hz, 1H), 8.20 (d, J = 7.9 Hz, 1H), 8.08 (dt, J = 1.5, 7.7 Hz, 1H), 7.66-7.56 (m, 3H), 7.28 (d, J = 4.2 Hz, 1H), 5.51 (br s, 1H), 3.90-3.83 (m, 1H), 2.39-2.31 (m, 1H), 2.26 (br dd, J = 3.2, 12.3 Hz, 1H), 2.15 (br d, J = 11.7 Hz, 1H), 1.99 (br d, J = 11.0 Hz, 1H), 1.91 (br d, J = 11.7 Hz, 2H), 1.56-1.37 (m, 2H) |
| 288 | $^1$H NMR (600 MHz, DMSO-$d_6$) δ = 8.85-8.80 (m, 1H), 8.70 (s, 1H), 8.47 (d, J = 7.6 Hz, 1H), 8.20 (d, J = 8.0 Hz, 1H), 8.08 (dt, J = 1.5, 7.7 Hz, 1H), 7.72-7.60 (m, 3H), 7.17 (d, J = 4.2 Hz, 1H), 5.51 (br s, 1H), 3.91-3.85 (m, 1H), 2.41-2.30 (m, 1H), 2.26 (br dd, J = 3.4, 12.5 Hz, 1H), 2.15 (br d, J = 11.7 Hz, 1H), 1.99 (br d, J = 11.0 Hz, 1H), 1.91 (br d, J = 11.7 Hz, 2H), 1.56-1.38 (m, 2H) |
| 244 | $^1$H NMR (600 MHz, DMSO-$d_6$) δ = 12.22-12.07 (m, 1H), 8.83 (d, J = 5.1 Hz, 1H), 8.53 (d, J = 8.3 Hz, 1H), 8.47 (s, 1H), 8.26 (d, J = 7.9 Hz, 1H), 8.12-8.06 (m, 3H), 7.63 (ddd, J = 1.1, 4.7, 7.7 Hz, 1H), 7.58 (d, J = 4.2 Hz, 1H), 7.57 (d, J = 3.8 Hz, 1H), 7.34 (d, J = 4.2 Hz, 1H), 7.27 (d, J = 4.2 Hz, 1H), 5.61 (br s, 1H), 3.93 (br dd, J = 3.8, 7.6 Hz, 1H), 2.60-2.53 (m, 1H), 2.36-2.26 (m, 1H), 2.17 (br d, J = 11.7 Hz, 1H), 2.08 (s, 1H), 2.04 (br s, 1H), 1.95 (br d, J = 9.4 Hz, 2H), 1.50 (br d, J = 7.9 Hz, 2H) |
| 245 | $^1$H NMR (600 MHz, DMSO-$d_6$) δ = 8.88-8.83 (m, 2H), 8.48 (s, 1H), 8.26 (d, J = 7.9 Hz, 1H), 8.21 (s, 1H), 8.13-8.08 (m, 2H), 7.97 (d, J = 4.2 Hz, 1H), 7.84 (d, J = 4.2 Hz, 1H), 7.64 (ddd, J = 1.1, 4.9, 7.6 Hz, 1H), 5.66-5.59 (m, 2H), 4.02-3.94 (m, 1H), 2.60-2.52 (m, 1H), 2.36-2.29 (m, 1H), 2.25-2.19 (m, 1H), 2.08 (s, 3H), 1.99-1.93 (m, 2H), 1.58-1.48 (m, 2H) |
| 246 | $^1$H NMR (600 MHz, DMSO-$d_6$) δ = 8.78 (d, J = 5.2 Hz, 1H), 8.55 (d, J = 7.9 Hz, 1H), 8.22-8.15 (m, 2H), 8.03 (dt, J = 1.7, 7.8 Hz, 1H), 7.71 (s, 1H), 7.68 (s, 1H), 7.62 (d, J = 4.2 Hz, 1H), 7.56 (ddd, J = 1.1, 4.9, 7.6 Hz, 1H), 7.27 (d, J = 4.2 Hz, 1H), 5.55 (br s, 1H), 3.93-3.85 (m, 1H), 2.79 (d, J = 4.5 Hz, 3H), 2.55-2.52 (m, 3H), 2.42 (q, J = 12.1 Hz, 1H), 2.37-2.28 (m, 1H), 2.15-2.07 (m, 1H), 1.97-1.89 (m, 3H), 1.55-1.42 (m, 2H), 0.99 (s, 1H) |
| 247 | $^1$H NMR (600 MHz, DMSO-$d_6$) δ = 8.82-8.75 (m, 1H), 8.57 (d, J = 7.9 Hz, 1H), 8.24-8.14 (m, 2H), 8.03 (dt, J = 1.5, 7.7 Hz, 1H), 7.74-7.64 (m, 3H), 7.56 (ddd, J = 1.1, 4.9, 7.6 Hz, 1H), 7.17 (d, J = 4.2 Hz, 1H), 5.55 (br t, J = 12.3 Hz, 1H), 3.96-3.82 (m, 1H), 2.79 (d, J = 4.5 Hz, 3H), 2.55-2.52 (m, 3H), 2.42 (q, J = 11.8 Hz, 1H), 2.37-2.28 (m, 1H), 2.17-2.02 (m, 1H), 1.99-1.87 (m, 3H), 1.56-1.42 (m, 2H) |
| 248 | $^1$H NMR (600 MHz, DMSO-$d_6$) δ = 8.87 (d, J = 7.9 Hz, 1H), 8.78 (s, 1H), 8.21-8.16 (m, 2H), 8.03 (dt, J = 1.9, 7.7 Hz, 1H), 7.97 (d, J = 4.2 Hz, 1H), 7.88 (d, J = 4.2 Hz, 1H), 7.72-7.68 (m, 2H), 7.56 (ddd, J = 1.3, 4.6, 7.6 Hz, 1H), 5.56 (br t, J = 12.3 Hz, 1H), 3.93 (dt, J = 3.6, 7.5 Hz, 1H), 2.79 (d, J = 4.5 Hz, 3H), 2.55-2.52 (m, 3H), 2.44 (q, J = 12.1 Hz, 1H), 2.35 (br dd, J = 3.4, 12.5 Hz, 1H), 2.14 (br d, J = 11.7 Hz, 1H), 1.99-1.91 (m, 3H), 1.58-1.44 (m, 2H), 0.99 (s, 1H) |
| 249 | $^1$H NMR (600 MHz, DMSO-$d_6$) δ = 8.69-8.57 (m, 1H), 8.53 (d, J = 8.3 Hz, 1H), 8.17 (s, 1H), 8.00 (br dd, J = 0.9, 2.8 Hz, 1H), 7.94 (br s, 1H), 7.64 (d, J = 4.2 Hz, 1H), 7.19 (d, J = 4.2 Hz, 1H), 4.92-4.74 (m, 1H), 4.16 (dtd, J = 4.0, 7.7, 11.6 Hz, 1H), 3.45-3.35 (m, 1H), 2.84 (d, J = 4.5 Hz, 3H), 2.42-2.31 (m, 1H), 2.31-2.20 (m, 1H), 2.18-2.06 (m, 1H), 2.02-1.84 (m, 8H), 1.78 (br d, J = 12.5 Hz, 1H), 1.73-1.61 (m, 3H), 1.59-1.48 (m, 3H), 1.34-1.24 (m, 1H) |
| 250 | $^1$H NMR (600 MHz, DMSO-$d_6$) δ = 8.69 (br d, J = 7.6 Hz, 1H), 8.37 (br s, 1H), 8.15 (s, 1H), 7.94 (d, J = 4.2 Hz, 1H), 7.92-7.88 (m, 1H), 7.88-7.85 (m, 1H), 7.85-7.82 (m, 1H), 4.76 (br t, J = 11.9 Hz, 1H), 4.21-4.15 (m, 1H), 3.37-3.27 (m, 1H), 2.87-2.80 (m, 3H), 2.45-2.35 (m, 1H), 2.26 (dq, J = 4.0, 12.7 Hz, 1H), 2.14 (br d, J = 11.7 Hz, 1H), 2.03-1.85 (m, 7H), 1.79 (br d, J = 13.2 Hz, 1H), 1.75-1.65 (m, 3H), 1.60-1.50 (m, 3H), 1.37-1.26 (m, 1H) |
| 251 | $^1$H NMR (600 MHz, DMSO-$d_6$) δ = 8.61 (br s, 1H), 8.51 (d, J = 7.9 Hz, 1H), 8.17 (s, 1H), 8.00 (br s, 1H), 7.98-7.88 (m, 1H), 7.60 (d, J = 4.2 Hz, 1H), 7.29 (d, J = 3.8 Hz, 1H), 4.90-4.72 (m, 1H), 4.19-4.11 (m, 2H), 3.46-3.38 (m, 1H), 2.84 (d, J = 4.5 Hz, 3H), 2.43-2.31 (m, 1H), 2.31-2.19 (m, 1H), 2.17-2.10 (m, 1H), 2.02-1.84 (m, 9H), 1.78 (br d, J = 12.5 Hz, 1H), 1.73-1.61 (m, 3H), 1.59-1.48 (m, 3H), 1.34-1.24 (m, 1H) |

-continued

| Compound No. | Peak list |
|---|---|
| 253 | ¹H NMR (600 MHz, DMSO-$d_6$) δ = 9.41 (dd, J = 1.5, 4.9 Hz, 1H), 8.55-8.51 (m, 2H), 8.42 (dd, J = 1.7, 8.5 Hz, 1H), 8.31 (d, J = 1.1 Hz, 1H), 7.99-7.96 (m, 2H), 7.91 (dd, J = 1.9, 8.7 Hz, 1H), 7.65 (d, J = 3.8 Hz, 1H), 7.17 (d, J = 4.2 Hz, 1H), 5.49 (br s, 1H), 3.95-3.77 (m, 4H), 2.85 (d, J = 4.5 Hz, 3H), 2.46 (d, J = 12.5 Hz, 1H), 2.32 (br d, J = 12.5 Hz, 1H), 2.21 (br d, J = 12.1 Hz, 1H), 2.04 (br d, J = 11.0 Hz, 1H), 1.93 (br d, J = 9.8 Hz, 2H), 1.54-1.44 (m, 2H) |
| 254 | ¹H NMR (600 MHz, DMSO-$d_6$) δ = 9.41 (dd, J = 1.5, 4.9 Hz, 1H), 8.52 (d, J = 7.1 Hz, 2H), 8.41 (dd, J = 1.7, 8.5 Hz, 1H), 8.31 (d, J = 1.1 Hz, 1H), 7.97 (dd, J = 4.7, 8.5 Hz, 2H), 7.91 (dd, J = 1.5, 8.7 Hz, 1H), 7.60 (d, J = 3.8 Hz, 1H), 7.27 (d, J = 4.2 Hz, 1H), 5.53-5.46 (m, 1H), 3.92-3.90 (m, 1H), 2.85 (d, J = 4.5 Hz, 3H), 2.50-2.41 (m, 1H), 2.39-2.27 (m, 1H), 2.20 (br d, J = 11.7 Hz, 1H), 2.04 (br d, J = 11.0 Hz, 1H), 1.93 (br d, J = 10.2 Hz, 2H), 1.55-1.43 (m, 2H) |
| 255 | ¹H NMR (600 MHz, DMSO-$d_6$) δ = 9.41 (dd, J = 1.7, 5.1 Hz, 1H), 8.86 (s, 1H), 8.52 (s, 1H), 8.42 (dd, J = 1.7, 8.5 Hz, 1H), 8.31 (d, J = 1.5 Hz, 1H), 8.00-7.96 (m, 3H), 7.92-7.90 (m, 1H), 7.86 (d, J = 4.2 Hz, 1H), 5.50 (br t, J = 12.3 Hz, 1H), 3.98-3.91 (m, 2H), 2.84 (d, J = 4.5 Hz, 3H), 2.49-2.46 (m, 1H), 2.33 (br dd, J = 3.4, 12.5 Hz, 1H), 2.24 (br s, 1H), 2.04 (br d, J = 10.6 Hz, 1H), 1.99-1.90 (m, 2H), 1.60-1.44 (m, 2H) |
| 256 | ¹H NMR (600 MHz, DMSO-$d_6$) δ = 8.74-8.59 (m, 1H), 8.48 (d, J = 7.6 Hz, 1H), 8.40 (s, 1H), 8.08 (s, 2H), 8.05 (dt, J = 1.1, 9.3 Hz, 1H), 7.77 (td, J = 4.3, 8.7 Hz, 1H), 7.59 (d, J = 4.2 Hz, 1H), 7.26 (d, J = 3.8 Hz, 1H), 4.63 (tt, J = 4.1, 12.4 Hz, 1H), 3.90-3.80 (m, 1H), 2.36 (q, J = 12.0 Hz, 1H), 2.26-2.16 (m, 1H), 2.13 (br d, J = 11.7 Hz, 1H), 1.96 (br d, J = 12.5 Hz, 1H), 1.92-1.82 (m, 2H), 1.48-1.38 (m, 2H) |
| 257 | ¹H NMR (600 MHz, DMSO-$d_6$) δ = 9.45-9.40 (m, 1H), 9.06 (d, J = 5.3 Hz, 1H), 8.84 (d, J = 7.9 Hz, 1H), 8.53 (q, J = 4.4 Hz, 1H), 8.32 (d, J = 1.5 Hz, 1H), 8.28 (dd, J = 1.3, 5.1 Hz, 1H), 8.00-7.95 (m, 2H), 7.90 (dd, J = 1.5, 8.7 Hz, 1H), 7.86 (d, J = 4.2 Hz, 1H), 5.77-5.64 (m, 1H), 4.05-3.92 (m, 1H), 2.84 (d, J = 4.5 Hz, 4H), 2.48-2.42 (m, 1H), 2.38-2.29 (m, 1H), 2.23-2.15 (m, 1H), 2.03 (br d, J = 12.1 Hz, 1H), 1.99-1.92 (m, 2H), 1.61-1.46 (m, 2H) |
| 258 | ¹H NMR (600 MHz, DMSO-$d_6$) δ = 8.53 (d, J = 7.6 Hz, 1H), 8.48 (q, J = 4.5 Hz, 1H), 8.46 (d, J = 4.9 Hz, 1H), 8.26 (d, J = 1.5 Hz, 1H), 7.94-7.89 (m, 1H), 7.85 (dd, J = 1.5, 8.7 Hz, 1H), 7.62 (d, J = 4.2 Hz, 1H), 7.33 (d, J = 4.9 Hz, 1H), 7.30-7.25 (m, 3H), 6.97 (br s, 2H), 6.59 (br s, 2H), 5.78-5.63 (m, 1H), 4.00 (dtd, J = 3.8, 7.5, 11.5 Hz, 1H), 2.83 (d, J = 4.2 Hz, 3H), 2.36-2.30 (m, 2H), 2.27 (br s, 1H), 1.97-1.88 (m, 3H), 1.69-1.59 (m, 1H), 1.57-1.48 (m, 1H) |
| 259 | ¹H NMR (600 MHz, DMSO-$d_6$) δ = 9.43 (d, J = 1.1 Hz, 1H), 9.06 (d, J = 5.3 Hz, 1H), 8.59-8.48 (m, 2H), 8.32 (d, J = 1.1 Hz, 1H), 8.28 (dd, J = 1.1, 5.3 Hz, 1H), 7.98-7.94 (m, 1H), 7.90 (dd, J = 1.5, 8.7 Hz, 1H), 7.65 (d, J = 4.2 Hz, 1H), 7.18 (d, J = 4.2 Hz, 1H), 5.76-5.66 (m, 1H), 3.98-3.91 (m, 4H), 2.84 (d, J = 4.5 Hz, 3H), 2.45 (br d, J = 11.7 Hz, 1H), 2.31 (dt, J = 8.7, 12.3 Hz, 1H), 2.21-2.14 (m, 1H), 2.02 (br d, J = 11.0 Hz, 1H), 1.94 (td, J = 3.4, 6.5 Hz, 2H), 1.59-1.45 (m, 2H) |
| 263 | ¹H NMR (600 MHz, DMSO-$d_6$) δ = 8.54 (d, J = 7.9 Hz, 1H), 8.49 (q, J = 4.5 Hz, 1H), 8.28 (d, J = 1.5 Hz, 1H), 7.91-7.83 (m, 2H), 7.60 (d, J = 4.2 Hz, 1H), 7.52 (d, J = 0.8 Hz, 1H), 7.28 (d, J = 4.2 Hz, 1H), 7.23 (d, J = 0.8 Hz, 1H), 5.69-5.59 (m, 1H), 4.02 (s, 3H), 3.93-3.84 (m, 1H), 2.83 (d, J = 4.5 Hz, 3H), 2.39 (q, J = 12.1 Hz, 1H), 2.30-2.21 (m, 1H), 2.12 (br d, J = 11.3 Hz, 1H), 1.99-1.88 (m, 3H), 1.55-1.40 (m, 2H) |
| 264 | ¹H NMR (600 MHz, DMSO-$d_6$) δ = 8.67 (dd, J = 1.1, 4.5 Hz, 1H), 8.45 (d, J = 7.6 Hz, 1H), 8.29-8.22 (m, 1H), 8.06-7.97 (m, 2H), 7.76 (td, J = 4.4, 8.5 Hz, 1H), 7.59 (d, J = 3.8 Hz, 1H), 7.28 (d, J = 4.2 Hz, 1H), 4.60 (tt, J = 3.8, 12.4 Hz, 1H), 3.89-3.80 (m, 1H), 2.83 (d, J = 4.5 Hz, 3H), 2.28 (q, J = 11.8 Hz, 1H), 2.19-2.05 (m, 2H), 1.91 (br d, J = 10.6 Hz, 1H), 1.87-1.81 (m, 2H), 1.49-1.36 (m, 2H) |
| 265 | ¹H NMR (600 MHz, DMSO-$d_6$) δ = 8.67 (td, J = 1.2, 4.7 Hz, 1H), 8.46 (d, J = 7.9 Hz, 1H), 8.26 (br dd, J = 2.5, 4.3 Hz, 1H), 8.06-7.97 (m, 2H), 7.87-7.78 (m, 1H), 7.76 (td, J = 4.4, 8.5 Hz, 1H), 7.64 (d, J = 4.2 Hz, 1H), 7.17 (d, J = 4.2 Hz, 1H), 4.60 (tt, J = 4.0, 12.5 Hz, 1H), 3.90-3.80 (m, 1H), 2.83 (d, J = 4.5 Hz, 4H), 2.28 (q, J = 11.8 Hz, 1H), 2.19-2.05 (m, 2H), 1.91 (br d, J = 11.0 Hz, 1H), 1.87-1.81 (m, 2H), 1.49-1.36 (m, 2H) |
| 266 | ¹H NMR (600 MHz, DMSO-$d_6$) δ = 8.77 (d, J = 7.9 Hz, 1H), 8.69-8.65 (m, 1H), 8.30-8.22 (m, 1H), 8.04 (dt, J = 1.3, 9.2 Hz, 1H), 8.00-7.96 (m, 2H), 7.87-7.81 (m, 2H), 7.76 (td, J = 4.4, 8.5 Hz, 1H), 4.62 (tt J = 4.0, 12.4 Hz, 1H), 3.93-3.85 (m, 1H), 2.83 (d, J = 4.5 Hz, 3H), 2.29 (q, J = 12.1 Hz, 1H), 2.22-2.05 (m, 2H), 1.95-1.82 (m, 3H), 1.53-1.36 (m, 2H) |
| 267 | ¹H NMR (600 MHz, DMSO-$d_6$) δ = 8.66 (td, J = 1.2, 4.7 Hz, 1H), 8.47 (d, J = 7.9 Hz, 1H), 8.26-8.20 (m, 1H), 8.10 (s, 1H), 8.01 (ddd, J = 1.3, 8.5, 9.8 Hz, 1H), 7.74 (td, J = 4.3, 8.7 Hz, 1H), 7.60 (d, J = 3.8 Hz, 1H), 7.35 (s, 1H), 7.27 (d, J = 4.2 Hz, 1H), 4.67-4.57 (m, 1H), 4.04 (s, 3H), 3.92-3.83 (m, 1H), 2.84 (d, J = 4.5 Hz, 3H), 2.23 (br d, J = 11.7 Hz, 1H), 2.15-2.03 (m, 2H), 1.95-1.80 (m, 3H), 1.48-1.32 (m, 2H) |

-continued

| Compound No. | Peak list |
|---|---|
| 268 | $^1$H NMR (600 MHz, DMSO-$d_6$) δ = 8.67-8.65 (m, 1H), 8.48 (d, J = 7.9 Hz, 1H), 8.23 (d, J = 4.9 Hz, 1H), 8.10 (s, 1H), 8.02 (ddd, J = 1.3, 8.5, 9.8 Hz, 1H), 7.77-7.72 (m, 1H), 7.65 (d, J = 4.2 Hz, 1H), 7.36 (s, 1H), 7.17 (d, J = 4.2 Hz, 1H), 5.30-5.26 (m, 1H), 4.62 (s, 1H), 4.04 (s, 3H), 3.87 (s, 1H), 2.84 (d, J = 4.5 Hz, 3H), 2.22 (q, J = 11.7 Hz, 1H), 2.15-2.01 (m, 2H), 1.98-1.79 (m, 3H), 1.56-1.31 (m, 2H) |
| 269 | $^1$H NMR (600 MHz, DMSO-$d_6$) δ = 8.79 (d, J = 7.6 Hz, 1H), 8.66 (d, J = 4.9 Hz, 1H), 8.26-8.11 (m, 1H), 8.10 (s, 1H), 8.04-7.99 (m, 1H), 7.98 (d, J = 4.2 Hz, 1H), 7.86 (d, J = 4.2 Hz, 1H), 7.74 (td, J = 4.2, 8.6 Hz, 1H), 7.36 (s, 1H), 4.64 (br t, J = 3.6 Hz, 1H), 4.05 (s, 3H), 3.92 (td, J = 3.7, 7.7 Hz, 1H), 2.84 (d, J = 4.9 Hz, 3H), 2.24 (br d, J = 12.1 Hz, 1H), 2.16-2.06 (m, 2H), 1.95-1.83 (m, 3H), 1.53-1.31 (m, 2H) |
| 270 | $^1$H NMR (600 MHz, DMSO-$d_6$) δ = 8.91-8.82 (m, 1H), 8.81 (ddd, J = 0.9, 1.8, 4.8 Hz, 1H), 8.34 (d, J = 1.5 Hz, 1H), 8.21 (td, J = 1.0, 7.7 Hz, 1H), 8.07 (dt, J = 1.5, 7.7 Hz, 1H), 8.01-7.99 (m, 1H), 7.98-7.97 (m, 1H), 7.96-7.93 (m, 1H), 7.86 (d, J = 4.2 Hz, 1H), 7.61 (ddd, J = 1.1, 4.8, 7.6 Hz, 1H), 5.57 (br s, 1H), 3.98-3.91 (m, 1H), 3.91 (s, 3H), 2.48-2.41 (m, 1H), 2.35-2.26 (m, 1H), 2.23-2.16 (m, 1H), 2.00 (br d, J = 11.3 Hz, 1H), 1.98-1.91 (m, 2H), 1.57-1.43 (m, 2H) |
| 271 | $^1$H NMR (600 MHz, DMSO-$d_6$) δ = 8.81 (d, J = 4.9 Hz, 1H), 8.55 (d, J = 7.6 Hz, 1H), 8.36-8.32 (m, 1H), 8.21 (d, J = 7.9 Hz, 1H), 8.06 (dt, J = 1.9, 7.7 Hz, 1H), 8.01-7.97 (m, 1H), 7.97-7.92 (m, 1H), 7.67-7.63 (m, 1H), 7.60 (ddd, J = 0.9, 4.7, 7.6 Hz, 1H), 7.17 (d, J = 4.2 Hz, 1H), 5.56 (br t, J = 12.5 Hz, 1H), 3.93-3.88 (m, 4H), 2.43 (q, J = 12.3 Hz, 1H), 2.35-2.22 (m, 1H), 2.17 (br d, J = 11.7 Hz, 1H), 2.08-1.97 (m, 1H), 1.96-1.89 (m, 2H), 1.54-1.43 (m, 2H) |
| 275 | $^1$H NMR (600 MHz, DMSO-$d_6$) δ = 8.81 (qd, J = 0.8, 4.8 Hz, 1H), 8.55 (d, J = 7.9 Hz, 1H), 8.34 (d, J = 1.1 Hz, 1H), 8.22-8.20 (m, 1H), 8.09-8.04 (m, 1H), 8.00-7.96 (m, 1H), 7.96-7.91 (m, 1H), 7.65 (d, J = 4.2 Hz, 1H), 7.61 (ddd, J = 1.1, 4.9, 7.6 Hz, 1H), 7.17 (d, J = 4.2 Hz, 1H), 5.62-5.51 (m, 1H), 4.42-4.31 (m, 2H), 3.95-3.86 (m, 1H), 2.46-2.38 (m, 1H), 2.34-2.24 (m, 1H), 2.17 (br d, J = 12.1 Hz, 1H), 2.00 (br d, J = 12.5 Hz, 1H), 1.93 (br d, J = 6.8 Hz, 2H), 1.55-1.43 (m, 2H), 1.37 (t, J = 7.2 Hz, 3H) |
| 276 | $^1$H NMR (600 MHz, DMSO-$d_6$) δ = 8.82-8.80 (m, 1H), 8.53 (d, J = 7.9 Hz, 1H), 8.34 (d, J = 1.1 Hz, 1H), 8.23-8.19 (m, 1H), 8.10-8.03 (m, 1H), 8.00-7.97 (m, 1H), 7.96-7.91 (m, 1H), 7.62-7.59 (m, 2H), 7.27 (d, J = 4.2 Hz, 1H), 5.57 (ddd, J = 3.8, 8.6, 12.2 Hz, 1H), 4.40-4.34 (m, 2H), 3.94-3.85 (m, 1H), 2.46-2.39 (m, 1H), 2.34-2.24 (m, 1H), 2.17 (br d, J = 11.7 Hz, 1H), 2.00 (br d, J = 11.7 Hz, 1H), 1.96-1.88 (m, 2H), 1.55-1.43 (m, 2H), 1.37 (t, J = 7.0 Hz, 3H) |
| 277 | $^1$H NMR (600 MHz, DMSO-$d_6$) δ = 8.86 (d, J = 7.9 Hz, 1H), 8.82-8.80 (m, 1H), 8.34 (d, J = 1.5 Hz, 1H), 8.23-8.20 (m, 1H), 8.07 (dt, J = 1.7, 7.8 Hz, 1H), 8.01-7.97 (m, 2H), 7.96-7.92 (m, 1H), 7.86 (d, J = 4.2 Hz, 1H), 7.61 (ddd, J = 1.1, 4.9, 7.6 Hz, 1H), 5.63-5.52 (m, 1H), 4.42-4.32 (m, 2H), 3.98-3.90 (m, 1H), 2.44 (q, J = 12.0 Hz, 1H), 2.40-2.27 (m, 1H), 2.26-2.17 (m, 1H), 2.00 (br d, J = 11.0 Hz, 1H), 1.98-1.91 (m, 2H), 1.51 (br d, J = 8.3 Hz, 2H), 1.37 (t, J = 7.2 Hz, 3H) |
| 299 | $^1$H NMR (600 MHz, DMSO-$d_6$) δ = 8.89 (d, J = 1.9 Hz, 1H), 8.85-8.80 (m, 1H), 8.64 (q, J = 4.5 Hz, 1H), 8.61 (d, J = 7.9 Hz, 1H), 8.55 (d, J = 1.9 Hz, 1H), 8.27-8.24 (m, 1H), 8.09 (dt, J = 1.9, 7.7 Hz, 1H), 7.65-7.61 (m, 2H), 7.28-7.25 (m, 1H), 5.62-5.56 (m, 1H), 3.90 (td, J = 7.7, 15.5 Hz, 1H), 2.90 (d, J = 12.1 Hz, 1H), 2.86 (d, J = 4.5 Hz, 3H), 2.63 (br d, J = 3.8 Hz, 1H), 2.14 (br d, J = 11.3 Hz, 1H), 1.98-1.86 (m, 3H), 1.50-1.43 (m, 2H) |
| 285 | $^1$H NMR (600 MHz, DMSO-$d_6$) δ = 9.75 (s, 1H), 8.51-8.43 (m, 1H), 8.39 (d, J = 7.9 Hz, 1H), 8.23-8.10 (m, 1H), 7.87 (br d, J = 3.8 Hz, 1H), 7.84 (d, J = 1.9 Hz, 1H), 7.66 (d, J = 4.2 Hz, 1H), 7.29 (d, J = 4.2 Hz, 1H), 7.17 (d, J = 4.2 Hz, 1H), 6.46 (d, J = 7.9 Hz, 1H), 4.07 (dtd, J = 4.0, 7.7, 11.6 Hz, 1H), 3.81 (dtd, J = 4.0, 7.8, 11.8 Hz, 1H), 2.75 (d, J = 4.5 Hz, 3H), 2.19-2.10 (m, 1H), 1.91 (br d, J = 10.6 Hz, 1H), 1.85 (br d, J = 11.3 Hz, 1H), 1.81-1.74 (m, 1H), 1.36 (br d, J = 12.1 Hz, 2H), 1.32-1.22 (m, 2H) |
| 278 | $^1$H NMR (600 MHz, DMSO-$d_6$) δ = 8.84 (d, J = 1.9 Hz, 1H), 8.62 (br d, J = 7.6 Hz, 2H), 8.47 (d, J = 1.9 Hz, 1H), 7.69 (d, J = 4.2 Hz, 1H), 7.60 (d, J = 4.2 Hz, 1H), 7.37 (d, J = 4.2 Hz, 1H), 7.16 (d, J = 4.2 Hz, 1H), 4.79 (tt, J = 3.8, 12.1 Hz, 1H), 4.03 (tdt, J = 3.9, 7.9, 11.8 Hz, 1H), 2.94-2.82 (m, 4H), 2.69-2.60 (m, 1H), 2.15 (br d, J = 11.7 Hz, 1H), 2.01-1.93 (m, 1H), 1.91 (td, J = 3.4, 6.8 Hz, 2H), 1.67-1.54 (m, 1H), 1.51-1.41 (m, 1H) |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties

What is claimed is:

1. A compound of Formula (I) or a pharmaceutically acceptable salt thereof:

(I)

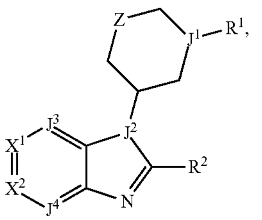

wherein

Z is $CH_2$, $CF_2$, O, or a bond;

each of $J^1$, $J^2$, $J^3$, and $J^4$ is independently CH or N;

$X^1$ is N or $CR^{5A}$;

$X^2$ is N or $CR^{5B}$;

$R^1$ is $—NR^3SO_2R^4$, $—NR^3C(O)R^4$, or $—C(O)(CH_2)_mNR^3R^4$;

$R^2$ is $—NR^6R^7$, $C_3$-$C_8$ cycloalkyl, $C_6$-$C_{10}$ aryl, or 5-10 membered heteroaryl, wherein each aryl or heteroaryl is optionally substituted with one, two, or three substituents $R^{2'}$ independently selected from halo, —CN, $—NO_2$, $C_1$-$C_6$ alkyl, $C_1$-$C_6$ alkoxy, halo$C_1$-$C_6$ alkyl, halo$C_1$-$C_6$ alkoxy, $C_2$-$C_6$ alkenyl, $C_2$-$C_6$ alkynyl, $—C(O)NR^6R^7$, $—C(O)R^6$, $—NR^6R^7$, $—NR^6C(O)R^7$, —OH, —S-(halo$C_1$-$C_6$ alkyl), $C_6$-$C_{10}$ aryl, and 5-10 membered heterocyclyl; or two $R^{2'}$ substituents together with the atoms to which they are attached form a five-membered heterocyclyl or $C_3$-$C_8$ cycloalkyl, each optionally substituted with halo;

$R^3$ is H or methyl;

$R^4$ is phenyl, thiophene, oxazole, isoxazole, thiazole, furan, pyrrole, or $C_2$-$C_6$ alkenyl, wherein each phenyl, thiophene, oxazole, isoxazole, thiazole, furan, or pyrrole is optionally substituted with one, two, or three substituents $R^{4'}$ independently selected from halo, —CN, $—NO_2$, $C_1$-$C_6$ alkyl, halo$C_1$-$C_6$ alkyl, $C_1$-$C_6$ alkoxy, $C_2$-$C_6$ alkenyl, $C_3$-$C_8$ cycloalkyl, $C_6$-$C_{10}$ aryl, $—(CH_2)_qNR^8C(O)R^9$, $—C(O)NR^8R^9$, $—C(O)OR^9$, $—C(O)R^9$, and 5-10 membered heterocyclyl;

$R^{5A}$ is F;

$R^{5B}$ is H, halo, —CN, $C_1$-$C_6$ alkyl, halo$C_1$-$C_6$ alkyl, $C_1$-$C_6$ alkoxy, $—(CH_2)$, OH, $—C(O)NR^8R^9$, $—NR^8COR^9$, 5-10 membered heteroaryl, $—C(O)R^8$, or $—C(O)OR^8$;

or $R^{5A}$ and $R^{5B}$ together with the atoms to which they are attached form a six-membered heterocyclyl ring optionally substituted with oxo;

$R^6$ and $R^7$ are independently H, $C_1$-$C_6$ alkyl, or $C_3$-$C_8$ cycloalkyl;

each $R^8$ is independently H, $C_1$-$C_6$ alkyl, or $C_3$-$C_8$ cycloalkyl;

each $R^9$ is independently H, $C_1$-$C_6$ alkyl, $C_2$-$C_6$ alkenyl, or $C_3$-$C_8$ cycloalkyl;

m is 0;

q is 0 or 1; and r is 0 or 1.

2. The compound of claim 1, wherein each of $J^2$, $J^3$, and $J^4$ is CH; $X^1$ is $CR^{5A}$, and $X^2$ is $CR^{5B}$.

3. The compound of claim 1, wherein $R^1$ is $—NR^3C(O)R^4$ or $—C(O)(CH_2)_mNR^3R^4$.

4. The compound of claim 3, wherein $R^4$ is phenyl thiophene, oxazole, isoxazole, thiazole, furan, or pyrrole, each optionally substituted with one, two, or three substituents $R^{4'}$.

5. The compound of claim 4, wherein $R^4$ is phenyl, thiophene, oxazole, isoxazole, thiazole, furan, or pyrrole, each of which is optionally substituted with one, two, or three substituents $R^{4'}$, wherein each $R^{4'}$ is independently selected from the group consisting of —F, —Cl, —Br, —CN, $—NO_2$, $—CF_3$, $—CH_3$, $—CH(CH_3)_2$, $—C(O)CH_3$, $—C(O)OCH_3$, phenyl, cyclopropyl, and morpholinyl.

6. The compound of claim 1, wherein $R^2$ is $C_6$-$C_{10}$ aryl or 5-10 membered heteroaryl, each optionally substituted with one, two, or three substituents $R^{2'}$.

7. The compound of claim 6, wherein $R^2$ is selected from the group consisting of phenyl, pyridine, pyrimidine, pyridazine, pyrazine, imidazole, and thiophene, each of which is optionally substituted with one, two, or three substituents $R^{2'}$, wherein each $R^{2'}$ is independently selected from the group consisting of —F, —Cl, —Br, —CN, $NO_2$, $—CH_3$, $—CF_2H$, —C≡CH, —C(O)H, $—CONH_2$, $—C(O)NHCH_3$, —OH, $—OCH_3$, $—OCF_3$, $—SCF_3$, $—NH_2$, $—NHC(O)CH_3$, and morpholine.

8. The compound of claim 1, wherein $X^2$ is $CR^{5B}$ and $R^{5B}$ is $—C(O)NR^8R^9$.

9. The compound of claim 1, wherein $X^2$ is $CR^{5B}$ and $R^{5B}$ is halo, —CN, $C_1$-$C_6$ alkyl, halo$C_1$-$C_6$ alkyl, $C_1$-$C_6$ alkoxy, $—(CH_2)_rOH$, $—NR^8COR^9$, 5-10 membered heteroaryl, $—C(O)R^8$, or $—C(O)OR^8$.

10. The compound of claim 9 wherein $X^2$ is $CR^{5B}$ and $R^{5B}$ is $—NR^8COR^9$ or $—C(O)OR^8$.

11. The compound of claim 1, wherein $X^2$ is $CR^{5B}$ and $R^{5B}$ is $—CF_3$, $—COCH_3$, $—CH_2OH$, —CN, or tetrazole.

12. The compound of claim 1, having a structure of Formula (III):

(III)

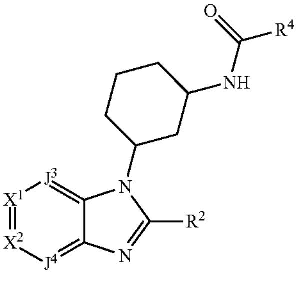

or a pharmaceutically acceptable salt thereof, wherein each $J^3$ and $J^4$ is independently CH or N;

$X^1$ is N or $CR^{5A}$;

$X^2$ is N or $CR^{5B}$;

wherein one, two, three, or four of $J^3$, $J^4$, $X^1$, and $X^2$ is N;

$R^2$ is $C_6$-$C_{10}$ aryl or 5-10 membered heteroaryl, wherein each aryl or heteroaryl is optionally substituted with one, two, or three substituents $R^{2'}$ independently selected from halo, —CN, —$NO_2$, $C_1$-$C_6$ alkyl, $C_1$-$C_6$ alkoxy, halo$C_1$-$C_6$ alkyl, halo$C_1$-$C_6$ alkoxy, $C_2$-$C_6$ alkenyl, $C_2$-$C_6$ alkynyl, —C(O)NR$^6$R$^7$, —C(O)R$^6$, —NR$^6$R$^7$, —NR$^6$C(O)R$^7$, —OH, —S-(halo$C_1$-$C_6$ alkyl), $C_6$-$C_{10}$ aryl, and 5-10 membered heterocyclyl; or two $R^{2'}$ substituents together with the atoms to which they are attached form a five-membered heterocyclyl or $C_3$-$C_8$ cycloalkyl, each optionally substituted with halo; and $R^4$ is phenyl, thiophene, oxazole, isoxazole, thiazole, furan, pyrrole, or $C_2$-$C_6$ alkenyl, wherein each phenyl, thiophene, oxazole, isoxazole, thiazole, furan, or pyrrole is optionally substituted with one, two, or three substituents $R^{4'}$ independently selected from halo, —CN, —$NO_2$, $C_1$-$C_6$ alkyl, halo$C_1$-$C_6$ alkyl, $C_1$-$C_6$ alkoxy, $C_2$-$C_6$ alkenyl, $C_3$-$C_8$ cycloalkyl, $C_6$-$C_{10}$ aryl, —$(CH_2)_q$NR$^8$C(O)R$^9$, —C(O)NR$^8$R$^9$, —C(O)OR$^9$, —C(O)R$^9$, and 5-10 membered heterocyclyl.

13. The compound of claim 12, wherein $R^2$ is phenyl optionally substituted with one, two, or three substituents $R^{2'}$ independently selected from halo, —CN, —$NO_2$, and $C_1$-$C_6$ alkyl.

14. The compound of claim 12, wherein $R^2$ is thiophene, oxazole, isoxazole, thiazole, furan, or pyrrole optionally substituted with one, two, or three substituents $R^{2'}$ independently selected from halo, —CN, —$NO_2$, and $C_1$-$C_6$ alkyl.

15. The compound of claim 12, wherein $R^4$ is thiophene optionally substituted with halo or phenyl.

16. The compound of claim 12, wherein $X^2$ is CR$^{5B}$;

$R^{5B}$ is H, halo, —C(O)NR$^8$R$^9$, —NR$^8$COR$^9$, or —C(O)OR$^8$; and $R^8$ and $R^9$ are each independently H or $C_1$-$C_6$ alkyl.

17. The compound of claim 1, having a structure of Formula (IV):

(IV)

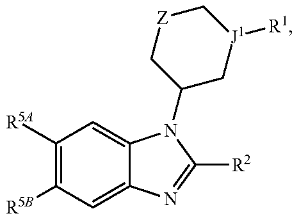

or a pharmaceutically acceptable salt thereof, wherein $R^1$ is —NR$^3$C(O)R$^4$ or —C(O)$(CH_2)_m$NR$^3$R$^4$; and $R^2$ is —NR$^6$R$^7$, $C_3$-$C_8$ cycloalkyl, $C_6$-$C_{10}$ aryl, or 5-10 membered heteroaryl, wherein each aryl or heteroaryl is substituted with one, two, or three substituents $R^{2'}$ independently selected from halo, —CN, —$NO_2$, $C_1$-$C_6$ alkoxy, halo$C_1$-$C_6$ alkyl, halo$C_1$-$C_6$ alkoxy, $C_2$-$C_6$ alkenyl, $C_2$-$C_6$ alkynyl, —C(O)NR$^6$R$^7$, —C(O)R$^6$, —NR$^6$R$^7$, —NR$^6$C(O)R$^7$, —OH, $C_6$-$C_{10}$ aryl, and 5-10 membered heterocyclyl; or two $R^{2'}$ substituents together with the atoms to which they are attached form a five-membered heterocyclyl or $C_3$-$C_8$ cycloalkyl, each optionally substituted with halo.

18. The compound of claim 1, having a structure of Formula (V), or a pharmaceutically acceptable salt thereof:

(V)

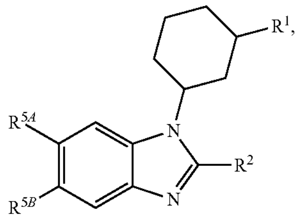

wherein $R^1$ is —NR$^3$SO$_2$R$^4$, —NR$^3$C(O)R$^4$, or —C(O)$(CH_2)_m$NR$^3$R$^4$;

$R^2$ is —NR$^6$R$^7$, $C_3$-$C_8$ cycloalkyl, $C_6$-$C_{10}$ aryl, or 5-10 membered heteroaryl, wherein each aryl or heteroaryl is optionally substituted with one, two, or three substituents $R^{2'}$ independently selected from halo, —CN, —$NO_2$, $C_1$-$C_6$ alkyl, $C_1$-$C_6$ alkoxy, halo$C_1$-$C_6$ alkyl, halo$C_1$-$C_6$ alkoxy, $C_2$-$C_6$ alkenyl, $C_2$-$C_6$ alkynyl, —C(O)NR$^6$R$^7$, —C(O)R$^6$, —NR$^6$R$^7$, —NR$^6$C(O)R$^7$, —OH, —S-(halo$C_1$-$C_6$ alkyl), $C_6$-$C_{10}$ aryl, and 5-10 membered heterocyclyl; or two $R^{2'}$ substituents together with the atoms to which they are attached form a five-membered heterocyclyl or $C_3$-$C_8$ cycloalkyl, each optionally substituted with halo;

$R^{5A}$ is F;

$R^{5B}$ is H, halo, —CN, $C_1$-$C_6$ alkyl, halo$C_1$-$C_6$ alkyl, $C_1$-$C_6$ alkoxy, —$(CH_2)$, OH, —C(O)NR$^8$R$^9$, —NR$^8$COR$^9$, 5-10 membered heteroaryl, —C(O)R$^8$, or —C(O)OR$^8$; and or $R^{5A}$ and $R^{5B}$ together with the atoms to which they are attached form a six-membered heterocyclyl ring optionally substituted with oxo.

19. The compound of claim 1, having a structure of Formula (VI) or a pharmaceutically acceptable salt thereof:

(VI)

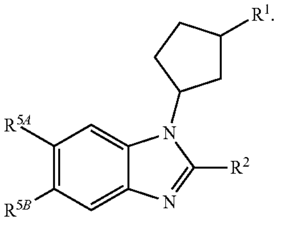

20. The compound of claim 1, having a structure of Formula (VII), or a pharmaceutically acceptable salt thereof:

(VII)

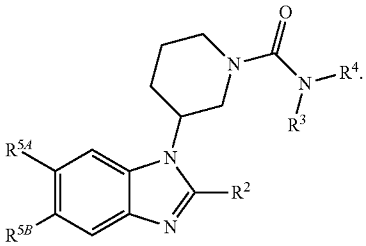

21. A compound, or pharmaceutically acceptable salt thereof, selected from the group consisting of:

155
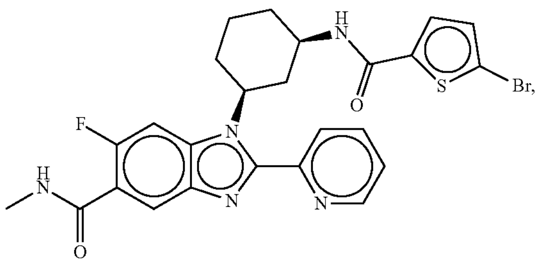
157
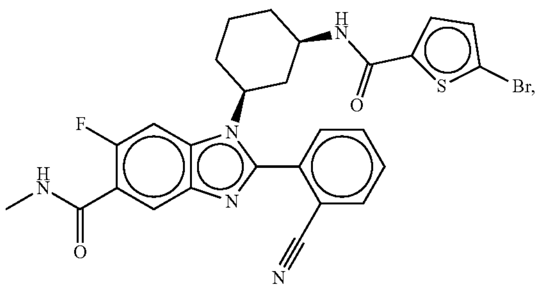
205
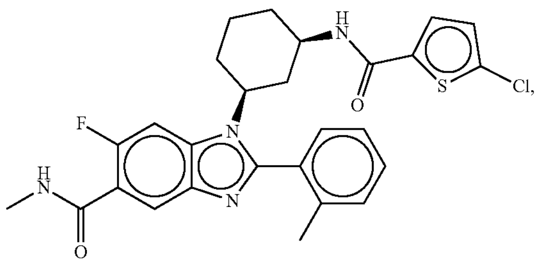
206
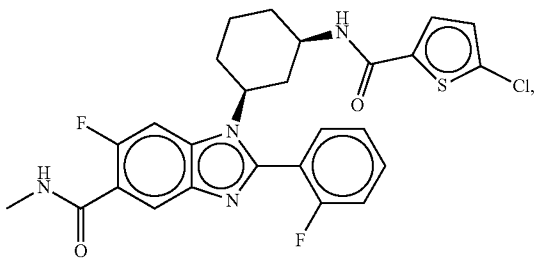
207
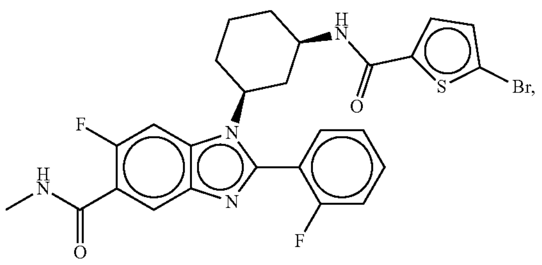
-continued
208
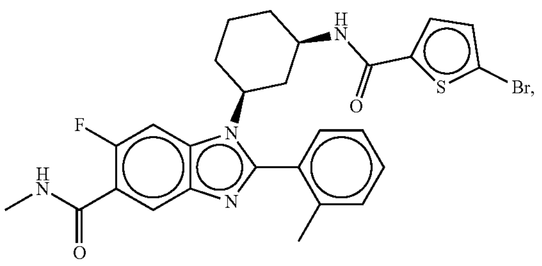
209
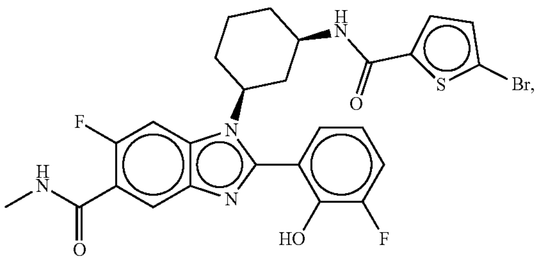
210
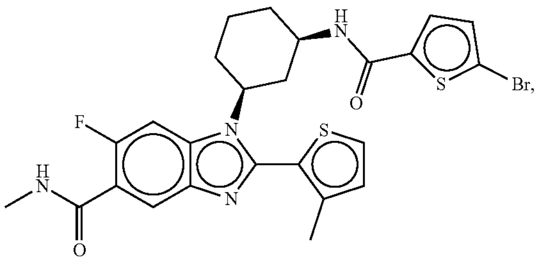
224
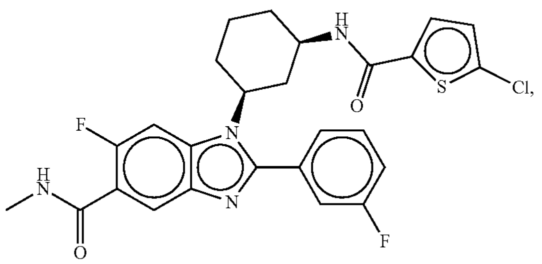
225
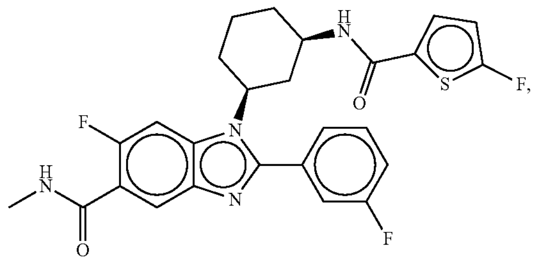

-continued
226
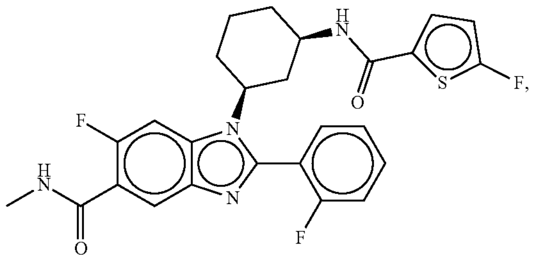
230
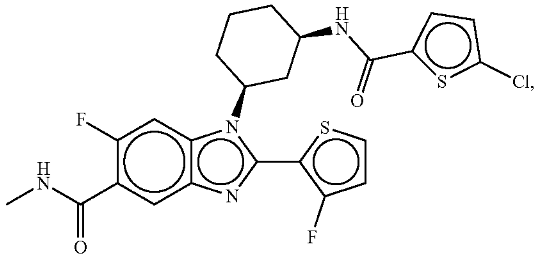
231
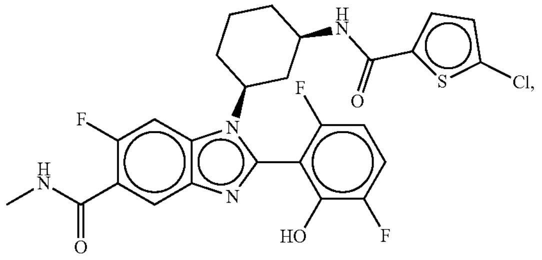
232
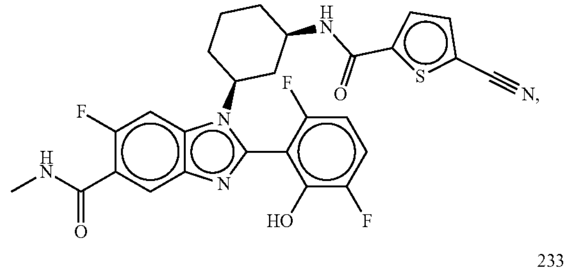
233
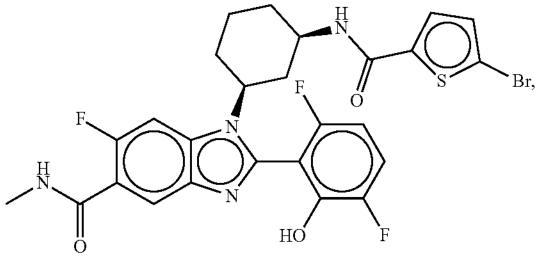
-continued
234
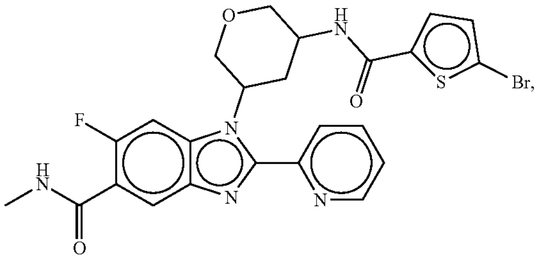
264
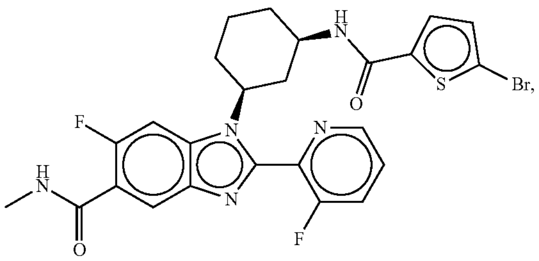
265
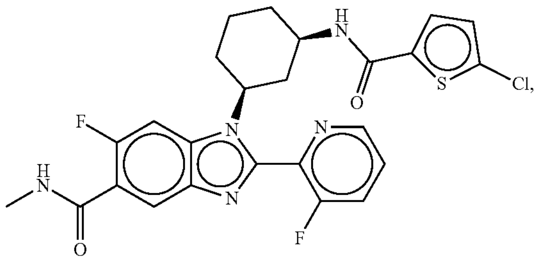
266
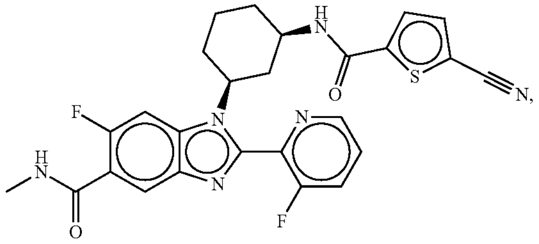
288
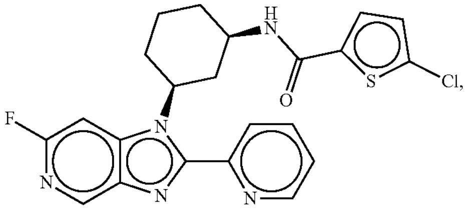
and
302
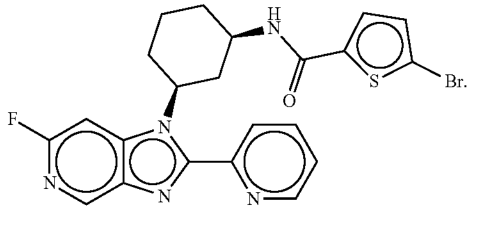
* * * * *